US011111277B2

(12) United States Patent
Young et al.

(10) Patent No.: US 11,111,277 B2
(45) Date of Patent: Sep. 7, 2021

(54) INFLUENZA VACCINES

(71) Applicants: InvVax, Inc., Pasadena, CA (US); The Regents of the University of California, Oakland, CA (US)

(72) Inventors: Arthur Young, Cypress, CA (US); Ren Sun, Los Angeles, CA (US); Nicholas C. Wu, Los Angeles, CA (US)

(73) Assignees: InvVax, Inc., Pasadena, CA (US); The Regents of the University of California, Oakland, CA (US)

( * ) Notice: Subject to any disclaimer, the term of this patent is extended or adjusted under 35 U.S.C. 154(b) by 75 days.

(21) Appl. No.: 15/857,436

(22) Filed: Dec. 28, 2017

(65) Prior Publication Data

US 2018/0230187 A1 Aug. 16, 2018

Related U.S. Application Data

(60) Provisional application No. 62/439,865, filed on Dec. 28, 2016, provisional application No. 62/550,167, filed on Aug. 25, 2017.

(51) Int. Cl.

| | |
|---|---|
| *C07K 14/11* | (2006.01) |
| *C07K 14/075* | (2006.01) |
| *A61K 39/145* | (2006.01) |
| *A61P 31/16* | (2006.01) |
| *A61K 39/12* | (2006.01) |
| *C07K 14/005* | (2006.01) |
| *C12N 15/86* | (2006.01) |
| *A61K 39/00* | (2006.01) |

(52) U.S. Cl.
CPC .............. *C07K 14/11* (2013.01); *A61K 39/12* (2013.01); *A61K 39/145* (2013.01); *A61P 31/16* (2018.01); *C07K 14/005* (2013.01); *C07K 14/075* (2013.01); *C12N 15/86* (2013.01); *A61K 2039/5256* (2013.01); *A61K 2039/5258* (2013.01); *A61K 2039/53* (2013.01); *A61K 2039/543* (2013.01); *A61K 2039/545* (2013.01); *A61K 2039/55555* (2013.01); *A61K 2039/57* (2013.01); *A61K 2039/6018* (2013.01); *A61K 2039/70* (2013.01); *C12N 2710/10343* (2013.01); *C12N 2760/16134* (2013.01); *C12N 2760/16234* (2013.01); *C12N 2760/16334* (2013.01)

(58) Field of Classification Search
None
See application file for complete search history.

(56) References Cited

U.S. PATENT DOCUMENTS

| | | | |
|---|---|---|---|
| 6,083,716 A | 7/2000 | Wilson et al. | |
| 6,171,820 B1 | 1/2001 | Short | |
| 6,337,186 B1 | 1/2002 | Krebber | |
| 6,596,539 B1 | 7/2003 | Stemmer et al. | |
| 6,696,275 B2 | 2/2004 | Short et al. | |
| 6,713,279 B1 | 3/2004 | Short | |
| 6,740,325 B1 | 5/2004 | Arnon et al. | |
| 6,740,506 B2 | 5/2004 | Short et al. | |
| 6,773,900 B2 | 8/2004 | Short et al. | |
| 7,488,491 B2 | 2/2009 | Tsuji et al. | |
| 7,537,768 B2 | 5/2009 | Luke et al. | |
| 7,569,225 B2 * | 8/2009 | Jackson | A61K 39/0006 424/184.1 |
| 7,785,603 B2 | 8/2010 | Luke et al. | |
| 7,790,374 B2 | 9/2010 | Schwaneberg | |
| 7,914,797 B2 | 3/2011 | Arnon et al. | |
| 8,128,938 B1 | 3/2012 | Luke et al. | |
| 8,444,995 B2 | 5/2013 | Soloff et al. | |
| 8,685,409 B2 | 4/2014 | Youn et al. | |
| 8,747,861 B2 | 6/2014 | Ben-Yedidia et al. | |
| 8,821,890 B2 | 9/2014 | Luke et al. | |
| 9,045,531 B2 | 6/2015 | Miyakawa et al. | |
| 9,265,822 B2 | 2/2016 | Hoft | |
| 9,303,070 B2 | 4/2016 | Ben-Yedidia et al. | |
| 9,353,159 B2 | 5/2016 | Ben-Yedidia et al. | |
| 9,446,116 B2 | 9/2016 | Stoloff et al. | |
| 9,603,920 B2 | 3/2017 | Diaz-Mitoma et al. | |
| 9,889,191 B2 | 2/2018 | Stoloff et al. | |
| 10,030,231 B2 * | 7/2018 | Dormitzer | C12N 7/00 |
| 1,017,917 A1 | 1/2019 | Zimmerman et al. | |
| 1,023,874 A1 | 3/2019 | Zimmerman | |
| 1,040,001 A1 | 9/2019 | Mahr et al. | |
| 1,042,682 A1 | 10/2019 | Uritski et al. | |

(Continued)

FOREIGN PATENT DOCUMENTS

| | | |
|---|---|---|
| CA | 2658559 A1 | 4/2008 |
| CA | 2566355 C | 4/2014 |

(Continued)

OTHER PUBLICATIONS

Alexander et al. (Human Immunology, 2010, p. 468-474).*
Ben-Yedidia et al. (International Immunology, 1999, p. 1043-1051).*
Cho et al. (Cancer Immunology Immunotherapy, 2012, p. 343-351).*
Aurielle et al. (Human Immunology, 2009, p. 711-721).*
Alexander, Jeff et al. "Identification of broad binding class I HLA supertype epitopes to provide universal coverage of influenza A virus." Human immunology vol. 71,5 (2010): 468-74. doi:10.1016/j.humimm.2010.02.014.
Amabel C. L. Tan et al., "Precursor Frequency and Competition Dictate the HLA-A2-Restricted CD8+ T Cell Responses to Influenza A Infection and Vaccination in HLA-A2.1 Transgenic Mice", J Immunol Aug. 15, 2011, 187 (4) 1895-1902; DOI: https://doi.org/10.4049/jimmunol.1100664.

(Continued)

*Primary Examiner* — Agnieszka Boesen
(74) *Attorney, Agent, or Firm* — Wilson Sonsini Goodrich & Rosati

(57) ABSTRACT

Provided herein are compositions related to vaccines, e.g., influenza vaccines, including, peptide based vaccines, nucleic acid based vaccines, recombinant virus based vaccines, antibody based vaccines, and virus based vaccines. Also provided herein are methods related to vaccines, e.g., influenza vaccines, including methods of identifying epitopes for the vaccines, producing, formulating, and administering the vaccines.

12 Claims, 6 Drawing Sheets

Specification includes a Sequence Listing.

(56) References Cited

U.S. PATENT DOCUMENTS

| | | |
|---|---|---|
| 2004/0116368 A1 | 6/2004 | Wen et al. |
| 2006/0079453 A1 | 4/2006 | Sidney et al. |
| 2007/0003576 A1 | 1/2007 | Gambotto et al. |
| 2007/0066534 A1 | 3/2007 | Jackson et al. |
| 2007/0122424 A1 | 5/2007 | Arnon et al. |
| 2007/0122430 A1 | 5/2007 | Shneider et al. |
| 2009/0191233 A1 | 7/2009 | Bonnet et al. |
| 2011/0087005 A1 | 4/2011 | Miyakawa et al. |
| 2014/0274806 A1 | 9/2014 | O'Hagan et al. |
| 2015/0140065 A1 | 5/2015 | Zimmerman et al. |
| 2017/0319671 A1 | 11/2017 | Faulkner et al. |
| 2019/0201519 A1 | 7/2019 | Stoloff et al. |

FOREIGN PATENT DOCUMENTS

| | | |
|---|---|---|
| EP | 1189624 A1 | 3/2002 |
| EP | 1578432 A2 | 9/2005 |
| EP | 1982992 B1 | 10/2010 |
| EP | 1917970 B1 | 6/2011 |
| EP | 2795321 A2 | 10/2014 |
| EP | 2173376 B1 | 3/2015 |
| EP | 2383284 B1 | 8/2016 |
| EP | 3263589 A2 | 1/2018 |
| WO | WO-9945954 A1 | 9/1999 |
| WO | WO-02092780 A2 | 11/2002 |
| WO | WO-2004014956 A1 | 2/2004 |
| WO | WO-2006113214 A2 | 10/2006 |
| WO | WO-2007051036 A2 | 5/2007 |
| WO | WO-2009016639 A2 | 2/2009 |
| WO | WO-2009029686 A1 | 3/2009 |
| WO | WO-2009117134 A2 | 9/2009 |
| WO | WO-2010117786 A1 | 10/2010 |
| WO | WO-2011041490 A1 | 4/2011 |
| WO | WO-2013093512 A2 | 6/2013 |
| WO | WO-2015157189 A1 | 10/2015 |
| WO | WO-2018126060 A1 | 7/2018 |
| WO | WO-2019046901 A1 | 3/2019 |

OTHER PUBLICATIONS

Babon, Jenny Aurielle B et al. "Genome-wide screening of human T-cell epitopes in influenza A virus reveals a broad spectrum of CD4(+) T-cell responses to internal proteins, hemagglutinins, and neuraminidases." Human immunology vol. 70,9 (2009): 711-21. doi:10.1016/j.humimm.2009.06.004.

Boon, A C M et al. "The magnitude and specificity of influenza A virus-specific cytotoxic T-lymphocyte responses in humans is related to HLA-A and -B phenotype." Journal of virology vol. 76,2 (2002): 582-90. doi:10.1128/jvi.76.2.582-590.2002.

Carreno BM et al., "The peptide binding specificity of HLA class I molecules is largely allele-specific and non-overlapping", Mol Immunol. Sep. 1992;29(9):1131-40.

Chaves, Francisco A et al. "The utility and limitations of current Web-available algorithms to predict peptides recognized by CD4 T cells in response to pathogen infection." Journal of immunology (Baltimore, Md. : 1950) vol. 188,9 (2012): 4235-48. doi:10.4049/jimmunol.1103640.

Chen, Li et al. "Broad-Based CD4+ T Cell Responses to Influenza A Virus in a Healthy Individual Who Lacks Typical Immunodominance Hierarchy." Frontiers in immunology vol. 8 375. Apr. 3, 2017, doi:10.3389/fimmu.2017.00375.

Currier JR et al., "A panel of MHC class I restricted viral peptides for use as a quality control for vaccine trial ELISPOT assays", J Immunol Methods. Feb. 1, 2002;260(1-2):157-72.

Di Mario, Giuseppina et al. "A heat-inactivated H7N3 vaccine induces cross-reactive cellular immunity in HLA-A2.1 transgenic mice." Virology journal vol. 13 56. Mar. 31, 2016, doi:10.1186/s12985-016-0513-7.

Di Mario, Giuseppina et al. "Protective immunity against influenza in HLA-A2 transgenic mice by modified vaccinia virus Ankara vectored vaccines containing internal influenza proteins." Pathogens and global health vol. 111,2 (2017): 76-82. doi:10.1080/20477724.2016.1275465.

Fløe, Andreas et al. "Development of an epitope panel for consistent identification of antigen-specific T-cells in humans." Immunology vol. 152,2 (2017): 298-307. doi:10.1111/imm.12769.

Gianfrani C et al., "Human memory CTL response specific for influenza A virus is broad and multispecific", Human Immunology, vol. 61, Issue 5, May 2000, pp. 438-452.

Gschoesser C et al., "CD4+ and CD8+ mediated cellular immune response to recombinant influenza nucleoprotein", Vaccine. Nov. 1, 2002;20(31-32):3731-8.

Herrmann VL et al., "Cytotoxic T cell vaccination with PLGA microspheres interferes with influenza A virus replication in the lung and suppresses the infectious disease", J Control Release. Oct. 28, 2015;216:121-31. doi: 10.1016/j.jconrel.2015.08.019.

Hoft, Daniel F et al. "Live and inactivated influenza vaccines induce similar humoral responses, but only live vaccines induce diverse T-cell responses in young children." The Journal of infectious diseases vol. 204,6 (2011): 845-53. doi:10.1093/infdis/jir436.

Hoppes, Rieuwert et al. "Altered peptide ligands revisited: vaccine design through chemically modified HLA-A2-restricted T cell epitopes." Journal of immunology (Baltimore, Md. : 1950) vol. 193,10 (2014): 4803-13. doi:10.4049/jimmunol.1400800.

Keskin, Derin B et al. "Physical detection of influenza A epitopes identifies a stealth subset on human lung epithelium evading natural CD8 immunity." Proceedings of the National Academy of Sciences of the United States of America vol. 112,7 (2015): 2151-6. doi:10.1073/pnas.1423482112.

Klinger, Mark et al. "Multiplex Identification of Antigen-Specific T Cell Receptors Using a Combination of Immune Assays and Immune Receptor Sequencing." PloS one vol. 10,10 e0141561. Oct. 28, 2015, doi:10.1371/journal.pone.0141561.

Lee, Jessica B et al. "Decline of influenza-specific CD8+ T cell repertoire in healthy geriatric donors." Immunity & ageing : I & A vol. 8 6. Aug. 16, 2011, doi:10.1186/1742-4933-8-6.

Lee, Laurel Yong-Hwa et al. "Memory T cells established by seasonal human influenza A infection cross-react with avian influenza A (H5N1) in healthy individuals." The Journal of clinical investigation vol. 118,10 (2008): 3478-90. doi:10.1172/JCI32460.

Nayak, Jennifer L, and Andrea J Sant. "Loss in CD4 T-cell responses to multiple epitopes in influenza due to expression of one additional MHC class II molecule in the host." Immunology vol. 136,4 (2012): 425-36. doi:10.1111/j.1365-2567.2012.03599.x.

Nayak, Jennifer L et al. "Analyses of the specificity of CD4 T cells during the primary immune response to influenza virus reveals dramatic MHC-linked asymmetries in reactivity to individual viral proteins." Viral immunology vol. 23,2 (2010): 169-80. doi:10.1089/vim.2009.0099.

Quiñones-Parra, Sergio et al. "Preexisting CD8+ T-cell immunity to the H7N9 influenza A virus varies across ethnicities." Proceedings of the National Academy of Sciences of the United States of America vol. 111,3 (2014): 1049-54. doi:10.1073/pnas.1322229111.

Richards, Katherine A et al. "Infection of HLA-DR1 transgenic mice with a human isolate of influenza a virus (H1N1) primes a diverse CD4 T-cell repertoire that includes CD4 T cells with heterosubtypic cross-reactivity to avian (H5N1) influenza virus." Journal of virology vol. 83,13 (2009): 6566-77. doi:10.1128/JVI.00302-09.

Rosendahl Huber, Sietske K et al. "Chemical Modification of Influenza CD8+ T-Cell Epitopes Enhances Their Immunogenicity Regardless of Immunodominance." PloS one vol. 11,6 e0156462. Jun. 22, 2016, doi:10.1371/journal.pone.0156462.

Soema, Peter C et al. "Whole-Inactivated Influenza Virus is a Potent Adjuvant for Influenza Peptides Containing CD8+ T Cell Epitopes." Frontiers in immunology vol. 9 525. Mar. 14, 2018, doi:10.3389/fimmu.2018.00525.

Tungatt, Katie et al. "Induction of influenza-specific local CD8 T-cells in the respiratory tract after aerosol delivery of vaccine antigen or virus in the Babraham inbred pig." PLoS pathogens vol. 14,5 e1007017. May 17, 2018, doi:10.1371/journal.ppat.1007017.

Valkenburg, Sophie A et al. "Molecular basis for universal HLA-A*0201-restricted CD8+ T-cell immunity against influenza viruses."

(56) References Cited

OTHER PUBLICATIONS

Proceedings of the National Academy of Sciences of the United States of America vol. 113,16 (2016): 4440-5. doi:10.1073/pnas.1603106113.
Voeten, J T et al. "Antigen processing for MHC class I restricted presentation of exogenous influenza A virus nucleoprotein by B-lymphoblastoid cells." Clinical and experimental immunology vol. 125,3 (2001): 423-31. doi:10.1046/j.1365-2249.2001.01613.x.
Voeten, J T et al. "Antigenic drift in the influenza a virus (H3N2) nucleoprotein and escape from recognition by cytotoxic T lymphocytes." Journal of virology vol. 74,15 (2000): 6800-7. doi:10.1128/jvi.74.15.6800-6807.2000.
Wei, Huiling et al. "DNA-vaccine platform development against H1N1 subtype of swine influenza A viruses." Viral immunology vol. 25,4 (2012): 297-305. doi:10.1089/vim.2011.0093.
Wilkinson TM et al., "Preexisting influenza-specific CD4+ T cells correlate with disease protection against influenza challenge in humans", Nat Med. Jan. 29, 2012;18(2):274-80. doi: 10.1038/nm.2612.
Wu, Chao et al. "Systematic identification of immunodominant CD8+ T-cell responses to influenza A virus in HLA-A2 individuals." Proceedings of the National Academy of Sciences of the United States of America vol. 108,22 (2011): 9178-83. doi:10.1073/pnas.1105624108.
Y. Adar et al., A universal epitope-based influenza vaccine and its efficacy against H5N1, vol. 27, Issue 15, Mar. 26, 2009, pp. 2099-2107.
Yk Cheung et al., "Human immunogenic T cell epitopes in nucleoprotein of human influenza A (H5N1) virus", Hong Kong Med J 2012;18(Suppl 2):517-21.
Zhang, Nianzhi et al. "Crystal structure of swine major histocompatibility complex class I SLA-1 0401 and identification of 2009 pandemic swine-origin influenza A H1N1 virus cytotoxic T lymphocyte epitope peptides." Journal of virology vol. 85,22 (2011): 11709-24. doi:10.1128/JVI.05040-11.
Arts, E. J. et al. HIV-1 antiretroviral drug therapy. Cold Spring Harbor Perspec Med vol. 2, pp. a007161 (2012).
Berg, P. Co-chairman's remarks: reverse genetics: directed modification of DNA for functional analysis. Gene. Dec. 15, 1993;135(1-2):261-4.
Breuer, et al. A cleavage enzyme-cytometric bead array provides biochemical profiling of resistance mutations in HIV-1 Gag and protease. Biochemistry. May 24, 2011;50(20):4371-81. doi: 10.1021/bi200031m. Epub Apr. 27, 2011.
Burnham, A. J. et al., Neuraminidase inhibitors for influenza B virus infection: etTicacy and resistance. Antiviral Res. vol. 100 pp. 520-534 (2013).
Burton, D. R., et al. Broadly neutralizing antibodies present new prospects to counter highly antigenically diverse viruses. Science vol. 337, pp. 183-186 (2012).
Chayama, K. & Hayes, C. N. Hepatitis C virus: How genetic variability affectspathobiology of disease. J Gastroenterol Hepatol vol. 1, pp. 83-95 (2011).
Chen, et al. Vaccine design of hemagglutinin glycoprotein against influenza. Trends Biotechnol. Sep. 2011;29(9):426-34. doi: 10.1016/j.tibtech.2011.04.007.
Choi et al. Viral vectors for vaccine applications. Clin Exp Vaccine Res. Jul. 2013; 2(2): 97-105.
Coffin, J. et al. HIV pathogenesis: dynamics and genetics of viral populations and infected cells. Cold Spring Harbor Perspec Med vol. 3, p. a012526 (2013).
Coffin, J. M. HIV population dynamics in vivo: implications for genetic variation, pathogenesis, and therapy. Science vol. 267, pp. 483-489 (1995).
DeGroot, A. S. et al. Further progress on defining highly conserved immunogenic epitopes for a global HIV vaccine: HLA-A3-restricted GAIA vaccine epitopes. Hum. Vaccin. Immunother vol. 8, pp. 987-1000 (2012).

Ekiert, et al. Antibody recognition of a highly conserved influenza virus epitope. Science. Apr. 10, 2009;324(5924):246-51. doi: 10.1126/science.1171491. Epub Feb. 26, 2009.
Engelhardt, OG. Many ways to make an influenza virus—review of influenza virus reverse genetics methods. Influenza Other Respir Viruses. May 2013;7(3):249-56. doi: 10.1111/j.1750-2659.2012.00392.x. Epub Jun. 19, 2012.
Epstein, et al. Protection against multiple influenza A subtypes by vaccination with highly conserved nucleoprotein. Vaccine, 2005. 23(46-47): p. 5404-10.
Fijalkowska, Iwona et al. DNA replication fidelity in *Escherichia coli*: a multi-DNA polymerase affair. FEMS Microbial Rev vol. 36, pp. 1105-1121 (2012).
Fodor, et al. Rescue of influenza A virus from recombinant DNA. J Virol. Nov. 1999;73(11):9679-82.
Genesca, M. et al. With minimal systemic T-cell expansion, CD8+ T cells mediate protection of rhesus macaques immunized with attenuated simian-human immunodeficiency virus SHIV89.6 from vaginal challenge with simian immunodeficiency virus. J. Viral. 82:11181-11196 (2008).
Gerhard, W. et al. Prospects for universal influenza virus vaccine. Emerg. Infect. Dis. vol. 12, pp. 569-574 (2006).
Gilbert, S.C. Advances in the development of universal influenza vaccines. Influenza Other Respi. Viruses vol. 7, Issue 5, pp. 750-758. Sep. 2013. (Epub Sep. 24, 2012).
Girard, et al. A review of vaccine research and development: human acute respiratory infections. Vaccine. Dec. 30, 2005;23(50):5708-24. Epub Aug. 3, 2005.
Goodman et al. A Human Multi-Epitope Recombinant Vaccinia Virus as a Universal T Cell Vaccine Candidate against Influenza Virus. PLoS ONE, 2011, 6(10): e25938. https://doi.org/10.1371/journal.pone.0025938.
Gout, J.-F. et al. Large-scale detection of in vivo transcription errors. Proc. Natl. Acad. Sci. USA 110:18584-18589 (2013).
Gray, Kevin A., et al. "Rapid Evolution of Reversible Denaturation and Elevated Melting Temperature in a Microbial Haloalkane Dehalogenase" Adv. Synth. Catal. vol. 343, No. 6-7, 2001.
Guan, et al. The emergence of pandemic influenza viruses. Protein Cell. Jan. 2010;1(1):9-13. doi: 10.1007/513238-010-0008-z. Epub Feb. 7, 2010.
Haut et al. A Partial E3 Deletion in Replication-Defective Adenoviral Vectors Allows for Stable Expression of Potentially Toxic Transgene Products. Hum Gene Ther Methods. Oct. 2016;27(5):187-196.
He, et al. Crystal structure of the polymerase PA(C)-PB1(N) complex from an avian influenza H5N1 virus. Nature. Aug. 28, 2008;454(7208):1123-6. doi: 10.1038/nature07120. Epub Jul. 9, 2008.
Hedskog, et al. Dynamics of HIV-1 quasispecies during antiviral treatment dissected using ultra-deep pyrosequencing. PLoS One. Jul. 7, 2010;5(7):e11345. doi: 10.1371/journal.pone.0011345.
Henderson et al. Recombinant Vaccinia Virus Vaccines. Vaccines. 3rd edition. Philadelphia: Saunders. 5 pages. 1999.
Hersperger, A. R. et al. Increased HIV-specific CD8+ T-cell cytotoxic potential in HIV elite controllers is associated with T-bet expression. Blood 117:3799-3808 (2011).
Hoffmann, E. et at. Rescue of influenza B virus from eight plasmids. Proc. Natl. Acad. Sci. USA vol. 99, pp. 11411-11416 (2002).
Hoffmann, et al. A DNA transfection system for generation of influenza A virus from eight plasmids. Proc Natl Acad Sci USA. vol. 97, Issue 11, pp. 6108-6113 (May 23, 2000).
Homer, et al. BFAST: an alignment tool for large scale genome resequencing. PLoS One. Nov. 11, 2009;4(11):e7767. doi: 10.1371/journal.pone.0007767.
Hoof, et al. NetMHCpan, a method for MHC class I binding prediction beyond humans. Immunogenetics. Jan. 2009;61(1):1-13. doi: 10.1007/s00251-008-0341-z. Epub Nov. 12, 2008.
Hwang, et al. Conserved herpesviral kinase promotes viral persistence by inhibiting the IRF-3-mediated type I interferon response. Cell Host Microbe. Feb. 19, 2009;5(2):166-78. doi: 10.1016/j.chom.2008.12.013.
Influenza Virus Resource Website. Accessed Nov. 10, 2014. http://www.ncbi.nlm.nih.gov/genomes/FLU/FLU.html.

(56) References Cited

OTHER PUBLICATIONS

Jin, X. et al. Dramatic rise in plasma viremia after CD8+ T cell depletion in simian immunodeficiency virus-infected macaques. J. Exp. Med. 189:991-998 (1999).
Kang, S. M., Song, J. M. & Compans, R. W. Novel vaccines against influenza viruses. Virus Res. vol. 162, pp. 31-38 (2011).
Kiepiela, K. et al. CD8+ T-cell responses to different HIV proteins have discordant associations with viral load. Nature Med. 13:46-53 (2007).
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Knapp, et al. In vitro selection of clinically relevant bevirimat resistance mutations revealed by "deep" sequencing of serially passaged, quasispecies-containing recombinant HIV-1. J Clin Microbiol. Jan. 2011;49(1):201-8. doi: 10.1128/JCM.01868-10. Epub Nov. 17, 2010.
Korber, Bet al. Evolutionary and immunological implications of contemporary HIV-1 variation. Br Med Bull vol. 58, pp. 19-42 (2001).
Kretz, Keith A., et al. "Gene Site Saturation Mutagenesis: A Comprehensive Mutagenesis Approach" Methods in enzymology, vol. 388, pp. 3-11 (2004).
Kuroda, et al. Characterization of quasispecies of pandemic 2009 influenza A virus (A/H1N1/2009) by de novo sequencing using a next-generation DNA sequencer. PLoS One. Apr. 23, 2010;5(4):e10256. doi: 10.1371/journal.pone.0010256.
Lambert, et al. Influenza vaccines for the future. New England Journal of Medicine. Nov. 18, 2010; vol. 363, Issue 21, pp. 2036-2044. doi: 10.1056/NEJMra1002842.
Levitz, L. et al. Conservation of HIV-1 T cell epitopes across time and clades: validation of immunogenic HLA-A2 epitopes selected for the GAIA HIV vaccine. Vaccine vol. 30, pp. 7547-7560 (2012).
Li et al. Recombinant protein comprising multi-neutralizing epitopes induced high titer of antibodies against Influenza A virus. Immunobiology. vol. 207, Issue 5, 2003, pp. 305-313.
Luytjes, et al. Amplification, expression, and packaging of foreign gene by influenza virus. Cell. Dec. 22, 1989;59(6):1107-13.
Lynch, RM, et al. Appreciating HIV type 1 diversity: subtype differences in Env. AIDS Res Human Retroviruses vol. 25, pp. 237-248 (2009).
Maier, et al. Differential role of the influenza A virus polymerase PA subunit for vRNA and cRNA promoter binding. Virology. Jan. 5, 2008;370(1):194-204. Epub Oct. 1, 2007.
Middleton, D. et al., New allele frequency database: http://www.allelefrequencies.net Tissue Antigens, vol. 61, pp. 403-407 (2003).
Neumann, et al. Generation of influenza A viruses entirely from cloned cDNAs. Proc Natl Acad Sci U S A. Aug. 3, 1999;96(16):9345-50.
Neumann, et al. The first influenza pandemic of the new millennium. Influenza Other. Respi. Viruses. vol. 5, pp. 157-166. (2011).
Ng, et al. Structure and sequence analysis of influenza A virus nucleoprotein. Sci China C Life Sci. May 2009;52(5):439-49. doi: 10.1007/s11427-009-0064-x. Epub May 27, 2009.
Nicholson, et al. "Influenza" Lancet. vol. 362, Issue 9397, pp. 1733-1745, Nov. 22, 2003.
Nielsen, M. et al. NetMHCpan, a method for quantitative predictions of peptide binding to any I-ILA-A and -B locus protein of known sequence. PLoS One vol. 2, p. 796 (2007).
Nobusawa, E. et al. Comparison of the mutation rates of human influenza A and B viruses. J Virol vol. 80, pp. 3675-3678 (2006).
O'Connell, R. J., et al., Human immunodeficiency virus vaccine trials. Cold Spring Harbor Perspec Med vol. 2, pp. a007351 (2012).
Peters, et al. Forward genetics and map-based cloning approaches. Trends Plant Sci. Oct. 2003;8(10):484-91.
Phillips, C. J. et al. Comparison of the effectiveness of trivalent inactivated influenza vaccine and live, attenuated influenza vaccine in preventing influenza-like illness among US military service members, 2006-2009. Clin. Infect. Dis. vol. 56, pp. 11-19 (2013).
Pica, et al. Toward a universal influenza virus vaccine: prospects and challenges. Ann. Rev. Med. vol. 64, pp. 189-202. (2013).
Poon, A. F. et al. Reconstructing the dynamics of HIV evolution within hosts from serial deep sequence data. PLoS Comput. Biol. 8:e1002753 (2012).
Price et al. Vaccination focusing immunity on conserved antigens protects mice and ferrets against virulent H1N1 and H5N1 influenza A viruses. Vaccine. Nov. 5, 2009;27(47):6512-21.
Rao et al. Comparative Efficacy of Hemagglutinin, Nucleoprotein, and Matrix 2 Protein Gene-Based Vaccination against H5N1 Influenza in Mouse and Ferret. PLoS One. 2010; 5(3): e9812.
Regan, et al. Defective assembly of influenza A virus due to a mutation in the polymerase subunit PA. J Virol. Jan. 2006;80(1):252-61.
Rolland, M. et al. HIV-1 conserved elements vaccines: Relationship between sequence conservation and replicative capacity. J. Virol. Epub ahead of print (2013).
Samiji, T. Influenza A: understanding the viral life cycle. Yale J Biol Med. Dec. 2009;82(4):153-9.
Samson, et al. Influenza virus resistance to neuraminidase inhibitors. Antiviral Res. vol. 98, Issue 2, pp. 174-185. May 2013.
Schmitz, J. E. et al. Control of viremia in simian immunodeficiency virus infection by CD8+ lymphocytes. Science 283:857-860 (1999).
Schnell, et al. Structure and mechanism of the M2 proton channel of influenza A virus. Nature. Jan. 31, 2008;451(7178):591-5. doi: 10.1038/nature06531.
Scorza et al. Universal influenza vaccines: Shifting to better vaccines. Vaccine. vol. 34, Issue 26, Jun. 3, 2016, pp. 2926-2933.
Sedova et al. Recombinant Influenza Vaccines. Acta Naturae. Oct.-Dec. 2012; 4(4): 17-27.
Shacklett, B. L. & Ferre, A. L. Mucosal immunity in HIV controllers: the right place at the right time. Curr. Opin. HIV AIDS 6:202-207 (2011).
Siloto, MP et al. Site Saturation mutagenesis: Methods and Applications in protein engineering. Biocatalysis and Agricultural Biotechnology vol. 1, pp. 181-189. 2012.
Soboleski et al. Cold-adapted influenza and recombinant adenovirus vaccines induce cross-protective immunity against pH1N1 challenge in mice. PLoS One. 2011;6(7):e21937.
Souza et al. Recombinant viruses as vaccines against viral diseases. Braz J Med Biol Res. Apr. 2005;38(4):509-22.
Staneková et al. Conserved epitopes of influenza A virus inducing protective immunity and their prospects for universal vaccine development. Virology Journal, 2010, 7:351.
Steel, et al. Influenza virus vaccine based on the conserved hemagglutinin stalk domain. MBio. May 18, 2010;1(1). pii: e00018-10. doi: 10.1128/mBio.00018-10.
Stoloff et al. Synthetic multi-epitope peptides identified in silico induce protective immunity against multiple influenza serotypes. Eur. J. Immunol., 37: 2441-2449, (2007).
Strait, et al. The Shannon information entropy of protein sequences. Biophys J. Jul. 1996;71(1):148-55.
Subbarao et al. The prospects and challenges of universal vaccines for influenza. Cell Press. Trends in Microbiology. vol. 21, Issue 7, Jul. 2013, pp. 350-358.
Takagi et al. Characterization of DNA polymerase from Pyrococcus sp. strain KOD1 and its application to PCR. Appl Environ Microbiol 63(11):4504-4510 (1997).
Tan, A. C.et al. Precursor frequency and competition dictate the HLA-A2-restricted CDS+ T cell responses to influenza A infection and vaccination in HLA-A2.1 transgenic mice. J Immunol. vol. 187, pp. 1895-1902 (2011).
Tan et al. The design and proof of concept for a CD8+ T cell-based vaccine inducing cross-subtype protection against influenza A virus. Immunology and Cell Biology (2013) 91, 96-104, (2013).
Tang et al. Adenovirus as a carrier for the development of influenza virus-free avian influenza vaccines. Expert Rev Vaccines. Apr. 2009;8(4):469-81.
Tang et al. Recombinant adenovirus encoding the HA gene from swine H3N2 influenza virus partially protects mice from challenge with heterologous virus: A/HK/1/68 (H3N2). Arch Virol. Nov. 2002;147(11):2125-41.

(56) References Cited

OTHER PUBLICATIONS

Tarendeau, et al. Structure and nuclear import function of the C-terminal domain of influenza virus polymerase PB2 subunit. Nat Struct Mol Biol. Mar. 2007;14(3):229-33. Epub Feb. 25, 2007.
Tatsis et al. Chimpanzee-origin adenovirus vectors as vaccine carriers. Gene Ther. Mar. 2006;13(5):421-9.
Tompkins et al. Matrix Protein 2 Vaccination and Protection against Influenza Viruses, Including Subtype H5N1. Emerg Infect Dis. Mar. 2007; 13(3): 426-435.
Toussaint, N.C.et al. Universal peptide vaccines—optimal peptide vaccine design based on viral sequence conservation. Vaccine vol. 29, pp. 8745-8753 (2011).
Tripp et al. Virus-Vectored Influenza Virus Vaccines. Viruses. Aug. 2014; 6(8): 3055-3079.
Tsibris, A. M. et al. Quantitative deep sequencing reveals dynamic HIV-1 escape and large population shifts during CCR5 antagonist therapy in vivo. PLoS One 4:e5683 (2009).
Uddback, et al. Combined local and systemic immunization is essential for durable T-cell mediated heterosubtypic immunity against influenza A virus. Scientific Reports 6, Article No. 20137. Published online: Feb. 1, 2016. doi:10.1038/srep20137.
Ura et al. Developments in Viral Vector-Based Vaccines. Vaccines (Basel). Sep. 2014; 2(3). 17 pages. 624-641.
Vemula et al. Broadly protective adenovirus-based multivalent vaccines against highly pathogenic avian influenza viruses for pandemic preparedness. PLoS One. Apr. 30, 2013;8(4):e62496.
Vemula et al. Production of adenovirus vectors and their use as a delivery system for influenza vaccines. Expert Opin Biol Ther. Oct. 2010;10(10):1469-87.
Vitiello et al. Analysis of the HLA-restricted influenza-specific cytotoxic T lymphocyte response in transgenic mice carrying a chimeric human-mouse class I major histocompatibility complex. J Exp Med 173:1007-1015 (1991).
Weaver et al. Low Seroprevalent Species D Adenovirus Vectors as Influenza Vaccines. PLoS One. 2013; 8(8): e73313.
Weber, et al. A classical bipartite nuclear localization signal on Thogoto and influenza A virus nucleoproteins. Virology. Oct. 10, 1998;250(1):9-18.
Wesley et al. Protection of weaned pigs by vaccination with human adenovirus 5 recombinant viruses expressing the hemagglutinin and the nucleoprotein of H3N2 swine influenza virus. Vaccine. Sep. 3, 2004;22(25-26):3427-34.
Wu, et al. High-throughput functional annotation of influenza A virus genome at single-nucleotide resolution. 2014. http://dx.doi.org/10.1101/005702.
Wu, et al. High-throughput profiling of influenza A virus hemagglutinin gene at single-nucleotide resolution. Scientific Reports, vol. 4, pp. 4942 (2014).
Wu, et al. Systematic identification of H274Y compensatory mutations in influenza A virus neuraminidase by high-throughput screening. J Virol. Jan. 2013;87(2):1193-9.
Yin, L. et al. High resolution deep sequencing reveals biodiversity, population structure, and persistence of HIV-1 quasispecies within host ecosystems. Retrovirology vol. 9, p. 108 (2012).
Zhang, Jianfeng. Advances and Future Challenges in Recombinant Adenoviral Vectored H5N1 Influenza Vaccines. Viruses. Nov. 2012; 4(11): 2711-2735.
Zhou et al. A Universal Influenza A Vaccine Based on Adenovirus Expressing Matrix-2 Ectodomain and Nucleoprotein Protects Mice From Lethal Challenge. Mol Ther. Dec. 2010; 18(12): 2182-2189.
Bloom, J.D., An Experimentally Determined Evolutionary Model Dramatically Improves Phylogenetic Fit. Mol Biol Evol. Aug. 2014; 31(8): 1956-1978.
Taft, et al., Identification of mammalian-adapting mutations in the polymerase complex of an avian H5N1 influenza virus. Nat Commun. 2015; 6: 7491.
Jackson David C Etal: "A totally synthetic vaccine of generic structure that targets Toll-like receptor 2 on dendritic cells and promotes antibody or cytotoxic T cell responses", Proceedings of Thenational Academy of Sciences (PNAS), National Academy of Sciences, US, vol. 101,No. 43, Oct. 26, 2004 (Oct. 26, 2004), pp. 15440-15445,XP002340337, ISSN: 0027-8424, DOI: 10.1073/PNAS. 0406740101.
Supplementary European Search Report dated Sep. 18, 2020 for Application Serial No. EP 17887439.2, (10 pages).
PCT/US2017/068800 International Search Report and Written Opinion dated May 8, 2018.
Roy et al. Rescue of chimeric adenoviral vectors to expand the serotype repertoire. J Virol Methods. Apr. 2007; 141(1): 14-21.
Tam, James P. Recent advances in multiple antigen peptides. J Immunol Methods. Sep. 13, 1996;196(1):17-32.

* cited by examiner

Fig. 1

```
┌─────────────────────────────┐      ┌─────────────────────────────┐
│ Mutation tolerance information for │  +   │ Immunogenicity information for │
│ influenza virus proteins           │      │ influenza epitopes             │
└─────────────────────────────┘      └─────────────────────────────┘
                                    │
                                    ▼
                    ┌─────────────────────────────┐
                    │ Identify influenza peptide sequences │
                    │ for use in vaccine                   │
                    └─────────────────────────────┘
                                    │
                                    ▼
                    ┌─────────────────────────────┐
                    │ Generate vaccine                     │
                    └─────────────────────────────┘
                                    │
                                    ▼
                    ┌─────────────────────────────┐
                    │ Administer vaccine to subject        │
                    └─────────────────────────────┘
```

Fig. 2
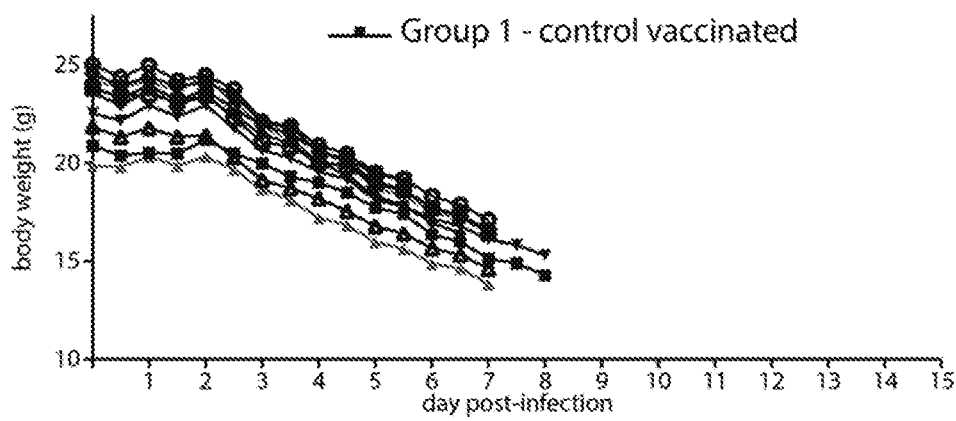
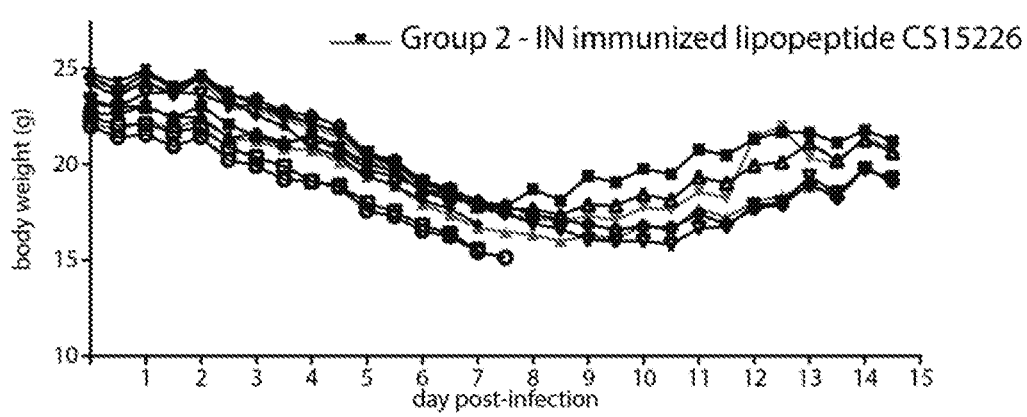
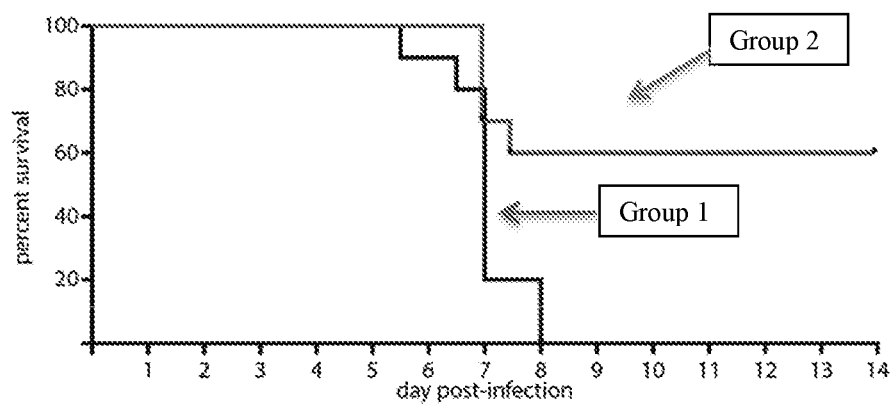

INFLUENZA VACCINES

CROSS-REFERENCE

This application claims the benefit of U.S. provisional application No. 62/439,865, filed Dec. 28, 2016, and U.S. provisional application No. 62/550,167, filed Aug. 25, 2017, which are herein incorporated by reference in their entirety.

SEQUENCE LISTING

The instant application contains a Sequence Listing which has been submitted electronically in ASCII format and is hereby incorporated by reference in its entirety. Said ASCII copy, created on Dec. 27, 2017, is named 46690-708_201_SL.txt and is 152,030 bytes in size.

BACKGROUND

Vaccines greatly promote human health by providing active adapted immunity to a particular disease. There is a need for improved vaccines, e.g., influenza vaccines. Improved vaccines may exhibit higher safety, increased immunogenicity, coverage of broader range of pathogens, or any combination thereof.

SUMMARY

One aspect of the present disclosure provides a polypeptide that comprises a first sequence selected from the group consisting of SEQ ID NOs: 2, 3, 8, 11, 12, 40, 41, 43, 51, 52, 58, 59, 61, 62, 84, and 92; and a second sequence selected from the group consisting of SEQ ID NOs: 17, 20, 21, 22, 24, 26, 29, 30, 32, 33, 34, 44, 45, 49, 53, 60, 70, 73, 74, 75, 76, 77, 78, 82, 83, 85, 86, 87, 88, 89, 90, 91, 93, and 94.

Another aspect of the present disclosure provides a polypeptide that comprises a first sequence selected from the group consisting of SEQ ID NOs: 2, 8, 11, 12, 40, 41, 43, 52, 58, 59, 61, 62, 84, and 92; and a second sequence selected from the group consisting of SEQ ID NOs: 17, 20, 21, 22, 24, 26, 29, 30, 31, 32, 33, 34, 44, 45, 49, 53, 60, 70, 73, 74, 75, 76, 77, 78, 82, 83, 85, 86, 87, 88, 89, 90, 91, 93, and 94.

Another aspect of the present disclosure provides a polypeptide that comprises: (a) a first sequence comprising at least 60%, at least 75%, at least 85%, or 100% sequence identity to at least 8 contiguous amino acids of SEQ ID NO: 8, 11, 12, 40, 41, 58, 59, 61, 62, 84, or 92, and a second sequence comprising at least 60%, at least 75%, at least 85%, or 100% sequence identity to at least 8 contiguous amino acids of SEQ ID NO: 2, 3, 17, 20, 21, 22, 24, 26, 29, 30, 31, 32, 33, 34, 43, 44, 45, 49, 51, 52, 53, 60, 70, 73, 74, 75, 76, 77, 78, 82, 83, 85, 86, 87, 88, 89, 90, 91, 93, or 94; or (b) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 17, 20, 21, 22, 24, 26, 29, 30, 31, 32, 33, 34, 40, 41, 44, 45, 49, 53, 58, 59, 60, 61, 62, 70, 73, 74, 75, 76, 77, 78, 82, 83, 84, 85, 86, 87, 88, 89, 90, 91, 92, 93, or 94; or (c) a first sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94, and a second sequence comprising at least 60%, at least 75%, at least 85%, or 100% sequence identity to at least 8 contiguous amino acids of SEQ ID NO: 2, 3, 8, 11, 12, 40, 41, 43, 51, 52, 58, 59, 61, 62, 84, or 92; or (d) a first sequence comprising at least 60%, at least 75%, at least 85%, or 100% sequence identity to at least 8 contiguous amino acids of SEQ ID NO: 17, 20, 29, 31, 33, 34, 44, 45, 73, 74, 75, 76, 77, 78, 82, 83, 87, 88, 89, 90, or 91 and a second sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92; or (e) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, or 94; or (f) a first sequence comprising at least 60%, at least 75%, at least 85%, or 100% sequence identity to at least 8 contiguous amino acids of SEQ ID NO: 3, 51, or 52, and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, 94; or (g) a first sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92, and a second sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94; or (h) a first sequence comprising at least 60%, at least 75%, at least 85%, or 100% sequence identity to at least 8 contiguous amino acids of SEQ ID NO: 2, 8, 11, 12, 21, 22, 24, 26, 30, 32, 40, 41, 43, 49, 53, 58, 59, 60, 61, 62, 70, 84, 85, 86, 92, 93, or 94, and a second different sequence comprising at least 60%, at least 75%, at least 85%, or 100% sequence identity to at least 8 contiguous amino acids of SEQ ID NO: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94, wherein a contiguous sequence comprising the first sequence and the second different sequence is not found in a PB1, PA, or NP.

Another aspect of the present disclosure provides a polypeptide that comprises a first sequence, second sequence, third sequence, fourth sequence, and a fifth sequence, wherein each of the first sequence, second sequence, third sequence, fourth sequence, and fifth sequence comprises at least 75% sequence identity to a different sequence selected from the group consisting of SEQ ID NOs: 2, 3, 8, 11, 12, 17, 20-22, 24, 26, 29-34, 40, 41, 43-45, 49, 51-53, 58-62, 70, 73-78, and 82-94, wherein the polypeptide is not naturally occurring.

In some cases, at least one of the first sequence, second sequence, third sequence, fourth sequence, and fifth sequence can comprise at least 75% sequence identity to a sequence selected from the group consisting of SEQ ID NOs: 17, 20-22, 24, 26, 29-34, 44, 45, 49, 53, 60, 70, 72-78, 82, 83, 85-91, 93, and 94. In some cases, at least one of the first sequence, second sequence, third sequence, fourth, and fifth sequence can comprise at least 75% sequence identity to a sequence selected from the group consisting of SEQ ID NOs: 2, 3, 43, 51, and 52. In some cases, at least one of the first sequence, second sequence, third sequence, fourth sequence, and fifth sequence can comprise at least 75% sequence identity to a sequence selected from the group consisting of SEQ ID NOs: 8, 11, 12, 40, 41, 58, 59, 61, 62, and 92.

A polypeptide provided herein can further comprise sequence with at least 50% sequence identity to at least 10% of the amino acid sequence of an NP protein of influenza B. A polypeptide provided herein can further comprise sequence with at least 50% sequence identity to at least 10% of the amino acid sequence of SEQ ID NO: 116, 117, or 118. In some cases, each sequence can be at most 10, 12, 15, 20, 25, 30, 35, 40, 45, or 50 amino acids in length. In some cases, the first sequence and second sequence can be directly linked. In some cases, the first sequence and the second sequence can be linked by a linker. In some cases, the linker can comprise a plurality of glycines, alanines, arginines, valines, or lysines. A linker can comprise the sequence RVKR (SEQ ID NO: 110). A polypeptide provided herein can further comprise sequence GALNNRFQIKGVELKSK (SEQ ID NO: 103). SEQ ID NO: 103 can be linked to an amino terminal portion of the polypeptide. A polypeptide provided herein can comprise SEQ ID NOs: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, and 94.

A polypeptide provided herein can be an isolated polypeptide.

Another aspect of the present disclosure provides a composition that comprises a polypeptide provided herein.

Another aspect of the present disclosure provides a polynucleotide encoding a polypeptide provided herein. A polynucleotide provided herein can be isolated.

Another aspect of the present disclosure provides a composition that comprises a polynucleotide provided herein.

Another aspect of the present disclosure provides a vector that comprises a polynucleotide provided herein. A vector provided herein can be a non-human primate vector. A vector provided herein can be an adenovirus vector. A vector provided herein can be a chimpanzee adenovirus vector. In some cases, the chimpanzee adenovirus vector can comprise at least 50% sequence identity to least 50% of the sequence of C68 (AdC68) (SEQ ID NO: 104), C7 (AdC7), C6 (AdC6) (SEQ ID NO: 105), Pan7, or Pan9.

A vector provided herein can be isolated.

Another aspect of the present disclosure provides a composition that comprises a vector provided herein.

Another aspect of the present disclosure provides a virus that comprises a polynucleotide provided herein.

Another aspect of the present disclosure provides a virus that comprises a vector provided herein.

A virus provided herein can be isolated. A virus can be an adenovirus.

Another aspect of the present disclosure provides a composition that comprises a virus provided herein.

Another aspect of the present disclosure provides a composition that comprises at least five different peptides, wherein each of the at least five different peptides comprises, consists of, or consists essentially of a sequence comprising at least 75% sequence identity to a sequence selected from the group consisting of SEQ ID NOs: 2, 3, 8, 11, 12, 17, 20-22, 24, 26, 29-34, 40, 41, 43-45, 49, 51-53, 58-62, 70, 73-78, and 82-94. In some cases of the composition, each peptide can be at most 10, 12, 15, 20, 25, 30, 35, 40, 45, or 50 amino acids in length. A composition provided herein can further comprise a peptide comprising a sequence with at least 50% sequence identity to at least 10% of the amino acid sequence of an NP protein of influenza B. A composition provided herein can further comprise a peptide comprising a sequence with at least 50% sequence identity to at least 10% of the amino acid sequence of SEQ ID NOs: 116, 117, or 118. A composition provided herein can further comprise a pharmaceutically acceptable excipient. A composition provided herein can be formulated for subcutaneous, intranasal, or intramuscular administration.

Another aspect of the present disclosure provides a method that comprises administering to a subject a composition provided herein. In some cases, the administration can be subcutaneous. In some cases, the administration can be intranasal. In some cases, the administration can be intramuscular. A method provided herein can further comprise administering the composition to the subject a second time. In some cases, an immune response can be induced following the administration. The immune response can be a systemic immune response. In some cases, the subject can be a human. In some cases, the subject can be infected with a virus. The virus can be an influenza virus. The influenza virus can be influenza A virus, influenza B virus, or influenza C virus. In some cases, the influenza virus can be influenza A virus. In some cases, the composition when administered can induce cross-protection against one or more subtypes of influenza A strains in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates a method for discovering vaccine epitopes.

FIG. 2 illustrates a result of an influenza challenge of vaccinated mice.

DETAILED DESCRIPTION

Figure 3A:
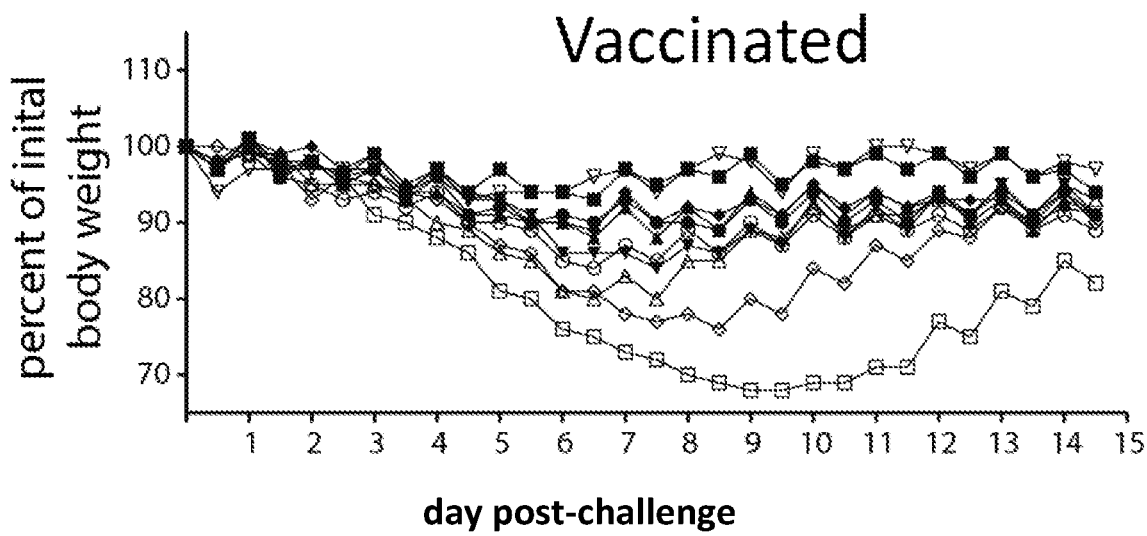
FIG. 3A illustrates the percent of initial body weight of vaccinated mice.

Provided herein are methods and compositions for forming vaccines, e.g., influenza vaccines. The methods can comprise, e.g., making a recombinant viral vaccine, e.g., recombinant adenoviral vaccine, using sequence encoding one or more influenza epitopes, e.g., one or more influenza A epitopes, e.g., one or more influenza A peptide epitopes. The one or more epitopes can comprise an "invariant" sequence, e.g., a sequence with a low tolerance for mutations. The one or more epitopes can comprise an experimentally verified human CD8 T cell influenza A virus epitope. The recombinant adenovirus can express at least 1, 5, 8, 10, 25, 50, 100, or 1000 peptide epitopes. In some cases, the expressed epitopes are linked, e.g., through covalent bonds, e.g., in a single polypeptide. In some cases, the expressed epitopes are not linked, e.g., each epitope can be expressed from a separate promoter, separate nucleic acid, or separate virus. In some cases, the one or more epitopes are described in the Immune Epitope Database and Analysis Resource (worldwideweb.iedb.org). A single polypeptide comprising one or more epitopes can be linked to one, two, or more copies of a full-length viral protein (or at least 10%, 20%, 30%, 40%, 50%, 60%, 70%, 80%, 90%, or 95% of a full-length viral protein, or a sequence having at least 50%, 60%, 70%, 80%, 90%, 95%, or 100% sequence identity to such proteins) from, e.g., influenza A, influenza B, or influenza C.

Definitions

The terminology used herein is for the purpose of describing particular cases only and is not intended to be limiting. As used herein, the singular forms "a", "an" and "the" can include the plural forms as well, unless the context clearly indicates otherwise. Furthermore, to the extent that the terms "contains," "containing," "including," "includes," "having," "has," "with," or variants thereof are used in either the detailed description and/or the claims, such terms can be inclusive in a manner similar to the term "comprising."

The term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" can mean an acceptable error range for the particular value, such as ±10% of the value modified by the term "about."

The term "polypeptide" and its grammatical equivalents, as used herein, can refer to a continuous and unbranched chain of amino acid monomers linked by peptide (amide) bonds, which can be covalent chemical bonds formed when the carboxyl group of one amino acid reacts with the amino group of another. Unless indicated otherwise, the terms "polypeptide" and "peptide" are interchangeable as used herein. The shortest polypeptide can be dipeptide with only two amino acids joined by a single peptide bond. For the purposes of the present disclosure, these terms should not to be construed as limiting with respect to an upper length. The terms can also encompass analogues of natural amino acids, as well as amino acids that are modified in the side chain, chirality, or properties.

The terms "nucleic acid," "polynucleotide," "polynucleic acid," and "oligonucleotide" and their grammatical equivalents can be used interchangeably and can refer to a deoxyribonucleotide or ribonucleotide polymer, in linear or circular conformation, and in either single- or double-stranded form. For the purposes of the present disclosure, these terms should not to be construed as limiting with respect to an upper length. The terms can also encompass analogues of natural nucleotides, as well as nucleotides that are modified in the base, sugar and/or phosphate moieties (e.g., phosphorothioate backbones). Modifications of the terms can also encompass demethylation, addition of CpG methylation, removal of bacterial methylation, and/or addition of mammalian methylation. In general, an analogue of a particular nucleotide can have the same base-pairing specificity, i.e., an analogue of A can base-pair with T.

The term "antigen" and its grammatical equivalents as used herein can refer to a molecule that contains one or more epitopes capable of being bound by one or more receptors. For example, an antigen can stimulate a host's immune system to make a cellular antigen-specific immune response when the antigen is presented, or a humoral antibody response. An antigen can also have the ability to elicit a cellular and/or humoral response by itself or when present in combination with another molecule. For example, an influenza A viral protein can be recognized by a TCR.

The term "epitope" and its grammatical equivalents as used herein can refer to a part of an antigen that can be recognized by antibodies, B cells, T cells or engineered cells. For example, an epitope can be an influenza A viral epitope that is recognized by a TCR. Multiple epitopes within an antigen can also be recognized. The epitope can also be mutated.

The term "mutation" and its grammatical equivalents, as used herein, can refer to a deletion, an insertion of a heterologous nucleic acid, an inversion or a substitution, including an open reading frame ablating mutation as commonly understood in the art.

The term "gene" and its grammatical equivalents, as used herein, can refer to a segment of nucleic acid that encodes an individual polypeptide, protein or RNA (also referred to as a "coding sequence" or "coding region"), optionally together with associated regulatory regions such as promoters, operators, terminators and the like, which can be located upstream or downstream of the coding sequence.

The term "naturally-occurring" and its grammatical equivalents, as used herein with reference to a virus, can indicate that the virus can be found in nature, i.e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter" and its grammatical equivalents, as used herein, can be a control sequence that is a region of a nucleic acid sequence at which initiation and rate of transcription are controlled. A promoter can contain genetic elements at which regulatory proteins and molecules can bind such as RNA polymerase and other transcription factors. The terms "operatively positioned," "operatively linked," "under control" and "under transcriptional control" can mean that a promoter is in a correct functional location and/or orientation in relation to a nucleic acid sequence to control transcriptional initiation and/or expression of that sequence. In some cases, a promoter may or may not be used in conjunction with an "enhancer," which can refer to a cis-acting regulatory sequence involved in the transcriptional activation of a nucleic acid sequence.

The term "subject" and its grammatical equivalents can refer to an animal, including, but not limited to, a primate (e.g., human), cow, sheep, goat, horse, dog, cat, rabbit, rat, or mouse. The terms "subject" and "patient" can be used interchangeably herein in reference, for example, to a mammalian subject, such as a human subject.

Methods of Identifying Epitopes for Use in a Vaccine

One aspect of the present disclosure provides methods of identifying epitopes for use in a vaccine. The methods can be used to identify an epitope sequence of a pathogen, e.g., a virus, e.g., an RNA virus, e.g., an influenza virus, e.g., an influenza A, influenza B, or influenza C virus. In some cases, the methods provided herein are used in connection with identification of epitope sequences of a pathogen, e.g., a virus, e.g., an RNA virus, e.g., an influenza virus, e.g., an influenza A influenza B, or influenza C virus, for use in a vaccine. The epitope sequences can be from one or more of, or have homology to one or more of, PB1, PB1-F2, PB2, PA, HA, NP, NA, M1, M2, NS1, or NEP/NS2.

Invariance, or invariant peptide regions, can be determined, e.g., as described in International PCT application publication WO/2015/157189, filed Apr. 6, 2015, which is herein incorporated by reference in its entirety. Invariance can describe the functional importance of an amino acid residue in the context of the fitness of a pathogen. Invariance can be a measurement of the fitness of a pathogen. At an amino acid residue level, invariance can be associated with how tolerant an amino acid residue is to a mutation and how adverse this mutation is to the ability of the pathogen to propagate, that is, fitness of the pathogen. Invariance can be correlated with the role of an amino acid residue in a pathogen's survival. For example, a mutation in a pathogen that exerts a deleterious effect on the proliferation of the pathogen can be considered a destructive mutation and would not be propagated within a pathogen population. An associated amino acid position correlated with the deleterious mutation can be characterized as invariant as its mutation would not be tolerated.

The methods can comprise generating a nucleic acid library. In some instances, the nucleic acid library can allow simulation of all possible mutations that can occur in a particular pathogen strain, for example, by generating a pool of mutant influenza A viruses or influenza B viruses. In some cases, the methods can further comprise introducing the library to cells to support production of a pool of pathogens, e.g. influenza A viruses. Sometimes, the methods can further comprise infection of cells with the pool of pathogens for a number of rounds (e.g., 1, 2, 3, 4, 5, 6, 7, 8, 9, 10 or more rounds), obtaining the resultant pool of pathogens, e.g. influenza A viruses, and generating a second sequencing library. The methods can further comprise obtaining the nucleic acid sequences of the second sequencing library. In some instances, the methods can further comprise comparing the sequences (e.g., comparing sequences from the library to sequences from the second library, or a library from the last round of infection) to obtain invariant sequence regions, e.g. invariant peptide regions. An invariant sequence region can have an average invariance ratio (frequency of mutant in final population/frequency in initial population) of $<0.05$, $<0.08$, $<0.1$, $<0.2$, $<0.3$, or $<0.4$ among all possible mutations in the stretch. The methods can further comprise evaluating the invariant sequence regions. In some cases, the methods can further comprise HLA affinity binding analysis of the invariant sequence regions, some additional immunogenicity analysis for vaccine development and treatment of patient, or any combination thereof. The term "immunogenicity," as used herein, can refer to the capability of a particular substance, e.g., antigen or epitope, to induce an immune response. In some cases, a first screen for epitope sequences for use in a vaccine comprises identifying immunogenicity peptide sequences and then evaluating the epitope sequences for sequence invariance.

HLA affinity binding analysis can be carried out using analysis programs such as NetMHCpan4.0 from the Center for Biological Sequences Analysis (CBS) at the Technical University of Denmark, HLA Peptide Binding Predictions server from the National Institute of Health, MHC-1 binding predictions server from the Immune Epitope Database (IEDB), and the like.

In some cases, candidate invariant sequences identified by a method provided herein can be further analyzed. For instance, the candidate invariant sequences can be compared against experimentally tested immunogenicity data of influenza virus epitopes, e.g., in various databases, such as Influenza Research Database (https://www.fludb.org). Upon the comparison, candidate invariant sequences with experimentally proven immunogenicity (e.g., deposited at https://fludb.org) can be identified and subject to either further analysis, or vaccine development. For instance, such candidate invariant sequences, or the variants thereof, can be chosen to be one of the constituent epitope sequences of a polypeptide as described herein, which can be expressed from a transgene as described herein, and the transgene can be part of a vector, e.g., a viral vector, for producing a virus-based vaccine, e.g., an adenoviral-based vaccine.

Additional Analysis

Additional analysis can be carried out to select candidate invariant sequences or peptides for vaccine development and for administration of the vaccine to a patient for treatment or prevention of a condition, e.g., influenza. These additional analysis or screenings can involve analysis of an immune response based on immunological assays. In some cases, test animals are first immunized (prime) with or without a second immunization (boost) following weeks after the prime and blood or tissue samples are collected, for example, two to four weeks after the last immunization. These studies can allow measurement of immune parameters that correlate to protective immunity, such as induction of specific antibodies (e.g., IgA, IgD, IgE, IgG, or IgM) and induction of specific T lymphocyte responses, in addition to determining whether an antigen or pools of antigens provides protective immunity.

Spleen cells, lung cells, cells from mediastinal lymph nodes, or peripheral blood mononuclear cells can be isolated from immunized test animals and measured for the presence of antigen-specific T cells and induction of cytokine synthesis. ELISA, ELISPOT, or cytoplasmic cytokine staining, alone or combined with flow cytometry, can provide such information on a single-cell level.

Immunological tests that can be used to identify the efficacy of immunization include antibody measurements, neutralization assays and analysis of activation levels or frequencies of antigen presenting cells or lymphocytes that are specific for the antigen or pathogen. The test animals that can be used in such studies include mice, rats, guinea pigs, hamsters, rabbits, cats, dogs, pigs, monkeys, or humans.

Monkey can be a useful test animal, e.g., due to the similarities of the MHC molecules between monkeys and humans. Virus neutralization assays can be useful for detection of antibodies that not only specifically bind to a pathogen, but also neutralize the function of the pathogen (e.g., virus). These can be based on detection of antibodies in the sera of immunized animal and analysis of these antibodies for their capacity to inhibit pathogen (e.g., virus) growth in tissue culture cells. Such assays are known to those skilled in the art. Virus neutralization assays can be used to screen for antigens that also provide protective immunity.

Polypeptides

One aspect of the present disclosure provides polypeptides that comprise, consist of, or consist essentially of, one or more influenza virus epitope sequences, for example, influenza A virus epitope sequences.

As used herein, a peptide or polypeptide that "comprises" a sequence according to a specified sequence or formula can be a peptide or polypeptide that can include additional amino acid residues, amino acid isomers, and/or amino acid analogs at its N-terminus, C-terminus, or both. The additional residues may or may not change its activity or function, e.g., increase or decrease the activity of the peptide as compared to the activity of a peptide consisting solely of the specified sequence or formula. As used herein, a peptide that "consists essentially of" a specified sequence or formula can mean that the peptide can include additional amino acid residues, amino acid isomers, and/or amino acid analogs at its N-terminus, C-terminus, or both, so long as the additional residues do not materially change its activity or function, e.g., increase or decrease the activity of the peptide as compared to the activity of a peptide consisting solely of the specified sequence or formula. As used herein, a peptide that "consists of" a specified sequence or formula can mean that the peptide does not include additional amino acid residues, amino acid isomers, and/or amino acid analogs at both its N-terminus and C-terminus.

The polypeptide can comprise, consist of, or consist essentially of, epitope sequences identified by the exemplary methods provided by the present disclosure. For instance, the polypeptide can comprise, consist of, or consist essentially of, one or more epitope sequences selected from the group consisting of: SEQ ID NOs: 1-94, or one or more epitope sequences selected from Table 1, Table 2, or Table 3. Tables 1, 2, and 3 below list epitope sequences, and viral proteins, which the epitope sequences are derived from, or variations of. Each of the polypeptides described herein can be chemically synthesized, or expressed in vivo, or in vitro. The polypeptide can be encoded by a nucleic acid, and the nucleic acid can be within a vector, e.g., viral vector, e.g., adenoviral vector. The vector, e.g. adenoviral vector, can be used to generate a recombinant virus, e.g. a recombinant adenovirus. Any of the polypeptides herein can be different than a full length viral protein. A polypeptide provided herein can be non-naturally occurring. A "non-naturally occurring polypeptide," as the term is used herein, can refer to a polypeptide whose primary sequence does not occur in nature, e.g., cannot be found in a single molecule in nature.

TABLE 1

| Protein | SEQ ID NO: | Sequences |
|---|---|---|
| PB1 | SEQ ID NO: 1 | GPATAQMAL |
| PB1 | SEQ ID NO: 2 | GTFEFTSFFY |
| PB1 | SEQ ID NO: 3 | YSHGTGTGY |
| PB1 | SEQ ID NO: 4 | GLPVGGNEKKAKLANVVR |
| PB1 | SEQ ID NO: 5 | GMMMGMFNMLSTVLGVS |
| PB1 | SEQ ID NO: 6 | LQLFIKDYRYTYRCHRG |

TABLE 1-continued

| Protein | SEQ ID NO: | Sequences |
|---|---|---|
| PB1 | SEQ ID NO: 7 | RRAIATPGM |
| PA | SEQ ID NO: 8 | FMYSDFHFI |
| PA | SEQ ID NO: 9 | MRRNYFTAEVSHCRATEY |
| PA | SEQ ID NO: 10 | QLMWALGENMA |
| PA | SEQ ID NO: 11 | DVVNFVSMEFSLTDPRL |
| PA | SEQ ID NO: 12 | KWGMEMRRCLLQSLQQI |
| NP | SEQ ID NO: 13 | AEIEDLIFLA |
| NP | SEQ ID NO: 14 | CTELKLSDY |
| NP | SEQ ID NO: 15 | CTELKLTDQ |
| NP | SEQ ID NO: 16 | CTELKLTDY |
| NP | SEQ ID NO: 17 | ELRSRYWAIRTRSG |
| NP | SEQ ID NO: 18 | ELKSRYWAIRTRSG |
| NP | SEQ ID NO: 19 | GMDPRMCSL |
| NP | SEQ ID NO: 20 | ILKGKFQTA |
| NP | SEQ ID NO: 21 | ILRGSIAHK |
| NP | SEQ ID NO: 22 | ILRGSVAHK |
| NP | SEQ ID NO: 23 | LELRSRYWAI |
| NP | SEQ ID NO: 24 | LIFLARSAL |
| NP | SEQ ID NO: 25 | RGINDRNFW |
| NP | SEQ ID NO: 26 | FLARSALILRGSVAHK |
| NP | SEQ ID NO: 27 | RMVLSAFDER |
| NP | SEQ ID NO: 28 | TLELRSGYWAIRTRSGGN |
| NP | SEQ ID NO: 29 | IAYERMCNILKGKFQTAA |
| NP | SEQ ID NO: 30 | FLARSALILRGSVAHKS |
| NP | SEQ ID NO: 31 | FQGRGVFEL |
| NP | SEQ ID NO: 32 | GQISIQPTFS |
| NP | SEQ ID NO: 33 | WHSNLNDATYQRTRALVRTGMDPRM |
| NP | SEQ ID NO: 34 | WHSNLNDTTYQRTRALVRTGMDPRM |
| NA | SEQ ID NO: 35 | CVNGSCFTV |
| M1 | SEQ ID NO: 36 | RMVLASTTAK |

TABLE 2

| SEQ ID NO: | Peptide | Protein | HLA (Experimentally Validated) | Additional HLA (NetMHCpan3.0 prediction) | Inv. Ratio |
|---|---|---|---|---|---|
| 35 | CVNGSCFTV | NA | A2 | | 0.044 |
| 38 | CVNGSCYTV | NA | | | |
| 17 | ELRSRYWAIRTRSG | NP | B27 | A3, A26, B8 | 0.053 |
| 39 | ELKSRYWAIRTRSG | NP | | | |
| 8 | FMYSDFHFI | PA | A2 | A24, B8, B39, B15 | 0.05 |

TABLE 2-continued

| SEQ ID NO: | Peptide | Protein | HLA (Experimentally Validated) | Additional HLA (NetMHCpan3.0 prediction) | Inv. Ratio |
|---|---|---|---|---|---|
| 40 | FMYSDLHFI | PA | | | |
| 41 | FMYTDFHFI | PA | | | |
| 19 | GMDPRMCSL | NP | A2 | B39 | 0.052 |
| 42 | GRDPRMCSL | NP | | | |
| 2 | GTFEFTSFFY | PB1 | A3 | A1, A24, A26, B58, B15 | 0.04 |
| 43 | GTFEFTSYFY | PB1 | | | |
| 20 | ILKGKFQTA | NP | B8 | | 0.056 |
| 44 | IIKGKFQTA | NP | | | |
| 45 | ILKGKFQIA | NP | | | |
| 21 | ILRGSIAHK | NP | A3 | | 0.03 |
| 46 | ILRGSVAHK | NP | | | |
| 47 | LQLRSRYWAI | NP | | B8 | |
| 48 | LELRSRHWAI | NP | | | |
| 24 | LIFLARSAL | NP | A2 | B7, B8, B15 | 0.056 |
| 49 | LVFLARSAL | NP | | | |
| 50 | RWINDRNFW | NP | | | |
| 3 | YSHGTGTGY | PB1 | A1 | A26, B15 | 0.055 |
| 51 | YSHWTGTGY | PB1 | | | |
| 52 | YSHGSGTGY | PB1 | | | |
| 26 | FLARSALILRGSVAHK | NP | | A2, A3, B7, B27, B8, B39, B15 | 0.033 |
| 53 | FLARSALVLRGSVAHK | NP | | | |
| 29 | IAYERMCNILKGKFQTAA | NP | B40 | A3, A24, B8, B27, B15 | 0.058 |
| 54 | IAYERMCNIIKGKFQTAA | NP | | | |
| 55 | IAYERMCNILKVKFQTAA | NP | | | |
| 56 | IAYERMCNILKGKFKTAA | NP | | | |
| 57 | IAYERMCNILKGKFQIAA | NP | | | |
| 11 | DVVNFVSMEFSLTDPRL | PA | | A1, A3, A24, A26, B8 B39, B40, B58, B15 | 0.021 |
| 58 | DVVNFVSMEFSLTYPRL | PA | | | |
| 59 | DVVNFVSMEFSLTDQRL | PA | | | |
| 30 | FLARSALILRGSVAHKS | NP | A3 | A2, B7, B8, B27, B39 B15 | 0.049 |
| 60 | FLARSALVLRGSVAHKS | NP | | | |

TABLE 2-continued

| SEQ ID NO: | Peptide | Protein | HLA (Experimentally Validated) | Additional HLA (NetMHCpan3.0 prediction) | Inv. Ratio |
|---|---|---|---|---|---|
| 12 | KWGMEMRRCLLQSLQQI | PA | | A2, A24, B7, B8, B27, B39, B40 | 0.031 |
| 61 | KLGMEMRRCLLQSLQQI | PA | | | |
| 62 | KWGMEMRRCLLQSLQQV | PA | | | |
| 6 | LQLFIKDYRYTYRCHRG | PB1 | | A26, B27, B15 | 0.05 |
| 63 | LQLFIKDFRYTYRCHRG | PB1 | | | |
| 64 | LQLFIKDYRYTYRCLRG | PB1 | | | |
| 65 | LQLFIKDYRYTYRCPRG | PB1 | | | |
| 66 | LQLFIKDYRYTYRCHRV | PB1 | | | |
| 31 | FQGRGVFEL | NP | A2 | B39, B40 | 0.04 |
| 67 | FQGPGVFEL | NP | | | |
| 32 | GQISIQPTFS | NP | | B40, B15 | 0.053 |
| 68 | SQISIQPTFS | NP | | | |
| 69 | GQVSIQPTFS | NP | | | |
| 70 | GQISVQPTFS | NP | | | |
| 71 | GQNSIQPTFS | NP | | | |
| 33 | WHSNLNDATYQRTRALVRTGMDPRM | NP | B27 | A1, A3, A24, A26, B7, B8, B39, B58, B15 | N/A |
| 72 | WHSNLNDTTYQRTRALVRTGMDPRM | NP | | | |
| 73 | WHSNLNDSTYQRTRALVRTGMDPRM | NP | | | |
| 74 | WHSNLNDATYQRKRALVRTGMDPRM | NP | | | |
| 75 | WHSNLNDATYQRTRSLVRTGMDPRM | NP | | | |
| 76 | WHSNLNDATYQRTRAIVRTGMDPRM | NP | | | |
| 77 | WHSNLNDATYQRTRALVRSGMDPRM | NP | | | |
| 78 | WHSNLNDATYQRTRALVRTGRDPRM | NP | | | |

TABLE 3

| SEQ ID NO: | Peptide | Protein | HLA (Experimentally Validated) | Additional HLA (NetMHCpan3.0 prediction) |
|---|---|---|---|---|
| 17 | ELRSRYWAIRTRSG | NP | B27 | B8 |
| 82 | ELRSREWAIRTRSG | NP | B27 | B8 |
| 83 | ELRSRYWASRTRSG | NP | | |

TABLE 3-continued

| SEQ ID NO: | Peptide | Protein | HLA (Experimentally Validated) | Additional HLA (NetMHCpan3.0 prediction) |
|---|---|---|---|---|
| 8 | FMYSDFHFI | PA | A2 | A24, B8, B39, B15 |
| 40 | FMYSDLHFI | PA | A2 | B8 4.00 pctl, A26 1.9 pctl |
| 41 | FMYTDFHFI | PA | A2 | A26 3.5 pctl, A24, B8, B39, B15 |
| 84 | FMFSDFHFI | PA | | |
| 2 | GTFEFTSFFY | PB1 | A3 | A1, A24, A26, B58, B15 |
| 43 | GTFEFTSYFY | PB1 | A3 | A1, A24, A26, B58, B15 |
| 20 | ILKGKFQTA | NP | B8 | |
| 44 | IIKGKFQTA | NP | B8 | |
| 45 | ILKGKFQIA | NP | B8 | |
| 21 | ILRGSIAHK | NP | A3 | |
| 22 | ILRGSVAKK | NP | A3 | |
| 85 | VLRGSIAHK | NP | | |
| 24 | LIFLARSAL | NP | A2 (negative on NetMHC) | B7, B8, B15 |
| 49 | LVFLARSAL | NP | | B7, B8, B15, B39 1.9 pctl |
| 86 | LTFLARSAL | NP | | |
| 3 | YSHGTGTGY | PB1 | A1 | A26, B15 |
| 51 | YSHWTGTGY | PB1 | A1 | A26, B15 |
| 52 | YSHGSGTGY | PB1 | A1 | A26, B15 |
| 26 | FLARSALILRGSVAHK | NP | | A2, A3, B7, B8, B39, B15 |
| 53 | FLARSALVLRGSVAHK | NP | | A2, A3, B7, B8, B39, B15 |
| 29 | IAYERMCNILKGKFQTAA | NP | B40 | A3, A24, B8, B27 |
| 87 | VAYERMCNILKGKFQTAA | NP | | |
| 88 | VAYERMCNIIKGKFQTAA | NP | B40 | A3, A24, B8, B27 |
| 89 | VAYERMCNILKGKFKTAA | NP | B40 | A3, A24, B8, B27 |
| 90 | VAYERMCNILKGKFQIAA | NP | B40 | A3, A24, B8, B27 |
| 91 | VAYERMCNILKGKFQTAY | NP | | |
| 11 | DVVINFVSMEFSLTDPRL | PA | | A1, A3, A24, A26, B8, B39, B40, B58, B15 |
| 58 | DVVNFVSMEFSLTYPRL | PA | | A1, A3, A24, A26, B8, B39, B40, B58, B15 |
| 59 | DVVNFVSMEFSLTDQRL | PA | | A3 2.5 pctl |
| 30 | FLARSALILRGSVAHKS | NP | A3 | A2, B7, B8, B39, B15 |

TABLE 3-continued

| SEQ ID NO: | Peptide | Protein | HLA (Experimentally Validated) | Additional HLA (NetMHCpan3.0 prediction) |
|---|---|---|---|---|
| 60 | FLARSALVLRGSVAHKS | NP | A3 | A2, B7, B8, B39, B15 |
| 12 | KWGMEMRRCLLQSLQQI | PA | | A2, B8, B27, B39 |
| 61 | KLGMEMRRCLLQSLQQI | PA | | A2, B8, B27, B39 |
| 62 | KWGMEMRRCLLQQQV | SL | PA | A2, B8, B27, B39 |
| 92 | KWGMELRRCLLQSLQQI | PA | | |
| 31 | FQGRGVFEL | NP | A2 | B39, B40 |
| 32 | GQISIQPTFS | NP | B40, B15 | |
| 93 | SQISVQPTFS | NP | | B39, B40, A24 (WB), B39 (WB) |
| 94 | GQVSVQPTFS | NP | | B39, B40 |
| 70 | GQISVQPTFS | NP | | B39, B40 |
| 33 | WHSNLNDATYQRTRALVRTGMDPRM | NP | B27 | A1, A3, A24, A26, B7, B8, B39, B58, B15 |
| 34 | WHSNLNDTTYQRTRALVRTGMDPRM | NP | B27 | A1, A3, A24, A26, B7, B8, B39, B58, B15 |
| 73 | WHSNLNDSTYQRTRALVRTGMDPRM | NP | B27 | A1, A3, A24, A26, B7, B8, B39, B58, B15 |
| 74 | WHSNLNDATYQRKRALVRTGMDPRM | NP | B27 | A1, A3, A24, A26, B7, B8, B39, B58, B15 |
| 75 | WHSNLNDATYQRTRSLVRTGMDPRM | NP | B27 | A1, A3, A24, A26, B7, B8, B39, B58, B15 |
| 76 | WHSNLNDATYQRTRAIVRTGMDPRM | NP | B27 | A3 2.5 pctl |
| 77 | WHSNLNDATYQRTRALVRSGMDPRM | NP | B27 | A1, A3, A24, A26, B7, B8, B39, B58, B15 |
| 78 | WHSNLNDATYQRTRALVRTGRDPRM | NP | B27 | A1, A3, A24, A26, B7, B8, B39, B58, B15 |

A polypeptide as described herein can comprise, consist of, or consist essentially of one or more epitope sequences. Sometimes, a polypeptide as described herein can comprise, consist of, or consist essentially of, more than one epitope sequence, among which some of the epitope sequences are the same, while others of the epitope sequences are different, or all the epitope sequences are the same, or all the epitope sequences are different. In some cases, one or more epitope sequences are repeated in a polypeptide, e.g., about, at least, or at most 2, 3, 4, 5, 6, 7, 8, 9, 10, 15, or 20 times. Sometimes, the polypeptide can comprise, consist of, or consist essentially of, one or more different epitope sequences. The polypeptide can comprise, consist of, or consist essentially of only one epitope sequence, and the one epitope sequence can be present in the polypeptide about, at least, or at most 1, 2, 3, 4, 5, 6, 7, 8, 9, 10, 15, or 20 times.

In some cases, a polypeptide can comprise, consist of, or consist essentially of one or more different epitope sequences, each of the one or more different epitope sequences comprising at least 70% sequence identity to at least 8 contiguous amino acids of a sequence selected from the group consisting of SEQ ID NOs: 1-94. A polypeptide provided herein can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 8 contiguous amino acids of a sequence selected from the group consisting of SEQ ID NOs: 1-94. In some embodiments, the polypeptide comprises, consists of, or consists essentially of one or more different epitope sequences, each of the one or more different epitope sequences comprising at least 70% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from the group consisting of SEQ ID NOs: 1-94. A polypeptide can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from the group consisting of SEQ ID NOs: 1-94.

In some cases, a polypeptide can comprise, consist of, or consist essentially of one or more different epitope sequences, each of the one or more different epitope sequences comprises at least 70% sequence identity to at least 8 contiguous amino acids of a sequence selected from Table 1, Table 2, Table 3, or any combination thereof. A polypeptide provided herein can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 8 contiguous amino acids of a sequence selected from Table 1, Table 2, Table 3, or any combination thereof. The polypeptide can comprise, consist of, or consist essentially of one or more different epitope sequences, each of the one or more different epitope sequences comprising at least 70% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from Table 1, Table 2, Table 3, or any combination thereof. A polypeptide can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from Table 1, Table 2, Table 3, or any combination thereof.

A polypeptide can comprise, consist of, or consist essentially of at least two different epitope sequences, each of the at least two different epitope sequences comprises at least 70% sequence identity to at least 8 contiguous amino acids of a sequence selected from the group consisting of SEQ ID NOs: 1-94 or of a sequence selected from Table 1, Table 2, or Table 3. The polypeptide can comprise, consist of, or consist essentially of at least three different epitope sequences, each of the at least three different epitope sequences comprising at least 70% sequence identity to at least 8 contiguous amino acids of SEQ ID NOs: 1-94 or of a sequence selected from Table 1, Table 2, or Table 3. The polypeptide can comprise, consist of, or consist essentially of at least four different epitope sequences, each of the at least four different epitope sequences comprising at least 70% sequence identity to at least 8 contiguous amino acids of SEQ ID NOs: 1-94 or of a sequence selected from Table 1, Table 2, or Table 3. The polypeptide can comprise, consist of, or consist essentially of at least five different epitope sequences, each of the at least five different epitope sequences comprises at least 70% sequence identity to at least 8 contiguous amino acids of SEQ ID NOs: 1-94 or of a sequence selected from Table 1, Table 2, or Table 3. The polypeptide can comprise, consist of, or consist essentially of at least 2, at least 3, at least 4, at least 5, at least 6, at least 7, at least 8, at least 9, at least 10, at least 15, at least 20, at least 25, at least 30, at least 35, at least 40, at least 50, or at least 51 different epitope sequences, each of the different epitope sequences comprising at least 70% sequence identity to at least 8 contiguous amino acids of SEQ ID NOs: 1-94 or of a sequence selected from Table 1, Table 2, or Table 3.

One non-limiting example relates to a polypeptide that comprises, consists of, or consists essentially of, at least 51 different epitope sequences, each of the 51 different epitope sequences comprises at least 70% sequence identity to at least 8 contiguous amino acids of a different sequence selected from Table 3. Sometimes, a polypeptide can comprise, consist of, or consist essentially of, at least 51 different epitope sequences, each of the 51 different epitope sequences comprises at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a different sequence selected from Table 3. In some cases, a polypeptide comprises, consists of, or consists essentially of each sequence from Table 3.

In some cases, the polypeptide comprises at least 8 amino acids. The polypeptide can comprise at least 8, at least 9, at least 10, at least 15, at least 20, at least 25, at least 30, at least 35, at least 40, at least 50, at least 60, at least 70, at least 80, at least 90, at least 100, at least 120, at least 140, at least 160, at least 180, at least 200, at least 250, at least 300, at least 400, at least 500, at least 1000, at least 1500, at least 2000, at least 2500, at least 3000, at least 4000, at least 5000, or more amino acids. In some cases, the polypeptide comprises, or consists of, at most 20, at most 30, at most 40, at most 50, at most 60, at most 70, at most 80, at most 90, at most 100, at most 150, at most 200, at most 250, at most 300, at most 500, at most 800, at most 1000, at most 1500, at most 2000, at most 2500, at most 3000, at most 4000, at most 5000 amino acids. The polypeptide can comprise, consist of, or consist essentially of about 8 to about 5000 amino acids, about 8 to about 4000 amino acids, about 8 to about 3000 amino acids, about 8 to about 2000 amino acids, about 8 to about 1000 amino acids, about 8 to about 500 amino acids, about 100 to about 5000 amino acids, about 100 to about 2500 amino acids, about 100 to about 1000 amino acids, about 1500 to about 3000 amino acids, about 1000 to about 3000 amino acids, or about 1000 to about 2500 amino acids. The polypeptide can consist of less than 5000, 4000, 3000, 2900, 2800, 2700, 2600, 2500, 2400, 2300, 2200, 2100, 2000, 1900, 1800, 1700, 1600 1500, 1400, 1300, 1200, 1100, 1000, 750, 500, 250, or 100 amino acids, e.g., when synthesized or initially expressed, e.g., in a cell.

Provided herein is an engineered polypeptide that comprises, consists of, or consists essentially of one or more different epitope sequences that can be derived from, or variants of, or fragments of, at least a portion of a viral protein, e.g., an influenza virus protein, e.g. an influenza A virus protein. In some embodiments, the influenza A virus protein can be PB1, PB1-F2, PB2, PA, HA, NP, NA, M1, M2, NS1, or NEP/NS2. PB2 can be a part of an RNA-dependent RNA polymerase complex, which can facilitate "cap-snatching" from host pre-mRNA molecules to initiate transcription, and can be conducive for replication. In certain situations, PB1 can be a RNA-dependent RNA polymerase, which can bind to terminal ends of vRNA and cRNA for initiation of transcription and replication and can catalyze the sequential addition of nucleotides during RNA chain elongation. PA can be used for viral transcription and replication and can have endonuclease activity. In some instances, PA does not correlate with polymerase activity. HA can bind sialic acid on cell surface for attachment, and can undergo conformational change with low pH exposing fusion peptide which can interact with the endosomal membrane, forming a pore through which the viral RNPs can be released into the cytoplasm. NP can coat viral RNA to form viral ribonucleoprotein (vRNP) complex, which can be critical for the trafficking of vRNPs into the nucleus. NA can be needed for the final release of virus through cleavage of the HA-sialic acid bond which can anchor virus to cell membrane. NA can also prevent virus particles from aggregating. M1 can form intermediate core of a virion and tether NP w/vRNPs, and can drive budding of virus from the cell membrane. M2 can have ion channel activity, and can conduct protons from acidified endosomes into viral particle resulting in pH dependent dissociation of vRNP from the remainder of viral components. NS1 can inhibit cellular antiviral Type 1 Interferon response, and can be dependent on binding to dsRNA. NEP/NS2 can be necessary for nuclear export of vRNP through recruitment of cellular export machinery. The influenza A virus protein can be NP, PB1, or PA.

One non-limiting example of the polypeptide provided herein comprises, consists of, or consists essentially of one or more different epitope sequences having at least 70%, 75%, 80%, 85%, 90%, or 100% sequence identity to at least 8 contiguous amino acids of a sequence derived from or variants of PB1 protein, such as, but not limited to a sequence selected from the group consisting of SEQ ID NOs: 1-7, 43, 51, 52, and 63-66, or a sequence selected from the group consisting of SEQ ID Nos: 2, 3, 43, 51, and 52. In some cases, the polypeptide further comprises one or more different epitope sequences having at least 70%, 75%, 80%, 85%, 90%, or 100% sequence identity to at least 8 contiguous amino acids of a sequence selected from the group consisting of SEQ ID NOs: 8-42, 44-50, 53-62, 67-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length PB1 sequence.

Another non-limiting example of the polypeptide provided herein comprises, consists of, or consists essentially of one or more different epitope sequences having at least 70% sequence identity to at least 8 contiguous amino acids of a sequence derived from or variants of PA protein, such as, but limited to a sequence selected from the group consisting of SEQ ID NOs: 8-12, 40, 41, 58, 59, 61, 62, 84, and 92, or a sequence selected from the group consisting of SEQ ID NOs: 8, 11, 12, 40, 41, 58, 59, 61, 62, 84, and 92. Sometimes, the polypeptide can further comprise one or more different epitope sequences having at least 70% sequence identity to at least 8 contiguous amino acids of a sequence selected from the group consisting of SEQ ID NOs: 1-7, 13-39, 42-57, 60, 63-80, 82, 83, 85-91, and 94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length PA sequence.

Another non-limiting example of the polypeptide provided herein comprises, consists of, or consists essentially of, one or more different epitope sequences having at least 70%, 75%, 80%, 85%, 90%, or 100% sequence identity to at least 8 contiguous amino acids of a sequence derived from or variants of NP protein, such as, but not limited to a sequence selected from the group consisting of SEQ ID NOs: 13-34, 37, 39, 42, 44-50, 53-57, 60, 67-80, 82, 83, 85-91, 93, and 94, or a sequence from the group consisting of SEQ ID NOs: 17, 20-22, 24, 26, 29-34, 44, 45, 49, 53, 60, 70, 73-78, 82, 83, 85-91, 93, and 94. Sometimes, the polypeptide can further comprise one or more different epitope sequences having at least 70%, 75%, 80%, 85%, 90%, or 100% sequence identity to at least 8 contiguous amino acids of a sequence selected from the group consisting of SEQ ID NOs: 1-12, 35, 36, 38, 43, 51, 52, 58, 59, 61-66, 84, and 92. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length NP sequence.

Another non-limiting example of the polypeptide provided herein comprises, consists of, or consists essentially of one or more different epitope sequences having at least 70%, 75%, 80%, 85%, 90%, or 100% sequence identity to at least 8 contiguous amino acids of a sequence derived from or variants of NA protein, such as, but not limited to, a sequence selected from SEQ ID NOs: 35 and 38. Sometimes, the polypeptide can further comprise one or more different epitope sequences having at least 70%, 75%, 80%, 85%, 90%, or 100% sequence identity to at least 8 contiguous amino acids of a sequence selected from the group consisting of SEQ ID NOs: 1-34, 36, 37, 39-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length NA sequence.

Another non-limiting example of the polypeptide provided herein comprises, consists of, or consists essentially of, one or more different epitope sequences having at least 70%, 75%, 80%, 85%, 90%, or 100% sequence identity to at least 8 contiguous amino acids of a sequence derived from or variants of M1 protein, such as, but not limited to SEQ ID NOs: 36. Sometimes, the polypeptide further comprises one or more different epitope sequences having at least 70%, 75%, 80%, 85%, 90%, or 100% sequence identity to at least 8 contiguous amino acids of a sequence selected from the group consisting of SEQ ID NOs: 1-35, 37-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length M1 sequence.

One non-limiting example of a polypeptide provided herein can comprise, consist of, or consist essentially of a first sequence selected from the group consisting of SEQ ID NOs: 2, 3, 8, 11, 12, 40, 41, 43, 51, 52, 58, 59, 61, 62, 84, and 92; and a second sequence selected from the group consisting of SEQ ID NOs: 17, 20, 21, 22, 24, 26, 29, 30, 32, 33, 34, 44, 45, 49, 53, 60, 70, 73, 74, 75, 76, 77, 78, 82, 83, 85, 86, 87, 88, 89, 90, 91, 93, and 94.

Another non-limiting example of a polypeptide provided herein can comprise, consist of, or consist essentially of a first sequence selected from the group consisting of SEQ ID NOs: 2, 8, 11, 12, 40, 41, 43, 52, 58, 59, 61, 62, 84, and 92; and a second sequence selected from the group consisting of SEQ ID NOs: 17, 20, 21, 22, 24, 26, 29, 30, 31, 32, 33, 34, 44, 45, 49, 53, 60, 70, 73, 74, 75, 76, 77, 78, 82, 83, 85, 86, 87, 88, 89, 90, 91, 93, and 94.

Another non-limiting example of a polypeptide provided herein can comprise, consist of, or consist essentially of: (a) a first sequence comprising at least 60%, at least 75%, at least 85%, or 100% sequence identity to at least 8 contiguous amino acids of SEQ ID NO: 8, 11, 12, 40, 41, 58, 59, 61, 62, 84, or 92, and a second sequence comprising at least 60%, at least 75%, at least 85%, or 100% sequence identity to at least 8 contiguous amino acids of SEQ ID NO: 2, 3, 17, 20, 21, 22, 24, 26, 29, 30, 31, 32, 33, 34, 43, 44, 45, 49, 51, 52, 53, 60, 70, 73, 74, 75, 76, 77, 78, 82, 83, 85, 86, 87, 88, 89, 90, 91, 93, or 94; or (b) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 17, 20, 21, 22, 24, 26, 29, 30, 31, 32, 33, 34, 40, 41, 44, 45, 49, 53, 58, 59, 60, 61, 62, 70, 73, 74, 75, 76, 77, 78, 82, 83, 84, 85, 86, 87, 88, 89, 90, 91, 92, 93, or 94; or (c) a first sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94, and a second sequence comprising at least 60%, at least 75%, at least 85%, or 100% sequence identity to at least 8 contiguous amino acids of SEQ ID NO: 2, 3, 8, 11, 12, 40, 41, 43, 51, 52, 58, 59, 61, 62, 84, or 92; or (d) a first sequence comprising at least 60%, at least 75%, at least 85%, or 100% sequence identity to at least 8 contiguous amino acids of SEQ ID NO: 17, 20, 29, 31, 33, 34, 44, 45, 73, 74, 75, 76, 77, 78, 82, 83, 87, 88, 89, 90, or 91 and a second sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92; or (e) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, or 94; or (f) a first sequence comprising at least 60%, at least 75%, at least 85%, or 100% sequence identity to at least 8 contiguous amino acids of SEQ ID NO: 3, 51, or 52, and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, 94; or (g) a first sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92, and a second sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94; or (h) a first sequence comprising at least 60%, at least 75%, at least 85%, or 100% sequence identity to at least 8 contiguous amino acids of SEQ ID NO: 2, 8, 11, 12, 21, 22, 24, 26, 30, 32, 40, 41, 43, 49, 53, 58, 59, 60, 61, 62, 70, 84, 85, 86, 92, 93, or 94, and a second different sequence comprising at least 60%, at least 75%, at least 85%, or 100% sequence identity to at least 8 contiguous amino acids of SEQ ID NO: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94, wherein a contiguous sequence comprising the first sequence and the second different sequence is not found in a PB1, PA, or NP.

Another non-limiting example of a polypeptide provided herein can comprise, consist of, or consist essentially of a sequence selected from at least two of the following groups: (a) a sequence comprising at least 60%, at least 75%, at least 85%, or 100% sequence identity to at least 8 contiguous amino acids of SEQ ID NO: 8, 40, 41, or 84; (b) a sequence comprising at least 60%, at least 75%, at least 85%, or 100% sequence identity to at least 8 contiguous amino acids SEQ ID NO: 11, 58, or 59; (c) a sequence comprising at least 60%, at least 75%, at least 85%, or 100% sequence identity to at least 8 contiguous amino acids SEQ ID NO: 12, 61, 62, or 92; (d) a sequence comprising at least 75%, at least 85%, or 100% sequence identity to at least 8 contiguous amino acids of SEQ ID NO: 2 or 43; (e) a sequence comprising at least 60%, at least 75%, at least 85%, or 100% sequence identity to at least 8 contiguous amino acids of SEQ ID NO: 3, 51, or 52; (f) a sequence comprising at least 60%, at least 75%, at least 85%, or 100% sequence identity to at least 8 contiguous amino acids of SEQ ID NO: 32, 93, 94, or 70; (g) a sequence comprising at least 60%, at least 75%, at least 85%, or 100% sequence identity to at least 8 contiguous amino acids of SEQ ID NO: 21, 22, or 85; (h) a sequence comprising at least 60%, at least 75%, at least 85%, or 100% sequence identity to at least 8 contiguous amino acids of SEQ ID NO: 24, 49, or 86; (i) a sequence comprising at least 60%, at least 75%, at least 85%, or 100% sequence identity to at least 8 contiguous amino acids of SEQ ID NO: 26, 53, 30, or 60; (j) a sequence comprising at least 60%, at least 75%, at least 85%, or 100% sequence identity to at least 8 contiguous amino acids of SEQ ID NO: 17, 82, or 83; (k) a sequence comprising at least 60%, at least 75%, at least 85%, or 100% sequence identity to at least 8 contiguous amino acids SEQ ID NO: 20, 44, or 45; (l) a sequence comprising at least 60%, at least 75%, at least 85%, or 100% sequence identity to at least 8 contiguous amino acids of SEQ ID NO: 29, 87, 88, 89, 90, or 91; (m) a sequence comprising at least 60%, at least 75%, at least 85%, or 100% sequence identity to at least 8 contiguous amino acids of SEQ ID NO: 31; and (n) a sequence comprising at least 60%, at least 75%, at least 85%, or 100% sequence identity to at least 8 contiguous amino acids of SEQ ID NO: 33, 34, 73, 74, 75, 76, 77, or 78; wherein at least one sequence is selected from groups (a)-(d) and at least one sequence is selected from groups (f)-(n).

Another non-limiting example of a polypeptide provided herein can comprise, consist of, or consist essentially of: (o) at least 1, 2, 3, or 4 sequences, each comprising at least 60%, at least 75%, at least 85%, or 100% sequence identity to at least 8 contiguous amino acids of any of SEQ ID NOs: 8, 40, 41, or 84, or at least 1, 2, 3, or 4 sequences, each comprising at least 55%, at least 66%, at least 77%, at least 88%, or 100% sequence identity to any of SEQ ID NOs: 8, 40, 41, or 84; (p) at least 1, 2, or 3 sequences, each comprising at least 60%, at least 75%, at least 85%, or 100% sequence identity to at least 8 contiguous amino acids of any of SEQ ID NOs: 11, 58, or 59, or at least 1, 2, or 3 sequences, each comprising at least 52%, at least 58%, at least 64%, at least 70%, and least 76%, at least 82%, at least 88%, at least 94%, or 100% sequence identity to at least 9, 10, 11, 12, 13, 14, 15, 16, or 17 contiguous amino acids of any of SEQ ID NOs: 11, 58, or 59; (q) at least 1, 2, 3, or 4 sequences, each comprising at least 60%, at least 75%, at least 85%, or 100% sequence identity to at least 8 contiguous amino acids of SEQ ID NOs: 12, 61, 62, or 92, or at least 1, 2, 3, or 4 sequences, each comprising at least 52%, at least 58%, at least 64%, at least 70%, and least 76%, at least 82%, at least 88%, at least 94%, or 100% sequence identity to at least 9, 10, 11, 12, 13, 14, 15, 16, or 17 contiguous amino acids of any of SEQ ID NOs: 12, 61, 62, or 92; (r) at least 1 or 2 sequences, each comprising at least 60%, at least 75%, at least 85%, or 100% sequence identity to at least 8 contiguous amino acids of any of SEQ ID NOs: 2 or 43, or at least 1 or 2 sequences, each comprising at least 60%, at least 70%, at least 80%, at least 90%, or 100% sequence identity to at least 9 or 10 contiguous amino acids of any of SEQ ID NOs: 2 or 43; (s) at least 1, 2, or 3 sequences, each comprising at least 60%, at least 75%, at least 85%, or 100% sequence identity to at least 8 contiguous amino acids of any of SEQ ID NOs: 3, 51, or 52, or at least 1, 2, or 3 sequences, each comprising at least 55%, at least 66%, at least 77%, at least 88%, or 100% sequence identity to at least 9 or 10 contiguous amino acids of any of SEQ ID NOs: 3, 51, or 52; (t) at least 1, 2, 3, or 4 sequences, each comprising at least 60%, at least 75%, at least 85%, or 100% sequence identity to at least 8 contiguous amino acids to any of SEQ ID NOs: 32, 93, 94, or 70, or at least 1, 2, 3, or 4 sequences, each comprising at least 60%, 70%, 80%, 90%, or 100% sequence identity to 9 or 10 contiguous amino acids of any of SEQ ID NOs: 32, 93, 94, or 70; (u) at least 1, 2, or 3 sequences, each comprising at least 60%, at least 75%, at least 85%, or 100% sequence identity to at least 8 contiguous amino acids any of SEQ ID NOs: 21, 22, or 85, or at least 1, 2, 3, or 4 sequences, each comprising at least 55%, at least 66%, at least 77%, at least 88%, or 100% sequence identity to 9 contiguous amino acids of any of SEQ ID NOs: 21, 22, or 85; (v) at least 1, 2 or 3 sequences, each comprising at least 60%, at least 75%, at least 85%, or 100% sequence identity to at least 8 contiguous amino acids of any of SEQ ID NOs: 24, 49, or 86, or at least 55%, at least 66%, at least 77%, at least 88%, or 100% sequence identity to 9 contiguous amino acids of any of SEQ ID NOs: 24, 49, or 86; (w) at least 1, 2, 3, or 4 sequences, each comprising at least 60%, at least 75%, at least 85%, or 100% sequence identity to at least 8 contiguous amino acids of any of SEQ ID NOs: 26, 53, 30, or 60, or at least 1, 2, 3, or 4 sequences, each comprising at least 50%, at least 56%, at least 62%, at least 68%, at least 75%, at least 81%, at least 87%, at least 93%, or at least 100% sequence identity to at least 9, 10, 11, 12, 13, 14, 15, or 16 contiguous amino acids of any of SEQ ID NOs: 26, 53, 30, or 60, or at least 9, 10, 11, 12, 13, 14, 15, 16, or 17 contiguous amino acids of any of SEQ ID NOs: 30 or 60; (x) at least 1, 2, or 3 sequences, each comprising at least 60%, at least 75%, at least 85%, or 100% sequence identity to at least 8 contiguous amino acids of any of SEQ ID NOs: 17, 82, or 83, or at least 1, 2, or 3 sequences, each comprising at least 50%, at least 57%, at least 60%, at least 71%, at least 78%, at least 85%, at least 92%, or 100% sequence identity to at least 9, 10, 11, 12, 13, or 14 contiguous amino acids of any of SEQ ID NOs: 17, 82, or 83; (y) at least 1, 2, or 3 sequences, each comprising at least 60%, at least 75%, at least 85%, or 100% sequence identity to at least 8 contiguous amino acids of any of SEQ ID NOs: 20, 44, or 45 or at least 1, 2, or 3 sequences, each comprising at least 55%, at least 66%, at least 77%, at least 88%, or 100% sequence identity to 9 contiguous amino acids of any of SEQ ID NOs: 20, 44, or 45; (z) at least 1, 2, 3, 4, 5, or 6 sequences, each comprising at least 60%, at least 75%, at least 85%, or 100% sequence identity to at least 8 contiguous amino acids of any of SEQ ID NOs: 29, 87, 88, 89, 90, or 91, or at least 1, 2, 3, 4, 5, or 6 sequences, each comprising at least 50%, at least 55%, at least 61%, at least 66%, at least 72%, at least 83%, at least 88%, at least 94%, or 100% sequence identity to at least 9, 10, 11, 12, 13, 14, 15, 16, 17, or 18 contiguous amino acids of any of SEQ ID NOs: 29, 87, 88, 89, 90, or 91; (aa) a sequence comprising at least 60%, at least 75%, at least 85%, or 100% sequence identity to at least 8 contiguous amino acids of SEQ ID NO: 31, or a sequence comprising at least 55%, at least 66%, at least 77%, at least 88%, or 100% sequence identity to 9 contiguous amino acids of SEQ ID NO: 31; (bb) at least 1, 2, 3, 4, 5, 6, 7, or 8 sequences, each comprising at least 60%, at least 75%, at least 85%, or 100% sequence identity to at least 8 contiguous amino acids of any of SEQ ID NOs: 33, 34, 73, 74, 75, 76, 77, or 78, or at least 1, 2, 3, 4, 5, 6, 7, or 8 sequences, each comprising at least 52%, at least 56%, at least 60%, at least 64%, at least 68%, at least 72%, at least 76%, at least 80%, at least 84%, at least 88%, at least 92%, at least 96%, or 100% sequence identity to at least 9, 10, 11, 12, 13, 14, 15, 16, 17, 18, 19, 20, 21, 22, 23, 24, or 25 contiguous amino acids of any of SEQ ID NOs: 33, 34, 73, 74, 75, 76, 77, or 78; or any combination of (o)-(bb).

Another non-limiting example of a polypeptide provided herein can comprise, consist of, consist essentially of: (cc) at least two sequences from the group consisting of SEQ ID NOs: 8, 40, 41, and 84; (dd) at least two sequences from the group consisting of SEQ ID NOs: 11, 58, and 59; (ee) at least two sequences from the group consisting of SEQ ID NO: 12, 61, 62, and 92; (ff) at least two sequences from the group consisting of SEQ ID NOs: 2 and 43; (gg) at least three sequences from the group consisting of SEQ ID NOs: 3, 51, and 52; (hh) at least two sequences from the group consisting of SEQ ID NOs: 32, 93, 94, and 70; (ii) at least two sequences from the group consisting of SEQ ID NOs: 21, 22, and 85; (jj) at least two sequences from the group consisting of SEQ ID NOs: 24, 49, and 86; (kk) at least two sequences from the group consisting of SEQ ID NOs: 26, 53, 30, and 60; (ll) at least two sequences from the group consisting of SEQ ID NOs: 17, 82, and 83; (mm) at least two sequences from the group consisting of SEQ ID NOs: 20, 44, and 45; (nn) at least two sequences from the group consisting of SEQ ID NOs: 29, 87, 88, 89, 90, and 91; or (oo) at least two sequences from the group consisting of SEQ ID NOs: 33, 34, 73, 74, 75, 76, 77, and 78.

In some cases, a polypeptide provided herein can further comprise a full-length amino acid sequence (or at least 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C. In some cases, a vaccine provided herein comprises a polypeptide comprising a full-length amino acid sequence (or at least 10%, 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C, e.g., or the polypeptide is expressed from a separate nucleic acid or virus in the vaccine, e.g., an adenovirus, A polypeptide provided herein can comprise 1, 2, 3, 4, or 5 or more copies of a sequence of a full-length amino acid sequence (or at least 50%, 60%, 70%, 80%, 90%, or 95% of the full-length sequence) of the viral protein. The full-length amino acid sequence (or at least 10%, 20%, 30%, 40%, 50%, 60%, 70%, 80%, 90%, or 95% of the full-length sequence) can be at the N-terminus of the polypeptide, the C-terminus of the polypeptide, internal in the polypeptide, or, e.g., if multiple copies are present, the N-terminus and C-terminus of the polypeptide. For example, a polypeptide can comprise at least 5, 10, 20, 30, 40, 50, or 51 sequences from Table 1, Table 2, or Table 3 (e.g., each sequence is from one of Table 1, Table 2, or Table 3), each sequence separated or not by a linker, and 1, 2, or 3 copies of a full-length amino acid sequence (or at least 10%, 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C.

In some cases, a polypeptide provided herein can further comprise a full length amino acid sequence (or at least 10%, 20%, 30%, 40%, 50%, 60%, 70%, 80%, 90%, or 95% of the full-length sequence) of NP protein of influenza, e.g., influenza A, or Influenza B, influenza C. In some cases, NP protein sequence (or at least 10%, 20%, 30%, 40%, 50%, 60%, 70%, 80%, 90%, or 95% of the full-length sequence of NP) can be from any appropriate strain of Influenza B. For instance, the sequence can be selected based the prevalent strain, or expected prevalent strain, for an influenza season. A strain of Influenza B from which an NP sequence is chosen can be chosen randomly. For instance, a polypeptide can comprise amino acid sequence of NP protein sequence (or at least 10%, 20%, 30%, 40%, 50%, 60%, 70%, 80%, 90%, or 95% of the full-length sequence of NP) from a particular strain of Influenza B, like B/Brisbane/60/2008-like that belong to B/Victoria lineage or B/Phuket/3073/2013-like or B/Pennsylvania/49/2015 that belongs to B/Yamagata lineage. A derivative (or fragment) of a full length amino acid sequence of NP protein of Influenza B can comprise at least 60% identity, at least 75% identity, at least 80% identity, at least 85% identity, at least 90% identity, at least 95% identity, at least 96% identity, at least 97% identity, at least 98% identity, at least 99% identity, at least 99.5% identity, at least 99.8% identity, at least 99.9% identity, at least 99.99% identity to the full length amino acid sequence of NP protein (or at least 10%, 20%, 30%, 40% 50%, 60%, 70%, 80%, 90%, or 95% of the full-length sequence of NP) of Influenza B. A derivative (or fragment) of a full length amino acid sequence of NP protein of Influenza B can comprise or consist of at most 100 amino acids, at most 80 amino acids, at most 60 amino acids, at most 50 amino acids, at most 40 amino acids, at most 30 amino acids, at most 20 amino acids, at most 15 amino acids, at most 10 amino acids, at most 9 amino acids, at most 8 amino acids, at most 7 amino acids, at most 6 amino acids, at most 5 amino acids, at most 4 amino acids, at most 3 amino acids, at most 2 amino acids, or only 1 amino acid different than the full length amino acid sequence of NP protein of Influenza B. A polypeptide can comprise all of the sequences in Table 1, with or without a linker between each sequence, and one or two copies of a full-length protein (or at least 10%, 20%, 30%, 40%, 50%, 60%, 70%, 80%, 90%, or 95% of the full-length sequence of the protein), e.g., NP protein from an influenza B strain. A polypeptide can comprise all of the sequences in Table 2, with or without a linker between each sequence, and one or two copies of a full-length protein (or at least 10%, 20%, 30%, 40%, 50%, 60%, 70%, 80%, 90%, or 95% of the full-length sequence of a protein), e.g., NP protein from an influenza B strain. A polypeptide can comprise all of the sequences in Table 3, with or without a linker between each sequence, and one or two copies of a full-length protein (or at least 10%, 20%, 30%, 40%, 50%, 60%, 70%, 80%, 90%, or 95% of the full-length sequence of a protein), e.g., NP protein from an influenza B strain.

In some cases, a polypeptide can comprise amino acid sequence (full-length or fragment) of NP protein from a virus that belongs to B/Victoria lineage. For example, a polypeptide can comprise amino acid sequence with at least 50%, 60%, 70%, 80%, 90%, 95%, or 100% sequence identity to full-length, or fragment, e.g., comprising amino acids 1 to 560, 38-557, 50 to 500, 100 to 500, 200 to 400, 1 to 100, 100 to 200, 200 to 300, 300 to 400, or 500 to 560, of NP protein (Accession NO.: AGK63064.1, SEQ ID NO: 116) from Influenza B/Brisbane/60/2008. In some cases, a polypeptide can comprise amino acid sequence (full-length or fragment) of NP protein from a virus that belongs to B/Yamagata lineage. For example, a polypeptide can comprise amino acid sequence with at least 50%, 60%, 70%, 80%, 90%, 95%, or 100% sequence identity to full-length, or fragment, e.g., comprising amino acids 1 to 560, 2 to 560, 50 to 500, 100 to 500, 200 to 400, 1 to 100, 2 to 100, 100 to 200, 200 to 300, 300 to 400, or 500 to 560, of NP protein (Accession NO.: ABL77260.1, SEQ ID NO: 117) from Influenza B/Yamagata/16/1988, or NP protein (Accession NO.: AOZ82278.1, SEQ ID NO: 118) from Influenza B/Pennsylvania/49/2015. In some cases, a polypeptide can comprise both an amino acid sequence (full-length or fragment) of NP protein from a virus that belongs to B/Victoria lineage, or a derivative thereof, and an amino acid sequence (full-length or fragment) of NP protein from a virus that belongs to B/Yamagata lineage, or a derivative thereof.

A polypeptide provided herein can comprise, consist of, or consist essentially of, one or more epitope sequences arranged in order. In some cases, epitope sequences are arranged in a particular order with the consideration of promoting immunogenicity, increasing expression, facilitating polypeptide stability, increasing polypeptide solubility, facilitating the in vivo cleavage of the polypeptide chain, or any other factors that may affect the vaccine performance, or any combination thereof. It is also possible to manipulate the order of the epitope sequences in the polypeptide in order to finely tune certain aspects of a vaccine, either upregulating or downregulating one or more certain parameters as one skilled in the art would be able to achieve.

In some embodiments, the polypeptide comprises more than one epitope sequence that are linked together directly, e.g., "back-to-back". Alternatively, the polypeptide can comprise, consist of, or consist essentially of, more than one epitope sequence, at least two neighboring epitope sequences among which are linked with a linker sequence. The polypeptide can comprise a single type of linker sequence throughout. The polypeptide can comprise more than one different type of linker sequence. The choice of linker sequence can vary depending on the selection of peptide sequences, the specific requirement for a number of different parameters, such as, but not limited to, expression level, folding and stability, solubility, cellular and subcellular targeting, immunogenicity, half-life in vitro and in vivo.

Linkers can be short amino acid sequences to separate multiple domains in a single polypeptide. In some cases, the linker sequence can comprise 3, 4, 5, 6, 7, 8, 9, 10, or more amino acids. The linker sequence can comprise at least 3, at least 4, at least 5, at least 6, at least 7, at least 8, at least 9, at least 10, at least 15, at least 20, or at least 50 amino acids. The linker sequence can comprise at most 4, at most 5, at most 6, at most 7, at most 8, at most 9, at most 10, at most 11, at most 12, at most 15, at most 20, at most 30, at most 40, at most 50, or at most 100 amino acids.

The linker sequence can comprise sequences occurring in natural multi-domain proteins that link the domains therein. The linker sequence can comprise an artificially created linker. The linker can also be a joined product of both a natural linker protein and an artificially created sequence. In some cases, specific linker sequences can be selected for in vivo cleavability of the polypeptide. For example, it can be desirable to cleave between certain epitope sequences, rendering the separated two or more parts of the polypeptide presented to the antigen-presenting cells separately. A linker can comprise a plurality of glycines, alanines, or any combinations thereof. A linker can comprise a plurality of arginines, valines, lysines, or any combinations thereof. Under such exemplary circumstances, linker sequences such as, LEAGCKNFFPRSFTSCGSLE (SEQ ID NO: 95), CRRRRRREAEAC (SEQ ID NO: 96), can be chosen. Sometimes, it can be desirable to use flexible linker sequences, such as, but not limited to, stretches of Gly and Ser residues ("GS" linker) like $(GGGGS)_n$ (n=1 to 10) (SEQ ID NO: 107), $(Gly)_8$ (SEQ ID NO: 97), GSAGSAAGSGEF (SEQ ID NO: 98), $(GGGGS)_4$ (SEQ ID NO: 99). In some cases, it can be desirable to use rigid linker sequences, such as, but not limited to, $(EAAAK)_n$ (SEQ ID NO: 108), Pro-rich sequences like $(XP)_n$ (SEQ ID NO: 109), with X designating any amino acid can be used (n=1 to 20). In some cases, the linker sequence RVKR (SEQ ID NO: 110) can be chosen. The linker sequence RVKR (SEQ ID NO: 110) can be immunostimulatory in some situations. The polypeptide can comprise, consist of, or consist essentially of, each sequence from Table 1, Table 2, or Table 3, wherein each sequence is separated by a linker. The polypeptide can comprise, consist of, or consist essentially of, each sequence from Table 1, Table 2, or Table 3, wherein each sequence is not separated by a linker. The polypeptide can comprise, consist of, or consist essentially of, each sequence from Table 1, Table 2, or Table 3, wherein some of the sequences are separated by a linker and some are not separated by a linker.

In certain aspects of the present disclosure, a polypeptide provided herein further comprises a CD4+ (helper) T cell epitope that is connected to one or more of the epitope sequences described above. A "connection" can be, e.g., a direct or indirect covalent linkage, or a direct or indirect non-covalent linkage. The CD4+ (helper) T cell epitope can be ISQAVHAAHAEINEAGR (SEQ ID NO: 100). In some cases, the CD4+ (helper) T cell epitope is AKFVAAWTL-KAAA (HLA DR-binding Epitope, PADRE) (SEQ ID NO: 101), or a non-natural amino acid derivative of the PADRE sequence, AKXVAAWTLKAAAZC (SEQ ID NO: 102), wherein X is L-cyclohexylalanine and Z is aminocaproic acid. In some cases, the CD4+ (helper) T cell epitope can be GALNNRFQIKGVELKSK (SEQ ID NO: 103). In some embodiments, the C-terminus of a polypeptide provided herein, e.g., a polypeptide comprising a sequence selected from SEQ ID NOs: 1-94 or a sequence selected from Table 1, Table 2, or Table 3, is attached to a lysine and the lysine is attached to the N-terminus of a CD4+ T cell epitope. The C-terminus of a CD4+ (helper) T cell epitope can be attached to a lysine and the lysine can be attached to the N-terminus of a peptide comprising a sequence selected from SEQ ID NOs: 1-94 or a sequence selected from Table 1, Table 2, or Table 3.

A polypeptide can be linked to a full length viral protein, e.g. full length PB1, PB1-F2, PB2, PA, HA, NP, NA, M1, M2, NS1, or NEP/NS2 protein, or the polypeptide can be link to a protein with at least 50%, 60%, 70%, 80%, 90%, 95%, or 100% sequence identity to at least 10%, 20%, 30%, 40%, 50%, 60%, 70%, 80%, 90%, or 95% of the full-length sequence of any of these proteins, from, e.g., influenza A, influenza B, or influenza C, e.g., via a linker described herein, or the connection can be without a linker.

A polypeptide provided herein can comprise one or more natural amino acids, unnatural amino acids, or a combination thereof. An amino acid residue can be a molecule containing both an amino group and a carboxyl group. Suitable amino acids for use in the peptides described include, without limitation, both the D- and L-isomers (amino acid isomer) of the naturally-occurring amino acids, as well as non-naturally occurring amino acids prepared by organic synthesis or other metabolic routes. An amino acid can be an α-amino acid, β-amino acid, natural amino acid, non-natural amino acid, or amino acid analog. An α-amino acid can be molecule containing both an amino group and a carboxyl group bound to a carbon which is designated the α-carbon. A α-amino acid can be a molecule containing both an amino group and a carboxyl group in a β configuration. A naturally occurring amino acid can be any one of the twenty amino acids commonly found in peptides synthesized in nature, and known by the one letter abbreviations A, R, N, C, D, Q, E, G, H, I, L, K, M, F, P, S, T, W, Y and V.

A polypeptide provided herein can comprise one or more hydrophobic, hydrophilic, polar, or charged amino acids. A hydrophobic amino acid can include small hydrophobic amino acids and large hydrophobic amino acids. A small hydrophobic amino acid can be glycine, alanine, proline, and analogs and isomers thereof. A large hydrophobic amino acid can be a valine, leucine, isoleucine, phenylalanine, methionine, tryptophan, and analogs and isomers thereof. A polar amino acid can be a serine, threonine, asparagine, glutamine, cysteine, tyrosine, and analogs and isomers thereof. A charged amino acid can be a lysine, arginine, histidine, aspartate, glutamate, or analog thereof.

A polypeptide as provided herein can comprise one or more amino acid analogs. An amino acid analog can be a molecule which is structurally similar to an amino acid and which can be substituted for an amino acid in the formation of a peptidomimetic macrocycle. Amino acid analogs include β-amino acids and amino acids where the amino or carboxyl group is substituted by a similarly reactive group (e.g., substitution of the primary amine with a secondary or tertiary amine, or substitution of the carboxyl group with an ester).

A polypeptide provided herein can comprise one or more non-natural amino acids. A non-natural amino acid can be an amino acid which is not one of the twenty amino acids commonly found in peptides synthesized in nature, and known by the one letter abbreviations A, R, N, C, D, Q, E, G, H, I, L, K, M, F, P, S, T, W, Y and V.

Amino acid analogs can include β-amino acid analogs. Amino acid analogs can include analogs of alanine, valine, glycine, leucine, arginine, lysine, aspartic acids, glutamic acids, cysteine, methionine, phenylalanine, tyrosine, proline, serine, threonine, and/or tryptophan.

Amino acid analogs can be racemic. In some embodiments, the D isomer of the amino acid analog is used. In some cases, the L isomer of the amino acid analog is used. In some embodiments, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

A polypeptide provided herein can comprise a non-essential amino acid. A non-essential amino acid residue can be a residue that can be altered from the wild-type sequence of a peptide without abolishing or substantially altering its essential biological or biochemical activity (e.g., receptor binding or activation). A peptide provided herein can comprise an essential amino acid. An essential amino acid residue can be a residue that, when altered from the wild-type sequence of the peptide, results in abolishing or substantially abolishing the peptide's essential biological or biochemical activity.

A polypeptide provided herein can comprise a conservative amino acid substitution. A conservative amino acid substitution can be one in which the amino acid residue is replaced with an amino acid residue having a similar side chain. Families of amino acid residues having similar side chains have been defined in the art. These families can include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a peptide, for example, can be replaced with another amino acid residue from the same side chain family. Other examples of acceptable substitutions can be substitutions based on isosteric considerations (e.g., norleucine for methionine) or other properties (e.g., 2-thienylalanine for phenylalanine, or 6-C1-tryptophan for tryptophan).

Vaccine Compositions

Individual epitope sequences provided herein, polypeptides in which individual epitope sequences are linked, as provided herein, nucleic acid expressing individual epitope sequences or polypeptides provided herein, vectors comprising nucleic acid expressing individual epitope sequences or polypeptides provided herein, or viruses comprises such nucleic acid or vectors, can be formulated as vaccines. Vaccines provided herein can be any substance used to stimulate the production of antibodies and provide immunity against one or more diseases, e.g., influenza. The vaccines can be prepared from live pathogens, live attenuated pathogens, or inactivated pathogens that have been inactivated by e.g., chemicals, heat, or radiation. The vaccines can contain subunits or portions of a pathogen, in which these subunits can be optionally conjugated. The vaccine can also be prepared as a peptide-based vaccine, a nucleic acid-based vaccine, a viral vector-based vaccine, an antibody based vaccine, or an antigen-presenting cell based vaccine.

The vaccines can protect against pathogens, for example. A pathogen can be any infectious organism, including bacteria, fungi, viruses, protozoa, and others. The vaccines can also include tumor or cancer vaccines. A composition, e.g., a vaccine, provided herein can induce a systemic immune response, when administered into a subject body, e.g. human body. A composition, e.g., a vaccine, provided herein can induce a mucosal immune response, e.g., in the respiratory tract, in addition to systemic immune response, when administered into a subject body, e.g. human body.

The vaccines can be a traditional vaccine or a universal vaccine. A traditional vaccine can be a vaccine that can target a specific pathogen. Measles vaccine is one example of a traditional vaccine. It can target epitopes present on the hemagglutinin (H) protein of the Measles virus that have remained conserved over 50 years.

Seasonal vaccines can be another type of traditional vaccine. For example, an influenza vaccine can be modified annually and is tailored to the population of influenza viruses present at a given year. In some cases, an influenza vaccine is generated as a trivalent vaccine, which can include two subtypes of the influenza A virus, H1N1 and H3N2, and one strain of the influenza B virus. Sometimes, the influenza vaccine is generated as a quadrivalent vaccine, which can include two subtypes of influenza A virus and two strains of influenza B virus. The specific strains of the influenza A and B viruses can be chosen based on surveillance-based forecasts that can predict the pathogenicity of the circulating strains each year and can vary from country to country.

A universal vaccine can be a vaccine that offers broad-based protection against multiple strains of a pathogen, and/or against multiple pathogens within the same family. Exemplary universal vaccines include SynCon® influenza vaccines from Inovio Pharmaceuticals, M-001 from BiondVax, and FP-01 from Immune Targeting Systems. These universal vaccines can target conserved regions or epitopes that exist within the influenza viral proteins. Conserved regions or epitopes can exhibit at least 70%, 80%, 90%, 95%, 99% sequence homology or sequence identity.

Vaccine compositions can be formulated using one or more physiologically acceptable carriers including excipients and auxiliaries which facilitate processing of one or more active agents, such as one or more peptides, nucleic acids, proteins (e.g., antibodies or fragments thereof), APCs, or viruses described herein, into preparations which can be used pharmaceutically. Proper formulation can be dependent upon the route of administration chosen.

In some cases, the vaccine composition is formulated as a peptide-based vaccine, a nucleic acid-based vaccine, an antibody based vaccine, a cell based vaccine, or a virus-based vaccine. For example, a vaccine composition can include naked cDNA in cationic lipid formulations; lipopeptides (see e.g., Vitiello, A. et al, J. Clin. Invest. 95:341, 1995), naked cDNA or peptides, encapsulated e.g., in poly (DL-lactide-co-glycolide) ("PLG") microspheres (see, e.g., Eldridge, et al, Molec. Immunol. 28:287-294, 1991: Alonso et al, Vaccine 12:299-306, 1994; Jones et al, Vaccine 13:675-681, 1995); peptide composition contained in immune stimulating complexes (ISCOMS) (see, e.g. Takahashi et al, Nature 344:873-875, 1990; Hu et al, Clin Exp Immunol. 113:235-243, 1998); or multiple antigen peptide systems (MAPs) (see e.g., Tarn, J. P., Proc. Natl Acad. Sci. U.S.A. 85:5409-5413, 1988; Tam, J. P., J. Immunol. Methods 196: 17-32, 1996). Sometimes, a vaccine is formulated as a peptide-based vaccine, or nucleic acid based vaccine in which the nucleic acid encodes the peptides. Sometimes, a vaccine is formulated as an antibody based vaccine. Sometimes, a vaccine is formulated as a cell based vaccine.

Vaccine compositions can be formulated using one or more physiologically acceptable carriers including excipients and auxiliaries which facilitate processing of one or more active agents, such as one or more peptides, nucleic acids, proteins (e.g., antibodies or fragments thereof), APCs, or viruses described herein, into preparations which can be used pharmaceutically. Proper formulation can be dependent upon the route of administration chosen.

Peptide-Based Vaccine

Provided herein is a peptide-based vaccine that comprises one or more epitope sequences or one or more polypeptides described herein. For instance, the polypeptide can comprise, consist of, or consist essentially of, one or more epitope sequences selected from the group consisting of:

SEQ ID NOs: 1-94, or one or more epitope sequences selected from Table 1, Table 2, or Table 3. The peptide-based vaccine can comprise one polypeptide. The peptide-based vaccine can comprises at least 2, 3, 4, 5, 6, 7, 8, 9, 10, 15, 20, 25, 30, 35, 40, 45, 50, 51, or more different peptide sequences, e.g., each peptide can have at least 70%, 75%, 80%, 85%, 90%, 95%, or 100% sequence identity to at least 8, 9, 10, 14, 16, 17, 18, or 25 amino acids of SEQ ID NOs: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94. The peptide-based vaccine can be used to treat or prevent an influenza infection.

In some embodiments, a composition comprises, consists essentially of, or consists of one or more peptides or polypeptides, which may or may not be purified peptides or polypeptides as described herein. As used herein, a composition "comprising" one or more peptides or polypeptides as described herein can mean that the composition can contain other compounds, including one or more proteins that are not described herein. As used herein, a composition "consisting essentially of" one or more peptides or polypeptides can mean that the composition can comprise other compounds in addition to the peptides or polypeptides described herein so long as the additional compounds do not materially change the activity or function of the one or more peptides or polypeptides that are contained in the composition. As used herein, a composition "consisting of" one or more peptides or polypeptides as described herein can mean that the composition does not contain other proteins in addition to the one or more peptides or polypeptides described herein. Compositions consisting of one or more peptides or polypeptides described herein can comprise ingredients other than proteins, e.g., pharmaceutically acceptable carriers, surfactants, preservatives, etc. In some embodiments, compositions consisting of one or more peptides or polypeptides described herein can contain insignificant amounts of contaminants, which can include peptide or polypeptide contaminants, e.g., smaller fragments of the one or more peptides or polypeptides described herein, which can result from, for example, the synthesis of the one or more peptides or polypeptides described herein, subsequent processing, storage conditions, and/or protein degradation.

Peptide-based vaccine can be formulated using techniques, carriers, and excipients as suitable. The peptide-based vaccines can be formulated to improve their biological half-life, stability, efficacy, bioavailability, bioactivity, or a combination thereof.

Sometimes, a vaccine can comprises a cocktail of multiple polypeptides described herein containing the same sequence, or a cocktail of multiple copies of different polypeptides described herein. The polypeptides can be modified, such as by lipidation, or attachment to a carrier protein. Lipidation can be the covalent attachment of a lipid group to a polypeptide. Lipidated polypeptides can stabilize structures and can enhance efficacy of the vaccine treatment.

Lipidation can be classified into several different types, such as N-myristoylation, palmitoylation, GPI-anchor addition, prenylation, and several additional types of modifications. N-myristoylation can be the covalent attachment of myristate, a C14 saturated acid, to a glycine residue. Palmitoylation can be thioester linkage of long-chain fatty acids (CI 6) to cysteine residues. GPI-anchor addition can be glycosyl-phosphatidylinositol (GPI) linkage via amide bond. Prenylation can be the thioether linkage of an isoprenoid lipid (e.g., farnesyl (C-15), geranylgeranyl (C-20)) to cysteine residues. Additional types of modifications can include attachment of S-diacylglycerol by a sulfur atom of cysteines, O-octanoyl conjugation via serine or threonine residues, S-archaeol conjugation to cysteine residues, and cholesterol attachment.

Fatty acids for generating a lipidated polypeptide can include C2 to C30 saturated, monounsaturated, or polyunsaturated fatty acyl groups. Exemplary fatty acids can include palmitoyl, myristoyl, stearoyl, and decanoyl groups.

In some embodiments, a lipid moiety that has adjuvant property is attached to a peptide of interest to elicit or enhance immunogenicity in the absence of an extrinsic adjuvant. A lipidated peptide or lipopeptide can be referred to as a self-adjuvant lipopeptide.

Any of the fatty acids described above and elsewhere herein can elicit or enhance immunogenicity of a peptide of interest. A fatty acid that can elicit or enhance immunogenicity can include palmitoyl, myristoyl, stearoyl, lauroyl, octanoyl, and decanoyl groups. In some cases, a fatty acid that can elicit or enhance immunogenicity can include palmitoyl groups. Non-limiting examples of palmitoyl group include $Pam_2Cys$, $Pam_3Cys$, or $Pam_3OH$.

$Pam_2Cys$, also known as dipalmitoyl-S-glyceryl-cysteine or S-[2,3 bis(palmitoyloxy) propyl]cysteine, corresponds to the lipid moiety of MALP-2, a macrophage-activating lipopeptide isolated from *Mycoplasma fermentans*.

$Pam_3Cys$, also known as $Pam_3OH$ or N-palmitoyl-S-[2, 3-bis(palmitoyloxy)propyl]cysteine, is a synthetic version of the N-terminal moiety of Braun's lipoprotein that spans the inner and outer membranes of Gram negative bacteria.

Other fatty acid groups contemplated for use include Set2Cys (also known as S-(2,3-bis(stearoyloxy)propyl) cysteine or distearoyl-S-glyceryl-cysteine), Lau2Cys (also known as S-[2,3-bis(lauroyloxy) propyl] cysteine or dilauroyl-S-glyceryl-cysteine); and Oct2Cys (also known as S-[2, 3-bis(octanoyloxy)propyl]cysteine or dioctanoyl-S-glyceryl-cysteine).

Additional suitable fatty acid groups include synthetic triacylated and diacylated lipopeptides, FSL-I (a synthetic lipoprotein derived from *Mycoplasma salivarium* I), $Pam_3Cys$ (tripaltnitoyl-S-glyceryl cysteine) and S-[2,3-bis (palmitoyloxy)-(2RS)-propyl]-N-palmitoyl-(R)-cysteine, where "$Pam_3$" is "tripalmitoyl-S-glyceryl". Derivatives of $Pam_3Cys$ are also suitable for use, in which derivatives include S-[2,3-bis(palmitoyloxy)-(2-R, S)-propyl]-N-palmitoyl-(R)-Cys-(S)-Ser-(Lys)4-hydroxytrihydrochloride("(R)-Cys-(S)-Ser-(Lys)4" disclosed as SEQ ID NO: 111); Pam3Cys-Ser-Ser-Asn-Ala (SEQ ID NO: 112); PaM3Cys-Ser-(Lys)4 (SEQ ID NO: 113); Pam3Cys-Ala-Gly; PamsCys-Ser-Gly; Pam3Cys-Ser; PaM3CyS-OMe; Pam3Cys-OH; PamCAG, palmitoyl-Cys((RS)-2,3-di(palmitoyloxy)-propyl)-Ala-Gly-OH; and the like. Another non-limiting examples include Pam2CSK4 (SEQ ID NO: 114) (dipalmitoyl-S-glyceryl cysteine-serine-(lysine)4; or Pam2Cys-Ser-(Lys)4 (SEQ ID NO: 114)).

Peptides such as naked peptides or lipidated peptides can be incorporated into a liposome. For example, the lipid portion of the lipidated peptide can spontaneously integrate into the lipid bilayer of a liposome. Thus, a lipopeptide can be presented on the "surface" of a liposome. A lipidated peptide can be a peptide that is encapsulated within a liposome.

Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

Depending on the method of preparation, liposomes can be unilamellar or multilamellar, and can vary in size with diameters ranging from about 0.02 μm to greater than about 10 μm. Sometimes, the liposomes can be small unilamellar vesicles (25-50 nm), large unilamellar vesicles (100-200 nm), giant unilamellar vesicles (1-2 μm), and multilamellar vesicles (MLV; 1 μm-2 μm). The peptides being delivered can be either encapsulated into liposomes or adsorbed on the surface. The size and surface properties of liposomes can be optimized for a desired result. For example, unilamellar and multilamellar liposomes provide sustained release from several hours to days after intravascular administration. The prolonged drug release can be achieved by multivesicular liposomes, also known as DepoFoam® technology. Unlike ULV and MLV, multivesicular liposomes are composed of nonconcentric multiple aqueous chambers surrounded by a network of lipid layers which confers an increased level of stability and longer duration of drug release. The liposomes can be further modified to achieve a desired result. For example, the liposomes can be PEGylated or have other surface modifications in order to interfere with recognition and uptake by the reticuloendothelial system and provide increased circulation times.

Liposomes can adsorb many types of cells and then release an incorporated agent (e.g., a polypeptide described herein). In some cases, the liposomes fuse with the target cell, whereby the contents of the liposome then empty into the target cell. A liposome can be endocytosed by cells that are phagocytic. Endocytosis can be followed by intralysosomal degradation of liposomal lipids and release of the encapsulated agents.

The liposomes provided herein can also comprise carrier lipids. In some embodiments the carrier lipids are phospholipids. Carrier lipids capable of forming liposomes include, but are not limited to dipalmitoylphosphatidylcholme (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSP A), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

A polypeptide as described herein can also be attached to a carrier protein for delivery as a vaccine. The carrier protein can be an immunogenic carrier element and can be attached by any recombinant technology. Exemplary carrier proteins include Mariculture keyhole limpet hemocyanin (mcKLH), PEGylated mcKLH, Blue Carrier* Proteins, bovine serum albumin (BSA), cationized BSA, ovalbumin, and bacterial proteins such as tetanus toxoid (TT).

A polypeptide as described herein can also be prepared as multiple antigenic peptides (MAPs). Polypeptides can be attached at the N-terminus or the C-terminus to small non-immunogenic cores. Polypeptides built upon this core can offer highly localized peptide density. The core can be a dendritic core residue or matrix composed of bifunctional units. Suitable core molecules for constructing MAPs can include ammonia, ethylenediamine, aspartic acid, glutamic acid, and lysine. For example, a lysine core molecule can be attached via peptide bonds through each of its amino groups to two additional lysines. This second generation molecule has four free amino groups, each of which can be covalently linked to an additional lysine to form a third generation molecule with 8 free amino groups. A polypeptide can be attached via its C-terminus to each of these free groups to form an octavalent multiple antigenic peptide (also referred to as a "MAP8" structure). The second generation molecule having four free amino groups can be used to form a tetravalent or tetrameric MAP, e.g., a MAP having four peptides covalently linked to the core (also referred to as a "MAP4" structure). The carboxyl group of the first lysine residue can be left free, amidated, or coupled to β-alanine or another blocking compound. As used herein, the "linear portion or molecule" of a MAP system structure can refer to antigenic peptides that are linked to the core matrix. Thus, a cluster of antigenic epitopes can form the surface of a MAP and a small matrix forms its core. The dendritic core, and the entire MAP can be synthesized on a solid resin using a classic Merrifield synthesis procedure.

The polypeptides used for MAP preparation can be identical or can comprise multiple different sequences and lengths. The polypeptides can be derived from a bacterium, a virus, or a fungus. The peptides can be derived from a virus, such as influenza A virus, influenza B virus, influenza C virus, hepatitis B virus, hepatitis C virus, or HIV.

Sometimes, a polypeptide as described herein can be subjected to cyclization to result in a cyclic peptide which is resistant to proteolytic degradation. Cyclization can be carried out between side chains or ends of the peptide sequences through disulfide bonds, lanthionine, dicarba, hydrazine, or lactam bridges using methods known in the art.

In some embodiments, the polypeptide as described herein are conjugated to a molecule such as vitamin B12, a lipid, or an ethylene oxide compound, e.g., polyethylene glycol (PEG), polyethylene oxide (PEO), and polyoxyethylene (POE), methoxypolyethylene glycol (MPEG), monomethoxy PEG (mPEG), and the like. The ethylene oxide compound can be further functionalized with, for example, amine binding terminal functional groups such as N-hydroxysuccinimide esters, N-hydroxysuccinimide carbonates, and aliphatic aldehyde, or thiol binding groups such as maleimide, pyridyl disulphides, and vinyl sulfonates. Since amino groups (α-amino and ε-lysine amino) and cysteine residues are well suited for conjugation, the peptides provided herein can further include one or more amino acid residues for conjugation to an ethylene oxide molecule or a carrier compound known in the art. The pharmacokinetic and pharmacodynamic properties of a conjugated peptide can be further modified by the use of a particular linker. For example, propyl and amyl linkers can be used to provide a conjugate having a loose conformation whereas a phenyl linker can be used to provide a denser conformation as well as shield domains adjacent to the C-terminus. In some instances, dense conformations can be more efficient in maintaining bioactivity, prolonging plasma half-life, lowering proteolytic sensitivity, and immunogenicity relative to loose conformations.

In some embodiments, the polypeptides as described herein can be hyperglycosylated using methods known in the art, e.g., in situ chemical reactions or site-directed mutagenesis. Hyperglycosylation can result in either N-linked or O-linked protein glycosylation. The clearance rate of a given peptide can be optimized by the selection of the particular saccharide. For example, polysialic acid (PSA) is available in different sizes and its clearance depends on type and molecular size of the polymer. Thus, for example, PSAs having high molecular weights can be suitable for the delivery of low-molecular-weight peptides, and PSAs having low molecular weights can be suitable for the delivery of peptides having high molecular weights. The type of saccharide can be used to target the peptide to a particular tissue or cell. For example, polypeptides conjugated with mannose can be recognized by mannose-specific lectins, e.g., mannose receptors and mannose binding proteins, and are taken up by the liver. In some embodiments, the polypeptides can be hyperglycosylated to improve their physical and chemical stability under different environmental conditions, e.g., to inhibit inactivation under stress conditions and reduce aggregation resulting from production and storage conditions.

In some embodiments, a drug delivery system, such as microparticles, nanoparticles (particles having sizes ranging from 10 to 1000 nm), nanoemulsions, liposomes, and the like, can be used to provide protection of sensitive proteins, prolong release, reduce administration frequency, increase patient compliance, and control plasma levels. Various natural or synthetic microparticles and nanoparticles, which can be biodegradable and/or biocompatible polymers, can be used. Microparticles and nanoparticles can be fabricated from lipids, polymers, and/or metal. Polymeric microparticles and nanoparticles can be fabricated from natural or synthetic polymers, such as starch, alginate, collagen, chitosan, polycaprolactones (PCL), polylactic acid (PLA), poly(lactide-co-glycolide) (PLGA), and the like. In some embodiments, the nanoparticles are solid lipid nanoparticles (SLNs), carbon nanotubes, nanospheres, nanocapules, and the like. In some embodiments, the polymers are hydrophilic. In some embodiments, the polymers are thiolated polymers.

Since the rate and extent of drug release from microparticles and nanoparticles can depend on the composition of polymer and fabrication methods one can select a given composition and fabrication method, e.g., spray drying, lyophilization, microextrusion, and double emulsion, to confer a desired drug release profile. Since peptides incorporated in or on microparticles or nanoparticles can be prone to denaturation at aqueous-organic interface during formulation development, different stabilizing excipients and compositions can be used to prevent aggregation and denaturation. For example, PEG and sugars, e.g., PEG (MW 5000) and maltose with a-chymotrypsin, can be added to the composition to reduce aggregation and denaturation. Additionally, chemically modified peptides, e.g., conjugated peptides and hyperglycosylated peptides, as described herein, can be employed.

Protein stability can also be achieved by the selected fabrication method. For example, to prevent degradation at aqueous-organic interface, non-aqueous methodology called ProLease® technology can be used. Peptides in solid state can also be encapsulated using solid-in-oil-in-water (s/o/w) methods, e.g., spray- or spray-freeze-dried peptides or peptide-loaded solid nanoparticles can be encapsulated in microspheres using s/o/w methods.

Hydrophobic ion-pairing (HIP) complexation can be used to enhance protein stability and increase encapsulation efficiency into microparticles and nanoparticles. In hydrophobic ion-pairing (HIP) complexation, ionizable functional groups of a peptide are complexed with ion-pairing agents (e.g., surfactant or polymer) containing oppositely charged functional groups leading to formation of HIP complex where hydrophilic protein molecules exist in a hydrophobic complex form.

A polypeptide described herein can be chemically synthesized, or recombinantly expressed in a cell system or a cell-free system. A polypeptide can be synthesized, such as by a liquid-phase synthesis, a solid-phase synthesis, or by microwave assisted peptide synthesis. A polypeptide as described herein can be modified, such as by acylation, alkylation, amidation, arginylation, polyglutamylation, polyglycylation, butyrylation, gamma-carboxylation, glycosylation, malonylation, hydroxylation, iodination, nucleotide addition (e.g., ADP-ribosylation), oxidation, phosphorylation, adenylylation, propionylation, S-glutathionylation, S-nitrosylation, succinylation, sulfation, glycation, palmitoylation, myristoylation, isoprenylation or prenylation (e.g., farnesylation or geranylgeranylation), glypiation, lipoylation, attachement of flavin moiety (e.g., FMN or FAD), attachment of heme C, phosphopantetheinylation, retinylidene Schiff base formation, diphthamide formation, ethanolamine phosphoglycerol attachment, hypusine formuation, biotinylation, pegylation, ISGylation, SUMOylation, ubiquitination, Neddylation, Pupylation, citrullination, deamidation, eliminylation, carbamylation, or a combination thereof.

After generation of a polypeptide, the polypeptide can be subjected to one or more rounds of purification steps to remove impurities. The purification step can be a chromatographic step utilizing separation methods such as affinity-based, size-exclusion based, ion-exchange based, or the like. In some cases, the peptide is at most 30%, 40%, 50%, 60%, 70%, 80%, 90%, 95%, 99%, 99.9%, or 100% pure or without the presence of impurities. In some cases, the peptide is at least 30%, 40%, 50%, 60%, 70%, 80%, 90%, 95%, 99%, 99.9%, or 100% pure or without the presence of impurities. In some cases, the amount of the peptides in the peptide composition is at least 30%, 40%, 50%, 60%, 70%, 80%, 90%, 95%, 99%, 99.9%, or 100% by weight of the total composition. As used herein, a "purified" peptide of polypeptide can mean that an amount of the macromolecular components that are naturally associated with the peptide have been removed from the peptide. As used herein, a composition comprising, consisting essentially of, or consisting of one or more purified peptides of the present invention can mean that the composition does not contain an amount of the macromolecular components that are naturally associated with the one or more peptides or polypeptides and/or the reagents used to synthesize the peptides or polypeptides. In some embodiments, the compositions described herein consist solely of one or more peptides or polypeptides described herein, e.g., one or more peptides or polypeptides in a solid or crystalized form.

In some embodiments, the peptides or polypeptides or nucleic acid molecules of described herein can be isolated. As used herein, an "isolated" compound (e.g., peptide, polypeptide, nucleic acid molecule) can refer to a compound which is isolated from its native environment. For example, an isolated peptide or polypeptide can be one which does not have its native amino acids which correspond to the full length polypeptide, flanking the N-terminus, C-terminus, or both. As another example, an isolated peptide can be one which is immobilized to a substrate with which the peptide is not naturally associated. As a further example, an isolated peptide or polypeptide can be one which is linked to another molecule, e.g., a PEG compound, with which the peptide is not naturally associated. Similarly, an "isolated" nucleic acid molecule can be one which does not have its native nucleic acid basses which correspond to the full length nucleic acid molecule, flanking its 5' end, 3' end, or both. As another example, an isolated nucleic acid molecule can be one which is bound to a substrate or a compound, e.g., a label such as a fluorescent tag, with which the nucleic acid molecule is not naturally associated. As a further example, with respect to nucleic acid molecules, the term isolated can mean that it is separated from the nucleic acid and cell in which it naturally occurs.

A peptide-based vaccine can comprise about, at least, or at most 1, 2, 3, 4, 5, 6, 7, 8, 9, 10, 15, 20, 25, 30, 35, 40, 45, 50, 51, 55, 60, 65, 70, of 75 different peptide sequences. The different peptide sequences can include any polypeptide described herein.

Nucleic Acid-Based Vaccine

Provided herein is a nucleic acid-based vaccine that codes for about, at least, or at most 1, 2, 3, 4, 5, 6, 7, 8, 9, 10, 15, 20, 25, 30, 35, 40, 45, 50, 51, 55, 60, 65, 70, of 75 polypeptides as described herein. The nucleic acid-based vaccine can be used to treat or prevent an influenza infection.

A nucleic acid-based vaccine can be formulated using techniques, carriers, and excipients as suitable. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. The vaccine can be a DNA-based vaccine, an RNA-based vaccine, a hybrid DNA/RNA based vaccine, or a hybrid nucleic acid/peptide based vaccine. The peptide can be a polypeptide that has a sequence with at least 40%, 50%, 60%, 70%, 80%, 90%, 95%, or 100% sequence homology or identity to a peptide selected from the group consisting of SEQ ID NOs: 1-94 or of a sequence selected from Table 1, Table 2, or Table 3. The peptide can be a polypeptide that has a sequence with at most 40%, 50%, 60%, 70%, 80%, 90%, 95%, or 100% sequence homology or identity to a peptide selected from the group consisting of SEQ ID NOs: 1-94 or of a sequence selected from Table 1, Table 2, or Table 3.

Nucleic acid molecules can refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide, phosphorothioate, phosphorodithioate, O-methylphosphoroamidite linkages, and peptide nucleic acid (also referred to herein as "PNA") backbones and linkages. Other analog nucleic acids include those with bicyclic structures including locked nucleic acids (also referred to herein as "LNA"); positive backbones; non-ionic backbones and non-ribose backbones. Nucleic acids containing one or more carbocyclic sugars are also included within the definition of nucleic acids (see e.g., Jenkins et al, Chem. Soc. Rev. (1995) pp 169 176). Several nucleic acid analogs are described, e.g., in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-0 atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

Provided herein is a vector that comprises a polynucleotide that codes for a polypeptide as described herein. In some cases, the vector can be used to treat or prevent influenza infection. In some cases, the vector can be used to produce one or more of the polypeptides described herein.

A polynucleotide encoding a polypeptide provided herein can be codon optimized for a target subject, such as human being, mouse, pig, or dog. For example, a polynucleotide provided herein can be codon optimized for mice for pre-clinical animal experiments. In some cases, the subject matter may find use in preventing influenza for agriculture, for example, for preventing swine flu, or avian flu. This type of optimization can entail the mutation of foreign-derived (e.g., recombinant) DNA to mimic the codon preferences of the intended host organism or cell while encoding the same protein.

The vector can be a circular plasmid or a linear nucleic acid. The circular plasmid or linear nucleic acid can be capable of directing expression of a particular nucleotide sequence in an appropriate subject cell. The vector can have a promoter operably linked to the peptide-encoding nucleotide sequence, which can be operably linked to termination signals. The vector can also contain sequences required for proper translation of the nucleotide sequence. The vector comprising the nucleotide sequence of interest can be chimeric, meaning that at least one of its components is heterologous with respect to at least one of its other components. The expression of the nucleotide sequence in the expression cassette can be under the control of a constitutive promoter or of an inducible promoter, which can initiate transcription only when the host cell is exposed to some particular external stimulus.

The vector can be a plasmid. The plasmid can be useful for transfecting cells with nucleic acid encoding the peptide, which the transformed host cells can be cultured and maintained under conditions wherein expression of the peptide takes place.

The plasmid can comprise a nucleic acid sequence that encodes one or more of the various polypeptides disclosed herein. A single plasmid can contain coding sequence for a single polypeptide, or coding sequence for more than one polypeptide. Sometimes, the plasmid can further comprise coding sequence that encodes an adjuvant, such as an immune stimulating molecule, such as a cytokine.

The plasmid can further comprise an initiation codon, which can be upstream of the coding sequence, and a stop codon, which can be downstream of the coding sequence. The initiation and termination codon can be in frame with the coding sequence. The plasmid can also comprise a promoter that is operably linked to the coding sequence, and an enhancer upstream of the coding sequence. The enhancer can be human actin, human myosin, human hemoglobin, human muscle creatine, or a viral enhancer such as one from CMV, FMDV, RSV, or EBV.

The plasmid can also comprise a mammalian origin of replication in order to maintain the plasmid extrachromosomally and produce multiple copies of the plasmid in a cell. The plasmid can be pVAXI, pCEP4, or pREP4 from Invitrogen (San Diego, Calif.).

The plasmid can also comprise a regulatory sequence, which can be well suited for gene expression in a cell into which the plasmid is administered. The coding sequence can comprise a codon that can allow more efficient transcription of the coding sequence in the host cell.

The plasmid can be pSE420 (Invitrogen, San Diego, Calif.), pYES2 (Invitrogen, San Diego, Calif.), MAXBAC™ complete baculovirus expression system (Invitrogen, San Diego, Calif.), pcDNA I or pcDNA3 (Invitrogen, San Diego, Calif.).

The vector can be circular plasmid, which can transform a target cell by integration into the cellular genome or exist extrachromosomally (e.g., autonomous replicating plasmid with an origin of replication). Exemplary vectors include pVAX, pcDNA3.0, or provax, or any other expression vector capable of expressing DNA encoding the antigen and enabling a cell to translate the sequence to an antigen that is recognized by the immune system.

The nucleic acid based vaccine can also be a linear nucleic acid vaccine, or linear expression cassette ("LEC"), that can be efficiently delivered to a subject via electroporation and expressing one or more peptides disclosed herein. The LEC can be any linear DNA devoid of any phosphate backbone. The DNA can encode one or more peptides disclosed herein. The LEC can contain a promoter, an intron, a stop codon, and/or a polyadenylation signal. The expression of the peptide can be controlled by the promoter. It is also possible that the LEC does not contain any antibiotic resistance genes and/or a phosphate backbone. The LEC cannot contain other nucleic acid sequences unrelated to the polypeptide expression.

The LEC can be derived from any plasmid capable of being linearized. The plasmid can express the peptide. Exemplary plasmids include: pNP (Puerto Rico/34), pM2 (New Caledonia/99), WLV009, pVAX, pcDNA3.0, provax, or any other expression vector capable of expressing DNA encoding the antigen and enabling a cell to translate the sequence to an antigen that is recognized by the immune system.

The nucleic acid based vaccine can be delivered to a subject through a parenteral delivery method. A parenteral delivery can include intravenous, transdermal, oral, intrabiliary, intraparenchymal, intra-hepatic artery, intra-portal vein, intratumoral, or transvenous delivery. Sometimes, a parenteral delivery can utilize a needle (e.g., a hypodermic needle) for delivery of the nucleic acid based vaccine. The nucleic acid based vaccine can be formulated in an aqueous solution, e.g., saline. The delivery can be further assisted by electroporation. Sometimes, a parenteral delivery can utilize a gene gun as a delivery method. The nucleic acid based vaccine can be formulated as a DNA-coated microparticle, e.g., a DNA-coated gold or tungsten bead. The gene gun delivery method can use a ballistical delivery method to accelerate nucleic acid into target cells. Sometimes, a parenteral delivery can utilize a pneumatic injection as a delivery method. The nucleic acid based vaccine can be formulated as an aqueous solution.

The nucleic acid based vaccine can also be delivered to a subject through a topical delivery method. Topical nucleic acid based vaccine can be formulated as aerosol instillation of naked DNA to be delivered onto mucosal surfaces, such as the nasal and lung mucosa, ocular administration, or vaginal mucosa.

The nucleic acid based vaccine can further be delivered to a subject through a lipid-mediated delivery method. Sometimes, the lipid-mediated delivery method can be a cytofectin-mediated delivery method. Cytofectin can be cationic lipids that can bind and transport nucleic acid molecules across cell membranes. The nucleic acid can be incorporated by cytofectin-based liposomes. Sometimes, the lipid-mediated delivery method can be a neutral lipid-mediated delivery method.

A composition provided herein, e.g., a vaccine, can comprise at least 5, 10, 25, 50, 100, or 1000 different nucleic acids.

Recombinant Virus-Based Vaccine

Provided herein is a recombinant virus-based vaccine.

A vector as described above can be a viral vector, e.g. a recombinant viral vector. In some cases, a nucleic acid-based vaccine as described above can be in the form of a recombinant virus. The recombinant virus can comprise a recombinant viral vector as described herein that is encapsulated by a capsid protein, typically derived from the viral vector and from other viral origin than influenza virus.

The viral vector can be based on a range of different viruses, such as, but not limited to, adenoviruses, adeno-associated viruses (AAV), alphaviruses, baculoviruses, Newcastle Disease viruses (NDV), poxviruses. Parainfluenza Virus 5 (PIV5), and Vesicular Stomatitis Viruses (VSV). In some cases, the vector can be a recombinant viral vector that comprises polynucleotide that codes for one or more (e.g., 1, 2, 3, 4, 5, 6, 7, 8, 9, 10) of the polypeptides described herein and polynucleotide sequences that code for viral proteins from viruses other than influenza virus. A vaccine can comprise one or more (e.g., 2, 3, 4, 5, 6, 7, 8, 9, 10) different viral vectors, each vector expressing a polypeptide with a different sequence.

An adenovirus based vaccine can infect broad range of hosts. In some cases, an adenovirus vaccine can induce high levels of transgene expression without the potential of viral genes being integrated into the host genome. Due to their ability to grow in high titers in cell culture, an adenovirus vaccine described herein can be manufactured safely and inexpensively. In some cases, adenoviral vectors that are used for a vaccine provided herein can inherently stimulate innate immune responses via Toll-like receptor-dependent and Toll-like receptor-independent pathways. In some cases, an adenovirus vaccine can also infect dendritic cells (DCs), thereby leading to more effective antigen presentation to immune cells, through e.g., up-regulation of co-stimulatory molecules, increased cytokine and chemokine production by the infected DCs, or both.

An adenoviral vector described herein can be generated in two different forms: replication-defective or replication-competent. Replication-defective adenoviral vectors can be rendered by deletion of the E1 genes, which can be essential for replication. Sometimes, replication-defective adenoviral vectors can be rendered to lack E3 genes as well in order to create more space for foreign gene inserts. An expression cassette with desired transgene, e.g., a polynucleotide that encodes one or more polypeptide described herein, can be inserted. Replication-competent adenoviral vectors can be rendered with the deletion of E3 genes. Sometimes, replication-competent Ad-vectors can mimic the natural viral infection, thereby a potent adjuvant effect can be exerted due to the inherent stimulation of various elements of innate and adaptive immunity.

In some embodiments of the present disclosure, the vector can be an adenoviral vector. In some instances, the vector is a non-human adenoviral vector. In some cases, the vector can be a non-human primate adenoviral vector. In some cases, the vector can be a chimpanzee adenoviral vector.

In certain embodiments, Chimpanzee adenovirus vector can be used for expressing one or more polypeptides, such as C68 (AdC68) (SEQ ID NO: 104), e.g., that is disclosed in U.S. Pat. No. 6,083,716, C7 (AdC7), e.g., that is disclosed in Tatsis, et al., "Chimpanzee-origin adenovirus vectors as vaccine carriers," Gene Therapy 13: 421-429 (2006), C6(AdC6) (SEQ ID NO: 105) that is disclosed in Haut et al., "A Partial E3 Deletion in Replication-Defective Adenoviral Vectors Allows for Stable Expression of Potentially Toxic Transgene Products", Human Gene Therapy Methods DOI: 10.1089/hgtb.2016.044 (2016), Pan7 and Pan9, which are both disclosed in Roy, et al., "Rescue of chimeric adenoviral vectors to expand the serotype repertoire," J Virol Methods 141(a): 14-21 (2007).

Alternatively, the vector can be based on AAV. Recombination AAV can have broad tropism infecting a variety of hosts, tissues, and proliferating and non-proliferating cell types. AAVs that can be used in connection with the present disclosure can include, but not limited to, AAV serotype 2 (AAV2), AAV5, AAV7, AAV1, and AAV6.

The vector can also be based on a baculovirus. Baculoviruses that can be used as vector for the vaccine provided herein, e.g., influenza vaccine, can include, but not limited to, alphabaculoviruses, betabaculoviruses, gammabaculoviruses, and deltabaculoviruses.

Alternatively, the vector can be based on a poxvirus. Poxviruses can be double-stranded DNA viruses. Poxvirus genome can be very large; mammalian poxviruses can possess a genome of approximately 130 kb, and avian poxvirus genome is even larger at approximately 300 kb. Such large genome size can enable the insertion of more than 10 kb of foreign DNA without compromising the infectivity or other essential viral functions. Poxviruses can have their own transcription machinery, viral DNA-dependent RNA polymerase and post-transcriptional modifying enzymes, thereby allowing self-sufficient cytoplasmic replication. As a result, inserted transgene products can be expressed at high levels, resulting in potent cellular immune responses.

Recombinant vaccinia virus can be created to express the polypeptide as described herein. Non-replicating poxviral vectors that can be used in connection with the present disclosure include, but not limited to, modified vaccinia virus Ankara (MVA), NYVAC, and ALVAC strains. MVA was rendered replication-deficient by loss of approximately 15% of its original genome resulting from repetitive passaging in chick embryo fibroblasts. NYVAC strain, derived from the Copenhagen strain of vaccinia, was rendered replication-defective by deletion of 18 different open reading frames from the original viral genome. ALVAC is a canarypoxviral vector that does not replicate in human cells with further attenuation induced via over 200 passages in chicken embryo fibroblasts.

Alternatively, the vector can be based on an alphavirus. Alphaviruses can be single-stranded positive-sense RNA viruses that can replicate in the cytoplasm of infected cells. Alphaviruses that can be used in connection with the present disclosure include, but are not limited to, Venezuelan equine encephalitis virus (VEE), Sindbis virus (SIN), Semliki forest virus (SFV), and VEE-SIN chimeras.

Alphaviral vectors can be designed with the deletion of genes encoding structural proteins. Such alphavirus vectors are known as "replicons". Alphavirus vectors can potentially target antigen presenting cells, such as dendritic cells, in the draining lymph nodes, which can lead to the efficient generation of antigen-specific immune responses. Also, alphavirus vectors can create a proper environment for the cross-priming of vaccine antigen by inducing apoptosis in some cells. Vaccine immunity can also be further enhanced by the alphavirus vector itself.

VEE can be pathogenic in humans, but SIN is not. VEE/SIN chimeras can be used to avoid safety concerns when human is the vaccination subject. In a VEE/SIN chimera, VEE can function as the replicon component and SIN as the structural and packaging components.

Other RNA viruses that can be used as a vector for producing a vaccine as described herein can include, but not limited to, NDV, PIV5, and VSV.

Figure 5:
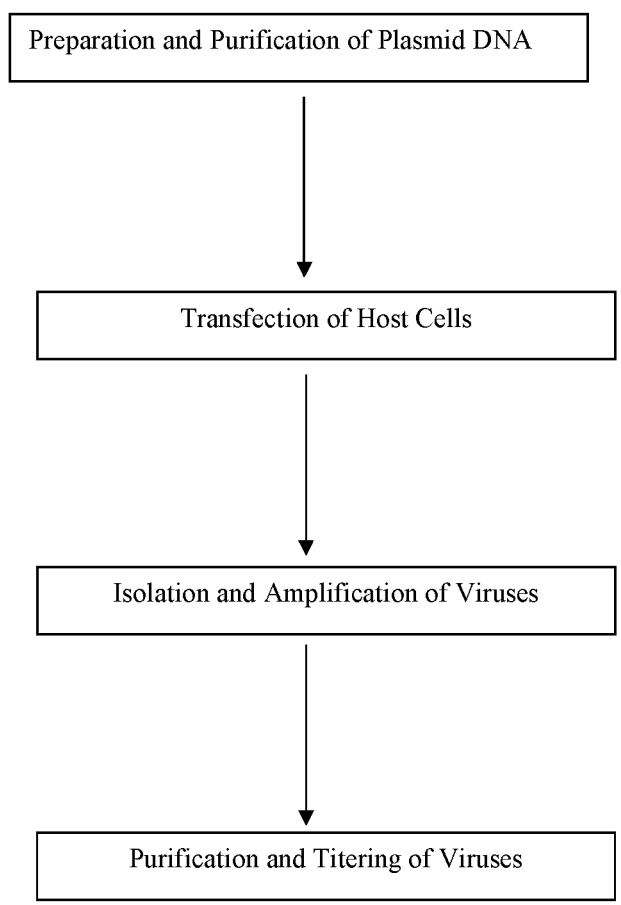
FIG. 5 illustrates a method of producing an adenovirus-based vaccine provided herein.

An adenoviral vector or an adenovirus based vaccine as described herein can be produced by a method provided herein, e.g., in accordance with procedures depicted in FIG. 5.

A method of producing an adenovirus based vaccine can comprise preparation and purification of plasmid DNA. The plasmid DNA herein can be a recombinant adenoviral vector DNA that comprises a polynucleotide encoding a polypeptide that comprises one or more epitope sequences as described herein. As discussed above, a recombinant adenoviral vector can lack E region genes, e.g. E1, E3, E5, or a combination thereof. The deletion of the endogenous viral genes can offer genomic space for insertion of gene of interest, e.g., polynucleotide expressing the polypeptide described herein. An E1-deleted Recombinant Adenoviral vector, as an example, can be constructed either by an in vitro ligation method or a homologous recombination method.

The in vitro ligation method can use whole adenoviral DNA genomes and a plasmid containing the left end of Ad with the right inverted terminal repeat (ITR), the packaging signal and E1A enhancer sequence. After the gene of interest, e.g., the polynucleotide encoding the polypeptide as described herein, can be inserted into the downstream of the viral sequence of the plasmid, the fragment containing viral sequence and gene of interest can be excised and ligated to a restriction site, replacing a portion of the viral E1 region, thereby producing a recombinant adenoviral DNA vector.

Alternatively, recombinant adenoviral vector can also be made by using homologous recombination method. Two or more plasmids with overlapping fragments that recombine in vivo can be used. An exemplary first plasmid can contain the entire Adenoviral genome with a deletion of the DNA packaging region and E1 region. An exemplary second plasmid (shuttle vector) can contain right ITR, packaging signal, overlapping sequence with the first plasmid. After the gene of interest, e.g. polynucleotide expressing a polypeptide described herein, can be introduced into the second plasmid, the two plasmids can be co-transfected into recombination cells. In the cells, homologous recombination can take place between the first and second plasmids, thereby producing a recombinant adenoviral vector. Non-limiting examples of cells for homologous recombination can include yeast, bacteria, and mammalian cell lines, such as, 293 cells, 293T cells, Hela cells. In some case, the recombinant adenoviral vector can be purified from the recombination cells. Alternatively, the recombination process can be conducted in vitro.

A method of producing an adenovirus based vaccine can further comprise transfection of host cells with the purified DNA plasmid. In some embodiments, the DNA plasmid, e.g. the recombinant adenoviral vector, is linearized before the transfection. In some cases, the transfection can generate adenoviral plaques.

In some cases, the recombinant adenoviral vector lack E1 gene, which can mediate the replication of adenovirus. Therefore, in some cases, it is necessary to supplement the E1 gene for the recombinant adenovirus to replicate. In some cases, 293 cell line, which have been generated using adenoviral infection and has E1 gene in the genome, can be used. Other cell lines that are engineered to produce E1 gene product can also be used for this purpose. In some cases, DNA fragments containing other viral genomic elements or one or more helper viruses can also be used for the production of recombinant adenovirus. For example, a helper virus can provide packaging signal for virus packaging, while the recombinant viral vector can lack the packaging signal. Alternatively, DNA fragment that contains the packaging signal can be co-transfected into the host cells for the production of the recombinant adenovirus. One or more plasmid vectors or helper virus used herein that contribute genomic materials for the production of the recombinant adenoviral vector can comprise reporter genes, selection markers, or any other genes that may be useful for the viral production.

Cell transfection can be performed using any transfection approach available to one skilled in the art. The transfection approach can include, but not limited to, electroporation, microinjection, calcium phosphate precipitation, cationic polymers, dendrimers, liposome, microprojectile bombardment, fugene, direct sonic loading, cell squeezing, optical transfection, protoplast fusion, impalefection, magnetofection, nucleofection, or any combination thereof.

A method of producing adenovirus based vaccine can further comprise isolation and amplification of viruses. Isolation of viruses can comprise isolating adenoviral plaques, which can be followed by screening of plaques. In some cases, the screening can be conducted by sequencing of the viral nucleic acids. In some cases, the plaques can be screened for the full, unaltered transgene sequence. A correct plaque can be further amplified by infection of successively larger number of cells. A method can further comprise isolating, and optionally lysing, the infected cells, which can be followed by purification of viral particles. The purification can be performed via various approaches, such as, but not limited to, ultracentrifugation and dialysis. A method can further comprise determining infectious titer, by e.g., plaque assay. A method can further comprise determining viral particle concentration, by e.g., ultraviolet absorbance measurement.

The recombinant virus based vaccine can be delivered to a subject through a parenteral delivery method. A parenteral delivery can include intravenous, transdermal, oral, intrabiliary, intraparenchymal, intra-hepatic artery, intra-portal vein, intratumoral, or transvenous delivery. Sometimes, a parenteral delivery can utilize a needle (e.g., a hypodermic needle) for delivery of the recombinant virus based vaccine. The recombinant virus based vaccine can be formulated in an aqueous solution, e.g., saline. Sometimes, a parenteral delivery can utilize a pneumatic injection as a delivery method. The nucleic acid based vaccine can be formulated as an aqueous solution.

The recombinant virus based vaccine can also be delivered to a subject through a topical delivery method. The vaccine can be applied directly onto an infected area, e.g., the nasal cavity.

Antibody Based Vaccine

Provided herein is an antibody based vaccine that can comprise an entity that binds a peptide or polypeptide sequence described herein. The antibody based vaccine can be used against influenza infection. The entity can be an antibody.

Antibody-based vaccine can be formulated using any techniques, carriers, and excipients as suitable. The antibody can be a natural antibody, a chimeric antibody, a humanized antibody, or can be an antibody fragment. The antibody can recognize one or more of the epitope sequences described herein. The antibody can recognize one or more sequences selected from SEQ ID NOs: 1-94 or a sequence selected from Table 1, Table 2, or Table 3. The antibody can recognize a sequence that has at most 40%, 50%, 60%, 70%, 80%, 90%, 95%, or 100% sequence homology or identity to a sequence selected from the group consisting of SEQ ID NOs: 1-94 or a sequence selected from Table 1, Table 2, or Table 3. The antibody can recognize a sequence with at least 40%, 50%, 60%, 70%, 80%, 90%, 95%, or 100% sequence homology or identity to a sequence selected from the group consisting of SEQ ID NOs: 1-94 or a sequence selected from Table 1, Table 2, or Table 3. The antibody can recognize a sequence length at least 30%, 40%, 50%, 60%, 70%, 80%, 90%, 95%, or 100%, or more of a sequence length of a sequence selected from the group consisting of SEQ ID NOs: 1-94 or a sequence selected from Table 1, Table 2, or Table 3. The antibody can recognize a sequence length at most 30%, 40%, 50%, 60%, 70%, 80%, 90%, 95%, or 100% the sequence length of a sequence selected from the group consisting of SEQ ID NOs: 1-94 or a sequence selected from Table 1, Table 2, or Table 3. In some embodiments, the antibody recognizes epitopes from multiple strains of influenza virus, such as influenza A virus, influenza B virus, influenza C virus.

An antibody can include fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the foregoing.

An antibody can be a monoclonal antibody. The preparation of monoclonal antibodies is known in the art and can be accomplished by fusing spleen cells from a host sensitized to the antigen with myeloma cells in accordance with known techniques or by transforming the spleen cells with an appropriate transforming vector to immortalize the cells. The cells can be cultured in a selective medium, cloned, and screened to select monoclonal antibodies that bind the designated antigens. Numerous references can be found on the preparation of monoclonal and polyclonal antibodies.

A native antibody (native immunoglobulin) can be heterotetrameric glycoproteins of about 150,000 daltons, composed of two identical light (L) chains and two identical heavy (H) chains. Each light chain can be linked to a heavy chain by one covalent disulfide bond, while the number of disulfide linkages can vary among the heavy chains of different immunoglobulin isotypes. Each heavy and light chain can also have regularly spaced intrachain disulfide bridges. Each heavy chain has at one end a variable domain (VH) followed by a number of constant domains. Each light chain can have a variable domain at one end (VL) and a constant domain at its other end; the constant domain of the light chain can be aligned with the first constant domain of the heavy chain, and the light chain variable domain can be aligned with the variable domain of the heavy chain. Particular amino acid residues can form an interface between the light and heavy-chain variable domains.

Variable regions can confer antigen-binding specificity. In some cases, the variability is not evenly distributed throughout the variable domains of antibodies. Variability can be concentrated in three segments called complementarity determining regions (CDRs) or hypervariable regions, both in the light chain and the heavy-chain variable domains. The more highly conserved portions of variable domains can be located in the framework (FR) regions. The variable domains of native heavy and light chains each can comprise four FR regions, largely adopting a β-pleated-sheet configuration, connected by three CDRs, which form loops connecting, and in some cases forming part of, the β-pleated-sheet structure. The CDRs in each chain can be held together in close proximity by the FR regions and, with the CDRs from the other chain, contribute to the formation of the antigen-binding site of antibodies. In some cases, the constant domains cannot be involved directly in binding an antibody to an antigen, but can exhibit various effector functions, such as Fc receptor (FcR) binding, participation of the antibody in antibody-dependent cellular toxicity, initiation of complement dependent cytotoxicity, and mast cell degranulation.

A hypervariable region can refer to the amino acid residues of an antibody that are responsible for antigen-binding. The hypervariable region can comprise amino acid residues from a complementarily determining region or CDR and/or those residues from a "hypervariable loop." Framework or FR residues can be those variable domain residues other than the hypervariable region residues, as herein deemed.

Antibody fragments can comprise a portion of an intact antibody, e.g., the antigen-binding or variable region of the intact antibody. Examples of antibody fragments include Fab, Fab, F(ab')2, and Fv fragments; diabodies; minibodies; linear antibodies; single-chain antibody molecules; and multispecific antibodies formed from antibody fragments. Papain digestion of antibodies can produce two identical antigen-binding fragments, called Fab fragments, each with a single antigen-binding site, and a residual Fc fragment, whose name reflects its ability to crystallize readily. Pepsin treatment yields an F(ab')2 fragment that has two antigen-combining sites and is still capable of cross-linking antigen.

Fv can be the minimum antibody fragment that contains a complete antigen recognition and binding site. This region can consist of a dimer of one heavy- and one light-chain variable domain in tight, non-covalent association. It is in this configuration that the three CDRs of each variable domain can interact to define an antigen-binding site on the surface of the VH-VL dimer. Collectively, the six CDRs can confer antigen-binding specificity to the antibody. However, even a single variable domain (or half of an Fv comprising only three CDRs specific for an antigen) can have the ability to recognize and bind antigen, although at a lower affinity than the entire binding site.

The Fab fragment can contain the constant domain of the light chain and the first constant domain (CHI) of the heavy chain. Fab fragment can differ from Fab' fragments by the addition of a few residues at the carboxy terminus of the heavy chain CHI domain including one or more cysteines from the antibody hinge region. Fab'-SH can be used herein for Fab' in which the cysteine residue(s) of the constant domains bear a free thiol group. Fab' fragments can be produced by reducing the F(ab')2 fragment's heavy chain disulfide bridge. Other chemical couplings of antibody fragments are also known.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Five major classes of human immunoglobulins include: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes can have different effector functions. For example, human IgG1 and IgG3 isotypes have ADCC (antibody dependent cell-mediated cytotoxicity) activity.

Monoclonal antibodies can be obtained from any suitable species e.g., murine, rabbit, sheep, goat, or human monoclonal antibodies.

A composition, e.g., vaccine, can comprise at about or at least or at most 5, 10, 25, 50 or 100 different antibodies.

Antigen Presenting Cell (APC) Based Vaccine

Provided herein is an APC based vaccine that presents a polypeptide described herein. The APC based vaccine can be used against influenza infection. The APC based vaccine can be formulated using any of the known techniques, carriers, and excipients as suitable and as understood in the art. APCs may include monocytes, monocyte-derived cells, macrophages, and dendritic cells. Sometimes, APC based vaccine can be a dendritic cell-based vaccine.

A dendritic cell (DC)-based vaccine can be prepared by any methods known in the art. In some cases, dendritic cell-based vaccines can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the peptides described herein. The DC-based vaccine can further comprise DC activators such as TLR3, TLR-7-8, and CD40 agonists. The DC-based vaccine can further comprise adjuvants, and a pharmaceutically acceptable carrier.

Virus-Based Vaccine

A virus-based vaccine can be generated based on live virus or on inactivated virus. Viruses can be engineered to express one or more proteins that comprise any of the sequences described herein. Vaccines based on live virus can use an attenuated virus, or a virus that can be cold-adapted. Vaccines based on inactivated virus can comprise whole virion, split virion, or purified surface antigens (e.g., HA and/or N from influenza A virus). Chemical means for inactivating a virus can include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as UV light, heat inactivation, or gamma irradiation.

Virions can be harvested from virus-containing fluids by various methods. For example, a purification process can involve zonal centrifugation using a linear sucrose gradient solution that includes detergent to disrupt the virions. Antigens can be purified, after optional dilution, by diafiltration.

Split virions can be obtained by treating purified virions with detergents (e.g., ethyl ether, polysorbate 80, deoxycholate, tri-N-butyl phosphate, Triton X-100, Triton N101, cetyltrimethylammonium bromide, Tergitol NP9, etc.) to produce subvirion preparations, including the "Tween-ether" splitting process. Methods of splitting influenza viruses are well known in the art. Splitting of the virus can be carried out by disrupting or fragmenting whole virus, whether infectious or non-infectious with a disrupting concentration of a splitting agent. The disruption can result in a full or partial solubilization of the virus proteins, altering the integrity of the virus. Splitting agents can be non-ionic or ionic (e.g., cationic) surfactants e.g., alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g., the Triton surfactants, such as Triton X-100 or Triton N101), polyoxyethylene sorbitan esters (the Tween surfactants), polyoxyethylene ethers, polyoxyethlene esters, etc. One exemplary splitting procedure can use the consecutive effects of sodium deoxycholate and formaldehyde, and splitting can take place during initial virion purification (e.g., in a sucrose density gradient solution). Thus a splitting process can involve clarification of the virion-containing material (to remove non-virion material), concentration of the harvested virions (e.g., using an adsorption method, such as CaHP04 adsorption), separation of whole virions from non-virion material, splitting of virions using a splitting agent in a density gradient centrifugation step (e.g., using a sucrose gradient that contains a splitting agent such as sodium deoxycholate), and then filtration (e.g., ultrafiltration) to remove undesired materials. Split virions can usefully be resuspended in sodium phosphate-buffered isotonic sodium chloride solution. The BEGRIVAC™, FLUARIX™, FLUZONE™, and FLUSHIELD™ products are split vaccines.

Purified surface antigen vaccines can comprise the influenza surface antigens haemagglutinin and, typically, also neuraminidase. Processes for preparing these proteins in purified form are well known in the art. The FLUVIRIN™, AGRIPPAL™, and INFLUVAC™ products are examples.

Vaccine based on inactivated virus can include the virosome (nucleic acid free viral-like liposomal particles). Virosomes can be prepared by solubilization of influenza virus with a detergent followed by removal of the nucleocapsid and reconstitution of the membrane containing the viral glycoproteins. Virosomes can also be prepared by adding viral membrane glycoproteins to excess amounts of phospholipids, to yield liposomes with viral proteins in their membrane.

Pharmaceutical Composition and Administration

Provided herein is a pharmaceutical composition that can be used to provide immunity against influenza virus infection. In certain aspects of the disclosure, the pharmaceutical composition can be a vaccine.

A composition can comprise one or more polypeptides, nucleic acids, proteins (e.g., antibodies or fragments thereof), APCs, or viruses described herein, or a combination thereof, and a pharmaceutically acceptable excipient. In some embodiments, a composition can further comprise carriers for the polypeptide, polynucleotide, or vector. A composition can further comprise a preservative. In some cases, a composition can further comprise other reagents to maintain appropriate physical or chemical properties, such as, but not limited to, salt concentration, osmolality, pH, hydrophobicity/hydrophility, and solubility. A composition can further comprise appropriate penetration enhancer for enhanced delivery. A composition can further comprise appropriate adjuvant(s) that can enhance the immunogenicity of the polypeptide, polynucleotide, or vector.

Formulations

A composition provided herein, e.g., a vaccine, can be formulated based, in part, on the intended route of administration of the composition. The composition, e.g., vaccine, can comprise one or more active agents, such as one or more peptides, nucleic acids, proteins (e.g., antibodies or fragments thereof), APCs, viruses described herein, or a combination thereof. A composition comprising one or more active agents in combination with one or more adjuvants can be formulated in conventional manner using one or more physiologically acceptable carriers, comprising excipients, diluents, and/or auxiliaries, e.g., which facilitate processing of the one or more active agents into preparations that can be administered. The one or more active agents described herein can be delivered to a subject using a number of routes or modes of administration described herein, e.g., oral, buccal, topical, rectal, transdermal, transmucosal, subcutaneous, intravenous, and intramuscular applications, as well as by inhalation.

A composition described herein, e.g., a vaccine, can be a liquid preparation such as a suspension, syrup, or elixir. The composition, e.g., vaccine, can also be a preparation for parenteral, subcutaneous, intradermal, intramuscular, or intravenous administration (e.g., injectable administration), such as a sterile suspension or emulsion. In some cases, aqueous solutions can be packaged for use as is, or lyophilized, and the lyophilized preparation being combined with a sterile solution prior to administration. The composition, e.g., vaccine, can be delivered as a solution or as a suspension. In general, formulations such as jellies, creams, lotions, suppositories and ointments can provide an area with more extended exposure to one or more active agents, while formulations in solution, e.g., sprays, can provide more immediate, short-term exposure.

Formulations for Inhalation (e.g., Nasal Administration or Oral Inhalation)

A composition described herein, e.g., a vaccine, can be formulated for administration via the nasal passages of a subject. Formulations suitable for nasal administration, wherein the carrier is a solid, can include a coarse powder having a particle size, for example, in the range of about 10 to about 500 microns which can be administered in the manner in which snuff is taken, e.g., by rapid inhalation through the nasal passage from a container of the powder held close up to the nose. The formulation can be a nasal spray, nasal drops, or by aerosol administration by nebulizer. The formulation can include aqueous or oily solutions of the vaccine.

A composition provided herein, e.g., a vaccine, can be formulated as an aerosol formulation. The aerosol formulation can be, e.g., an aerosol solution, suspension or dry powder. The aerosol can be administered through the respiratory system or nasal passages. For example, the composition can be suspended or dissolved in an appropriate carrier, e.g., a pharmaceutically acceptable propellant, and administered directly into the lungs using a nasal spray or inhalant. For example, an aerosol formulation comprising one or more active agents can be dissolved, suspended or emulsified in a propellant or a mixture of solvent and propellant, e.g., for administration as a nasal spray or inhalant. The aerosol formulation can contain any acceptable propellant under pressure, such as a cosmetically or dermatologically or pharmaceutically acceptable propellant.

An aerosol formulation for nasal administration can be an aqueous solution designed to be administered to the nasal passages in drops or sprays. Nasal solutions can be similar to nasal secretions in that they can be isotonic and slightly buffered to maintain a pH of about 5.5 to about 6.5. In some cases, pH values outside of this range can be used. Antimicrobial agents or preservatives can also be included in the formulation.

An aerosol formulation for inhalation can be designed so that one or more active agents are carried into the respiratory system of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Hydrocarbon propellants can include, for example, propane, isobutane, n-butane, pentane, isopentane, and neopentane. A blend of hydrocarbons can also be used as a propellant. Ether propellants include, for example, dimethyl ether as well as ethers. An aerosol formulation can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. A composition described herein, e.g., vaccine, can also be dispensed with a compressed gas, e.g., an inert gas such as carbon dioxide, nitrous oxide, or nitrogen.

The aerosol formulation can also include other components, for example, ethanol, isopropanol, propylene glycol, as well as surfactants or other components, such as oils and detergents. These components can serve to stabilize the formulation and/or lubricate valve components.

The aerosol formulation can be packaged under pressure and can be formulated as an aerosol using solutions, suspensions, emulsions, powders, and semisolid preparations. For example, a solution aerosol formulation can comprise a solution of an active agent such in (substantially) pure propellant or as a mixture of propellant and solvent. The solvent can be used to dissolve one or more active agents and/or retard the evaporation of the propellant. Solvents can include, for example, water, ethanol, and glycols. Any combination of suitable solvents can be use, optionally combined with preservatives, antioxidants, and/or other aerosol components.

An aerosol formulation can be a dispersion or suspension. A suspension aerosol formulation can comprise a suspension of one or more active agents, e.g., peptides, and a dispersing agent. Dispersing agents can include, for example, sorbitan trioleate, oleyl alcohol, oleic acid, lecithin, and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water, and a propellant, as well as an active agent or combination of active agents, e.g., one or more peptides. The surfactant used can be nonionic, anionic, or cationic. One example of an emulsion aerosol formulation comprises, for example, ethanol, surfactant, water, and propellant. Another example of an emulsion aerosol formulation comprises, for example, vegetable oil, glyceryl monostearate, and propane.

Formulations for Parenteral Administration

A composition, e.g., vaccine, comprising one or more active agents can be formulated for parenteral administration and can be presented in unit dose form in ampoules, pre-filled syringes, small volume infusion or in multi-dose containers with an added preservative. The composition can take such forms as suspensions, solutions, or emulsions in oily or aqueous vehicles, for example solutions in aqueous polyethylene glycol.

For injectable formulations, a vehicle can be chosen from those known in the art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of active agent in injection grade water, liposomes, and vehicles suitable for lipophilic substances and those known in the art.

Parenteral injection can include subcutaneous, intramuscular, intravenous, intraperitoneal, and intracardiac administration. A subcutaneous administration can be administered as a bolus into the subcutis. Subcutaneous injection sites on a human subject can include the outer area of the upper arm, abdomen, the front of the thigh, the upper back, the upper area of the buttock. Intramuscular administration can be an injection directly into muscle. Intramuscular injection sites can include deltoid, dorsogluteal, rectus femoris, vastus lateralis and ventrogluteal muscles. Intravenous administration can be delivery of a liquid formulation directly into a vein. Intravenous administration can be applied on a peripheral vein (e.g. the veins in the arms, hands, legs, and feet) or a central vein (e.g. superior vena cava, inferior vena cava, and the right atrium of the heart). Intraperitoneal administration can be injection into the peritoneum. Intracardiac administration can be injection directly into heart muscles or ventricles.

Sometimes, the composition, e.g., vaccine, can be formulated for intravenous administration to mammalian subjects, like human beings. The composition, e.g., vaccine, for intravenous administration can be a solution in sterile isotonic aqueous buffer. In some cases, the composition, e.g., vaccine, can include a solubilizing agent and a local anesthetic such as lidocaine to ease pain at the site of the injection. The ingredients can be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, a composition, e.g., vaccine, comprising one or more active agents can be formulated in aqueous solutions, specifically in physiologically compatible buffers such as Hanks solution, Ringer's solution, or physiological saline buffer. The solution can contain formulatory agents such as suspending, stabilizing, and/or dispersing agents. Alternatively, the one or more active agents can be in powder form for constitution with a suitable vehicle, e.g., sterile pyrogen-free water, before use. In another embodiment, the composition, e.g., vaccine, does not comprise an adjuvant or any other substance added to enhance the immune response stimulated by the active agent. In another embodiment, the composition, e.g., vaccine, can comprise a substance that inhibits an immune response to the one or more active agents.

In some embodiments, one or more active agents are formulated as a depot preparation. Such long acting formulations can be administered by implantation or transcutaneous delivery (e.g., subcutaneously or intramuscularly), intramuscular injection or use of a transdermal patch. Thus, for example, one or more active agents can be formulated with suitable polymeric or hydrophobic materials (e.g., as an emulsion in an acceptable oil) or ion exchange resins, or as sparingly soluble derivatives, for example, as a sparingly soluble salt.

Formulations for Topical Administration

In certain aspects of the disclosure, a composition provided herein, e.g., a vaccine, can comprise one or more agents that exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). In some embodiments, local/topical formulations comprising one or more active agents are used to treat epidermal or mucosal viral infections.

A composition provided herein, e.g., a vaccine, can contain a dermatologically acceptable carrier. Such carriers are compatible with skin, nails, mucous membranes, tissues, and/or hair, and can include any dermatological carrier meeting these requirements. Such carriers can be readily selected by one of ordinary skill in the art. In formulating skin ointments, one or more agents can be formulated in an oleaginous hydrocarbon base, an anhydrous absorption base, a water-in-oil absorption base, an oil-in-water water-removable base and/or a water-soluble base. Examples of such carriers and excipients include humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. The construction and use of transdermal patches for the delivery of pharmaceutical agents is known in the art. Such patches can be constructed for continuous, pulsatile, or on demand delivery of pharmaceutical agents.

Lubricants which can be used to form compositions and dosage forms can include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

A composition provided herein, e.g., a vaccine, can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. Other than the one or more active agents, the amounts of the various constituents of the compositions provided herein can be those used in the art. These compositions can constitute protection, treatment or care creams, milks, lotions, gels or foams for the face, for the hands, for the body and/or for the mucous membranes, or for cleansing the skin. The compositions can also consist of solid preparations constituting soaps or cleansing bars.

A composition provided herein, e.g., a vaccine, for local/topical application can include one or more antimicrobial preservatives such as quaternary ammonium compounds, organic mercurials, p-hydroxy benzoates, aromatic alcohols, chlorobutanol, and the like.

Formulations for Oral Administration

Sometimes, a composition provided herein, e.g., a vaccine, can be formulated for oral administration.

For oral administration, a composition as provided herein can be formulated readily by combining the one or more active agents with pharmaceutically acceptable carriers known in the art. Such carriers enable active agents to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier can be a finely divided solid which is a mixture with the finely divided active component. In tablets, the active component generally is mixed with the carrier having the desired binding capacity in suitable proportions and compacted in the shape and size desired. The powders and tablets can contain from about one (1) to about seventy (70) percent of the one or more active agents. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the one or more active agents can be included at concentration levels ranging from about 0.5%, about 5%, about 10%, about 20%, or about 30% to about 50%, about 60%, about 70%, about 80%, or about 90% by weight of the total composition of oral dosage forms, in an amount sufficient to provide a desired unit of dosage.

Aqueous suspensions for oral use can contain one or more active agents with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring the one or more active agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. Ligands can also be attached to the liposomes to direct these compositions to particular sites of action.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration can be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating compounds for oral administration, it can be desirable to utilize gastroretentive formulations to enhance absorption from the gastrointestinal (GI) tract. A formulation which is retained in the stomach for several hours can release an active agent slowly and provide a sustained release that can be used herein. Expandable, floating and bioadhesive techniques can be utilized to maximize absorption an active agent.

Formulations for Ophthalmic Administration

In some instances, a composition provided herein can be administered through eyes, e.g. delivered in eye drops. Eye drops can be prepared by dissolving the one or more active agents in a sterile aqueous solution such as physiological saline, buffering solution, etc., or by combining powder compositions to be dissolved before use. Other vehicles can be chosen, as is known in the art, including but not limited to: balance salt solution, saline solution, water soluble poly ethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose, or other agents known to those skilled in the art).

Other Formulations

In some embodiments, a composition provided herein is administered in otic solutions, suspensions, ointments, or inserts. In some embodiments, a composition described herein, e.g., a vaccine, is formulated for administration as a suppository. For example, a low melting wax, such as a mixture of triglycerides, fatty acid glycerides, Witepsol S55 (trademark of Dynamite Nobel Chemical, Germany), or cocoa butter can be first melted and the active component can be dispersed homogeneously, for example, by stirring. The molten homogeneous mixture can then be poured into convenient sized molds, allowed to cool, and to solidify. In some embodiments, a composition described herein, e.g., a vaccine, is formulated for vaginal administration. In some cases, pessaries, tampons, creams, gels, pastes, foams, or sprays contain one or compositions, e.g., vaccines described herein.

Ingredients, e.g., Carriers, Excipients

A composition provided herein, e.g., a vaccine, can include one or more carriers and excipients (including but not limited to buffers, carbohydrates, mannitol, proteins, peptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In another instance, the composition is substantially free of preservatives. In other embodiments, the composition, e.g., vaccine, contains at least one preservative. General methodology on pharmaceutical dosage forms can be found in Ansel et ah, Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the pharmaceutical compositions described herein, the type of carrier can vary depending on the mode of administration. Suitable formulations and additional carriers are described in Remington "The Science and Practice of Pharmacy" ($20^{th}$ Ed., Lippincott Williams & Wilkins, Baltimore Md.), the teachings of which are incorporated by reference in their entirety herein.

Liposomes and Microspheres

A composition provided herein, e.g., a vaccine, can be encapsulated within liposomes. Biodegradable microspheres can also be employed as carriers for the composition.

A composition provided herein, e.g., a vaccine, can be administered in liposomes or microspheres (or microparticles). Methods for preparing liposomes and microspheres for administration to a patient are known to those of skill in the art. For example, U.S. Pat. No. 4,789,734, the contents of which are hereby incorporated by reference, describes methods for encapsulating biological materials in liposomes. The material can be dissolved in an aqueous solution, the appropriate phospholipids and lipids added, along with surfactants if required, and the material dialyzed or sonicated, as desired. Microspheres formed of polymers or proteins are known to those skilled in the art, and can be tailored for passage through the gastrointestinal tract directly into the blood stream. Alternatively, the compound can be incorporated and the microspheres, or composite of microspheres, implanted for slow release over a period of time ranging from days to months.

Preservatives/Sterility

A composition provided herein, e.g., a vaccine, can include material for a single administration (e.g., immunization), or can include material for multiple administrations (e.g., immunizations) (e.g., a "multidose" kit). The composition, e.g., vaccine, can include one or more preservatives such as thiomersal or 2-phenoxyethanol. In some embodiments, the vaccine is substantially free from (e.g., <10 µg/ml) mercurial material e.g., thiomersal-free. In some embodiments, a-Tocopherol succinate is used as an alternative to mercurial compounds. Preservatives can be used to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In ophthalmic products, e.g., such preservatives can be employed at a level of from 0.004% to 0.02%. In the compositions of the present application the preservative, e.g., benzalkonium chloride, can be employed at a level of from 0.001% to less than 0.01%, e.g., from 0.001% to 0.008%, preferably about 0.005% by weight. A concentration of benzalkonium chloride of 0.005% can be sufficient to preserve a composition provided herein from microbial attack.

As an alternative (or in addition) to including a preservative in multidose compositions, the composition, e.g., vaccine, can be contained in a container having an aseptic adaptor for removal of material.

In some cases, a composition provided herein, e.g., a vaccine, can be sterile. The composition, e.g., vaccine, can be non-pyrogenic e.g., containing <1 EU (endotoxin unit, a standard measure) per dose, and can be <0.1 EU per dose. The composition, e.g., vaccine, can be formulated as a sterile solution or suspension, in suitable vehicles, known in the art. The composition, e.g., vaccine, can be sterilized by conventional, known sterilization techniques, e.g., the composition can be sterile filtered.

Salts/Osmolality

In some embodiments, a composition provided herein, e.g., vaccine, comprises one or more salts. For controlling the tonicity, a physiological salt such as sodium salt can be included a composition provided herein, e.g., vaccine. Other salts can include potassium chloride, potassium dihydrogen phosphate, disodium phosphate, and/or magnesium chloride, or the like. In some embodiments, the composition, e.g., vaccine, is formulated with one or more pharmaceutically acceptable salts. The one or more pharmaceutically acceptable salts can include those of the inorganic ions, such as, for example, sodium, potassium, calcium, magnesium ions, and the like. Such salts can include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid, or maleic acid. If an active agent (e.g., polypeptide) contains a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexylamine, ethanolamine, diethanolamine, triethanolamine, and the like.

A composition, e.g., vaccine, can have an osmolality of between 200 mOsm/kg and 400 mOsm/kg, between 240-360 mOsm/kg, or within the range of 290-310 mOsm/kg.

Buffers/pH

A composition provided herein, e.g., vaccine, can comprise one or more buffers, such as a Tris buffer; a borate buffer; a succinate buffer; a histidine buffer (e.g., with an aluminum hydroxide adjuvant); or a citrate buffer. Buffers, in some cases, are included in the 5-20 mM range.

A composition provided herein, e.g., vaccine, has a pH between about 5.0 and about 8.5, between about 6.0 and about 8.0, between about 6.5 and about 7.5, or between about 7.0 and about 7.8.

Detergents/Surfactants

A composition provided herein, e.g., vaccine, includes one or more detergents and/or surfactants, e.g., polyoxyethylene sorbitan esters surfactants (commonly referred to as "Tweens"), e.g., polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1, 2-ethanediyl) groups, e.g., octoxynol-9 (Triton X-100, or t-octylphenoxypolyethoxyethanol); (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as "SPANs"), such as sorbitan trioleate (Span 85) and sorbitan monolaurate, an octoxynol (such as octoxynol-9 (Triton X-100) or t-octylphenoxypolyethoxyethanol), a cetyl trimethyl ammonium bromide ("CTAB"), or sodium deoxycholate, particularly for a split or surface antigen vaccine. The one or more detergents and/or surfactants can be present only at trace amounts. In some cases, the composition, e.g., vaccine, can include less than 1 mg/ml of each of octoxynol-10 and polysorbate 80. Non-ionic surfactants can be used herein. Surfactants can be classified by their "HLB" (hydrophile/lipophile balance). In some cases, surfactants have a HLB of at least 10, at least 15, and/or at least 16.

In some embodiments, mixtures of surfactants is used in a composition e.g., vaccine, e.g., Tween 80/Span 85 mixtures. A combination of a polyoxyethylene sorbitan ester and an octoxynol can also be suitable. Another combination can comprise laureth 9 plus a polyoxyethylene sorbitan ester and/or an octoxynol. The amounts of surfactants (% by weight) can be: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Adjuvants

A composition provided herein, e.g., vaccine, can comprise one or more adjuvants. An adjuvant can be used to enhance the immune response (humoral and/or cellular) elicited in a subject receiving the vaccine. Sometimes, an adjuvant can elicit a Th1-type response. In some cases, an adjuvant can elicit a Th2-type response. A Th1-type response can be characterized by the production of cytokines such as IFN-γ as opposed to a Th2-type response which can be characterized by the production of cytokines such as IL-4, IL-5, and IL-10.

Lipid-based adjuvants, such as MPL and MDP, can be used with a composition, e.g., vaccine, disclosed herein. Monophosphoryl lipid A (MPL), for example, is an adjuvant that can cause increased presentation of liposomal antigen to specific T Lymphocytes. In addition, a muramyl dipeptide (MDP) can also be used as a suitable adjuvant in conjunction with a composition, e.g., vaccine, described herein.

Adjuvant can also comprise stimulatory molecules such as cytokines. Non-limiting examples of cytokines include: CCL20, a-interferon(IFN-a), β-interferon (IFN-β), γ-interferon, platelet derived growth factor (PDGF), TNFa, TNFp, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC 5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, and TAP2.

Additional adjuvants can include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2 and functional fragments thereof.

In some cases, the one or more adjuvants can be a modulator of a toll like receptor. Examples of modulators of toll-like receptors include TLR-9 agonists and TLR-2 agonists and are not limited to small molecule modulators of toll-like receptors such as Imiquimod (R837). Other examples of adjuvants that can be used a composition described herein, e.g., a vaccine, include saponin, CpG ODN and the like.

In some cases, the one or more adjuvants is selected from bacteria toxoids, polyoxypropylene-polyoxyethylene block polymers, aluminum salts, liposomes, CpG polymers, oil-in-water emulsions, or a combination thereof.

Sometimes, the one or more adjuvants can be based on aluminum salts (alum) or derivatives thereof. Exemplary Alums can comprise aluminum hydroxide, aluminum phosphate, potassium aluminum sulfate, sodium aluminum sulfate, ammonium aluminum sulfate, cesium aluminum sulfate, or a mixture of aluminum and magnesium hydroxide. Alum can also comprise crystalline aluminum oxyhydroxide (AlOOH). Sometimes, AlOOH adjuvants can compose of nanolength scale plate-like primary particles that form aggregates, representing the functional subunits in the material. These aggregates can be porous and can have irregular shapes that range from about 1 to about 20 µm in diameter. Upon mixing with antigen, the aggregates can be broken into smaller fragments that can reaggregate to distribute the absorbed antigen throughout the vaccine. In some embodiments, the adjuvant comprises ordered rod-like AlO(OH) naonparticles.

In some embodiments, the one or more adjuvants are an oil-in-water emulsion. The oil-in-water emulsion can include at least one oil and at least one surfactant, with the oil(s) and surfactant(s) being biodegradable and biocompatible. The oil droplets in the emulsion can be less than 5 µm in diameter, and can even have a sub-micron diameter, with these small sizes being achieved with a microfluidiser to provide stable emulsions. Droplets with a size less than 220 nm can be preferred as they can be subjected to filter sterilization.

The oils used can include such as those from an animal (such as fish) or vegetable source. Sources for vegetable oils can include nuts, seeds, and grains. Peanut oil, soybean oil, coconut oil, and olive oil, the most commonly available, exemplify the nut oils. Jojoba oil can be used e.g., obtained from the jojoba bean. Seed oils include safflower oil, cottonseed oil, sunflower seed oil, sesame seed oil, etc. The grain group can include: corn oil and oils of other cereal grains such as wheat, oats, rye, rice, teff, triticale, and the like. 6-10 carbon fatty acid esters of glycerol and 1,2-propanediol, while not occurring naturally in seed oils, can be prepared by hydrolysis, separation and esterification of the appropriate materials starting from the nut and seed oils. Fats and oils from mammalian milk can be metabolizable and can be used in with the compositions, e.g., vaccines described herein. The procedures for separation, purification, saponification, and other means for obtaining pure oils from animal sources are known in the art. Fish can contain metabolizable oils which can be readily recovered. For example, cod liver oil, shark liver oils, and whale oil such as spermaceti can exemplify several of the fish oils which can be used herein. A number of branched chain oils can be synthesized biochemically in 5-carbon isoprene units and can be generally referred to as terpenoids. Shark liver oil contains a branched, unsaturated terpenoid known as squalene, 2,6,10,15,19,23-hexamethyl-2,6,10,14,18,22-tetracosahexaene. Squalane, the saturated analog to squalene, can also be used. Fish oils, including squalene and squalane, can be readily available from commercial sources or can be obtained by methods known in the art.

Other useful oils include tocopherols, which can be included in a composition described herein, e.g., a vaccine, for use in elderly patients (e.g., aged 60 years or older), as vitamin E can have a positive effect on the immune response in this subject group. Further, tocopherols can have antioxidant properties that can help to stabilize the emulsions. Various tocopherols exist (α, β, γ, δ, ε or ξ); in some cases, α is used. An example of a-tocopherol is DL-a-tocopherol. a-tocopherol succinate can be compatible with compositions provided herein, e.g., influenza vaccines, and can be a useful preservative as an alternative to mercurial compounds. In some embodiments, mixtures of oils can be used e.g., squalene and a-tocopherol. An oil content in the range of 2-20% (by volume) can be used.

Specific oil-in-water emulsion adjuvants include, e.g., a submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as "MF59". The MF59 emulsion advantageously includes citrate ions e.g., 10 mM sodium citrate buffer.

An oil-in water emulsion can be a submicron emulsion of squalene, a tocopherol, and polysorbate 80. These emulsions can have from 2 to 10% squalene, from 2 to 10% tocopherol and from 0.3 to 3% polysorbate 80, and the weight ratio of squalene:tocopherol can be preferably ≤1 (e.g., 0.90) as this can provide a more stable emulsion. Squalene and polysorbate 80 can be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-a-tocopherol and 5 ml squalene), then microfluidising the mixture. The resulting emulsion has submicron oil droplets e.g., with an average diameter of between 100 and 250 nm, preferably about 180 nm. The emulsion may also include a 3-de-O-acylated monophosphoryl lipid A (3d-MPL). Another useful emulsion of this type can comprise, per human dose, 0.5-10 mg squalene, 0.5-11 mg tocopherol, and 0.1-4 mg polysorbate 80.

An oil-in water emulsion can be an emulsion of squalene, a tocopherol, and a Triton detergent (e.g., Triton X-100). The emulsion can also include a 3d-MPL (see below). The emulsion can contain a phosphate buffer.

An oil-in water emulsion can be an emulsion comprising a polysorbate (e.g., polysorbate 80), a Triton detergent (e.g., Triton X-100) and a tocopherol (e.g., an a-tocopherol succinate). The emulsion can include these three components at a mass ratio of about 75:11:10 (e.g., 750 µ/ml polysorbate 80, 110 u/ml Triton X-100 and 100 µ/ml α-tocopherol succinate), and these concentrations should include any contribution of these components from antigens. The emulsion can also include squalene. The emulsion can also include a 3d-MPL. The aqueous phase can contain a phosphate buffer.

An oil-in water emulsion can be an emulsion of squalane, polysorbate 80, and poloxamer 401 ("Pluronic™ L121"). The emulsion can be formulated in phosphate buffered saline, pH 7.4. This emulsion can be a useful delivery vehicle for muramyl dipeptides, and can be used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80).

An oil-in water emulsion can be an emulsion comprising squalene, an aqueous solvent, a polyoxyethylene alkyl ether hydrophilic nonionic surfactant (e.g., polyoxyethylene (12) cetostearyl ether) and a hydrophobic nonionic surfactant (e.g., a sorbitan ester or mannide ester, such as sorbitan monoleate or "Span 80"). The emulsion can be thermoreversible and/or has at least 90% of the oil droplets (by volume) with a size less than 200 nm. The emulsion can also include one or more of: alditol; a cryoprotective agent (e.g., a sugar, such as dodecylmaltoside and/or sucrose); and/or an alkylpolyglycoside. The emulsion can include a TLR4 agonist. Such emulsions can be lyophilized.

An oil-in water emulsion can be an emulsion of squalene, poloxamer 105 and Abil-Care. The final concentration (weight) of these components in adjuvanted vaccines can be 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An oil-in water emulsion can be an emulsion having from 0.5-50% of an oil, 0.1-10% of a phospholipid, and 0.05-5% of a non-ionic surfactant. Phospholipid components can include phosphatidylcholine, phosphatidylethanolamine, phosphatidylserine, phosphatidylinositol, phosphatidylglycerol, phosphatidic acid, sphingomyelin, and cardiolipin. Submicron droplet sizes can be advantageous.

An oil-in water emulsion can be a submicron oil-in-water emulsion of a non-metabolisable oil (such as light mineral oil) and at least one surfactant (such as lecithin, Tween 80 or Span 80). Additives can include, QuilA saponin, cholesterol, a saponin-lipophile conjugate (such as GPI-O1OO, produced by addition of aliphatic amine to desacylsaponin via the carboxyl group of glucuronic acid), dimethyldioctadecylammonium bromide, and/or N,N-dioctadecyl-N,N-bis (2-hydroxyethyl) propanediamine.

In some embodiments, a composition provided herein, e.g., vaccine, contains adjuvants such as hydrophilic or lipophilic gelling agents, hydrophilic or lipophilic active agents, preserving agents, antioxidants, solvents, fragrances, fillers, sunscreens, odor-absorbers, and dyestuffs. The amounts of these various adjuvants can be those used in the fields considered and, for example, are from about 0.01% to about 20% of the total weight of the composition. Depending on their nature, these adjuvants can be introduced into a fatty phase, into an aqueous phase and/or into lipid vesicles.

A composition provided herein, e.g., a vaccine, comprising one or more active agent such as a peptide, a nucleic acid molecule, an antibody or fragments thereof, an APC, and/or virus described herein, in combination with one or more adjuvants, can be formulated to comprise certain molar ratios. For example, molar ratios of about 99:1 to about 1:99 of an active agent in combination with one or more adjuvants can be used. In some embodiments, the range of molar ratios of an active agent in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent in combination with one or more adjuvants can be about 1:9, and in some cases can be about 1:1. The active agent such as a peptide or polypeptide, a nucleic acid molecule, an antibody or fragments thereof, an APC, and/or virus described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

A composition provided herein, e.g., vaccine, can comprise one or more adjuvants selected from the list Alum, monophosphoryl lipid A (MPL), imiquimod (R837) (a small synthetic antiviral molecule-TLR7 ligand), Pam2Cys, and ordered rod-like AIO(OH) nanoparticles (Rod). In some embodiments, a composition provided herein, e.g., vaccine, comprises Alum. In some embodiments, a composition, e.g., vaccine, provided herein comprises Rod. In some embodiments, a composition provided herein, e.g., vaccine, comprises Rod, MPL, and R837. In some embodiments, a composition provided herein, e.g., vaccine, comprises MPL and R837. In some embodiments, a composition provided herein, e.g., vaccine, comprises Alum, MPL, and R837. In some embodiments, a composition provided herein, e.g., vaccine, comprises Pam2Cys.

Additional Agents

A composition provided herein, e.g., a vaccine, can be administered with an additional active agent. The choice of the additional active agent can depend, at least in part, on the condition being treated. The additional active agent can include, for example, any active agent having a therapeutic effect for a pathogen infection (e.g., viral infection), including, e.g., drugs used to treat inflammatory conditions such as an NSAID, e.g., ibuprofen, naproxen, acetaminophen, ketoprofen, or aspirin. In some embodiments, a formulation for treating or preventing an influenza infection can contain one or more conventional influenza antiviral agents, such as Vitamin D, amantadine, arbidol, laninamivir, rimantadine, zanamivir, peramivir, and oseltamivir. In treatments for retroviral infections, such as HIV, formulations can contain one or more conventional antiviral drugs, such as protease inhibitors (lopinavir/ritonavir (Kaletra®), indinavir (Crixivan®), ritonavir (Norvir®), nelfmavir (Viracept®), saquinavir hard gel capsules (Invirase®), atazanavir (Reyataz®), amprenavir (Agenerase®), fosamprenavir (Telzir®), tipranavir (Aptivus®)), reverse transcriptase inhibitors, including non-Nucleoside and Nucleoside/nucleotide inhibitors (AZT (zidovudine, Retrovir®), ddl (didanosine, Videx®), 3TC (lamivudine, Epivir®), d4T (stavudine, Zerit®), abacavir (Ziagen®), FTC (emtricitabine, Emtriva®), tenofovir (Viread®), efavirenz (Sustiva®) and nevirapine (Viramune®)), fusion inhibitors T20 (enfuvirtide, Fuzeon®), integrase inhibitors (MK-0518 and GS-9137), and maturation inhibitors (PA-457 (Bevirimat®)). As another example, formulations can additionally contain one or more supplements, such as vitamin C, vitamin E, and other vitamins and anti-oxidants.

A composition provided herein, e.g., a vaccine, can include one or more antibiotics (e.g., neomycin, kanamycin, polymyxin B).

In some embodiments, the composition, e.g., a vaccine, can be gluten free.

Co-Solvents

The solubility of the components of a composition provided herein can be enhanced by a co-solvent in the composition. Such co-solvents include polysorbate 20, 60, and 80, Pluronic F68, F-84 and P-103, cyclodextrin, or other agents known to those skilled in the art. Such co-solvents can be employed at a level of from about 0.01% to 2% by weight.

Penetration Enhancers

In some embodiments, a composition provided herein, e.g., a vaccine, can include one or more penetration enhancers. For example, the composition can comprise suitable solid or gel phase carriers or excipients that increase penetration or help delivery of agents or combinations of agents across a permeability barrier, e.g., the skin. Examples of penetration-enhancing compounds include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-a-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, a-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the compositions will include one or more such penetration enhancers.

Additives for Sustained Release Formulations

In some embodiments, one or more active agents can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation. The controlled release from a biocompatible polymer, such as PLGA microspheres or nanospheres, can be utilized in a formulation suitable for intra ocular implantation or injection for sustained release administration. Any suitable biodegradable and biocompatible polymer can be used.

Administration Routes

A composition described herein, e.g., a vaccine, can be delivered via a variety of routes to a subject, e.g., a human. Delivery routes can include oral (including buccal and sublingual), rectal, nasal, topical, transdermal, transmucosal, pulmonary, vaginal, suppository, or parenteral (including intramuscular, intra-arterial, intrathecal, intradermal, intraperitoneal, subcutaneous and intravenous) administration or in a form suitable for administration by aerosolization, inhalation or insufflation. The composition, e.g., vaccine, can be administered to muscle, or can be administered via intradermal or subcutaneous injections, or transdermally, such as by iontophoresis. The composition, e.g., vaccine, can be delivered to a subject by epidermal administration.

Therapeutic Regimens

A composition provided herein, e.g., a vaccine, can be administered to a subject in a dosage volume of about 0.1, 0.15, 0.2, 0.25, 0.3, 0.35, 0.4, 0.45, 0.5, 0.55, 0.6, 0.7, 0.8, 0.9, 1.0 mL, or more. A half dose, e.g., about 0.25 mL, can be administered to a child. Sometimes the vaccine can be administered in a higher dose, e.g., about 1 mL.

The composition, e.g., vaccine, can be administered as a 1, 2, 3, 4, 5, 6, 7, 8, 9, 10, or more dose-course regimen. Sometimes, the vaccine can be administered as a 2, 3, or 4 dose-course regimen. Sometimes the vaccine can be administered as a 2 dose-course regimen.

The administration of the first dose and second dose of the 2 dose-course regimen can be separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, 5 years, 10 years, 20 years, or more. A composition described herein, e.g., vaccine, can be administered to a subject once a year, twice a year, three times a year, every 1, 2, 3, 4, 5, 6, 7, 8, 9, 10, or more years. Sometimes, the composition, e.g., vaccine, can be administered to a subject every 2, 3, 4, 5, 6, 7, or more years. Sometimes, the composition, e.g., vaccine, can be administered every 4, 5, 6, 7, or more years. Sometimes, the composition, e.g., vaccine, can be administered to a subject once. Sometimes, the composition, e.g., vaccine, can be taken by a subject as a multiple dose vaccine over a period of time, e.g., a 2-dose vaccine wherein the second dose can be taken 4-5 years after the first dose. In some cases, a composition, e.g., vaccine, is administered at a time from August to March, from September to February, from October to January, from November to December, e.g. in a region in the North Hemisphere. In some cases, a composition, e.g., vaccine, is administered at a time from March to October, from April to September, from May to August, from June to July, e.g. in a region in the South Hemisphere.

The dosage examples are not limiting and are only used to exemplify particular dosing regiments for administering a composition, e.g., vaccine, described herein. In some embodiments, a "therapeutically effective amount" for use in a human can be determined from an animal model. For example, a dose for a human can be formulated to achieve circulating, liver, topical, and/or gastrointestinal concentrations that have been found to be therapeutically effective in an animal. Based on animal data, and other types of similar data, those skilled in the art can determine a therapeutically effective amount of a composition, e.g., vaccine, appropriate for administration to a human.

A composition described herein, e.g., a vaccine, can be used to treat or prevent seasonal influenza or pandemic influenza. In some embodiments, the methods and compositions described herein can target an influenza virus subtype. Influenza A virus can be subtyped based on hemagglutinin (HA) and neuraminidase (N), two proteins expressed on the surface of the viral envelope. Influenza A virus can display about 18 HA subtypes: HI, H2, H3, H4, H5, H6, H7, H8, H9, H10, H11, H12, H13, H14, H15, H16, H17, and H18; and about eleven N subtypes: N1, N2, N3, N4, N5, N6, N7, N8, N9, N10, and N11. Together, the HA and N subtypes can be combined in any combination. Non-limiting examples of the HA and N subtype combinations that have been observed include: H1N1, H1N2, H1N7, H2N2, H3N2, H3N8, H4N8, H5N1, H5N2, H5N8, H5N9, H6N5, H7N1, H7N2, H7N3, H7N4, H7N7, H7N9, H8N4, H9N2, H10N7, HI 1N6, H12N5, H13N6, and H14N5. In some embodiments, the vaccines described herein can target an influenza A virus that has a combination of the HA and N subtypes disclosed herein. In some cases, the combination can be represented by HxNy, wherein x represents any HI-HI 8 subtypes, and y represents any N1-N1 1 subtypes. For example, in some embodiments, vaccines disclosed herein can target a subtype represented as H1Ny, which is HI in combination with any N subtype described herein, or a subtype represented as H2Ny, and the like. In some embodiments, a vaccine described herein can target an influenza A virus that has the HA and N subtype combinations H1N1, H1N2, H1N7, H2N2, H3N2, H3N8, H4N8, H5N1, H5N2, H5N8, H5N9, H6N5, H7N1, H7N2, H7N3, H7N4, H7N7, H7N9, H8N4, H9N2, H10N7, H11N6, H12N5, H13N6, or H14N5.

In some embodiments, a composition, e.g., vaccine, described herein can target an influenza B virus. Influenza B viruses can be classified into lineages and strains. An influenza B virus can belong to either the B/Yamagata or the B/Victoria lineage. Exemplary influenza B virus strains include Brisbane/60/2008, Massachusetts/2/2012, and Wisconsin/1/2010.

In some embodiments, a composition, e.g., vaccine, described herein can target an influenza A virus, influenza B virus, and/or an influenza C virus. In some embodiments, a composition, e.g., vaccine, described herein can target strains of influenza A virus, influenza B virus, influenza C virus, or a combination thereof.

In some embodiments, a composition, e.g., vaccine, described herein can be used to treat a patient who has an influenza infection, such as an influenza A virus infection, an influenza B virus infection, or an influenza C virus infection. Sometimes, a composition, e.g., vaccine, described herein can be used as a vaccination method against the infection of influenza A virus, influenza B virus, or influenza C virus. Sometimes, a composition, e.g., vaccine, described herein offers cross-protection against the different strains associated with the influenza A virus, the influenza B virus, and/or the influenza C virus.

The term "therapeutically effective amount" as used herein can mean an amount which is effective to alleviate, ameliorate, or prevent a symptom or sign of a disease or condition to be treated. For example, in some embodiments, a therapeutically effective amount can be an amount which has a beneficial effect in a subject having signs and/or symptoms of a viral infection, e.g., an influenza infection, e.g., an influenza A infection. In some embodiments, a therapeutically effective amount can be an amount which inhibits or reduces signs and/or symptoms of a viral infection, e.g., an influenza infection, e.g., an influenza A infection, as compared to a control. Signs and symptoms of an influenza infection, e.g., an influenza A infection, are well-known in the art and can include fever, cough, sore throat, runny nose, stuffy nose, headache, muscle aches, chills, fatigue (tiredness), nausea, vomiting, diarrhea, pain (e.g., abdominal pain), conjunctivitis, shortness of breath, difficulty breathing, pneumonia, acute respiratory distress, viral pneumonia, respiratory failure, neurologic change (e.g., altered mental status, seizure), or a combination thereof. In some embodiments, the therapeutically effective amount can be one which is sufficient to reduce any of the signs and/or symptoms by about, or at least 10%, 20%, 30%, 40%, 50%, 60%, 70%, 80%, 90%, 95%, or 100% in a subject as compared to a control.

A therapeutically effective amount, when referring to one or more active agents, can be a dose range, mode of administration, formulation, etc., that has been recommended or approved by any of the various regulatory or advisory organizations in the medical or pharmaceutical arts (e.g., FDA, AMA) or by the manufacturer or supplier.

In some aspects of the present disclosure, the composition can comprise a peptide based formulation. The composition comprising a polypeptide described herein can be administered to a subject between about 1 nmol/dose and about 1000 µmol/dose. In some embodiments, the composition can be administered to a subject at a dose about 1 nmol/dose, about 5 nmol/dose, about 10 nmol/dose, about 20 nmol/dose, about 30 nmol/dose, about 40 nmol/dose, about 50 nmol/dose, about 60 nmol/dose, about 70 nmol/dose, about 80 nmol/dose, about 90 nmol/dose, about 100 nmol/dose, about 200 nmol/dose, about 300 nmol/dose, about 400 nmol/dose, about 500 nmol/dose, about 600 nmol/dose, about 700 nmol/dose, about 800 nmol/dose, about 900 nmol/dose, about 1 µmol/dose, about 1 µmol/dose, about 2 µmol/dose, about 3 µmol/dose, about 4 µmol/dose, about 5 µmol/dose, about 6 µmol/dose, about 7 µmol/dose, about 8 µmol/dose, about 9 µmol/dose, about 10 µmol/dose, about 20 µmol/dose, about 50 µmol/dose, about 100 µmol/dose, about 200 µmol/dose, about 300 µmol/dose, about 400 µmol/dose, about 500 µmol/dose, about 750 µmol/dose, about 1000 µmol/dose, or any dose between any two thereof. In some cases, the composition can be administered to a subject at a dose about 50 nmol/dose.

In some aspects of the present disclosure, the composition can comprise a polynucleotide encoding a polypeptide described herein. The composition administered to a subject can comprise the polynucleotide at a dose between about 1 pmol/dose and about 1000 µmol/dose. In some embodiments, the composition administered to a subject can comprise the polynucleotide at a dose between about 1 pmol/dose, about 5 pmol/dose, about 10 pmol/dose, about 20 pmol/dose, about 30 pmol/dose, about 40 pmol/dose, about 50 pmol/dose, about 60 pmol/dose, about 70 pmol/dose, about 80 pmol/dose, about 90 pmol/dose, about 100 pmol/dose, about 200 pmol/dose, about 300 pmol/dose, about 400 pmol/dose, about 500 pmol/dose, about 600 pmol/dose, about 700 pmol/dose, about 800 pmol/dose, about 900 pmol/dose, 1 nmol/dose, about 5 nmol/dose, about 10 nmol/dose, about 20 nmol/dose, about 30 nmol/dose, about 40 nmol/dose, about 50 nmol/dose, about 60 nmol/dose, about 70 nmol/dose, about 80 nmol/dose, about 90 nmol/dose, about 100 nmol/dose, about 200 nmol/dose, about 300 nmol/dose, about 400 nmol/dose, about 500 nmol/dose, about 600 nmol/dose, about 700 nmol/dose, about 800 nmol/dose, about 900 nmol/dose, about 1 µmol/dose, about 1 µmol/dose, about 2 µmol/dose, about 3 µmol/dose, about 4 µmol/dose, about mol/dose, about 6 µmol/dose, about 7 µmol/dose, about 8 µmol/dose, about 9 µmol/dose, about 10 µmol/dose, about 20 µmol/dose, about 50 µmol/dose, about 100 µmol/dose, about 200 µmol/dose, about 300 µmol/dose, about 400 µmol/dose, about 500 µmol/dose, about 750 µmol/dose, about 1000 µmol/dose, or any dose between any two thereof.

In some aspects of the present disclosure, the composition can comprise a recombinant virus containing a polynucleotide encoding a polypeptide as described herein. The composition comprising recombinant virus can be administered to a subject between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a virus vaccine of this disclosure administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. Sometimes, a virus vaccine of this disclosure administered to a subject can be administered at a dose about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. A virus vaccine of this disclosure administered to a subject can comprise about $2 \times 10^3$ PFU/dose, $3 \times 10^3$ PFU/dose, $4 \times 10^3$ PFU/dose, $5 \times 10^3$ PFU/dose, $6 \times 10^3$ PFU/dose, $7 \times 10^3$ PFU/dose, $8 \times 10^3$ PFU/dose, $9 \times 10^3$ PFU/dose, about $10^4$ PFU/dose, about $2 \times 10^4$ PFU/dose, about $3 \times 10^4$ PFU/dose, about $4 \times 10^4$ PFU/dose, about $5 \times 10^4$ PFU/dose, about $6 \times 10^4$ PFU/dose, about $7 \times 10^4$ PFU/dose, about $8 \times 10^4$ PFU/dose, about $9 \times 10^4$ PFU/dose, about $10^5$ PFU/dose, $2 \times 10^5$ PFU/dose, $3 \times 10^5$ PFU/dose, $4 \times 10^5$ PFU/dose, $5 \times 10^5$ PFU/dose, $6 \times 10^5$ PFU/dose, $7 \times 10^5$ PFU/dose, $8 \times 10^5$ PFU/dose, $9 \times 10^5$ PFU/dose, about $10^6$ PFU/dose, about $2 \times 10^6$ PFU/dose, about $3 \times 10^6$ PFU/dose, about $4 \times 10^6$ PFU/dose, about $5 \times 10^6$ PFU/dose, about $6 \times 10^6$ PFU/dose, about $7 \times 10^6$ PFU/dose, about $8 \times 10^6$ PFU/dose, about $9 \times 10^6$ PFU/dose, about $10^7$ PFU/dose, about $2 \times 10^7$ PFU/dose, about $3 \times 10^7$ PFU/dose, about $4 \times 10^7$ PFU/dose, about $5 \times 10^7$ PFU/dose, about $6 \times 10^7$ PFU/dose, about $7 \times 10^7$ PFU/dose, about $8 \times 10^7$ PFU/dose, about $9 \times 10^7$ PFU/dose, about $10^8$ PFU/dose, about $2 \times 10^8$ PFU/dose, about $3 \times 10^8$ PFU/dose, about $4 \times 10^8$ PFU/dose, about $5 \times 10^8$ PFU/dose, about $6 \times 10^8$ PFU/dose, about $7 \times 10^8$ PFU/dose, about $8 \times 10^8$ PFU/dose, about $9 \times 10^8$ PFU/dose, about $10^9$ PFU/dose, about $2 \times 10^9$ PFU/dose, about $3 \times 10^9$ PFU/dose, about $4 \times 10^9$ PFU/dose, about $5 \times 10^9$ PFU/dose, about $6 \times 10^9$ PFU/dose, about $7 \times 10^9$ PFU/dose, about $8 \times 10^9$ PFU/dose, about $9 \times 10^9$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{11}$ PFU/dose, about $2\times10^{11}$ PFU/dose, about $3\times10^{11}$ PFU/dose, about $4\times10^{11}$ PFU/dose, about $5\times10^{11}$ PFU/dose, about $6\times10^{11}$ PFU/dose, about $7\times10^{11}$ PFU/dose, about $8\times10^{11}$ PFU/dose, about $9\times10^{11}$ PFU/dose, or about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose, or any dose between any two thereof.

Sometimes, a virus vaccine of this disclosure administered to a subject can be administered at a dose about $10^4$ viral particles/dose, about $10^4$ viral particles/dose to about $10^5$ viral particles/dose, about $10^5$ viral particles/dose to about $10^6$ viral particles/dose, about $10^7$ viral particles/dose to about $10^8$ viral particles/dose, about $10^9$ viral particles/dose to about $10^{10}$ viral particles/dose, about $10^{10}$ viral particles/dose to about 1011 viral particles/dose, about $10^{11}$ viral particles/dose to about $10^{12}$ viral particles/dose, about $10^{12}$ viral particles/dose to about $10^{13}$ viral particles/dose, about $10^{13}$ viral particles/dose to about $10^{14}$ viral particles/dose, or about $10^{14}$ viral particles/dose to about $10^{15}$ viral particles/dose. In some embodiments, a virus vaccine of this disclosure administered to a subject can be administered at a dose about $1\times10^9$ viral particles/dose, about $1.5\times10^9$ viral particles/dose, about $2\times10^9$ viral particles/dose, about $2.5\times10^9$ viral particles/dose, about $3\times10^9$ viral particles/dose, about $3.5\times10^9$ viral particles/dose, about $4\times10^9$ viral particles/dose, about $4.5\times10^9$ viral particles/dose, about $5\times10^9$ viral particles/dose, about $5.5\times10^9$ viral particles/dose, about $6\times10^9$ viral particles/dose, about $6.5\times10^9$ viral particles/dose, about $7\times10^9$ viral particles/dose, about $7.5\times10^9$ viral particles/dose, about $8\times10^9$ viral particles/dose, about $8.5\times10^9$ viral particles/dose, about $9\times10^9$ viral particles/dose, about $1\times10^{10}$ viral particles/dose, about $2\times10^{10}$ viral particles/dose, about $3\times10^{10}$ viral particles/dose, about $4\times10^{10}$ viral particles/dose, about $5\times10^{10}$ viral particles/dose, about $6\times10^{10}$ viral particles/dose, about $7\times10^{10}$ viral particles/dose, about $8\times10^{10}$ viral particles/dose, about $9\times10^{10}$ viral particles/dose, or any dose in between any two thereof. In some embodiments, a virus vaccine of this disclosure administered to a subject can be administered at a dose about $7.5\times10^9$ viral particles/dose.

A composition provided herein, e.g., a vaccine can be administered before, during, or after the onset of a symptom associated with a pathogen infection, e.g., an influenza A infection. Exemplary symptoms can include fever, cough, sore throat, runny nose, stuffy nose, headache, muscle aches, chills, fatigue, nausea, vomiting, diarrhea, pain (e.g., abdominal pain), conjunctivitis, shortness of breath, difficulty breathing, pneumonia, acute respiratory distress, viral pneumonia, respiratory failure, neurologic change (e.g., altered mental status, seizure), or a combination thereof. In some cases, the composition, e.g., vaccine, can be administered to a subject in order to treat a pathogen infection, e.g., influenza infection, e.g., influenza A infection. Sometimes, the composition, e.g., vaccine, can be administered to a subject for a preventive purpose, such as a prophylactic treatment of a pathogen infection, e.g., influenza infection, e.g., influenza A infection. The composition, e.g., vaccine, can be administered to a subject to illicit an immune response from a subject. The composition, e.g., vaccine, can be administered to a subject to illicit an immune response from the subject prior to a pathogen infection, during a pathogen infection, or as a prophylactic measure against a pathogen infection. Following administration of a composition provided herein, e.g., a vaccine, a symptom associated with a pathogen can be reduced about, at least, or at most 5%, 10%, 20%, 30%, 40%, 50%, 60%, 70%, 80%, 90%, or 100%, with about, at least, or at most 1 day, 5 days, 1 week, 2 weeks, 3 weeks, or 1 month.

A complication from an influenza infection, e.g. an influenza A infection, can be, e.g., pneumonia, bronchitis, sinus infection, or an ear infection. In some cases, an influenza infection, e.g., an influenza A infection, can make a chronic health problem worse, e.g., a person with asthma may experience an asthma attack while the person has an influenza infection, or a person with chronic congestive heart failure can experience worsening of this condition while the person has an influenza infection. In some embodiments, a therapeutically effective amount of a composition, e.g., a vaccine described herein, can be administered to a subject with a complication from an influenza infection. In some embodiments, a therapeutically effective amount of a composition, e.g., a vaccine described herein, can be administered to a subject with an influenza infection (e.g., an influenza A infection) and one or more chronic health problems.

A composition provided herein, e.g., a vaccine, or a kit described herein can be stored at between 2° C. and 8° C. Sometimes, the composition, e.g., vaccine, can be stored at room temperature. In some embodiments, the composition, e.g., vaccine, may not be stored frozen. In some embodiments, the composition, e.g., vaccine, can be stored in a temperature such as at −20° C. or −80° C. In some embodiments, the composition, e.g., vaccine, can be stored away from sunlight.

EXAMPLE

The following examples are offered by way of illustration, not by way of limitation.

Example 1

The peptide sequence TYQRTRALV (SEQ ID NO: 37) was selected based on 1) being an experimentally validated BALB/C influenza A virus CD8 T-cell epitope in worldwideweb.fludb.org and 2) having an average invariance ratio (frequency of mutant in final population/frequency in initial population) of <0.08 among all possible mutations in the stretch (generally each residue has 6-7 possible mutations from single nucleotide changes within the codon). Peptide was conjugated to Pam2Cys (a liposomal adjuvant that activates TLR2 and is covalently linked to the peptide) and a CD4 T cell epitope from HA (GALNNRFQIKGVELKS (SEQ ID NO: 115)) (epitopes connected via a central lysine, and Pam2Cys conjugated to central lysine via two serines). (CS Bio, Menlo Park, Calif. synthesized the lipopeptides) A formulation was made with 50 nmol of Pam2Cys-peptide having the sequence TYQRTRALV (SEQ ID NO: 37) per 20 μL of phosphate buffered saline (PBS) (2.5 μM). A volume of 20 μL of the formulation was administered intranasally to each of 10 BALB/C mice ("Group 2"). A volume of 20 μl of PBS was administered intranasally to each of 10 control BALB/C mice ("Group 1"). Four weeks after the administrations, the mice in both groups were challenged with 100 $TCID_{50}$ PR8 influenza A virus. 60% (6 of 10) of mice in the vaccine group (Group 2) compared to 0% (0 of 10) in the control group (Group 1) survived after 9 days from the lethal challenge of influenza A virus, showing statistically significant protection by vaccine (see FIG. 2).

Example 2

Figure 4:
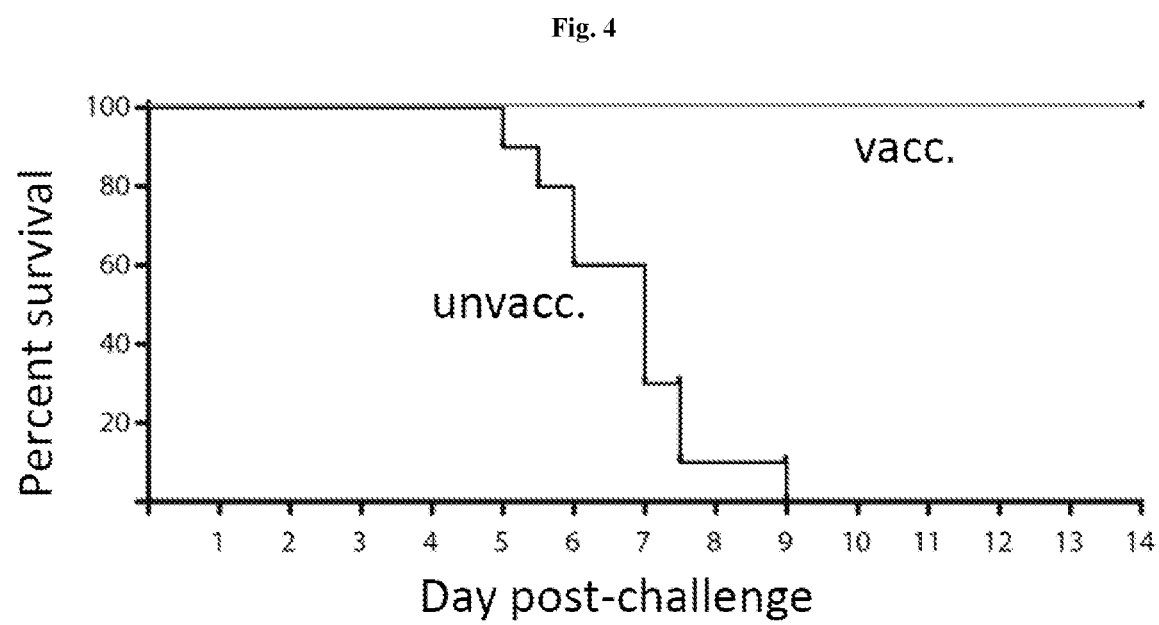
FIG. 4 illustrates percent survival of vaccinated and unvaccinated mice in FIGS. 3A and 3B.

This example describes vaccination with a vaccine comprising 4 influenza virus epitopes. A recombinant adenovirus carrying 4 influenza virus epitopes: ELRSRYWAIRTRSG (NP) (SEQ ID NO: 17), FYIQMCTEL (NP) (SEQ ID NO: 79), TYNAELLVLL (HA) (SEQ ID NO: 80), and TYQRTRALV (NP) (SEQ ID NO: 37) was generated. The recombinant adenovirus contained a single transgene with the four peptides encoded in tandem and separated by the linker RVKR (SEQ ID NO: 110). The sequence of the transgene product is GALNNRFQIKGVELKSKTYQRTRALVRVKRELRSRYWAIRTRSGRVKRFYIQMCTELRVKRTYNAELLVLL (SEQ ID NO: 81). For generating the recombinant adenoviral vector, the transgene was codon optimized for expression in mouse cells. The recombinant adenovirus was administered subcutaneously and intranasally simultaneously to Group 1 mice (10 BALB/C mice) at a dose of $2 \times 10^7$ pfu (plaque-forming units) in 20 μl ($7.5 \times 10^9$ viral particles to each s.c. and i.n). The mice were challenged 28 days later with a lethal dose of 5-10 LD50 (lethal dose 50) (~100 TCID50 or tissue culture infectious dose 50) of H1N1 flu. All 10 mice in this group survived. 9 out of the 10 mice initially lost weight but regained most of their weight by day 12 post-challenge. See FIG. 3A and FIG. 4.

Figure 3B:
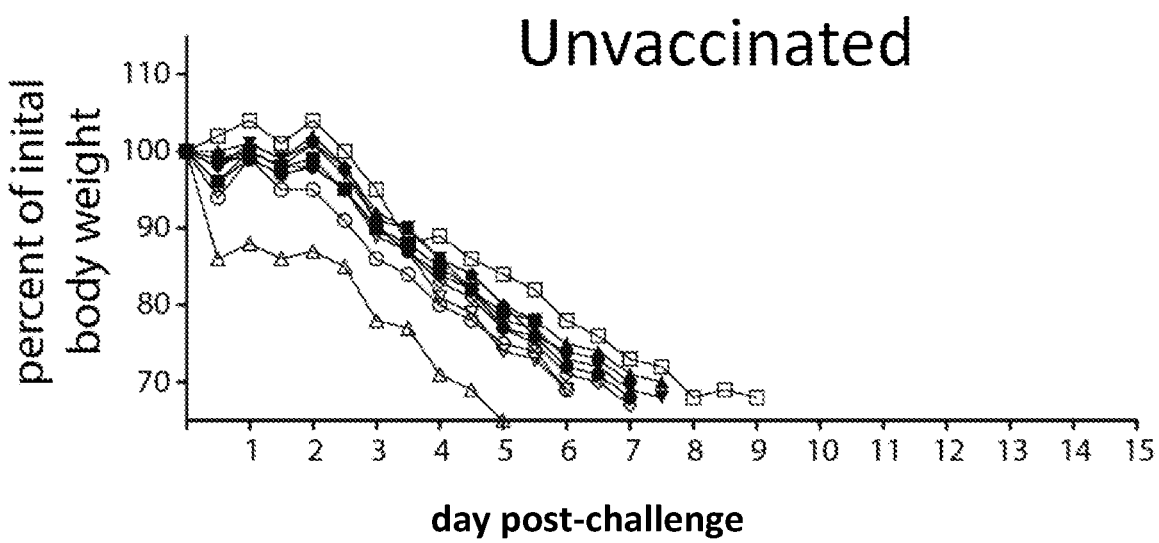
FIG. 3B illustrates the percent of initial body weight of unvaccinated mice.

In a control group (Group 2, unvaccinated, injected with saline s.c. and i.n.), 10 BALB/C mice were challenged with a lethal dose of 5-10 LD50 (lethal dose 50) (~100 TCID50 or tissue culture infectious dose 50) of H1N1 flu. 0 of 10 mice survived, all of the mice died by day 9 post-challenge. See FIG. 3B and FIG. 4.

Figure 3C:
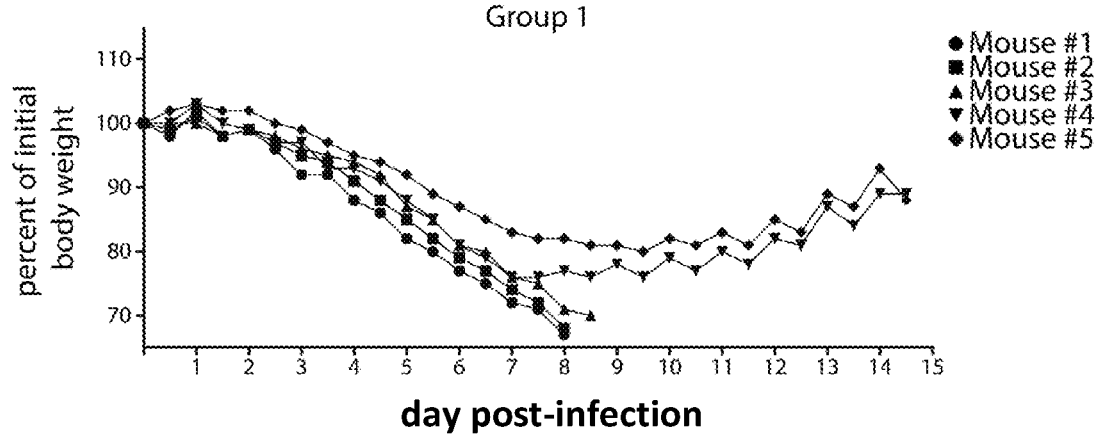
FIG. 3C illustrates the percent of initial body weight of Group 1 (AdCre-injected) mice.
Figure 3D:
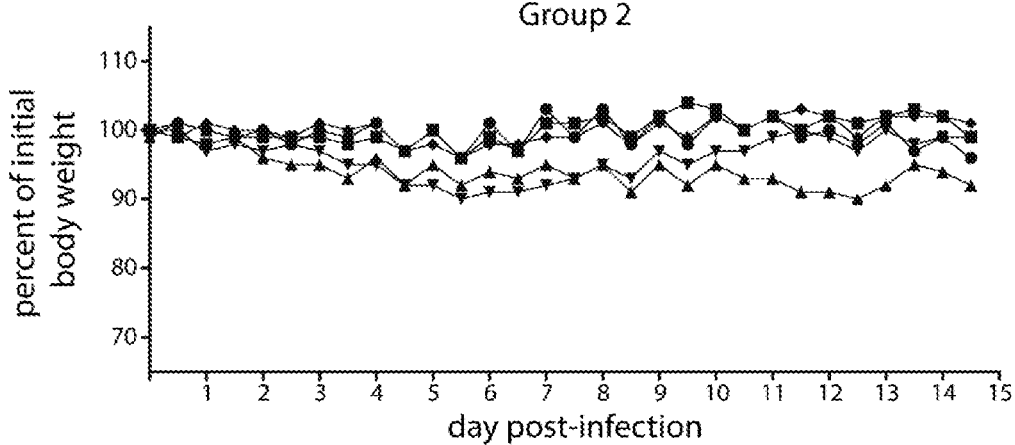
FIG. 3D illustrates the percent of initial body weight of Group 2 vaccinated mice.

In another set of experiments, AdCre-injected mice were used as control group (Group 1 in FIG. 3C) for the Ad vector. AdCre is an adenovirus produced using the same adenoviral vector as the recombinant adenovirus vaccine, but inserted with a Cre recombinase gene instead of the nucleotide sequence expressing the 4 epitopes. As shown in FIG. 3C, 3 of 5 mice in the control group perished, and the other 2 5 mice lost substantial weight. In contrast, in the vaccinated group (Group 2 in FIG. 3D), 0 of 5 mice lost >10% body weight. All 5 mice in AdCre had symptom scores of 3 or greater (not shown), whereas all 5 mice in the vaccine group had no higher than 1.

Example 3

This example describes vaccination with a vaccine comprising 9 influenza virus epitopes. A recombinant adenovirus carrying 9 influenza virus epitopes is generated. A vaccine cocktail of peptides comprising 9 influenza virus epitopes can also be used. Influenza virus epitopes can comprise any combination of the epitopes listed in Table 1.

Vaccination can be performed utilizing HLA-B44-transgenic mice. A prime-boost regimen can be employed. Priming can be with 9 Pam2Cys-adjuvanted peptides. Boosting can be with a recombinant adenovirus carrying 9 influenza virus epitopes or with a universal helper T cell epitope. Following vaccination, mice are challenged with the PR8 strain of influenza virus. Mice are monitored for health, weight, and survival to assess protection conferred by vaccination.

Example 4

This example describes experimental procedures and materials for heterosubtypic protection test of influenza virus.

Kill Curve

A kill curve experiment (a lethal dose curve) can be performed to determine the LD50 (a dose at which 50% of subject animals die), so that a challenge dose of 5-10LD50 can be used for the protection experiment.

Day 1: 3 mice in each Group, i.n. in 25 ul
Vict 1d is H3N2, and is $3.2 \times 10^7$ TCID50/ml
1) Group A: 10 TCID50 Vict 1d (H3N2) (Make this 5th: Dilution #5: 50 ul Dilution #4+450 ul PBS)
2) Group B: 100 TCID50 Vict 1d (Make this 4th: Dilution #4: 50 ul Dilution #3+450 ul PBS)
3) Group C: 1,000 TCID50 Vict 1d (Make this 3rd: Dilution #3: 50 ul Dilution #2+450 ul PBS)
4) Group D: 10,000 TCID50 Vict 1d (Make this 2nd: Dilution #2: 50 ul Dilution #1+450 ul PBS)
5) Group E: 100,000 TCID50 Vict 1d (Make this 1st: Dilution #1: 100 ul virus stock+700 ul PBS)

Heterosubtypic Protection

Day 1: Immunize mice:
1) Group 1: 10 mice with 20 ul saline i.n. (intranasal) and 20 ul saline s.c. (subcutaneous)
2) Group 2: 10 mice with $2 \times 10^7$ pfu in 20 ul AdBALB i.n. and same s.c.
   For 2×10 pfu AdBALAB: To 3 vials AdBALB, add 115 ul PBS each. Mix vials together (should be 420 ul total, just enough; can also use some from vial in Group 6) and administer above.
3) Group 3: 5 mice with $2 \times 10^7$ pfu in 20 ul AdBALB5-pep i.n. and same s.c.
   For 2×10 pfu AdBALAB5-pep: To 1 vial AdBALB5-pep, add 230 ul PBS and administer above.
4) Group 4: 5 mice with $7.5 \times 10^9$ viral particles in 20 ul i.n. and same s.c.
   For $10 \times 10^9$ pfu AdBALAB5-pep: To 1 vial AdBALB5-pep, add 722 ul PBS and administer above.
5) Group 5: 5 mice with 20 ul AdCre i.m. (intramuscular)
   For 20 ul AdCre: To 1 vial AdCre, add 653 ul PBS and administer above.
6) Group 6: 5 mice with 20 ul AdBALB i.m.
   For 20 ul AdBALB: To 1 vial AdBALB, add 115 ul PBS and administer above.

Days 2-15: Monitor body weight, survival, and clinical scores

Day 29: Challenge mice: All i.n. in 20 ul
1) Groups 1-4: 5-10 LD50 (selected on the basis of kill curve) Vict 1d
2) Groups 5-6: 100 TCID50 PR8 (Dilute virus stock 1/10,000: 10 ul virus stock+990 ul PBS; 10 ul of this dilution+990 ul PBS for working stock)

Days 30-43: Monitor body weight, survival, and clinical scores

Reagents

Total 55 BALB/C 6-12 wk-old female mice.
Adenoviruses: AdBALB (control virus with no epitope sequences); AdBALB5-pep (vaccine carrying 5 different influenza epitope sequences); AdCre (control virus with no epitope sequences but Cre transgene). Influenza viruses: PR8; Vict 1d (H3N2).

Example 5

This example describes a recombinant adenovirus based vaccine (AdFlu51pep) having 51 different influenza virus epitopes. The recombinant adenovirus is engineered with a single transgene that expresses all 51 epitope sequences in Table 3, which are encoded in tandem and separated by a linker RVKR (SEQ ID NO: 110). The order of the 51 epitope sequences can be random, thereby generating a variety of different transgene sequences. The sequence of one example of the transgene products, or a portion of the transgene product, is as listed in Table 4.

TABLE 4

SEQ ID NO: 106

ELRSRYWAIRTRSGRVKRELRSRHWAIRTRSGRVKRELRSRYWASRTRSG
RVKRFMYSDFHFIRVKRFMYSDLHFIRVKRFMYTDFHFIRVKRFMFSDFH
FIRVKRGTFEFTSFFYRVKRGTFEFTSYFYRVKRILKGKFQTARVKRIIK
GKFQTARVKRILKGKFQIARVKRILRGSIAHKRVKRILRGSVAHKRVKRV
LRGSIAHKRVKRLIFLARSALRVKRLVFLARSALRVKRLTFLARSALRVK
RYSHGTGTGYRVKRYSHWTGTGYRVKRYSHGSGTGYRVKRFLARSALILR
GSVAHKRVKRFLARSALVLRGSVAHKRVKRIAYERMCNILKGKFQTAARV
KRVAYERMCNILKGKFQTAARVKRVAYERMCNIIKGKFQTAARVKRVAYE
RMCNILKGKFKTAARVKRVAYERMCNILKGKFQIAARVKRVAYERMCNIL
KGKFQTAVRVKRDVVNFVSMEFSLTDPRLRVKRDVVNFVSMEFSLTYPRL
RVKRDVVNFVSMEFSLTDQRLRVKRFLARSALILRGSVAHKSRVKRFLAR
SALVLRGSVAHKSRVKRKWGMEMRRCLLQSLQQIRVKRKLGMEMRRCLLQ
SLQQIRVKRKWGMEMRRCLLQSLQQVRVKRKWGMELRRCLLQSLQQIRVK
RFQGRGVFELRVKRGQISIQPTFSRVKRSQISVQPTFSRVKRGQVSVQPT
FSRVKRGQISVQPTFSRVKRWHSNLNDATYQRTRALVRTGMDPRMRVKRW
HSNLNDTTYQRTRALVRTGMDPRMRVKRWHSNLNDSTYQRTRALVRTGMD
PRMRVKRWHSNLNDATYQRKRALVRTGMDPRMRVKRWHSNLNDATYQRTR
SLVRTGMDPRMRVKRWHSNLNDATYQRTRAIVRTGMDPRMRVKRWHSNLN
DATYQRTRALVRSGMDPRMRVKRWHSNLNDATYQRTRALVRTGRDPRM

The transgene can express the polypeptide linked to one or more copies (e.g., 2, 3, 4, or 5) of influenza B virus NP protein, e.g., SEQ ID NO: 116, 117 or 118, or fragments of the influenza B virus NP protein (e.g., amino acids 2-560 of SEQ ID NO: 116, 117 or 118). In some cases, the vaccine comprises a second adenovirus with a second transgene that can expresses a polypeptide comprising one or more copies (e.g., 2, 3, 4, 5) of influenza B virus NP protein, e.g., SEQ ID NO: 116, 117 or 118, or fragments of influenza B virus NP protein. In some cases, an adenovirus can comprise a transgene that can express a polypeptide comprising SEQ ID NO: 106 and a second polypeptide comprising one or more copies (e.g., 2, 3, 4, or 5) of influenza B virus NP protein, e.g., SEQ ID NO: 116, 117 or 118, or fragments of the influenza B virus NP protein.

Example 6

This example describes production of an adenovirus based influenza vaccine as described in Example 5.

First, shuttle vector (Add2) containing the transgene that expresses SEQ ID NO: 106 can be constructed using conventional molecular cloning techniques. The transgene is driven by CMV promoter. Expression of the transgene can be checked at this point by transfection into 293T cells. Vector construct will be optimized if no polypeptide expression can be observed in transfected 293T cells.

Maxiprep pAdFlu51pep will then be linearized and transfected into 293 cells for generation of adenoviral plaques. A replication defective C68 helper virus or C6 virus will be supplemented to the transfected 293 cells for adenovirus packaging. Viral plaques will form 7-10 days after plating. Plaques can then be picked, frozen for later use, or subject to expansion of the viruses. Laboratory scale expansion of the pAdFlu51pep virus can be performed by serial passage of subconfluent 293 cells through different sizes of cell culture flasks, like T25, T75, or even T150.

Cell culture media and lysed cells will be subject to centrifugation for viral stock. Titering will be performed according to routine virus tittering procedures.

Example 7

This example describes clinical studies for the adenovirus based vaccine as described in Example 5 in human subject.

An open-label, uncontrolled Phase 1 study is carried out to evaluate the adenovirus based vaccine (AdFlu51pep vaccine) containing the 51 different epitope sequences in Table 3 in healthy adults.

Objectives:

Evaluate the safety, tolerability and immunogenicity of the AdFlu51pep vaccine in healthy adult volunteers of both sexes between the ages of 18 and 55 years.

Dose

The starting dose for AdFlu51pep vaccine ranges from $3 \times 10^5$ to $1 \times 10^9$ PFU by intramuscular injection into deltoid once, including dose levels at $3 \times 10^5$ PFU, $3 \times 10^6$ PFU, $3 \times 10^7$ PFU, $3 \times 10^8$ PFU, and $1 \times 10^9$ PFU.

Each dose level enrolls between 6 and 12 evaluable healthy adults.

Safety Monitoring

Injection-site and systemic reactogenicity and medication use can be recorded for 7 days after injection and at follow-up (days 14 and 28). Clinical and laboratory evaluations can be performed during each study visit. Laboratory analyses can include a complete blood count and measurements of creatinine, C-reactive protein, and liver function. Adverse events will be listed for each participant.

Immunogenicity

Immunogenicity can be assessed by assaying serum samples of the participants. IFN-γ ELISPOT to assay T cell immunogenicity will be conducted with participants' serum samples collected at baseline (before vaccination) and at 28 and 180 days after injection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A polypeptide comprising influenza virus epitopes, wherein the polypeptide comprises the sequences of SEQ ID NOs: 2, 3, 8, 11, 12, 17, 21, 22, 24, 32, 33, 34, 40, 41, 43, 49, 51, 52, 58, 59, 61, 62, 70, 73, 74, 75, 76, 77, 78, 82, 84, 85, 86, 92, 93, and 94.

2. A polypeptide comprising influenza virus epitopes, wherein the polypeptide comprises:
   a first sequence comprising at least 75% sequence identity to the sequence of SEQ ID NO: 8;
   a second sequence comprising at least 75% sequence identity to the sequence of SEQ ID NO: 11;

a third sequence comprising at least 75% sequence identity to the sequence of SEQ ID NO: 12;
a fourth sequence comprising at least 75% sequence identity to the sequence of SEQ ID NO: 2;
a fifth sequence comprising at least 75% sequence identity to the sequence of SEQ ID NO: 3;
a sixth sequence comprising at least 75% sequence identity to the sequence of SEQ ID NO: 32;
a seventh sequence comprising at least 75% sequence identity to the sequence of SEQ ID NO: 24;
an eighth sequence comprising at least 75% sequence identity to the sequence of SEQ ID NO: 17;

a ninth sequence comprising at least 75% sequence identity to the sequence of SEQ ID NO: 29; and a tenth sequence comprising at least 75% sequence identity to the sequence of SEQ ID NO: 33.

3. The polypeptide of claim 2, wherein the first sequence and second sequence are directly linked.

4. The polypeptide of claim 2, wherein at least two of the first, second, third, fourth, fifth, sixth, seventh, eighth, ninth, or tenth sequence are linked by a linker.

5. The polypeptide of claim 4, wherein the linker comprises the sequence RVKR (SEQ ID NO: 110).

6. The polypeptide of claim 2, comprising the sequence of SEQ ID NO: 106.

7. A polypeptide comprising influenza virus epitopes, wherein the polypeptide comprises:

at least 3 sequences comprising at least 75% sequence identity to the sequence of SEQ ID NO: 8;

at least 3 sequences comprising at least 75% sequence identity to the sequence of SEQ ID NO: 11;

at least 4 sequences comprising at least 75% sequence identity to the sequence of SEQ ID NO: 12;

at least 2 sequences comprising at least 75% sequence identity to the sequence of SEQ ID NO: 2;

at least 3 sequences comprising at least 75% sequence identity to the sequence of SEQ ID NO: 3;

at least 4 sequences comprising at least 75% sequence identity to the sequence of SEQ ID NO: 32;

at least 3 sequences comprising at least 75% sequence identity to the sequence of SEQ ID NO: 21;

at least 3 sequences comprising at least 75% sequence identity to the sequence of SEQ ID NO: 24;

at least 3 sequences comprising at least 75% sequence identity to the sequence of SEQ ID NO: 17;

at least 5 sequences comprising at least 75% sequence identity to the sequence of SEQ ID NO: 29; and at least 8 sequences comprising at least 75% sequence identity to the sequence of SEQ ID NO: 33.

8. A polynucleotide encoding the polypeptide of claim 2.

9. A composition comprising the polynucleotide of claim 8.

10. A vector comprising the polynucleotide of claim 8.

11. A composition comprising the vector of claim 10.

12. A method comprising administering to a subject the composition of claim 11.

* * * * *

SEQUENCE LISTING

<160> NUMBER OF SEQ ID NOS: 118

<210> SEQ ID NO 1
<211> LENGTH: 9
<212> TYPE: PRT

<213> ORGANISM: Artificial Sequence
<220> FEATURE:
<223> OTHER INFORMATION: Description of Artificial Sequence: Synthetic peptide

<400> SEQUENCE: 1

Gly Pro Ala Thr Ala Gln Met Ala Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Gly Thr Phe Glu Phe Thr Ser Phe Phe Tyr
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Tyr Ser His Gly Thr Gly Thr Gly Tyr
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Leu Pro Val Gly Gly Asn Glu Lys Lys Ala Lys Leu Ala Asn Val
1               5                   10                  15

Val Arg

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gly Met Met Met Gly Met Phe Asn Met Leu Ser Thr Val Leu Gly Val
1               5                   10                  15

Ser

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 6

Leu Gln Leu Phe Ile Lys Asp Tyr Arg Tyr Thr Tyr Arg Cys His Arg
1               5                   10                  15

Gly

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Ala Ile Ala Thr Pro Gly Met
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Met Tyr Ser Asp Phe His Phe Ile
1               5

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Arg Asn Tyr Phe Thr Ala Glu Val Ser His Cys Arg Ala Thr
1               5                   10                  15

Glu Tyr

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Leu Met Trp Ala Leu Gly Glu Asn Met Ala
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Val Val Asn Phe Val Ser Met Glu Phe Ser Leu Thr Asp Pro Arg
1               5                   10                  15
```

Leu

```
<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Trp Gly Met Glu Met Arg Arg Cys Leu Leu Gln Ser Leu Gln Gln
1               5                   10                  15

Ile

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Glu Ile Glu Asp Leu Ile Phe Leu Ala
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Thr Glu Leu Lys Leu Ser Asp Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Thr Glu Leu Lys Leu Thr Asp Gln
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Glu Leu Lys Leu Thr Asp Tyr
1               5

<210> SEQ ID NO 17
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 17

Glu Leu Arg Ser Arg Tyr Trp Ala Ile Arg Thr Arg Ser Gly
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Leu Lys Ser Arg Tyr Trp Ala Ile Arg Thr Arg Ser Gly
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Met Asp Pro Arg Met Cys Ser Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Leu Lys Gly Lys Phe Gln Thr Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Leu Arg Gly Ser Ile Ala His Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Leu Arg Gly Ser Val Ala His Lys
1               5
```

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Glu Leu Arg Ser Arg Tyr Trp Ala Ile
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Ile Phe Leu Ala Arg Ser Ala Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Ile Asn Asp Arg Asn Phe Trp
1               5

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Leu Ala Arg Ser Ala Leu Ile Leu Arg Gly Ser Val Ala His Lys
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Met Val Leu Ser Ala Phe Asp Glu Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Thr Leu Glu Leu Arg Ser Gly Tyr Trp Ala Ile Arg Thr Arg Ser Gly
1               5                   10                  15

Gly Asn

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Ala Tyr Glu Arg Met Cys Asn Ile Leu Lys Gly Lys Phe Gln Thr
1               5                   10                  15

Ala Ala

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Leu Ala Arg Ser Ala Leu Ile Leu Arg Gly Ser Val Ala His Lys
1               5                   10                  15

Ser

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Gln Gly Arg Gly Val Phe Glu Leu
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gln Ile Ser Ile Gln Pro Thr Phe Ser
1               5                   10

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp His Ser Asn Leu Asn Asp Ala Thr Tyr Gln Arg Thr Arg Ala Leu
```

```
                1               5                   10                  15
Val Arg Thr Gly Met Asp Pro Arg Met
            20                  25

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp His Ser Asn Leu Asn Asp Thr Thr Tyr Gln Arg Thr Arg Ala Leu
1               5                   10                  15
Val Arg Thr Gly Met Asp Pro Arg Met
            20                  25

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Val Asn Gly Ser Cys Phe Thr Val
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Met Val Leu Ala Ser Thr Thr Ala Lys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Tyr Gln Arg Thr Arg Ala Leu Val
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Val Asn Gly Ser Cys Tyr Thr Val
1               5
```

```
<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Leu Lys Ser Arg Tyr Trp Ala Ile Arg Thr Arg Ser Gly
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Met Tyr Ser Asp Leu His Phe Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Met Tyr Thr Asp Phe His Phe Ile
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Arg Asp Pro Arg Met Cys Ser Leu
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Thr Phe Glu Phe Thr Ser Tyr Phe Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Ile Ile Lys Gly Lys Phe Gln Thr Ala
1               5
```

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ile Leu Lys Gly Lys Phe Gln Ile Ala
1               5
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ile Leu Arg Gly Ser Val Ala His Lys
1               5
```

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Leu Gln Leu Arg Ser Arg Tyr Trp Ala Ile
1               5                   10
```

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Leu Glu Leu Arg Ser Arg His Trp Ala Ile
1               5                   10
```

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Leu Val Phe Leu Ala Arg Ser Ala Leu
1               5
```

<210> SEQ ID NO 50
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 50

Arg Trp Ile Asn Asp Arg Asn Phe Trp
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Ser His Trp Thr Gly Thr Gly Tyr
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Ser His Gly Ser Gly Thr Gly Tyr
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Leu Ala Arg Ser Ala Leu Val Leu Arg Gly Ser Val Ala His Lys
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Ala Tyr Glu Arg Met Cys Asn Ile Ile Lys Gly Lys Phe Gln Thr
1               5                   10                  15

Ala Ala

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ala Tyr Glu Arg Met Cys Asn Ile Leu Lys Val Lys Phe Gln Thr
```

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Ala Tyr Glu Arg Met Cys Asn Ile Leu Lys Gly Lys Phe Lys Thr
1               5                   10                  15

Ala Ala

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Ala Tyr Glu Arg Met Cys Asn Ile Leu Lys Gly Lys Phe Gln Ile
1               5                   10                  15

Ala Ala

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Val Val Asn Phe Val Ser Met Glu Phe Ser Leu Thr Tyr Pro Arg
1               5                   10                  15

Leu

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Val Val Asn Phe Val Ser Met Glu Phe Ser Leu Thr Asp Gln Arg
1               5                   10                  15

Leu

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Phe Leu Ala Arg Ser Ala Leu Val Leu Arg Gly Ser Val Ala His Lys
1               5                   10                  15

Ser

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Leu Gly Met Glu Met Arg Arg Cys Leu Leu Gln Ser Leu Gln Gln
1               5                   10                  15

Ile

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Trp Gly Met Glu Met Arg Arg Cys Leu Leu Gln Ser Leu Gln Gln
1               5                   10                  15

Val

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Gln Leu Phe Ile Lys Asp Phe Arg Tyr Thr Tyr Arg Cys His Arg
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Gln Leu Phe Ile Lys Asp Tyr Arg Tyr Thr Tyr Arg Cys Leu Arg
1               5                   10                  15

Gly

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Leu Gln Leu Phe Ile Lys Asp Tyr Arg Tyr Thr Tyr Arg Cys Pro Arg
1               5                   10                  15
Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Gln Leu Phe Ile Lys Asp Tyr Arg Tyr Thr Tyr Arg Cys His Arg
1               5                   10                  15
Val

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Gln Gly Pro Gly Val Phe Glu Leu
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Gln Ile Ser Ile Gln Pro Thr Phe Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gln Val Ser Ile Gln Pro Thr Phe Ser
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gln Ile Ser Val Gln Pro Thr Phe Ser
1               5                   10
```

```
<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gln Asn Ser Ile Gln Pro Thr Phe Ser
1               5                   10

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp His Ser Asn Leu Asn Asp Thr Thr Tyr Gln Arg Thr Arg Ala Leu
1               5                   10                  15

Val Arg Thr Gly Met Asp Pro Arg Met
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp His Ser Asn Leu Asn Asp Ser Thr Tyr Gln Arg Thr Arg Ala Leu
1               5                   10                  15

Val Arg Thr Gly Met Asp Pro Arg Met
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp His Ser Asn Leu Asn Asp Ala Thr Tyr Gln Arg Lys Arg Ala Leu
1               5                   10                  15

Val Arg Thr Gly Met Asp Pro Arg Met
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp His Ser Asn Leu Asn Asp Ala Thr Tyr Gln Arg Thr Arg Ser Leu
1               5                   10                  15

Val Arg Thr Gly Met Asp Pro Arg Met
```

```
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp His Ser Asn Leu Asn Asp Ala Thr Tyr Gln Arg Thr Arg Ala Ile
1               5                   10                  15

Val Arg Thr Gly Met Asp Pro Arg Met
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp His Ser Asn Leu Asn Asp Ala Thr Tyr Gln Arg Thr Arg Ala Leu
1               5                   10                  15

Val Arg Ser Gly Met Asp Pro Arg Met
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp His Ser Asn Leu Asn Asp Ala Thr Tyr Gln Arg Thr Arg Ala Leu
1               5                   10                  15

Val Arg Thr Gly Arg Asp Pro Arg Met
            20                  25

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Tyr Ile Gln Met Cys Thr Glu Leu
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Tyr Asn Ala Glu Leu Leu Val Leu Leu
```

<210> SEQ ID NO 81
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ala Leu Asn Asn Arg Phe Gln Ile Lys Gly Val Glu Leu Lys Ser
1               5                   10                  15

Lys Thr Tyr Gln Arg Thr Arg Ala Leu Val Arg Val Lys Arg Glu Leu
            20                  25                  30

Arg Ser Arg Tyr Trp Ala Ile Arg Thr Arg Ser Gly Arg Val Lys Arg
        35                  40                  45

Phe Tyr Ile Gln Met Cys Thr Glu Leu Arg Val Lys Arg Thr Tyr Asn
    50                  55                  60

Ala Glu Leu Leu Val Leu Leu
65                  70

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Leu Arg Ser Arg His Trp Ala Ile Arg Thr Arg Ser Gly
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Leu Arg Ser Arg Tyr Trp Ala Ser Arg Thr Arg Ser Gly
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Met Phe Ser Asp Phe His Phe Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 85

Val Leu Arg Gly Ser Ile Ala His Lys
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Thr Phe Leu Ala Arg Ser Ala Leu
1               5

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ala Tyr Glu Arg Met Cys Asn Ile Leu Lys Gly Lys Phe Gln Thr
1               5                   10                  15

Ala Ala

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Ala Tyr Glu Arg Met Cys Asn Ile Ile Lys Gly Lys Phe Gln Thr
1               5                   10                  15

Ala Ala

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Ala Tyr Glu Arg Met Cys Asn Ile Leu Lys Gly Lys Phe Lys Thr
1               5                   10                  15

Ala Ala

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Ala Tyr Glu Arg Met Cys Asn Ile Leu Lys Gly Lys Phe Gln Ile
```

```
1               5                   10                  15

Ala Ala

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Ala Tyr Glu Arg Met Cys Asn Ile Leu Lys Gly Lys Phe Gln Thr
1               5                   10                  15

Ala Val

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Trp Gly Met Glu Leu Arg Arg Cys Leu Leu Gln Ser Leu Gln Gln
1               5                   10                  15

Ile

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Gln Ile Ser Val Gln Pro Thr Phe Ser
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gln Val Ser Val Gln Pro Thr Phe Ser
1               5                   10

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Glu Ala Gly Cys Lys Asn Phe Phe Pro Arg Ser Phe Thr Ser Cys
1               5                   10                  15

Gly Ser Leu Glu
```

20

```
<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Arg Arg Arg Arg Arg Arg Glu Ala Glu Ala Cys
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Gly Gly Gly Gly
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Ala Gly Ser Ala Ala Gly Ser Gly Glu Phe
1               5                   10

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Ser Gly Gly Gly Ser Gly
1               5                   10                  15

Gly Gly Gly Ser
            20

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Ser Gln Ala Val His Ala Ala His Ala Glu Ile Asn Glu Ala Gly
1               5                   10                  15

Arg

<210> SEQ ID NO 101
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Lys Phe Val Ala Ala Trp Thr Leu Lys Ala Ala Ala
1               5                  10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: L-cyclohexylalanine
<220> FEATURE:
<221> NAME/KEY: MOD_RES
<222> LOCATION: (14)..(14)
<223> OTHER INFORMATION: Aminocaproic acid

<400> SEQUENCE: 102

Ala Lys Xaa Val Ala Ala Trp Thr Leu Lys Ala Ala Ala Xaa Cys
1               5                  10                  15

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ala Leu Asn Asn Arg Phe Gln Ile Lys Gly Val Glu Leu Lys Ser
1               5                  10                  15

Lys

<210> SEQ ID NO 104
<211> LENGTH: 36519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
ccatcttcaa taatatacct caaactttt  gtgcgcgtta atatgcaaat gaggcgtttg       60
aatttgggga ggaagggcgg tgattggtcg agggatgagc gaccgttagg ggcggggcga      120
gtgacgtttt gatgacgtgg ttgcgaggag gagccagttt gcaagttctc gtgggaaaag      180
tgacgtcaaa cgaggtgtgg tttgaacacg gaaatactca attttcccgc gctctctgac      240
aggaaatgag gtgtttctgg gcggatgcaa gtgaaaacgg gccattttcg cgcgaaaact      300
gaatgaggaa gtgaaaatct gagtaatttc gcgtttatgg cagggaggag tatttgccga      360
gggccgagta gactttgacc gattacgtgg gggtttcgat taccgtgttt ttcacctaaa      420 ttccgcgta cggtgtcaaa gtccggtgtt tttacgtagg tgtcagctga tcgccagggt       480
atttaaacct gcgctctcca gtcaagaggc cactcttgag tgccagcgag aagagttttc      540
```

```
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gcccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc ataccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
accccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtgggt tgaacctttg gacttgtgta cccggaaacg ccccaggcac   1440
taagtgccac acatgtgtgt ttacttgagg tgatgtcagt atttataggg tgtggagtgc   1500
aataaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tcttttgac gctcttaact   1800
tgggccatca gtctcacttt aaccagagga tttcgagagc ccttgatttt actactcctg   1860
gcagaaccac tgcagcagta gcctttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttcttggg tttaataaca cctgcatcga ggcctggggt caggtcggtg tgaggggctg   2760
cagttttttca gccaactgga tggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
```

```
gcataaatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga ggggaggggta ttcagcccttt atctgacggg   3540
gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg aatggccat   3720
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata ataaacgga gacggttgtt gattttaaca   3960
cagagtctga atctttattt gatttttcgc gcgcggtagg ccctgaccg ccggtctcga   4020
tcattgagca cccggtggat cttttccagg acccggtaga ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
tctttgagga ggagactgat ggccacgggc agcccttttgg tgtaggtgtt tacaaatctg   4260
ttgagctggg agggatgcat gcggggggag atgaggtgca tcttggcctg gatcttgaga   4320
ttggcgatgt taccgcccag atcccgcctg gggttcatgt tgtgcaggac caccagcacg   4380
gtgtatccgg tgcacttggg gaatttatca tgcaacttgg aagggaaggc gtgaaagaat   4440
ttggcgacgc ctttgtgccc gcccaggttt ccatgcact catccatgat gatggcgatg   4500
ggcccgtggg cggcggcctg ggcaaagacg tttcgggggt cggacacatc atagttgtgg   4560
tcctgggtga ggtcatcata ggccatttta atgaatttgg ggcggagggt gccggactgg   4620
gggacaaagg taccctcgat cccggggcg tagttccct cacagatctg catctcccag   4680
gctttgagct cggaggggg gatcatgtcc acctgcgggg cgataaagaa cacggttccc   4740
ggggcggggg agatgagctg ggccgaaagc aagttccgga gcagctggga cttgccgcag   4800
ccggtgggc cgtagatgac cccgatgacc ggctgcaggt ggtagttgag ggagagacag   4860
ctgccgtcct cccggaggag gggggccacc tcgttcatca tctcgcgcac gtgcatgttc   4920
tcgcgcacca gttccgccag gaggcgctct ccccccaggg ataggagctc ctggagcgag   4980
gcgaagtttt tcagcggctt gagtccgtcg gccatgggca ttttggagag ggtttgttgc   5040
aagagttcca ggcggtccca gagctcgtg atgtgctcta cggcatctcg atccagcaga   5100
cctcctcgtt tcgcggggttg gacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
```

```
tggtcgaaaa ccgctcccga tcggcgccct gcgcgtcggc caggtagcaa ttgaccatga      5340
gttcgtagtt gagcgcctcg gccgcgtggc ctttggcgcg gagcttacct ttggaagtct      5400
gcccgcaggc gggacagagg agggacttga gggcgtagag cttgggggcg aggaagacgg      5460
actcgggggc gtaggcgtcc cgcgccgcagt gggcgcagac ggtctcgcac tccacgagcc      5520
aggtgaggtc gggctggtcg gggtcaaaaa ccagtttccc gccgttcttt ttgatgcgtt      5580
tcttaccttt ggtctccatg agctcgtgtc cccgctgggt gacaaagagg ctgtccgtgt      5640
ccccgtagac cgactttatg ggccggtcct cgagcggtgt gccgcggtcc tcctcgtaga      5700
ggaaccccgc ccactccgag acgaaagccc gggtccaggc cagcacgaag gaggccacgt      5760
gggacgggta gcggtcgttg tccaccagcg ggtccacctt ttccagggta tgcaaacaca      5820 tgtcccccctc gtccacatcc aggaaggtga ttggcttgta agtgtaggcc acgtgaccgg      5880
gggtcccggc cggggggggta taaaagggtg cgggtccctg ctcgtcctca ctgtcttccg      5940
gatcgctgtc caggagcgcc agctgttggg gtaggtattc cctctcgaag gcgggcatga      6000
cctcggcact caggttgtca gtttctagaa acgaggagga tttgatattg acggtgccgg      6060
cggagatgcc tttcaagagc ccctcgtcca tctggtcaga aaagacgatc ttttttgttgt      6120 cgagcttggt ggcgaaggag ccgtagaggg cgttggagag gagcttggcg atggagcgca      6180
tggtctggtt tttttccttg tcggcgcgct ccttggcggc gatgttgagc tgcacgtact      6240
cgcgcgccac gcacttccat tcggggaaga cggtggtcag ctcgtcgggc acgattctga      6300
cctgccagcc ccgattatgc agggtgatga ggtccacact ggtggccacc tcgccgcgca      6360
ggggctcatt agtccagcag aggcgtccgc ccttgcgcga gcagaagggg ggcagggggt      6420
ccagcatgac ctcgtcgggg gggtcggcat cgatggtgaa gatgccgggc aggaggtcgg      6480
ggtcaaagta gctgatggaa gtggccagat cgtccagggc agcttgccat cgcgcacgg      6540 ccagcgcgcg ctcgtaggga ctgaggggcg tgccccaggg catgggatgg gtaagcgcgg      6600
aggcgtacat gccgcagatg tcgtagacgt agagggctc ctcgaggatg ccgatgtagg      6660
tggggtagca gcgcccccg cggatgctgg cgcgcacgta gtcatacagc tcgtgcgagg      6720
gggcgaggag ccccgggccc aggttggtgc gactgggctt tcggcgcgg tagacgatct      6780 ggcggaaaat ggcatgcgag ttggaggaga tggtgggcct ttggaagatg ttgaagtggg      6840
cgtggggcag tccgaccgag tcgcggatga agtgggcgta ggagtcttgc agcttggcga      6900
cgagctcggc ggtgactagg acgtccagag cgcagtagtc gagggtctcc tggatgatgt      6960
catacttgag ctgtcccttt tgtttccaca gctcgcggtt gagaaggaac tcttcgcggt      7020
ccttccagta ctcttcgagg gggaacccgt cctgatctgc acggtaagag cctagcatgt      7080
agaactggtt gacggccttg taggcgcagc agcccttctc cacggggagg gcgtaggcct      7140
gggcggcctt gcgcagggag gtgtgcgtga gggcgaaagt gtccctgacc atgaccttga      7200
ggaactggtg cttgaagtcg atatcgtcgc agccccctg ctcccagagc tggaagtccg      7260
tgcgcttctt gtaggcgggg ttgggcaaag cgaaagtaac atcgttgaag aggatcttgc      7320
ccgcgcgggg cataaagttg cgagtgatgc ggaaaggttg gggcacctcg gcccggttgt      7380
tgatgacctg ggcggcgagc acgatctcgt cgaagccgtt gatgttgtgg cccacgatgt      7440
agagttccac gaatcgcgga cggcccttga cgtggggcag tttcttgagc tcctcgtagg      7500
tgagctcgtc ggggtcgctg agcccgtgct gctcgagcgc ccagtcggcg agatgggggt      7560
tggcgcggag gaaggaagtc cagagatcca cggccagggc ggtttgcaga cggtcccggt      7620
actgacggaa ctgctgcccg acggccattt tttcgggggt gacgcagtag aaggtgcggg      7680
```

```
ggtccccgtg ccagcgatcc catttgagct ggagggcgag atcgaggggcg agctcgacga    7740 gccggtcgtc cccggagagt ttcatgacca gcatgaaggg gacgagctgc ttgccgaagg    7800
accccatcca ggtgtaggtt tccacatcgt aggtgaggaa gagcctttcg gtgcgaggat    7860
gcgagccgat ggggaagaac tggatctcct gccaccaatt ggaggaatgg ctgttgatgt    7920
gatggaagta gaaatgccga cggcgcgccg aacactcgtg cttgtgttta tacaagcggc    7980
cacagtgctc gcaacgctgc acgggatgca cgtgctgcac gagctgtacc tgagttcctt    8040
tgacgaggaa tttcagtggg aagtggagtc gtggcgcctg catctcgtgc tgtactacgt    8100
cgtggtggtc ggcctggccc tcttctgcct cgatggtggt catgctgacg agcccgcgcg    8160
ggaggcaggt ccagacctcg gcgcgagcgg gtcggagagc gaggacgagg gcgcgcaggc    8220
cggagctgtc cagggtcctg agacgctgcg gagtcaggtc agtgggcagc ggcggcgcgc    8280
ggttgacttg caggagtttt tccagggcgc gcgggaggtc cagatggtac ttgatctcca    8340
ccgcgccatt ggtggcgacg tcgatggctt gcagggtccc gtgcccctgg ggtgtgacca    8400
ccgtcccccg tttcttcttg ggcggctggg gcgacggggg cggtgcctct tccatggtta    8460
gaagcggcgg cgaggacgcg cgccgggcgg caggggcggc tcggggcccg gaggcagggg    8520
cggcaggggc acgtcggcgc cgcgcgcggg taggttctgg tactgcgccc ggagaagact    8580
ggcgtgagcg acgacgcgac ggttgacgtc ctggatctga cgcctctggg tgaaggccac    8640
gggacccgtg agtttgaacc tgaaagagag ttcgacagaa tcaatctcgg tatcgttgac    8700
ggcggcctgc cgcaggatct cttgcacgtc gcccgagttg tcctggtagg cgatctcggt    8760
catgaactgc tcgatctcct cctcttgaag gtctccgcgg ccggcgcgct ccacggtggc    8820
cgcgaggtcg ttggagatgc ggcccatgag ctgcagaaag cgttcatgc ccgcctcgtt    8880 ccagacgcgg ctgtagacca cgacgccctc gggatcgccg gcgcgcatga ccacctgggc    8940
gaggttgagc tccacgtggc gcgtgaagac cgcgtagttg cagaggcgct ggtagaggta    9000
gttgagcgtg gtggcgatgt gctcggtgac gaagaaatac atgatccagc ggcggagcgg    9060
catctcgctg acgtcgccca cgcgctccaa acgttccatg gcctcgtaaa agtccacggc    9120
gaagttgaaa aactgggagt tgcgcgccga cacggtcaac tcctcctcca gaagacggat    9180
gagctcggcg atggtggcgc gcacctcgcg ctcgaaggcc cccgggagtt cctccacttc    9240
ctcttcttcc tcctccacta acatctcttc tacttcctcc tcaggcggca gtggtggcgg    9300
gggagggggc ctgcgtcgcc ggcggcgcac gggcagacgg tcgatgaagc gctcgatggt    9360
ctcgccgcgc cggcgtcgca tggtctcggt gacggcgcgc ccgtcctcgc ggggccgcag    9420
cgtgaagacg ccgccgcgca tctccaggtg gccgggggggg tccccgttgg gcaggagag    9480 ggcgctgacg atgcatctta tcaattgccc cgtagggact ccgcgcaagg acctgagcgt    9540
ctcgagatcc acgggatctg aaaaccgctg aacgaaggct tcgagccagt cgcagtcgca    9600
aggtaggctg agcacggttt cttctggcgg gtcatgttgg ttgggagcgg ggcgggcgat    9660
gctgctggtg atgaagttga aataggcggt tctgagacgg cggatggtgg cgaggagcac    9720
caggtctttg ggcccggctt gctggatgcg cagacggtcg gccatgcccc aggcgtggtc    9780
ctgacacctg gccaggtcct tgtagtagtc ctgcatgagc cgctccacgg gcacctcctc    9840
ctcgcccgcg cggccgtgca tgcgcgtgag cccgaagccg cgctggggct ggacgagcgc    9900
caggtcggcg acgacgcgct cggcgaggat ggcttgctgg atctgggtga gggtggtctg    9960
gaagtcatca aagtcgacga agcggtggta ggctccggtt ttgatggtgt aggagcagtt    10020
```

```
ggccatgacg gaccagttga cggtctggtg gcccggacgc acgagctcgt ggtacttgag   10080
gcgcgagtag gcgcgcgtgt cgaagatgta gtcgttgcag gtgcgcacca ggtactggta   10140
gccgatgagg aagtgcggcg gcggctggcg gtagagcggc catcgctcgg tggcgggggc   10200
gccgggcgcg aggtcctcga gcatggtgcg gtggtagccg tagatgtacc tggacatcca   10260
ggtgatgccg gcgcggtgg tggaggcgcg cgggaactcg cggacgcggt tccagatgtt   10320
gcgcagcggc aggaagtagt tcatggtggg cacggtctgg cccgtgaggc gcgcgcagtc   10380
gtggatgctc tatacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtattg gcactcccgt ctcgacccaa gcctgcacca accctccagg   10560
atacggaggc gggtcgtttt gcaactttt tttggaggcc ggatgagact agtaagcgcg   10620
gaaagcggcc gaccgcgatg gctcgctgcc gtagtctgga gaagaatcgc cagggttgcg   10680
ttgcggtgtg ccccggttcg aggccggccg gattccgcgg ctaacgaggg cgtggctgcc   10740
ccgtcgtttc caagaccca tagccagccg acttctccag ttacgagcg agccctctt   10800 ttgttttgtt tgttttgcc agatgcatcc cgtactgcgg cagatgcgcc cccaccaccc   10860
tccaccgcaa caacagcccc ctccacagcc ggcgcttctg cccccgcccc agcagcaact   10920
tccagccacg accgccgcgg ccgccgtgag cggggctgga cagagttatg atcaccagct   10980
ggccttggaa gagggcgagg ggctggcgcg cctgggggcg tcgtcgccgg agcggcaccc   11040
gcgcgtgcag atgaaaaggg acgctcgcga ggcctacgtg cccaagcaga acctgttcag   11100
agacaggagc ggcgaggagc ccgaggagat gcgcgcggcc cggttccacg cggggcggga   11160
gctgcggcgc ggcctggacc gaaagagggt gctgagggac gaggatttcg aggcggacga   11220
gctgacgggg atcagccccg cgcgcgcgca cgtggccgcg gccaacctgg tcacggcgta   11280
cgagcagacc gtgaaggagg agagcaactt ccaaaaatcc ttcaacaacc acgtgcgcac   11340
cctgatcgcg cgcgaggagg tgaccctggg cctgatgcac ctgtgggacc tgctggaggc   11400
catcgtgcag aaccccacca gcaagccgct gacggcgcag ctgttcctgg tggtgcagca   11460
tagtcgggac aacgaagcgt tcagggaggc gctgctgaat atcaccgagc ccgagggccg   11520
ctggctcctg gacctggtga acattctgca gagcatcgtg gtgcaggagc gcgggctgcc   11580
gctgtccgag aagctggcgg ccatcaactt ctcggtgctg agtttgggca agtactacgc   11640
taggaagatc tacaagaccc cgtacgtgcc catagacaag gaggtgaaga tcgacgggtt   11700
ttacatgcgc atgaccctga aagtgctgac cctgagcgac gatctggggg tgtaccgcaa   11760
cgacaggatg caccgtgcgg tgagcgccag caggcggcgc gagctgagcg accaggagct   11820
gatgcatagt ctgcagcggg ccctgaccgg ggccgggacc gagggggaga gctactttga   11880
catgggcgcg gacctgcact ggcagcccag ccgccgggcc ttggaggcgg cggcaggacc   11940
ctacgtagaa gaggtggacg atgaggtgga cgaggagggc gagtacctgg aagactgatg   12000
gcgcgaccgt attttgcta gatgcaacaa caacagccac ctcctgatcc cgcgatgcgg   12060
gcggcgctgc agagccagcc gtccggcatt aactcctcgg acgattggac ccaggccatg   12120
caacgcatca tggcgctgac gacccgcaac cccgaagcct ttagacagca gcccaggcc   12180 aaccggctct cggccatcct ggaggccgtg gtgccctcgc gctccaaccc cacgcacgag   12240
aaggtcctgg ccatcgtgaa cgcgctggtg gagaacaagg ccatccgcgg cgacgaggcc   12300
ggcctggtgt acaacgcgct gctggagcgc gtggcccgct acaacagcac caacgtgcag   12360
accaacctgg accgcatggt gaccgacgtg cgcgaggccg tggcccagcg cgagcggttc   12420
```

```
caccgcgagt ccaacctggg atccatggtg gcgctgaacg ccttcctcag cacccagccc   12480
gccaacgtgc cccggggcca ggaggactac accaacttca tcagcgccct gcgcctgatg   12540
gtgaccgagg tgccccagag cgaggtgtac cagtccgggc cggactactt cttccagacc   12600
agtcgccagg gcttgcagac cgtgaacctg agccaggctt tcaagaactt gcagggcctg   12660
tggggcgtgc aggccccggt cggggaccgc gcgacggtgt cgagcctgct gacgccgaac   12720
tcgcgcctgc tgctgctgct ggtggccccc ttcacggaca cgcgcagcat caaccgcaac   12780
tcgtacctgg gctacctgat taacctgtac cgcgaggcca tcggccaggc gcacgtggac   12840
gagcagacct accaggagat cacccacgtg agccgcgccc tgggccagga cgacccgggc   12900
aacctggaag ccaccctgaa cttttttgctg accaaccggt cgcagaagat cccgccccag   12960
tacgcgctca gcaccgagga ggagcgcatc ctgcgttacg tgcagcagag cgtgggcctg   13020
ttcctgatgc aggaggggc cacccccagc gccgcgctcg acatgaccgc gcgcaacatg   13080
gagcccagca tgtacgccag caaccgcccg ttcatcaata aactgatgga ctacttgcat   13140
cgggcggccg ccatgaactc tgactatttc accaacgcca tcctgaatcc ccactggctc   13200
ccgccgccgg ggttctacac gggcgagtac gacatgcccg accccaatga cgggttcctg   13260
tgggacgatg tggacagcag cgtgttctcc ccccgaccgg gtgctaacga gcgcccttg   13320 tggaagaagg aaggcagcga ccgacgcccg tcctcggcgc tgtccggccg cgagggtgct   13380
gccgcggcgg tgcccgaggc cgccagtcct ttcccgagct tgcccttctc gctgaacagt   13440
atccgcagca gcgagctggg caggatcacg cgcccgcgct tgctgggcga agaggagtac   13500
ttgaatgact cgctgttgag acccgagcgg gagaagaact tccccaataa cgggatagaa   13560
agcctggtgg acaagatgag ccgctggaag acgtatgcgc aggagcacag ggacgatccc   13620
cgggcgtcgc aggggccac gagccggggc agcgccgccc gtaaacgccg gtggcacgac   13680
aggcagcggg gacagatgtg ggacgatgag gactccgccg acgacagcag cgtgttggac   13740
ttgggtggga gtggtaaccc gttcgctcac ctgcgccccc gtatcgggcg catgatgtaa   13800
gagaaaccga aaataaatga tactcaccaa ggccatggcg accagcgtgc gttcgtttct   13860
tctctgttgt tgttgtatct agtatgatga ggcgtgcgta cccggagggt cctcctccct   13920
cgtacgagag cgtgatgcag caggcgatgg cggcggcggc gatgcagccc ccgctggagg   13980
ctccttacgt gccccgcgg tacctggcgc ctacggaggg gcggaacagc attcgttact   14040
cggagctggc acccttgtac gataccaccc ggttgtacct ggtggacaac aagtcggcgg   14100
acatcgcctc gctgaactac cagaacgacc acagcaactt cctgaccacc gtggtgcaga   14160
acaatgactt caccccccacg gaggccagca cccagaccat caactttgac gagcgctcgc   14220
ggtggggcgg ccagctgaaa accatcatgc acaccaacat gccaacgtg aacgagttca   14280 tgtacagcaa caagttcaag gcgcgggtga tggtctcccg caagaccccc aatggggtga   14340
cagtgacaga ggattatgat ggtagtcagg atgagctgaa gtatgaatgg gtggaatttg   14400
agctgcccga aggcaacttc tcggtgacca tgaccatcga cctgatgaac aacgccatca   14460
tcgacaatta cttggcggtg gggcggcaga acgggtgct ggagagcgac atcggcgtga   14520
agttcgacac taggaacttc aggctgggct gggaccccgt gaccgagctg gtcatgcccg   14580
gggtgtacac caacgaggct ttccatcccg atattgtctt gctgcccggc tgcggggtgg   14640
acttcaccga gagccgcctc agcaacctgc tgggcattcg caagaggcag cccttccagg   14700
aaggcttcca gatcatgtac gaggatctgg agggggcaa catccccgcg ctcctggatg   14760
```

```
tcgacgccta tgagaaaagc aaggaggatg cagcagctga agcaactgca gccgtagcta    14820
ccgcctctac cgaggtcagg ggcgataatt ttgcaagcgc cgcagcagtg gcagcggccg    14880
aggcggctga aaccgaaagt aagatagtca ttcagccggt ggagaaggat agcaagaaca    14940
ggagctacaa cgtactaccg gacaagataa acaccgccta ccgcagctgg tacctagcct    15000
acaactatgg cgaccccgag aagggcgtgc gctcctggac gctgctcacc acctcggacg    15060
tcacctgcgg cgtggagcaa gtctactggt cgctgcccga catgatgcaa gacccggtca    15120
ccttccgctc cacgcgtcaa gttagcaact acccggtggt gggcgccgag ctcctgcccg    15180
tctactccaa gagcttcttc aacgagcagg ccgtctactc gcagcagctg cgcgccttca    15240
cctcgcttac gcacgtcttc aaccgcttcc ccgagaacca gatcctcgtc cgcccgcccg    15300
cgcccaccat taccaccgtc agtgaaaacg ttcctgctct cacagatcac gggaccctgc    15360
cgctgcgcag cagtatccgg ggagtccagc gcgtgaccgt tactgacgcc agacgccgca    15420
cctgccccta cgtctacaag gccctgggca tagtcgcgcc gcgcgtcctc tcgagccgca    15480
ccttctaaat gtccattctc atctcgccca gtaataacac cggttgggc ctgcgcgcgc    15540 ccagcaagat gtacggaggc gctcgccaac gctccacgca acaccccgtg cgcgtgcgcg    15600
ggcacttccg cgctccctgg ggcgccctca agggccgcgt gcggtcgcgc accaccgtcg    15660
acgacgtgat cgaccaggtg gtggccgacg cgcgcaacta cacccccgcc gccgcgcccg    15720
tctccaccgt ggacgccgtc atcgacgcg tggtggcgga cgcgcgccgg tacgcccgcg    15780
ccaagagccg gcggcggcgc atcgcccggc ggcaccggag cacccccgcc atgcgcgcgg    15840
cgcgagcctt gctgcgcagg gccaggcgca cgggacgcag ggccatgctc agggcggcca    15900
gacgcgcggc ttcaggcgcc agcgccggca ggacccggag acgcgcggcc acggcggcgg    15960
cagcggccat cgccagcatg tcccgcccgc ggcgagggaa cgtgtactgg gtgcgcgacg    16020
ccgccaccgg tgtgcgcgtg cccgtgcgca cccgcccccc tcgcacttga agatgttcac    16080
ttcgcgatgt tgatgtgtcc cagcggcgag gaggatgtcc aagcgcaaat tcaaggaaga    16140
gatgctccag gtcatcgcgc ctgagatcta cggccctgcg gtggtgaagg aggaaagaaa    16200
gccccgcaaa atcaagcggg tcaaaaagga caaaaaggaa gaagaaagtg atgtggacgg    16260
attggtggag tttgtgcgcg agttcgcccc ccggcggcgc gtgcagtggc gcgggcggaa    16320
ggtgcaaccg gtgctgagac ccggcaccac cgtggtcttc acgcccggcg agcgctccgg    16380
caccgcttcc aagcgctcct acgacgaggt gtacgggat gatgatattc tggagcaggc    16440
ggccgagcgc ctgggcgagt ttgcttacgg caagcgcagc cgttccgcac cgaaggaaga    16500
ggcggtgtcc atcccgctgg accacggcaa ccccacgccg agcctcaagc ccgtgacctt    16560
gcagcaggtg ctgccgaccg cggcgccgcg ccggggttc aagcgcgagg gcgaggatct    16620
gtaccccacc atgcagctga tggtgcccaa cgccagaag ctggaagacg tgctggagac    16680
catgaaggtg gacccggacg tgcagcccga ggtcaaggtg cggcccatca agcaggtggc    16740
cccgggcctg ggcgtgcaga ccgtggacat caagattccc acggagccca tggaaacgca    16800
gaccgagccc atgatcaagc ccagcaccag caccatggag gtgcagacgg atccctggat    16860
gccatcggct cctagtcgaa gaccccgcg caagtacggc gcggccagcc tgctgatgcc    16920
caactacgcg ctgcatcctt ccatcatccc cacgccgggc taccgcggca cgcgcttcta    16980
ccgcggtcat accagcagcc gccgccgcaa gaccaccact cgccgccgcc gtcgccgcac    17040
cgccgctgca accaccccctg ccgccctggt gcggagagtg taccgccgcg gccgcgcacc    17100 tctgacccctg ccgcgcgcgc gctaccaccc gagcatcgcc atttaaactt cgccagctt    17160
```

```
tgcagatcaa tggccctcac atgccgcctt cgcgttccca ttacgggcta ccgaggaaga    17220
aaaccgcgcc gtagaaggct ggcggggaac gggatgcgtc gccaccacca ccggcggcgg    17280
cgcgccatca gcaagcggtt gggggggaggc ttcctgcccg cgctgatccc catcatcgcc   17340
gcggcgatcg gggcgatccc cggcattgct tccgtggcgg tgcaggcctc tcagcgccac    17400
tgagacacac ttggaaacat cttgtaataa acccatggac tctgacgctc ctggtcctgt    17460
gatgtgtttt cgtagacaga tggaagacat caattttcg tccctggctc cgcgacacgt     17520
cacgcggccg ttcatgggca cctggagcga catcggcacc agccaactga acggggcgc     17580 cttcaattgg agcagtctct ggagcgggct taagaatttc gggtccacgc ttaaaaccta    17640
tggcagcaag gcgtggaaca gcaccacagg gcaggcgctg agggataagc tgaaagagca    17700
gaacttccag cagaaggtgg tcgatgggct cgcctcgggc atcaacgggg tggtggacct    17760
ggccaaccag gccgtgcagc ggcagatcaa cagccgcctg acccggtgc cgcccgccgg     17820 ctccgtggag atgccgcagg tggaggagga gctgcctccc ctggacaagc ggggcgagaa    17880 gcgacccgc ccgatgcgg aggagacgct gctgacgcac acggacgagc cgccccgta      17940 cgaggaggcg gtgaaactgg gtctgcccac cacgcgcccc atcgcgcccc tggccaccgg    18000
ggtgctgaaa cccgaaaagc ccgcgaccct ggacttgcct cctccccagc cttcccgccc    18060
ctctacagtg gctaagcccc tgccgccggt ggccgtggcc cgcgcgcgac ccggggggcac   18120 cgcccgccct catgcgaact ggcagagcac tctgaacagc atcgtgggtc tgggagtgca    18180
gagtgtgaag cgccgccgct gctattaaac ctaccgtagc gcttaacttg cttgtctgtg    18240
tgtgtatgta ttatgtcgcc gccgccgctg tccaccagaa ggaggagtga agaggcgcgt    18300
cgccgagttg caagatggcc acccccatcga tgctgcccca gtgggcgtac atgcacatcg    18360
ccggacagga cgcttcggag tacctgagtc cgggtctggt gcagtttgcc cgcgccacag    18420
acacctactt cagtctgggg aacaagttta ggaaccccac ggtggcgccc acgcacgatg    18480
tgaccaccga ccgcagccag cggctgacgc tgcgcttcgt gcccgtggac cgcgaggaca    18540
acacctactc gtacaaagtg cgctacacgc tggccgtggg cgacaaccgc gtgctggaca    18600
tggccagcac ctactttgac atccgcggcg tgctggatcg gggccctagc ttcaaaccct    18660
actccggcac cgcctacaac agtctggccc ccaagggagc acccaacact tgtcagtgga    18720
catataaagc cgatggtgaa actgccacag aaaaaaccta tacatatgga aatgcacccg    18780
tgcagggcat taacatcaca aaagatggta ttcaacttgg aactgacacc gatgatcagc    18840
caatctacgc agataaaacc tatcagcctg aacctcaagt gggtgatgct gaatggcatg    18900
acatcactgg tactgatgaa aagtatggag gcagagctct taagcctgat accaaaatga    18960
agccttgtta tggttctttt gccaagccta ctaataaaga aggaggtcag gcaaatgtga    19020
aaacaggaac aggcactact aaagaatatg acatagacat ggctttcttt gacaacagaa    19080
gtgcggctgc tgctggccta gctccagaaa ttgttttgta tactgaaaat gtggatttgg    19140
aaactccaga tacccatatt gtatacaaag caggcacaga tgacagcagc tcttctatta    19200
atttgggtca gcaagccatg cccaacagac taactacat tggtttcaga gacaactta       19260 tcgggctcat gtactacaac agcactggca atatgggggt gctggccggt caggcttctc    19320
agctgaatgc tgtggttgac ttgcaagaca gaaacaccga gctgtcctac cagctcttgc    19380
ttgactctct gggtgacaga acccggtatt tcagtatgtg gaatcaggcg gtggacagct    19440
atgatcctga tgtgcgcatt attgaaaatc atggtgtgga ggatgaactt cccaactatt    19500
```

```
gtttccctct ggatgctgtt ggcagaacag atacttatca gggaattaag gctaatggaa    19560
ctgatcaaac cacatggacc aaagatgaca gtgtcaatga tgctaatgag ataggcaagg    19620
gtaatccatt cgccatggaa atcaacatcc aagccaacct gtggaggaac ttcctctacg    19680
ccaacgtggc cctgtacctg cccgactctt acaagtacac gccggccaat gttaccctgc    19740
ccaccaacac caacacctac gattacatga acggcgggt ggtggcgccc tcgctggtgg    19800
actcctacat caacatcggg gcgcgctggt cgctggatcc catggacaac gtgaacccct    19860
tcaaccacca ccgcaatgcg gggctgcgct accgctccat gctcctgggc aacgggcgct    19920
acgtgccctt ccacatccag gtgccccaga aattttttcgc catcaagagc ctcctgctcc    19980
tgcccgggtc ctacacctac gagtggaact tccgcaagga cgtcaacatg atcctgcaga    20040
gctccctcgg caacgacctg cgcacggacg gggcctccat ctccttcacc agcatcaacc    20100
tctacgccac cttcttcccc atggcgcaca acacggcctc cacgctcgag gccatgctgc    20160
gcaacgacac caacgaccag tccttcaacg actacctctc ggcggccaac atgctctacc    20220
ccatcccggc caacgccacc aacgtgccca tctccatccc ctcgcgcaac tgggccgcct    20280
tccgcggctg gtccttcacg cgtctcaaga ccaaggagac ccctcgctg ggctccgggt    20340 tcgaccccta cttcgtctac tcgggctcca tcccctacct cgacggcacc ttctacctca    20400
accacacctt caagaaggtc tccatcacct tcgactcctc cgtcagctgg cccggcaacg    20460
accggctcct gacgcccaac gagttcgaaa tcaagcgcac cgtcgacggc gagggctaca    20520
acgtggccca gtgcaacatg accaaggact ggttcctggt ccagatgctg gcccactaca    20580
acatcggcta ccagggcttc tacgtgcccg agggctacaa ggaccgcatg tactccttct    20640
tccgcaactt ccagcccatg agccgccagg tggtggacga ggtcaactac aaggactacc    20700
aggccgtcac cctggcctac cagcacaaca actcgggctt cgtcggctac ctcgcgccca    20760
ccatgcgcca gggccagccc taccccgcca actacccta cccgctcatc ggcaagagcg    20820
ccgtcaccag cgtcacccag aaaaagttcc tctgcgacag ggtcatgtgg cgcatccct    20880 tctccagcaa cttcatgtcc atgggcgcgc tcaccgacct cggccagaac atgctctatg    20940
ccaactccgc ccacgcgcta gacatgaatt tcgaagtcga ccccatggat gagtccaccc    21000
ttctctatgt tgtcttcgaa gtcttcgacg tcgtccgagt gcaccagccc caccgcggcg    21060
tcatcgaggc cgtctacctg cgcacccct tctcggccgg taacgccacc acctaagctc    21120
ttgcttcttg caagccatgg ccgcgggctc cggcgagcag gagctcaggg ccatcatccg    21180
cgacctgggc tgcgggccct acttcctggg caccttcgat aagcgcttcc cgggattcat    21240
ggccccgcac aagctggcct gcgccatcgt caacacggcc ggccgcgaga ccgggggcga    21300
gcactggctg gccttcgcct ggaacccgcg ctcgaacacc tgctacctct tcgacccctt    21360
cgggttctcg gacgagcgcc tcaagcagat ctaccagttc gagtacgagg gcctgctgcg    21420
ccgcagcgcc ctggccaccg aggaccgctg cgtcaccctg gaaaagtcca cccagaccgt    21480
gcagggtccg cgctcggccg cctgcgggct cttctgctgc atgttcctgc acgccttcgt    21540
gcactggccc gaccgcccca tggacaagaa ccccaccatg aacttgctga cggggtgcc    21600 caacggcatg ctccagtcgc cccaggtgga acccaccctg cgccgcaacc aggaggcgct    21660
ctaccgcttc ctcaactccc actccgccta ctttcgctcc caccgcgcgc gcatcgagaa    21720
ggccaccgcc ttcgaccgca tgaatcaaga catgtaaacc gtgtgtgtat gttaaatgtc    21780
tttaataaac agcactttca tgttacacat gcatctgaga tgatttattt agaaatcgaa    21840
agggttctgc cgggtctcgg catggcccgc gggcagggac acgttgcgga actggtactt    21900
```

```
ggccagccac ttgaactcgg ggatcagcag tttgggcagc ggggtgtcgg ggaaggagtc    21960
ggtccacagc ttccgcgtca gttgcagggc gcccagcagg tcgggcgcgg agatcttgaa    22020
atcgcagttg ggacccgcgt tctgcgcgcg ggagttgcgg tacacggggt tgcagcactg    22080
gaacaccatc agggccgggt gcttcacgct cgccagcacc gtcgcgtcgg tgatgctctc    22140
cacgtcgagg tcctcggcgt tggccatccc gaaggggatc atcttgcagg tctgccttcc    22200
catggtgggc acgcacccgg gcttgtggtt gcaatcgcag tgcaggggga tcagcatcat    22260
ctgggcctgg tcggcgttca tccccgggta catggccttc atgaaagcct ccaattgcct    22320
gaacgcctgc tgggccttgg ctccctcggt gaagaagacc ccgcaggact tgctagagaa    22380
ctggttggtg gcgcacccgg cgtcgtgcac gcagcagcgc gcgtcgttgt tggccagctg    22440
caccacgctg cgccccccagc ggttctgggt gatcttggcc cggtcggggt tctccttcag    22500
cgcgcgctgc ccgttctcgc tcgccacatc catctcgatc atgtgctcct tctggatcat    22560
ggtggtcccg tgcaggcacc gcagcttgcc ctcggcctcg gtgcacccgt gcagccacag    22620
cgcgcacccg gtgcactccc agttcttgtg ggcgatctgg gaatgcgcgt gcacgaagcc    22680
ctgcaggaag cggcccatca tggtggtcag ggtcttgttg ctagtgaagg tcagcggaat    22740
gccgcggtgc tcctcgttga tgtacaggtg gcagatgcgg cggtacacct cgccctgctc    22800
gggcatcagc tggaagttgg cttttcaggtc ggtctccacg cggtagcggt ccatcagcat    22860
agtcatgatt tccatacccct tctcccaggc cgagacgatg ggcaggctca tagggttctt    22920
caccatcatc ttagcgctag cagccgcggc caggggggtcg ctctcgtcca gggtctcaaa    22980
gctccgcttg ccgtccttct cggtgatccg caccgggggg tagctgaagc ccacggccgc    23040
cagctcctcc tcggcctgtc tttcgtcctc gctgtcctgg ctgacgtcct gcaggaccac    23100
atgcttggtc ttgcggggtt tcttcttggg cggcagcggc ggcggagatg ttggagatgg    23160 cgaggggggag cgcagttct cgctcaccac tactatctct tcctcttctt ggtccgaggc    23220
cacgcggcgg taggtatgtc tcttcggggg cagaggcgga ggcgacgggc tctcgccgcc    23280
gcgacttggc ggatggctgg cagagcccct tccgcgttcg ggggtgcgct cccggcggcg    23340
ctctgactga cttcctccgc ggccggccat tgtgttctcc tagggaggaa caacaagcat    23400
ggagactcag ccatcgccaa cctcgccatc tgcccccacc gccgacgaga agcagcagca    23460
gcagaatgaa agcttaaccg ccccgccgcc cagccccgcc acctccgacg cggccgtccc    23520
agacatgcaa gagatggagg aatccatcga gattgacctg ggctatgtga cgcccgcgga    23580
gcacgaggag gagctggcag tgcgcttttc acaagaagag atacaccaag aacagccaga    23640
gcaggaagca gagaatgagc agagtcaggc tgggctcgag catgacggcg actacctcca    23700
cctgagcggg gggaggacg cgctcatcaa gcatctggcc cggcaggcca ccatcgtcaa    23760
ggatgcgctg ctcgaccgca ccgaggtgcc cctcagcgtg gaggagctca gccgcgccta    23820
cgagttgaac ctcttctcgc cgcgcgtgcc ccccaagcgc cagcccaatg gcacctgcga    23880
gcccaacccg cgcctcaact tctacccggt cttcgcggtg cccgaggccc tggccaccta    23940
ccacatcttt ttcaagaacc aaaagatccc cgtctcctgc cgcgccaacc gcacccgcgc    24000
cgacgccctt ttcaacctgg gtcccggcgc ccgcctacct gatatcgcct ccttggaaga    24060
ggttcccaag atcttcgagg gtctgggcag cgacgagact cgggccgcga acgctctgca    24120
aggagaagga ggagagcatg agcaccacag cgccctggtc gagttggaag gcgacaacgc    24180
gcggctggcg gtgctcaaac gcacggtcga gctgacccat ttcgcctacc cggctctgaa    24240
```

```
cctgcccccc aaagtcatga gcgcggtcat ggaccaggtg ctcatcaagc gcgcgtcgcc    24300
catctccgag gacagggggca tgcaagactc cgaggagggc aagcccgtgg tcagcgacga    24360
gcagctggcc cggtggctgg gtcctaatgc tagtcccag agtttggaag agcggcgcaa     24420
actcatgatg gccgtggtcc tggtgaccgt ggagctggag tgcctgcgcc gcttcttcgc    24480
cgacgcggag accctgcgca aggtcgagga aacctgcac tacctcttca ggcacgggtt     24540
cgtgcgccag gcctgcaaga tctccaacgt ggagctgacc aacctggtct cctacatggg    24600
catcttgcac gagaaccgcc tggggcagaa cgtgctgcac accaccctgc gcggggaggc    24660
ccggcgcgac tacatccgcg actgcgtcta cctctacctc tgccacacct ggcagacggg    24720
catgggcgtg tggcagcagt gtctggagga gcagaacctg aaagagctct gcaagctcct    24780
gcagaagaac ctcaagggtc tgtggaccgg gttcgacgag cgcaccaccg cctcggacct    24840
ggccgacctc attttccccg agcgcctcag gctgacgctg cgcaacggcc tgcccgactt    24900
tatgagccaa agcatgttgc aaaactttcg ctctttcatc ctcgaacgct ccggaatcct    24960
gcccgccacc tgctccgcgc tgccctcgga cttcgtgccg ctgaccttcc gcgagtgccc    25020
cccgccgctg tggagccact gctacctgct gcgcctggcc aactacctgg cctaccactc    25080
ggacgtgatc gaggacgtca gcggcgaggg cctgctcaga tgccactgcc gctgcaacct    25140
ctgcacgccg caccgctccc tggcctgcaa ccccccagctg ctgagcgaga cccagatcat    25200
cggcaccttc gagttgcaag ggcccagcga aggcgagggt tcagccgcca agggggggtct    25260
gaaactcacc ccggggctgt ggacctcggc ctacttgcgc aagttcgtgc ccgaggacta    25320
ccatcccttc gagatcaggt tctacgagga ccaatcccat ccgcccaagg ccgagctgtc    25380
ggcctgcgtc atcacccagg gggcgatcct ggcccaattg caagccatcc agaaatcccg    25440
ccaagaattc ttgctgaaaa agggccgcgg ggtctacctc gacccccaga ccggtgagga    25500
gctcaacccc ggcttccccc aggatgcccc gaggaaacaa gaagctgaaa gtggagctgc    25560
cgcccgtgga ggatttggag gaagactggg agaacagcag tcaggcagag gaggaggaga    25620
tggaggaaga ctgggacagc actcaggcag aggaggacag cctgcaagac agtctggagg    25680
aagacgagga ggaggcagag gaggaggtgg aagaagcagc cgccgccaga ccgtcgtcct    25740
cggcggggga gaaagcaagc agcacggata ccatctccgc tccgggtcgg ggtcccgctc    25800
gaccacacag tagatgggac gagaccggac gattcccgaa ccccaccacc cagaccggta    25860
agaaggagcg gcagggatac aagtcctggc gggggcacaa aaacgccatc gtctcctgct    25920
tgcaggcctg cgggggcaac atctccttca cccggcgcta cctgctcttc caccgcgggg    25980
tgaactttcc ccgcaacatc ttgcattact accgtcacct ccacagcccc tactacttcc    26040
aagaagaggc agcagcagca gaaaaagacc agcagaaaac cagcagctag aaaatccaca    26100
gcggcggcag caggtggact gaggatcgcg gcgaacgagc cggcgcaaac ccgggagctg    26160
aggaaccgga tctttcccac cctctatgcc atcttccagc agagtcgggg gcaggagcag    26220
gaactgaaag tcaagaaccg ttctctgcgc tcgctcaccc gcagttgtct gtatcacaag    26280
agcgaagacc aacttcagcg cactctcgag gacgccgagg ctctcttcaa caagtactgc    26340
gcgctcactc ttaaagagta gcccgcgccc gcccagtcgc agaaaaaggc gggaattacg    26400
tcacctgtgc ccttcgccct agccgcctcc acccatcatc atgagcaaag agattcccac    26460
gccttacatg tggagctacc agccccagat gggcctggcc gccggtgccg cccaggacta    26520
ctccacccgc atgaattggc tcagcgccgg gccgcgatg atctcacggg tgaatgacat    26580
ccgcgcccac cgaaaccaga tactcctaga acagtcagcg ctcaccgcca cgccccgcaa    26640
```

```
tcacctcaat ccgcgtaatt ggcccgccgc cctggtgtac caggaaattc cccagcccac    26700
gaccgtacta cttccgcgag acgcccaggc cgaagtccag ctgactaact caggtgtcca    26760
gctggcgggc ggcgccaccc tgtgtcgtca ccgccccgct cagggtataa agcggctggt    26820
gatccggggc agaggcacac agctcaacga cgaggtggtg agctcttcgc tgggtctgcg    26880
acctgacgga gtcttccaac tcgccggatc ggggagatct tccttcacgc ctcgtcaggc    26940
cgtcctgact ttggagagtt cgtcctcgca gccccgctcg ggtggcatcg gcactctcca    27000
gttcgtggag gagttcactc cctcggtcta cttcaacccc ttctccggct ccccggcca    27060 ctaccccggac gagttcatcc cgaacttcga cgccatcagc gagtcggtgg acggctacga    27120
ttgaatgtcc catggtggcg cagctgacct agctcggctt cgacacctgg accactgccg    27180
ccgcttccgc tgcttcgctc gggatctcgc cgagtttgcc tactttgagc tgcccgagga    27240
gcaccctcag ggcccggccc acggagtgcg gatcgtcgtc aagggggcc tcgactccca    27300 cctgcttcgg atcttcagcc agcgtccgat cctggtcgag cgcgagcaag acagaccct    27360 tctgactctg tactgcatct gcaaccaccc cggcctgcat gaaagtcttt gttgtctgct    27420
gtgtactgag tataataaaa gctgagatca gcgactactc cggacttccg tgtgttcctg    27480
aatccatcaa ccagtctttg ttcttcaccg ggaacgagac cgagctccag ctccagtgta    27540
agccccacaa gaagtacctc acctggctgt tccagggctc cccgatcgcc gttgtcaacc    27600
actgcgacaa cgacggagtc ctgctgagcg gccctgccaa ccttactttt tccacccgca    27660
gaagcaagct ccagctcttc caacccttcc tccccgggac ctatcagtgc gtctcgggac    27720
cctgccatca caccttccac ctgatcccga ataccacagc gtcgctcccc gctactaaca    27780
accaaactaa cctccaccaa cgccaccgtc gcgacctttc tgaatctaat actaccaccc    27840
acaccggagg tgagctccga ggtcaaccaa cctctgggat ttactacggc ccctgggagg    27900
tggttgggtt aatagcgcta ggcctagttg cgggtgggct tttggttctc tgctacctat    27960
acctcccttg ctgttcgtac ttagtggtgc tgtgttgctg gtttaagaaa tggggaagat    28020
caccctagtg agctgcggtg cgctggtggc ggtgttgctt tcgattgtgg gactgggcgg    28080
tgcggctgta gtgaaggaga aggccgatcc ctgcttgcat ttcaatccca acaaatgcca    28140
gctgagtttt cagcccgatg gcaatcggtg cgcggtactg atcaagtgcg gatgggaatg    28200
cgagaacgtg agaatcgagt acaataacaa gactcggaac aatactctcg cgtccgtgtg    28260
gcagcccggg gaccccgagt ggtacaccgt ctctgtcccc ggtgctgacg gctccccgcg    28320
caccgtgaat aatactttca ttttttgcgca catgtgcgac acggtcatgt ggatgagcaa    28380
gcagtacgat atgtggcccc ccacgaagga gaacatcgtg gtcttctcca tcgcttacag    28440
cctgtgcacg gcgctaatca ccgctatcgt gtgcctgagc attcacatgc tcatcgctat    28500
tcgccccaga aataatgccg aaaaagaaaa acagccataa cgttttttt cacaccttt    28560 tcagaccatg gcctctgtta aattttgct tttatttgcc agtctcattg ccgtcattca    28620
tggaatgagt aatgagaaaa ttactattta cactggcact aatcacacat tgaaaggtcc    28680 agaaaagcc acagaagttt catggtattg ttattttaat gaatcagatg tatctactga    28740
actctgtgga aacaataaca aaaaaaatga gagcattact ctcatcaagt ttcaatgtgg    28800
atctgactta accctaatta acatcactag agactatgta ggtatgtatt atggaactac    28860
agcaggcatt tcggacatgg aattttatca agtttctgtg tctgaaccca ccacgccag    28920 aatgaccaca accacaaaaa ctacacctgt taccactatg cagctcacta ccaataacat    28980
```

```
ttttgccatg cgtcaaatgg tcaacaatag cactcaaccc accccaccca gtgaggaaat    29040
tcccaaatcc atgattggca ttattgttgc tgtagtggtg tgcatgttga tcatcgcctt    29100
gtgcatggtg tactatgcct tctgctacag aaagcacaga ctgaacgaca agctggaaca    29160
cttactaagt gttgaatttt aattttttag aaccatgaag atcctaggcc ttttaatttt    29220
ttctatcatt acctctgctc tatgcaattc tgacaatgag gacgttactg tcgttgtcgg    29280
atcaaattat acactgaaag gtccagcgaa gggtatgctt tcgtggtatt gctattttgg    29340
atctgacact acagaaactg aattatgcaa tcttaagaat ggcaaaattc aaaattctaa    29400
aattaacaat tatatatgca atggtactga tctgatactc ctcaatatca cgaaatcata    29460
tgctggcagt tacacctgcc ctggagatga tgctgacagt atgatttttt acaaagtaac    29520
tgttgttgat cccactactc cacctccacc caccacaact actcacacca cacacacaga    29580
tcaaaccgca gcagaggagg cagcaaagtt agccttgcag gtccaagaca gttcatttgt    29640
tggcattacc cctacacctg atcagcggtg tccggggctg ctagtcagcg gcattgtcgg    29700
tgtgctttcg ggattagcag tcataatcat ctgcatgttc attttgctt gctgctatag     29760 aaggctttac cgacaaaaat cagacccact gctgaacctc tatgtttaat ttttccaga    29820 gtcatgaagg cagttagcgc tctagttttt tgttctttga ttggcattgt tttttgcaat    29880
cctattccta agttagctt tattaaagat gtgaatgtta ctgaggggg caatgtgaca     29940 ctggtaggtg tagagggtgc tgaaaacacc acctggacaa ataccacct caatgggtgg     30000 aaagatattt gcaattggag tgtattagtt tatacatgtg agggagttaa tcttaccatt    30060
gtcaatgcca cctcagctca aatggtaga attcaaggac aaagtgtcag tgtatctaat     30120
gggtatttta cccaacatac ttttatctat gacgttaaag tcataccact gcctacgcct    30180
agcccaccta gcactaccac acagacaacc cacactacac agacaaccac atacagtaca    30240
ttaaatcagc ctaccaccac tacagcagca gaggttgcca gctcgtctgg ggtccgagtg    30300 gcattttga tgtgggcccc atctagcagt cccactgcta gtaccaatga gcagactact     30360
gaatttttgt ccactgtcga gagccacacc acagctacct ccagtgcctt tctctagcacc    30420 gccaatctct cctcgctttc ctctacacca atcagtcccg ctactactcc tagccccgct    30480
cctcttccca ctcccctgaa gcaaacagac ggcggcatgc aatggcagat caccctgctc    30540
attgtgatcg ggttggtcat cctggccgtg ttgctctact acatcttctg ccgccgcatt     30600
cccaacgcgc accgcaagcc ggtctacaag cccatcattg tcgggcagcc ggagccgctt    30660
caggtggaag ggggtctaag gaatcttctc ttctcttta cagtatggtg attgaactat     30720
gattcctaga caattcttga tcactattct tatctgcctc ctccaagtct gtgccaccct    30780
cgctctggtg gccaacgcca gtccagactg tattgggccc ttcgcctcct acgtgctctt    30840
tgccttcacc acctgcatct gctgctgtag catagtctgc ctgcttatca ccttcttcca    30900
gttcattgac tggatctttg tgcgcatcgc ctacctgcgc caccacccc agtaccgcga    30960 ccagcgagtg gcgcggctgc tcaggctcct ctgataagca tgcgggctct gctacttctc    31020
gcgcttctgc tgttagtgct ccccgtccc gtcgaccccc ggtcccccac ccagtccccc    31080
gaggaggtcc gcaaatgcaa attccaagaa ccctggaaat tcctcaaatg ctaccgccaa    31140
aaatcagaca tgcatcccag ctggatcatg atcattggga tcgtgaacat tctggcctgc    31200
accctcatct cctttgtgat ttaccctgc tttgactttg gttggaactc gccagaggcg    31260
ctctatctcc cgcctgaacc tgacacacca ccacagcaac ctcaggcaca cgcactacca    31320
ccactacagc ctaggccaca atacatgccc atattagact atgaggccga gccacagcga    31380
```

```
cccatgctcc ccgctattag ttacttcaat ctaaccggcg gagatgactg acccactggc   31440
caacaacaac gtcaacgacc ttctcctgga catggacggc cgcgcctcgg agcagcgact   31500
cgcccaactt cgcattcgcc agcagcagga gagagccgtc aaggagctgc aggatgcggt   31560
ggccatccac cagtgcaaga gaggcatctt ctgcctggtg aaacaggcca agatctccta   31620
cgaggtcact ccaaacgacc atcgcctctc ctacgagctc ctgcagcagc gccagaagtt   31680
cacctgcctg gtcggagtca accccatcgt catcacccag cagtctggcg ataccaaggg   31740
gtgcatccac tgctcctgcg actcccccga ctgcgtccac actctgatca agaccctctg   31800
cggcctccgc gacctcctcc ccatgaacta atcacccccct tatccagtga aataaagatc   31860
atattgatga tgattttaca gaaataaaaa ataatcattt gatttgaaat aaagatacaa   31920
tcatattgat gatttgagtt taacaaaaaa ataaagaatc acttacttga aatctgatac   31980
caggtctctg tccatgtttt ctgccaacac cacttcactc ccctcttccc agctctggta   32040
ctgcaggccc cggcgggctg caaacttcct ccacacgctg aaggggatgt caaattcctc   32100
ctgtccctca atcttcattt tatcttctat cagatgtcca aaaagcgcgt ccgggtggat   32160
gatgacttcg accccgtcta cccctacgat gcagacaacg caccgaccgt gcccttcatc   32220
aaccccccct tcgtctcttc agatggattc caagagaagc ccctgggggt gttgtccctg   32280
cgactggccg accccgtcac caccaagaac ggggaaatca ccctcaagct gggagagggg   32340
gtggacctcg attcctcggg aaaactcatc tccaacacgg ccaccaaggc cgccgcccct   32400
ctcagttttt ccaacaacac catttcccct aacatggatc accccttta cactaaagat   32460 ggaaaattat ccttacaagt ttctccacca ttaaatatac tgagaacaag cattctaaac   32520
acactagctt taggttttgg atcaggttta ggactccgtg ctctgccctt ggcagtacag   32580
ttagtctctc cacttacatt tgatactgat ggaaacataa agcttacctt agacagaggt   32640
ttgcatgtta caacaggaga tgcaattgaa agcaacataa gctgggctaa aggtttaaaa   32700
tttgaagatg gagccatagc aaccaacatt ggaaatgggt tagagtttgg aagcagtagt   32760
acagaaacag gtgttgatga tgcttaccca atccaagtta aacttggatc tggccttagc   32820
tttgacagta caggagccat aatggctggt aacaaagaag acgataaact cactttgtgg   32880
acaacacctg atccatcacc aaactgtcaa atactcgcag aaaatgatgc aaaactaaca   32940
ctttgcttga ctaaatgtgg tagtcaaata ctggccactg tgtcagtctt agttgtagga   33000
agtggaaacc taaccccat tactggcacc gtaagcagtg ctcaggtgtt tctacgtttt   33060
gatgcaaacg gtgttctttt aacagaacat tctacactaa aaaatactg ggggtatagg   33120 cagggagata gcatagatgg cactccatat accaatgctg taggattcat gcccaattta   33180
aaagcttatc caaagtcaca aagttctact actaaaaata atatagtagg gcaagtatac   33240
atgaatggag atgtttcaaa acctatgctt ctcactataa ccctcaatgg tactgatgac   33300
agcaacagta catattcaat gtcattttca tacacctgga ctaatggaag ctatgttgga   33360
gcaacatttg gggctaactc ttataccttc tcatacatcg cccaagaatg aacactgtat   33420
cccaccctgc atgccaaccc ttcccacccc actctgtgga acaaactctg aaacacaaaa   33480
taaaataaag ttcaagtgtt ttattgattc aacagtttta caggattcga gcagttattt   33540
ttcctccacc ctcccaggac atggaataca ccaccctctc ccccgcaca gccttgaaca   33600 tctgaatgcc attggtgatg acatgctttt tggtctccac gttccacaca gtttcagagc   33660
gagccagtct cgggtcggtc agggagatga aaccctccgg gcactccgc atctgcacct   33720
```

```
cacagctcaa cagctgagga ttgtcctcgg tggtcgggat cacggttatc tggaagaagc   33780
agaagagcgg cggtgggaat catagtccgc gaacgggatc ggccggtggt gtcgcatcag   33840
gcccccgcag cagtcgctgcc gccgccgctc cgtcaagctg ctgctcaggg ggtccgggtc   33900
cagggactcc ctcagcatga tgcccacggc cctcagcatc agtcgtctgg tgcggcgggc   33960
gcagcagcgc atgcggatct cgctcaggtc gctgcagtac gtgcaacaca gaaccaccag   34020
gttgttcaac agtccatagt tcaacacgct ccagccgaaa ctcatcgcgg gaaggatgct   34080
acccacgtgg ccgtcgtacc agatcctcag gtaaatcaag tggtgccccc tccagaacac   34140
gctgcccacg tacatgatct ccttgggcat gtggcggttc accacctccc ggtaccacat   34200
caccctctgg ttgaacatgc agccccggat gatcctgcgg aaccacaggg ccagcaccgc   34260
cccgcccgcc atgcagcgaa gagacccccgg gtcccggcaa tggcaatgga ggacccaccg   34320
ctcgtacccg tggatcatct gggagctgaa caagtctatg ttggcacagc acaggcatat   34380
gctcatgcat ctcttcagca ctctcaactc ctcgggggtc aaaaccatat cccagggcac   34440
ggggaactct tgcaggacag cgaaccccgc agaacagggc aatcctcgca cagaacttac   34500
attgtgcatg gacagggtat cgcaatcagg cagcaccggg tgatcctcca ccagagaagc   34560
gcgggtctcg gtctcctcac agcgtggtaa gggggccggc cgatacgggt gatggcggga   34620
cgcggctgat cgtgttcgcg accgtgtcat gatgcagttg ctttcggaca ttttcgtact   34680
tgctgtagca gaacctggtc cgggcgctgc acaccgatcg ccggcggcgg tctcggcgct   34740
tggaacgctc ggtgttgaaa ttgtaaaaca gccactctct cagaccgtgc agcagatcta   34800
gggcctcagg agtgatgaag atcccatcat ggctgatggc tctgatcaca tcgaccaccg   34860
tggaatgggc cagacccagc cagatgatgc aattttgttg ggtttcggtg acggcggggg   34920
agggaagaac aggaagaacc atgattaact tttaatccaa acggtctcgg agtacttcaa   34980
aatgaagatc gcggagatgg cacctctcgc ccccgctgtg ttggtggaaa ataacagcca   35040
ggtcaaaggt gatacggttc tcgagatgtt ccacggtggc ttccagcaaa gcctccacgc   35100
gcacatccag aaacaagaca atagcgaaag cgggagggtt ctctaattcc tcaatcatca   35160
tgttacactc ctgcaccatc cccagataat tttcattttt ccagccttga atgattcgaa   35220
ctagttcgtg aggtaaatcc aagccagcca tgataaagag ctcgcgcaga gcgccctcca   35280
ccggcattct taagcacacc ctcataattc caagatattc tgctcctggt tcacctgcag   35340
cagattgaca agcggaatat caaaatctct gccgcgatcc ctgagctcct ccctcagcaa   35400
taactgtaag tactctttca tatcctctcc gaaatttta gccataggac caccaggaat   35460
aagattaggg caagccacag tacagataaa ccgaagtcct ccccagtgag cattgccaaa   35520
tgcaagactg ctataagcat gctggctaga cccggtgata tcttccagat aactggacag   35580
aaaatcgccc aggcaatttt taagaaaatc aacaaaagaa aaatcctcca ggtggacgtt   35640
tagagcctcg ggaacaacga tgaagtaaat gcaagcggtg cgttccagca tggttagtta   35700
gctgatctgt agaaaaaaca aaaatgaaca ttaaaccatg ctagcctggc gaacaggtgg   35760
gtaaatcgtt ctctccagca ccaggcaggc cacggggtct ccggcgcgac cctcgtaaaa   35820
attgtcgcta tgattgaaaa ccatcacaga gagacgttcc cggtggccgg cgtgaatgat   35880
tcgacaagat gaatacaccc ccggaacatt ggcgtccgcg agtgaaaaaa agcgcccgag   35940
gaagcaataa ggcactacaa tgctcagtct caagtccagc aaagcgatgc catgcggatg   36000
aagcacaaaa ttctcaggtg cgtacaaaat gtaattactc ccctcctgca caggcagcaa   36060
agcccccgat ccctccaggt acacatacaa agcctcagcg tccatagctt accgagcagc   36120
```

```
agcacacaac aggcgcaaga gtcagagaaa ggctgagctc taacctgtcc acccgctctc    36180
tgctcaatat atagcccaga tctacactga cgtaaaggcc aaagtctaaa ataccccgcc    36240
aaataatcac acacgcccag cacacgccca gaaaccggtg acacactcaa aaaatacgc    36300 gcacttcctc aaacgcccaa aactgccgtc atttccgggt tcccacgcta cgtcatcaaa    36360
acacgacttt caaattccgt cgaccgttaa aaacgtcacc cgccccgccc ctaacggtcg    36420
cccgtctctc agccaatcag cgccccgcat ccccaaattc aaacacctca tttgcatatt    36480
aacgcgcaca aaaagtttga ggtatattat tgatgatgg                           36519
```

<210> SEQ ID NO 105
<211> LENGTH: 36604
<212> TYPE: DNA
<213> ORGANISM: Simian adenovirus 23

<400> SEQUENCE: 105

```
catcatcaat aatatacctc aaacttttgg tgcgcgttaa tatgcaaatg agctgtttga      60
atttggggag ggaggaaggt gattggctgc gggagcggcg accgttaggg gcggggcggg     120
tgacgttttg atgacgtggc tatgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggc gtcagctgat cgccagggta     480
tttaaacctg cgctctctag tcaagaggcc actcttgagt gccagcgagt agagttttct     540
cctccgcgcc gcgagtcaga tctacacttt gaaagatgag gcacctgaga gacctgcccg     600 gtaatgttt cctggctact gggaacgaga ttctggaatt ggtggtggac gccatgatgg      660
gtgacgaccc tccagagccc cctaccccat ttgaggcgcc ttcgctgtac gatttgtatg     720
atctggaggt ggatgtgccc gagagcgacc ctaacgagga ggcggtgaat gatttgttta     780
gcgatgccgc gctgctggct gccgagcagg ctaatacgga ctctggctca gacagcgatt     840
cctctctcca taccccgaga cccggcagag gtgagaaaaa gatccccgag cttaaagggg     900
aagagctcga cctgcgctgc tatgaggaat gcttgcctcc gagcgatgat gaggaggacg     960
aggaggcgat cgagctgcg gtgaaccagg gagtgaaaac tgcgggcgag agctttagcc     1020
tggactgtcc tactctgccc ggacacggct gtaagtcttg tgaatttcat cgcatgaata     1080
ctggagataa gaatgtgatg tgtgccctgt gctatatgag agcttacaac cattgtgttt     1140
acagtaagtg tgattaactt tagttgggaa ggcagagggt gactgggtgc tgactggttt     1200
atttatgtat atgttttttt atgtgtaggt cccgtctctg acgtagatga gacccccact     1260
tcagagtgca tttcatcacc cccagaaatt ggcgaggaac cgcccgaaga tattattcat     1320
agaccagttg cagtgagagt caccgggcgg agagcagctg tggagagttt ggatgacttg     1380
ctacagggtg gggatgaacc tttggacttg tgtacccgga aacgcccag gcactaagtg     1440 ccacacatgt gtgtttactt aaggtgatgt cagtatttat agggtgtgga gtgcaataaa     1500
atccgtgttg actttaagtg cgtgttttat gactcagggg tggggactgt gggtatataa     1560
gcaggtgcag acctgtgtgg tcagttcaga gcaggactca tggagatctg gactgtcttg     1620
gaagactttc accagactag acagttgcta gagaactcat cggagggagt ctcttacctg     1680
```

```
tggagattct gcttcggtgg gcctctagct aagctagtct atagggccaa acaggattat    1740
aaggaacaat tgaggatat tttgagagag tgtcctggta tttttgactc tctcaacttg     1800
ggccatcagt ctcactttaa ccagagtatt ctgagagccc ttgactttc tactcctggc     1860 agaactaccg ccgcggtagc ctttttgcc tttattcttg acaaatggag tcaagaaacc     1920
catttcagca gggattaccg tctggactgc ttagcagtag ctttgtggag aacatggagg    1980
tgccagcgcc tgaatgcaat ctccggctac ttgccagtac agccggtaga cacgctgagg    2040
atcctgagtc tccagtcacc ccaggaacac caacgccgcc agcagccgca gcaggagcag    2100
cagcaagagg aggaccgaga agagaacccg agagccggtc tggaccctcc ggtggcggag    2160
gaggaggagt agctgacttg tttcccgagc tgcgccgggt gctgactagg tcttccagtg    2220
gacgggagag ggggattaag cgggagaggc atgaggagac tagccacaga actgaactga    2280
ctgtcagtct gatgagccgc aggcgcccag aatcggtgtg gtggcatgag gtgcagtcgc    2340
aggggataga tgaggtctcg gtgatgcatg agaaatattc cctagaacaa gtcaagactt    2400
gttggttgga gcccgaggat gattgggagg tagccatcag gaattatgcc aagctggctc    2460
tgaagccaga caagaagtac aagattacca aactgattaa tatcagaaat tcctgctaca    2520
tttcagggaa tggggccgag gtggagatca gtacccagga gagggtggcc ttcagatgtt    2580
gtatgatgaa tatgtacccg ggggtggtgg gcatggaggg agtcaccttt atgaacacga    2640
ggttcagggg tgatgggtat aatggggtgg tctttatggc caacaccaag ctgacagtgc    2700
acggatgctc cttctttggc ttcaataaca tgtgcatcga ggcctggggc agtgtttcag    2760
tgaggggatg cagcttttca gccaactgga tggggtcgt gggcagaacc aagagcaagg     2820
tgtcagtgaa gaaatgcctg ttcgagaggt gccacctggg ggtgatgagc gagggcgaag    2880
ccaaagtcaa acactgcgcc tctaccgaga cgggctgctt tgtgctgatc aagggcaatg    2940
cccaagtcaa gcataacatg atctgtgggg cctcggatga gcgcggctac cagatgctga    3000
cctgcgccgt tgggaacagc catatgctgg ccaccgtgca tgtggcctcg cacccccgca    3060
agacatggcc cgagttcgag cacaacgtca tgacccgctg caatgtgcac ctgggctccc    3120
gccgaggcat gttcatgccc taccagtgca acatgcaatt tgtgaaggtg ctgctggagc    3180
ccgatgccat gtccagagtg agcctgacgg gggtgtttga catgaatgtg gagctgtgga    3240
aaattctgag atatgatgaa tccaagacca ggtgccgggc ctgcgaatgc ggaggcaagc    3300
acgccaggct tcagcccgtg tgtgtggagg tgacggagga cctgcgaccc gatcatttgg    3360
tgttgtcctg caacgggacg gagttcggct ccagcgggga agaatctgac tagagtgagt    3420
agtgtttggg gctgggtgtg agcctgcatg aggggcagaa tgactaaaat ctgtggtttt    3480
ctgtgtgttg cagcagcatg agcggaagcg cctccttga gggagggta ttcagcccctt     3540 atctgacggg gcgtctcccc tcctgggcgg gagtgcgtca aatgtgatg ggatccacgg      3600 tggacggccg gcccgtgcag cccgcgaact cttcaaccct gacctacgcg accctgagct    3660
cctcgtccgt ggacgcagct gccgccgcag ctgctgcttc cgccgccagc gccgtgcgcg    3720
gaatggccct gggcgccggc tactacagct ctctggtggc caactcgagt tccaccaata    3780
atcccgccag cctgaacgag gagaagctgc tgctgctgat ggcccagctc gaggccctga    3840
cccagcgcct gggcgagctg acccagcagg tggctcagct gcaggcggag acgcgggccg    3900
cggttgccac ggtgaaaacc aaataaaaaa tgaatcaata ataaacgga gacggttgtt     3960 gatttttaaca cagagtcttg aatctttatt tgatttttcg cgcgcggtag gccctggacc    4020
accggtctcg atcattgagc acccggtgga tcttttccag gacccggtag aggtgggctt    4080
```

```
ggatgttgag gtacatgggc atgagcccgt cccggggggtg gaggtagctc cattgcaggg    4140
cctcgtgctc ggggatggtg ttgtaaatca cccagtcata gcaggggcgc agggcgtggt    4200
gctgcacgat gtccttgagg aggagactga tggccacggg cagccccttg gtgtaggtgt    4260
tgacgaacct gttgagctgg gagggatgca tgcgggggga gatgagatgc atcttggcct    4320
ggatcttgag attggcgatg ttcccgccca gatcccgccg ggggttcatg ttgtgcagga    4380
ccaccagcac ggtgtatccg gtgcacttgg ggaatttgtc atgcaacttg gaagggaagg    4440
cgtgaaagaa tttggagacg cccttgtgac cgcccaggtt ttccatgcac tcatccatga    4500
tgatggcgat gggcccgtgg gcggcggcct gggcaaagac gtttcggggg tcggacacat    4560
cgtagttgtg gtcctgggtg agctcgtcat aggccatttt aatgaatttg gggcggaggg    4620
tgcccgactg ggggacgaag gtgccctcga tcccggggc gtagttgccc tgcagatct    4680 gcatctccca ggccttgagc tcggaggggg ggatcatgtc cacctgcggg gcgatgaaaa    4740
aaacggtttc cggggcgggg gagatgagct gggccgaaag caggttccgg agcagctggg    4800
acttgccgca accggtgggg ccgtagatga ccccgatgac cggctgcagg tggtagttga    4860
gggagagaca gctgccgtcc tcgcggagga gggggccac ctcgttcatc atctcgcgca    4920
catgcatgtt ctcgcgcacg agttccgcca ggaggcgctc gccccccagc gagaggagct    4980
cttgcagcga ggcgaagttt ttcagcggct tgagtccgtc ggccatgggc attttggaga    5040
gggtctgttg caagagttcc agacggtccc agagctcggt gatgtgctct agggcatctc    5100
gatccagcag acctcctcgt ttcgcgggtt ggggcgactg cggagtagg gcaccaggcg    5160 atgggcgtcc agcgaggcca gggtccggtc cttccagggc cgcagggtcc gcgtcagcgt    5220
ggtctccgtc acggtgaagg ggtgcgcgcc gggctgggcg cttgcgaggg tgcgcttcag    5280
gctcatccgg ctggtcgaga accgctcccg gtcggcgccc tgcgcgtcgg ccaggtagca    5340
attgagcatg agttcgtagt tgagcgcctc ggccgcgtgg cccttggcgc ggagcttacc    5400
tttggaagtg tgtccgcaga cgggacagag gagggacttg agggcgtaga gcttggggc    5460 gaggaagacg gactcggggg cgtaggcgtc cgcgccgcag ctggcgcaga cggtctcgca    5520
ctccacgagc caggtgaggt cggggcggtt ggggtcaaaa acgaggtttc ctccgtgctt    5580
tttgatgcgt ttcttacctc tggtctccat gagctcgtgt ccccgctggg tgacaaagag    5640
gctgtccgtg tccccgtaga ccgactttat gggccggtcc tcgagcgggg tgccgcggtc    5700
ctcgtcgtag aggaaccccg cccactccga dacgaaggcc cgggtccagg ccagcacgaa    5760
ggaggccacg tgggaggggt agcggtcgtt gtccaccagc gggtccacct tctccagggt    5820
atgcaagcac atgtccccct cgtccacatc caggaaggtg attggcttgt aagtgtaggc    5880
cacgtgaccg ggggtcccgg ccgggggggt ataaaagggg gcgggcccct gctcgtcctc    5940
actgtcttcc ggatcgctgt ccaggagcgc cagctgttgg ggtaggtatt ccctctcgaa    6000
ggcgggcatg acctcggcac tcaggttgtc agtttctaga aacgaggagg atttgatatt    6060
gacggtgccg ttggagacgc ctttcatgag cccctcgtcc atttggtcag aaaagacgat    6120
ctttttgttg tcgagcttgg tggcgaagga gccgtagagg gcgttggaga gcagcttggc    6180
gatggagcgc atggtctggt tctttttcctt gtcggcgcgc tccttggcgg cgatgttgag    6240
ctgcacgtac tcgcgcgcca cgcacttcca ttcggggaag acggtggtga gctcgtcggg    6300
cacgattctg acccgccagc cgcggttgtg cagggtgatg aggtccacgc tggtggccac    6360
ctcgccgcgc aggggctcgt tggtccagca gaggcgcccg cccttgcgcg agcagaaggg    6420
```

```
gggcagcggg tccagcatga gctcgtcggg ggggtcggcg tccacggtga agatgccggg   6480
caggagctcg gggtcgaagt agctgatgca ggtgcccaga ttgtccagcg ccgcttgcca   6540
gtcgcgcacg gccagcgcgc gctcgtaggg gctgaggggc gtgccccagg gcatggggtg   6600
cgtgagcgcg gaggcgtaca tgccgcagat gtcgtagacg tagaggggct cctcgaggac   6660
gccgatgtag gtggggtagc agcgcccccc gcggatgctg gcgcgcacgt agtcgtacag   6720
ctcgtgcgag ggcgcgagga gccccgtgcc gaggttggag cgttgcggct tttcggcgcg   6780
gtagacgatc tggcggaaga tggcgtggga gttggaggag atggtgggcc tttggaagat   6840
gttgaagtgg gcgtggggca ggccgaccga gtccctgatg aagtgggcgt aggagtcctg   6900
cagcttggcg acgagctcgg cggtgacgag gacgtccagg gcgcagtagt cgagggtctc   6960
ttggatgatg tcatacttga gctggcccett ctgcttccac agctcgcggt tgagaaggaa   7020
ctcttcgcgg tccttccagt actcttcgag ggggaacccg tcctgatcgg cacggtaaga   7080
gcccaccatg tagaactggt tgacggcctt gtaggcgcag cagcccttct ccacggggag   7140
ggcgtaagct tgcgcggcct tgcgcaggga ggtgtgggtg agggcgaagg tgtcgcgcac   7200
catgaccttg aggaactggt gcttgaagtc gaggtcgtcg cagccgccct gctcccagag   7260
ttggaagtcc gtgcgcttct tgtaggcggg gttaggcaaa gcgaaagtaa catcgttgaa   7320
gaggatcttg cccgcgcggg gcatgaagtt gcgagtgatg cggaaaggct ggggcacctc   7380
ggcccggttg ttgatgacct gggcggcgag gacgatctcg tcgaagccgt tgatgttgtg   7440
cccgacgatg tagagttcca cgaatcgcgg gcggcccttg acgtggggca gcttcttgag   7500
ctcgtcgtag gtgagctcgg cggggtcgct gagcccgtgc tgctcgaggg cccagtcggc   7560
gacgtggggg ttggcgctga ggaaggaagt ccagagatcc acggccaggg cggtctgcaa   7620
gcggtcccgg tactgacgga actgttggcc cacggccatt ttttcggggg tgacgcagta   7680
gaaggtgcgg gggtcgccgt gccagcggtc ccacttgagc tggagggcga ggtcgtgggc   7740
gagctcgacg agcggcgggt ccccggagag tttcatgacc agcatgaagg ggacgagctg   7800
cttgccgaag gaccccatcc aggtgtaggt ttccacatcg taggtgagga agagcctttc   7860
ggtgcgagga tgcgagccga tggggaagaa ctggatctcc tgccaccagt tggaggaatg   7920
gctgttgatg tgatggaagt agaaatgccg acggcgcgcc gagcactcgt gcttgtgttt   7980
atacaagcgt ccgcagtgct cgcaacgctg cacgggatgc acgtgctgca cgagctgtac   8040
ctgggttcct ttggcgagga atttcagtgg gcagtggagc gctggcggct gcatctcgtg   8100
ctgtactacg tcttggccat cggcgtggcc atcgtctgcc tcgatggtgg tcatgctgac   8160
gagcccgcgc gggaggcagg tccagacctc ggctcggacg ggtcggagag cgaggacgag   8220
ggcgcgcagg ccggagctgt ccagggtcct gagacgctgc ggagtcaggt cagtgggcag   8280
cggcggcgcg cggttgactt gcaggagctt ttccagggcg cgcgggaggt ccagatggta   8340
cttgatctcc acggcgccgt tggtggctac gtccacggct tgcagggtgc cgtgcccctg   8400
gggcgccacc accgtgcccc gtttcttctt gggcgctgct tccatgtcgg tcagaagcgg   8460
cggcgaggac gcgcgccggg cggcaggggc ggctcggggc ccggaggcag gggcggcagg   8520
ggcacgtcgg cgccgcgcgc gggcaggttc tggtactgcg cccggagaag actggcgtga   8580
gcgacgacgc gacggttgac gtcctggatc tgacgcctct gggtgaaggc cacgggaccc   8640
gtgagtttga acctgaaaga gagttcgaca gaatcaatct cggtatcgtt gacggcggcc   8700
tgccgcagga tctcttgcac gtcgcccgag ttgtcctggt aggcgatctc ggtcatgaac   8760
tgctcgatct cctcctcctg aaggtctccg cggccggcgc gctcgacggt ggccgcgagg   8820
```

```
tcgttggaga tgcggcccat gagctgcgag aaggcgttca tgccggcctc gttccagacg   8880
cggctgtaga ccacggctcc gtcggggtcg cgcgcgcgca tgaccacctg ggcgaggttg   8940
agctcgacgt ggcgcgtgaa gaccgcgtag ttgcagaggc gctggtagag gtagttgagc   9000
gtggtggcga tgtgctcggt gacgaagaag tacatgatcc agcggcggag cggcatctcg   9060
ctgacgtcgc ccagggcttc aagcgttcc atggcctcgt agaagtccac ggcgaagttg    9120
aaaaactggg agttgcgcgc cgagacggtc aactcctcct ccagaagacg gatgagctcg   9180
gcgatggtgg cgcgcacctc gcgctcgaag gccccggggg gctcctcttc catctcctcc   9240
tcttcctcct ccactaacat ctcttctact tcctcctcag gaggcggtgg cggggggaggg   9300 gccctgcgtc gccggcggcg cacgggcaga cggtcgatga agcgctcgat ggtctccccg   9360
cgccggcgac gcatggtctc ggtgacggcg cgcccgtcct cgcggggccg cagcatgaag   9420
acgccgccgc gcatctccag gtggccgccg gggggtctc cgttgggcag ggagagggcg    9480
ctgacgatga tcttatcaa ttgacccgta gggactccgc gcaaggacct gagcgtctcg    9540
agatccacgg gatccgaaaa ccgctgaacg aaggcttcga gccagtcgca gtcgcaaggt   9600
aggctgagcc cggtttcttg ttcttcgggt atttggtcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgcccaggc gtggtcctga    9780 cacctggcga ggtccttgta gtagtcctgc atgagccgct ccacgggcac ctcctcctcg   9840
cccgcgcggc cgtgcatgcg cgtgagcccg aacccgcgct gcggctggac gagcgccagg   9900
tcggcgacga cgcgctcggt gaggatggcc tgctggatct gggtgagggt ggtctggaag   9960
tcgtcgaagt cgacgaagcg gtggtaggct ccggtgttga tggtgtagga gcagttggcc   10020
atgacggacc agttgacggt ctggtggccg ggtcgcacga gctcgtggta cttgaggcgc   10080
gagtaggcgc gcgtgtcgaa gatgtagtcg ttgcaggcgc gcacgaggta ctggtatccg   10140
acgaggaagt gcggcggcgg ctggcggtag agcggccatc gctcggtggc gggggcgccg   10200
ggcgcgaggt cctcgagcat gaggcggtgg tagccgtaga tgtacctgga catccaggtg   10260
atgccggcgg cggtggtgga ggcgcgcggg aactcgcgga cgcggttcca gatgttgcgc   10320
agcggcagga agtagttcat ggtggccgcg gtctggcccg tgaggcgcgc gcagtcgtgg   10380
atgctctaga catacgggca aaacgaaag cggtcagcgg ctcgactccg tggcctggag    10440
gctaagcgaa cgggttgggc tgcgcgtgta ccccggttcg aatctcgaat caggctggag   10500
ccgcagctaa cgtggtactg gcactcccgt ctcgacccaa gctgctaac gaaacctcca    10560 ggatacggag gcgggtcgtt ttttggcctt ggtcgctggt catgaaaaac tagtaagcgc   10620
ggaaagcggc cgcccgcgat ggctcgctgc cgtagtctgg agaaagaatc gccagggttg   10680
cgttgcggtg tgccccggtt cgagcctcag cgctcggcgc cggccggatt ccgcggctaa   10740
cgtgggcgtg gctgccccgt cgtttccaag accccttagc cagccgactt ctccagttac   10800
ggagcgagcc cctctttttt tttcttgtgt ttttgccaga tgcatcccgt actgcggcag   10860
atgcgccccc accctccacc acaaccgccc ctaccgcagc agcagcaaca gccggcgctt   10920 ctgccccgc cccagcagca gccagccact accgcgcgg ccgccgtgag cggagccggc    10980
gttcagtatg acctggcctt ggaagagggc gaggggctgg cgcggctggg ggcgtcgtcg   11040
ccggagcgga acccgcgcgt gcagatgaaa agggacgctc gcgaggccta cgtgcccaag   11100
cagaacctgt tcagagacag gagcggcgag gagcccgagg agatgcgcgc ctcccgcttc   11160
```

```
cacgcggggc gggagctgcg gcgcggcctg gaccgaaagc gggtgctgag ggacgaggat   11220
ttcgaggcgg acgagctgac ggggatcagc cccgcgcgcg cgcacgtggc cgcggccaac   11280
ctggtcacgg cgtacgagca gaccgtgaag gaggagagca acttccaaaa atccttcaac   11340
aaccacgtgc gcacgctgat cgcgcgcgag gaggtgaccc tgggcctgat gcacctgtgg   11400
gacctgctgg aggccatcgt gcagaacccc acgagcaagc cgctgacggc gcagctgttt   11460
ctggtggtgc agcacagtcg ggacaacgag acgttcaggg aggcgctgct gaatatcacc   11520
gagcccgagg gccgctggct cctggacctg gtgaacattt gcagagcat cgtggtgcag   11580
gagcgcgggc tgccgctgtc cgagaagctg gcggccatca acttctcggt gctgagtctg   11640
ggcaagtact acgctaggaa gatctacaag accccgtacg tgcccataga caaggaggtg   11700
aagatcgacg ggttttacat gcgcatgacc ctgaaagtgc tgaccctgag cgacgatctg   11760
ggggtgtacc gcaacgacag gatgcaccgc gcggtgagcg ccagccgccg gcgcgagctg   11820
agcgaccagg agctgatgca cagcctgcag cgggccctga ccggggccgg gaccgagggg   11880
gagagctact ttgacatggg cgcggacctg cgctggcagc ccagccgccg ggccttggaa   11940
gctgccggcg gttcccccta cgtggaggag gtggacgatg aggaggagga gggcgagtac   12000
ctggaagact gatggcgcga ccgtattttt gctagatgca gcaacagcca ccgccgccgc   12060
ctcctgatcc cgcgatgcgg gcggcgctgc agagccagcc gtccggcatt aactcctcgg   12120
acgattggac ccaggccatg caacgcatca tggcgctgac gacccgcaat cccgaagcct   12180
ttagacagca gcctcaggcc aaccggctct cggccatcct ggaggccgtg gtgccctcgc   12240
gctcgaaccc cacgcacgag aaggtgctgg ccatcgtgaa cgcgctggtg gagaacaagg   12300
ccatccgcgg tgacgaggcc gggctggtgt acaacgcgct gctggagcgc gtggcccgct   12360
acaacagcac caacgtgcag acgaacctgg accgcatggt gaccgacgtg cgcgaggcgg   12420
tgtcgcagcg cgagcggttc caccgcgagt cgaacctggg ctccatggtg gcgctgaacg   12480
ccttcctgag cacgcagccc gccaacgtgc ccgggggcca ggaggactac accaacttca   12540
tcagcgcgct gcggctgatg gtggccgagg tgccccagag cgaggtgtac cagtcggggc   12600
cggactactt cttccagacc agtcgccagg gcttgcagac cgtgaacctg agccaggctt   12660
tcaagaactt gcagggactg tggggcgtgc aggccccggt cggggaccgc gcgacggtgt   12720
cgagcctgct gacgccgaac tcgcgcctgc tgctgctgct ggtggcgccc ttcacggaca   12780
gcggcagcgt gagccgcgac tcgtacctgg gctacctgct taacctgtac cgcgaggcca   12840
tcggacaggc gcacgtggac gagcagacct accaggagat cacccacgtg agccgcgcgc   12900
tgggccagga ggacccgggc aacctggagg ccaccctgaa cttcctgctg accaaccggt   12960
cgcagaagat cccgcccag tacgcgctga gcaccgagga ggagcgcatc ctgcgctacg   13020
tgcagcagag cgtggggctg ttcctgatgc aggagggggc cacgcccagc gcggcgctcg   13080
acatgaccgc gcgcaacatg gagcccagca tgtacgcccg caaccgcccg ttcatcaata   13140
agctgatgga ctacttgcat cgggcggccg ccatgaactc ggactacttt accaacgcca   13200
tcttgaaccc gcactggctc ccgccgcccg ggttctacac gggcgagtac gacatgcccg   13260
accccaacga cgggttcctg tgggacgacg tggacagcag cgtgttctcg ccgcgtccag   13320
gaaccaatgc cgtgtggaag aaagagggcg gggaccggcg gccgtcctcg gcgctgtccg   13380
gtcgcgcggg tgctgccgcg gcggtgcccg aggccgccag cccccttcccg agcctgccct   13440
tttcgctgaa cagcgtgcgc agcagcgagc tgggtcggct gacgcgaccg cgcctgctgg   13500
gcgaggagga gtacctgaac gactccttgt tgaggcccga gcgcgagaag aacttcccca   13560
```

```
ataacgggat agagagcctg gtggacaaga tgagccgctg gaagacgtac gcgcacgagc   13620
acagggacga gccccgagct agcagcgcag gcacccgtag acgccagcgg cacgacaggc   13680 agcgggact ggtgtgggac gatgaggatt ccgccgacga cagcagcgtg ttggacttgg    13740
gtgggagtgg tggtaacccg ttcgctcacc tgcgcccccg tatcgggcgc ctgatgtaag   13800
aatctgaaaa aataaaagac ggtactcacc aaggccatgg cgaccagcgt gcgttcttct   13860
ctgttgtttg tagtagtatg atgaggcgcg tgtacccgga gggtcctcct ccctcgtacg   13920
agagcgtgat gcagcaggcg gtggcggcgg cgatgcagcc cccgctggag gcgccttacg   13980 tgccccgcg gtacctggcg cctacggagg ggcggaacag cattcgttac tcggagctgg    14040 caccctgta cgataccacc cggttgtacc tggtggacaa caagtcggca gacatcgcct    14100
cgctgaacta ccagaacgac cacagcaact tcctgaccac cgtggtgcag aacaacgatt   14160 tcaccccac ggaggccagc acccagacca tcaactttga cgagcgctcg cggtggggcg    14220
gccagctgaa aaccatcatg cacaccaaca tgcccaacgt gaacgagttc atgtacagca   14280
acaagttcaa ggcgcgggtg atggtctcgc gcaagacccc caacgggtg gatgatgatt    14340 atgatggtag tcaggacgag ctgacctacg agtgggtgga gtttgagctg cccgagggca   14400
acttctcggt gaccatgacc atcgatctga tgaacaacgc catcatcgac aactacttgg   14460
cggtggggcg gcagaacggg gtgctggaga gcgacatcgg cgtgaagttc gacacgcgca   14520
acttccggct gggctgggac cccgtgaccg agctggtgat gccgggcgtg tacaccaacg   14580
aggccttcca ccccgacatc gtcctgctgc ccggctgcgg cgtggacttc accgagagcc   14640
gcctcagcaa cctgctgggc atccgcaagc ggcagcccct ccaggagggc ttccagatcc   14700
tgtacgagga cctggagggg ggcaacatcc ccgcgctctt ggatgtcgaa gcctacgaga   14760
aaagcaagga ggatagcacc gccgcggcga ccgcagccgt ggccaccgcc tctaccgagg   14820
tgcggggcga taattttgct agcgctgcgg cagcggccga ggcggctgaa accgaaagta   14880
agatagtcat ccagccggtg gagaaggaca gcaaggacag gagctacaac gtgctcgcgg   14940
acaagaaaaa caccgcctac cgcagctggt acctggccta caactacggc gaccccgaga   15000
agggcgtgcg ctcctggacg ctgctccacc cctcggacgt cacctgcggc gtggagcaag   15060
tctactggtc gctgcccgac atgatgcaag acccggtcac cttccgctcc acgcgtcaag   15120
ttagcaacta cccggtggtg ggcgccgagc tcctgcccgt ctactccaag agcttcttca   15180
acgagcaggc cgtctactcg cagcagctgc gcgccttcac ctcgctcacg cacgtcttca   15240
accgcttccc cgagaaccag atcctcgtcc gcccgccccgc gcccaccatt accaccgtca   15300
gtgaaaacgt tcctgctctc acagatcacg ggaccctgcc gctgcgcagc agtatccggg   15360
gagtccagcg cgtgaccgtc actgacgcca gacgccgcac ctgcccctac gtctacaagg   15420
ccctgggcgt agtcgcgccg cgcgtcctct cgagccgcac cttctaaaaa atgtccattc   15480
tcatctcgcc cagtaataac accggttggg gcctgcgcgc gcccagcaag atgtacgag   15540 gcgctcgcca acgctccacg caacaccccg tgcgcgtgcg cgggcacttc cgcgctccct   15600
ggggcgccct caagggccgc gtgcgctcgc gcaccaccgt cgacgacgtg atcgaccagg   15660
tggtggccga cgcgcgcaac tacacgcccg ccgccgcgcc cgtctccacc gtggacgccg   15720
tcatcgacag cgtggtggcc gacgcgcgcc ggtacgcccg caccaagagc cggcggcggc   15780
gcatcgcccg gcggcaccgg agcaccccg ccatgcgcgc ggcgcgagcc ttgctgcgca    15840
gggccaggcg cacgggacgc agggccatgc tcagggcggc cagacgcgcg gcctccggca   15900
```

-continued

```
gcagcagcgc cggcaggacc cgcagacgcg cggccacggc ggcggcggcg gccatcgcca    15960
gcatgtcccg cccgcggcgc ggcaacgtgt actgggtgcg cgacgccgcc accggtgtgc    16020
gcgtgcccgt gcgcacccgc cccctcgca cttgaagatg ctgacttcgc gatgttgatg     16080
tgtcccagcg gcgaggagga tgtccaagcg caaatacaag gaagagatgc tccaggtcat    16140
cgcgcctgag atctacggcc ccgcggcggc ggtgaaggag gaaagaaagc cccgcaaact    16200
gaagcgggtc aaaaggaca aaaggagga ggaagatgac ggactggtgg agtttgtgcg       16260
cgagttcgcc ccccggcggc gcgtgcagtg gcgcgggcgg aaagtgaaac cggtgctgcg    16320
gcccggcacc acggtggtct tcacgcccgg cgagcgttcc ggctccgcct ccaagcgctc    16380
ctacgacgag gtgtacgggg acgaggacat cctcgagcag gcggtcgagc gtctgggcga    16440
gtttgcgtac ggcaagcgca gccgccccgc gcccttgaaa gaggaggcgg tgtccatccc    16500
gctggaccac ggcaaccca cgccgagcct gaagccggtg accctgcagc aggtgctacc      16560
gagcgcggcg ccgcgccggg gcttcaagcg cgagggcggc gaggatctgt acccgaccat    16620
gcagctgatg gtgcccaagc gccagaagct ggaggacgtg ctggagcaca tgaaggtgga    16680
ccccgaggtg cagcccgagg tcaaggtgcg gcccatcaag caggtggccc cgggcctggg    16740
cgtgcagacc gtggacatca agatccccac ggagcccatg gaaacgcaga ccgagcccgt    16800
gaagcccagc accagcacca tggaggtgca gacggatccc tggatgccag caccagcttc    16860
caccagcact cgccgaagac gcaagtacgg cgcggccagc ctgctgatgc caactacgc      16920 gctgcatcct tccatcatcc ccacgccggg ctaccgcggc acgcgcttct accgcggcta    16980
caccagcagc cgccgccgca agaccaccac ccgccgccgt cgtcgcagcc gccgcagcag    17040
caccgcgact tccgccttgg tgcggagagt gtatcgcagc gggcgcgagc ctctgaccct    17100
gccgcgcgcg cgctaccacc cgagcatcgc catttaacta ccgcctccta cttgcagata    17160
tggccctcac atgccgcctc cgcgtcccca ttacgggcta ccgaggaaga aagccgcgcc    17220
gtagaaggct gacggggaac gggctgcgtc gccatcacca ccggcggcgg cgcgccatca    17280
gcaagcggtt gggggggaggc ttcctgcccg cgctgatccc catcatcgcc gcggcgatcg    17340
gggcgatccc cggcatagct tccgtggcgg tgcaggcctc tcagcgccac tgagacacaa    17400
aaaagcatgg atttgtaata aaaaaaaaaa tggactgacg ctcctggtcc tgtgatgtgt    17460 gttttttagat ggaagacatc aattttttcgt ccctggcacc gcgacacggc acgcggccgt    17520
ttatgggcac ctggagcgac atcggcaaca gccaactgaa cggggcgcc ttcaattgga      17580 gcagtctctg gagcgggctt aagaatttcg ggtccacgct caaaacctat ggcaacaagg    17640
cgtggaacag cagcacaggg caggcgctga gggaaaagct gaaagaacag aacttccagc    17700
agaaggtggt tgatggcctg gcctcaggca tcaacgggt ggttgacctg gccaaccagg       17760
ccgtgcagaa acagatcaac agccgcctgg acgcggtccc gccgcggg tccgtggaga       17820 tgccccaggt ggaggaggag ctgcctcccc tggacaagcg cggcgacaag cgaccgcgtc    17880
ccgacgcgga ggagacgctg ctgacgcaca cggacgagcc gccccgtac gaggaggcgg     17940 tgaaactggg cctgcccacc acgcggcccg tggcgcctct ggccaccgga gtgctgaaac    18000
ccagcagcag ccagcccgcg accctggact tgcctccgcc tcgccctcc acagtggcta     18060 agcccctgcc gccggtggcc gtcgcgtcgc gcgcccccg aggccgccc caggcgaact       18120 ggcagagcac tctgaacagc atcgtgggtc tgggagtgca gagtgtgaag cgccgccgct    18180
gctattaaaa gacactgtag cgcttaactt gcttgtctgt gtgtatatgt atgtccgccg    18240
accagaagga ggagtgtgaa gaggcgcgtc gccgagttgc aagatggcca ccccatcgat    18300
```

```
gctgcccccag tgggcgtaca tgcacatcgc cggacaggac gcttcggagt acctgagtcc  18360
gggtctggtg cagttcgccc gcgccacaga cacctacttc agtctgggga caagtttag   18420 gaacccacg gtggcgccca cgcacgatgt gaccaccgac cgcagccagc ggctgacgct   18480
gcgcttcgtg cccgtggacc gcgaggacaa cacctactcg tacaaagtgc gctacacgct   18540
ggccgtgggc gacaaccgcg tgctggacat ggccagcacc tactttgaca tccgcggcgt   18600
gctggaccgg ggccctagct tcaaaccta ctctggcacc gcctacaaca gcctagctcc    18660
caagggagct cccaattcca gccagtggga gcaagcaaaa acaggcaatg ggggaactat   18720
ggaaacacac acatatggtg tggccccaat gggcggagag aatattacaa aagatggtct   18780
tcaaattgga actgacgtta cagcgaatca gaataaacca atttatgccg acaaaacatt   18840
tcaaccagaa ccgcaagtag gagaagaaaa ttggcaagaa actgaaaact tttatggcgg   18900
tagagctctt aaaaaagaca caaacatgaa accttgctat ggctcctatg ctagacccac   18960
caatgaaaaa ggaggtcaag ctaaacttaa agttggagat gatggagttc caaccaaaga   19020
attcgacata gacctggctt tctttgatac tcccggtggc accgtgaacg gtcaagacga   19080
gtataaagca gacattgtca tgtataccga aaacacgtat ttggaaactc cagacacgca   19140
tgtggtatac aaaccaggca aggatgatgc aagttctgaa attaacctgg ttcagcagtc   19200
tatgcccaac agaccaacct acattgggtt cagggacaac tttatcggtc ttatgtacta   19260
caacagcact ggcaatatgg gtgtgcttgc tggtcaggcc tcccagctga atgctgtggt   19320
tgatttgcaa gacagaaaca ccgagctgtc ctaccagctc ttgcttgact ctttgggtga   19380
cagaacccgg tatttcagta tgtggaacca ggcggtggac agttatgacc ccgatgtgcg   19440
catcatcgaa aaccatggtg tggaggatga attgccaaac tattgcttcc ccttggacgg   19500
ctctggcact aacgccgcat accaaggtgt gaaagtaaaa gatggtcaag atggtgatgt   19560
tgagagtgaa tgggaaaatg acgatactgt tgcagctcga aatcaattat gtaaaggtaa   19620
cattttcgcc atggagatta atctccaggc taacctgtgg agaagtttcc tctactcgaa   19680
cgtggccctg tacctgcccg actcctacaa gtacacgccg accaacgtca cgctgccgac   19740
caacaccaac acctacgatt acatgaatgg cagagtgaca cctccctcgc tggtagagcg   19800
ctacctcaac atcgggggcgc gctggtcgct ggaccccatg gacaacgtca ccccttcaa   19860 ccaccaccgc aacgcgggcc tgcgctaccg ctccatgctc ctgggcaacg ggcgctacg   19920 gcccttccac atccaggtgc cccaaaagtt tttcgccatc aagagcctcc tgctcctgcc   19980
cgggtcctac acctacgagt ggaacttccg caaggacgtc aacatgatcc tgcagagctc   20040
cctaggcaac gacctgcgca cggacggggc ctccatcgcc ttcaccagca tcaacctcta   20100
cgccaccttc ttccccatgg cgcacaacac cgcctccacg ctcgaggcca tgctgcgcaa   20160
cgacaccaac gaccagtcct tcaacgacta cctctcggcg ccaacatgc tctaccccat    20220 cccggccaac gccaccaacg tgcccatctc catcccctcg cgcaactggg ccgccttccg   20280
cggatggtcc ttcacgcgcc tgaagaccc ggagacgccc tcgctcggct ccgggttcga    20340
cccctacttc gtctactcgg gctccatccc ctacctagac ggcaccttct acctcaacca   20400
caccttcaag aaggtctcca tcaccttcga ctcctccgtc agctgccccg caacgaccg    20460 cctcctgacg cccaacgagt tcgaaatcaa gcgcaccgtc gacggagagg gatacaacgt    20520
ggcccagtgc aacatgacca aggactggtt cctggtccag atgctggccc actacaacat   20580
cggctaccag ggcttctacg tgcccgaggg ctacaaggac cgcatgtact ccttcttccg   20640
```

```
caacttccag cccatgagcc gccaggtcgt ggacgaggtc aactacaagg actaccaggc   20700
cgtcaccctg gcctaccagc acaacaactc gggcttcgtc ggctaccteg cgcccaccat   20760
gcgccagggc cagccctacc ccgccaacta ccctacccg ctcatcggca agagcgccgt   20820
cgccagcgtc acccagaaaa agttcctctg cgaccgggtc atgtggcgca tcccttctc   20880
cagcaacttc atgtccatgg gcgcgctcac cgacctcggc cagaacatgc tctacgccaa   20940
ctccgcccac gcgctagaca tgaatttcga agtcgacccc atggatgagt ccacccttct   21000
ctatgttgtc ttcgaagtct tcgacgtcgt ccgagtgcac cagccccacc gcggcgtcat   21060
cgaagccgtc tacctgcgca cgcccttctc ggccggcaac gccaccacct aagccgctct   21120
tgcttcttgc aagatgacgg cgggctccgg cgagcaggag ctcagggcca tcctccgcga   21180
cctgggctgc gggccctgct tcctgggcac cttcgacaag cgcttccctg gattcatggc   21240
cccgcacaag ctggcctgcg ccatcgtgaa cacggccggc cgcgagaccg ggggcgagca   21300
ctggctggcc ttcgcctgga cccgcgctc ccacacatgc tacctcttcg acccctttgg   21360
gttctcggac gagcgcctca gcagatcta ccagttcgag tacgagggcc tgctgcgtcg   21420
cagcgccctg gccaccgagg accgctgcgt caccctggaa aagtccaccc agaccgtgca   21480
gggtccgcgc tcggccgcct gcgggctctt ctgctgcatg ttcctgcacg ccttcgtgca   21540
ctggcccgac cgccccatgg acaagaaccc caccatgaac ttactgacgg gggtgcccaa   21600
cggcatgctc cagtcgcccc aggtggaacc caccctgcgc cgcaaccagg aagcgctcta   21660
ccgcttcctc aatgcccact ccgcctactt tcgctcccac cgcgcgcgca tcgagaaggc   21720
caccgccttc gaccgcatga atcaagacat gtaaaaaacc ggtgtgtgta tgtgaatgct   21780
ttattcataa taaacagcac atgtttatgc caccttctct gaggctctga ctttatttag   21840
aaatcgaagg ggttctgccg gctctcggca tggcccgcgg gcagggatac gttgcggaac   21900
tggtacttgg gcagccactt gaactcgggg atcagcagct tgggcacggg gaggtcgggg   21960
aacgagtcgc tccacagctt gcgcgtgagt tgcaggcgc ccagcaggtc gggcgcggag   22020
atcttgaaat cgcagttggg acccgcgttc tgcgcgcgag agttgcggta cacggggttg   22080
cagcactgga acaccatcag ggccgggtgc ttcacgcttg ccagcaccgt cgcgtcggtg   22140
atgccctcca cgtccagatc ctcggcgttg gccatcccga agggggtcat cttgcaggtc   22200
tgccgcccca tgctgggcac gcagccgggc ttgtggttgc aatcgcagtg caggggatc   22260
agcatcatct gggcctgctc ggagctcatg cccgggtaca tggccttcat gaaagcctcc   22320
agctggcgga aggcctgctg cgccttgccg ccctcggtga agaagacccc gcaggacttg   22380
ctagagaact ggttggtggc gcagccggcg tcgtgcacgc agcagcgcgc gtcgttgttg   22440
gccagctgca ccacgctgcg ccccagcgg ttctgggtga tcttggcccg gttgggttc   22500
tccttcagcg cgcgctgccc gttctcgctc gccacatcca tctcgatagt gtgctccttc   22560
tggatcatca cggtcccgtg caggcaccgc agcttgccct cggcttcggt gcagccgtgc   22620
agccacagcg cgcagccggt gcactcccag ttcttgtggg cgatctggga gtgcgagtgc   22680
acgaagccct gcaggaagcg gcccatcatc gcggtcaggg tcttgttgct ggtgaaggtc   22740
agcgggatgc cgcggtgctc ctcgttcaca tacaggtggc agatgcggcg gtacacctcg   22800
ccctgctcgg gcatcagctg gaaggcggac ttcaggtcgc tctccacgcg gtaccggtcc   22860
atcagcagcg tcatcacttc catgcccttc tcccaggccg aaacgatcgg caggctcagg   22920
gggttcttca ccgccattgt catcttagtc gccgccgccg aggtcagggg gtcgttctcg   22980
tccagggtct caaacactcg cttgccgtcc ttctcgatga tgcgcacggg gggaaagctg   23040
```

```
aagcccacgg ccgccagctc ctcctcggcc tgcctttcgt cctcgctgtc ctggctgatg   23100
tcttgcaaag gcacatgctt ggtcttgcgg ggtttctttt tgggcggcag aggcggcggc   23160
gatgtgctgg gagagcgcga gttctcgttc accacgacta tttcttcttc ttggccgtcg   23220
tccgagacca cgcggcggta ggcatgcctc ttctggggca gaggcggagg cgacgggctc   23280
tcgcggttcg gcgggcggct ggcagagccc cttccgcgtt cggggtgcg ctcctggcgg    23340 cgctgctctg actgacttcc tccgcggccg gccattgtgt tctcctaggg agcaacaaca   23400
agcatggaga ctcagccatc gtcgccaaca tcgccatctg ccccgccgc caccgccgac    23460 gagaaccagc agcagaatga aagcttaacc gccccgccgc ccagcccac ctccgacgcc    23520 gcggccccag acatgcaaga gatggaggaa tccatcgaga ttgacctggg ctacgtgacg   23580
cccgcggagc acgaggagga gctggcagcg cgcttttcag ccccggaaga gaaccaccaa   23640
gagcagccag agcaggaagc agagaacgag cagaaccagg ctgggcacga gcatggcgac   23700
tacctgagcg gggcagagga cgtgctcatc aagcatctgg cccgccaatg catcatcgtc   23760
aaggacgcgc tgctcgaccg cgccgaggtg cccctcagcg tggcggagct cagccgcgcc   23820
tacgagcgca acctcttctc gccgcgcgtg cccccaagc gccagcccaa cggcacctgt   23880
gagcccaacc cgcgcctcaa cttctacccg gtcttcgcgg tgcccgaggc cctggccacc   23940
taccacctct ttttcaagaa ccaaaggatc cccgtctcct gccgcgccaa ccgcacccgc   24000
gccgacgccc tgctcaacct gggccccggc gcccgcctac ctgatatcac ctccttggaa   24060
gaggttccca agatcttcga gggtctgggc agcgacgaga ctcggccgc gaacgctctg    24120 caaggaagcg gagaggagca tgagcaccac agcgccctgg tggagttgga aggcgacaac   24180
gcgcgcctgg cggtcctcaa gcgcacggtc gagctgaccc acttcgccta cccggcgctc   24240
aacctgcccc ccaaggtcat gagcgccgtc atggaccagg tgctcatcaa gcgcgcctcg   24300
cccctctcgg aggaggagat gcaggacccc gagagttcgg acgagggcaa gcccgtggtc   24360
agcgacgagc agctggcgcg ctggctggga gcgagtagca ccccccagag cctggaagag   24420
cggcgcaagc tcatgatggc cgtggtcctg gtgaccgtgg agctggagtg tctgcgccgc   24480
ttctttgccg acgcggagac cctgcgcaag gtcgaggaga acctgcacta cctcttcagg   24540
cacgggttcg tgcgccaggc ctgcaagatc tccaacgtgg agctgaccaa cctggtctcc   24600
tacatgggca tcctgcacga gaaccgcctg ggcaaaaacg tgctgcacac cacccctgcgc  24660 ggggaggccc gccgcgacta catccgcgac tgcgtctacc tgtacctctg ccacacctgg   24720
cagacgggca tgggcgtgtg gcagcagtgc ctggaggagc agaacctgaa agagctctgc   24780
aagctcctgc agaagaacct caaggccctg tggaccgggt tcgacgagcg taccaccgcc   24840
tcggacctgc ccgacctcat cttccccgag cgcctgcggc tgacgctgcg caacgggctg   24900
cccgacttta tgagccaaag catgttgcaa aactttcgct ctttcatcct cgaacgctcc   24960
gggatcctgc ccgccacctg ctccgcgctg ccctcggact tcgtgccgct gaccttccgc   25020
gagtgccccc cgccgctctg gagccactgc tacttgctgc gcctggccaa ctacctggcc   25080
taccactcgg acgtgatcga ggacgtcagc ggcgagggtc tgctggagtg ccactgccgc   25140
tgcaacctct gcacgccgca ccgctccctg gcctgcaacc cccagctgct gagcgagacc   25200
cagatcatcg gcaccttcga gttgcaaggc cccggcgacg gcgagggcaa ggggggtctg   25260
aaactcaccc cggggctgtg gacctcggcc tacttgcgca gttcgtgcc cgaggactac    25320 catcccttcg agatcaggtt ctacgaggac caatcccagc cgcccaaggc cgagctgtcg   25380
```

```
gcctgcgtca tcacccaggg ggccatcctg gcccaattgc aagccatcca gaaatcccgc    25440
caagaatttc tgctgaaaaa gggccacggg gtctacttgg accccccagac cggagaggag   25500 ctcaaccccca gcttccccca ggatgccccg aggaagcagc aagaagctga aagtggagct   25560
gccgccgccg gaggatttgg aggaagactg ggagagcagt caggcagagg aggaggagat   25620
ggaagactgg gacagcactc aggcagagga ggacagcctg caagacagtc tggaggagga   25680
agacgaggtg gaggaggcag aggaagaagc agccgccgcc agaccgtcgt cctcggcgga   25740
gaaagcaagc agcacggata ccatctccgc tccgggtcgg ggtcgcggcg gccgggccca   25800
cagtaggtgg gacgagaccg ggcgcttccc gaaccccacc acccagaccg gtaagaagga   25860
gcggcaggga tacaagtcct ggcgggggca caaaaacgcc atcgtctcct gcttgcaagc   25920
ctgcgggggc aacatctcct tcacccggcg ctacctgctc ttccaccgcg gggtgaactt   25980 ccccccgcaac atcttgcatt actaccgtca cctccacagc ccctactact gtttccaaga   26040
agaggcagaa acccagcagc agcagaaaac cagcggcagc agcagctaga aaatccacag   26100
cggcggcagg tggactgagg atcgcggcga acgagccggc gcagaccccgg gagctgagga   26160 accggatctt tcccaccctc tatgccatct ccagcagag tcggggggcag gagcaggaac   26220 tgaaagtcaa gaaccgttct ctgcgctcgc tcacccgcag ttgtctgtat cacaagagcg   26280
aagaccaact tcagcgcact ctcgaggacg ccgaggctct cttcaacaag tactgcgcgc   26340
tcactcttaa agagtagccc gcgcccgccc acacacggaa aaaggcggga attacgtcac   26400
cacctgcgcc cttcgcccga ccatcatgag caaagagatt cccacgcctt acatgtggag   26460
ctaccagccc cagatgggcc tggccgccgg cgccgcccag gactactcca cccgcatgaa   26520
ctggctcagt gccgggcccg cgatgatctc acgggtgaat gacatccgcg cccaccgaaa   26580
ccagatactc ctagaacagt cagcgatcac cgccacgccc cgccatcacc ttaatccgcg   26640
taattggccc gccgccctgg tgtaccagga aattccccag cccacgaccg tactacttcc   26700
gcgagacgcc caggccgaag tccagctgac taactcaggt gtccagctgg ccggcggcgc   26760
cgccctgtgt cgtcaccgcc ccgctcaggg tataaagcgg ctggtgatcc gaggcagagg   26820
cacacagctc aacgacgagg tggtgagctc ttcgctgggt ctgcgacctg acggagtctt   26880
ccaactcgcc ggatcgggga gatcttcctt cacgcctcgt caggccgtcc tgactttgga   26940
gagttcgtcc tcgcagcccc gctcgggcgg catcggcact ctccagttcg tggaggagtt   27000
cactccctcg gtctacttca accccttctc cggctccccc ggccactacc cggacgagtt   27060
catcccgaac ttcgacgcca tcagcgagtc ggtggacggc tacgattgaa tgtcccatgg   27120
tggcgcagct gacctagctc ggcttcgaca cctggaccac tgccgccgct tccgctgctt   27180
cgctcgggat ctcgccgagt ttgcctactt tgagctgccc gaggagcacc ctcagggccc   27240
agcccacgga gtgcggatca tcgtcgaagg gggcctcgac tcccacctgc ttcggatctt   27300
cagccagcga ccgatcctgg tcgagcgcga acaaggacag accccttctta ctttgtactg   27360 catctgcaac caccccggcc tgcatgaaag tctttgttgt ctgctgtgta ctgagtataa   27420
taaaagctga gatcagcgac tactccggac tcgattgtgg tgttcctgct atcaaccggt   27480
ccctgttctt caccgggaac gagaccgagc tccagctcca gtgtaagccc cacaagaagt   27540
acctcacctg gctgttccag ggctccccga tcgccgttgt caaccactgc gacaacgacg   27600
gagtcctgct gagcggccct gccaaccctta ctttttccac ccgcagaagc aagctccagc   27660
tcttccaacc cttcctcccc gggacctatc agtgcgtctc aggaccctgc catcacacct   27720
tccacctgat cccgaatacc acagcgccgc tccccgctac taacaaccaa actacccacc   27780
```

```
aacgccaccg tcgcgacctt tcctctgaat ctaataccac taccggaggt gagctccgag   27840
gtcgaccaac ctctgggatt tactacggcc cctgggaggt ggtggggtta atagcgctag   27900
gcctagttgc gggtgggctt ttggttctct gctacctata cctcccttgc tgttcgtact   27960
tagtggtgct gtgttgctgg tttaagaaat ggggaagatc accctagtga gctgcggtgc   28020
gctggtggcg gtgttgcttt cgattgtggg actgggcggc gcggctgtag tgaaggagaa   28080
ggccgatccc tgcttgcatt tcaatcccaa caaatgccag ctgagttttc agcccgatgg   28140
caatcggtgc gcggtactga tcaagtgcgg atgggaatgc gagaacgtga gaatcgagta   28200
caataacaag actcggaaca atactctcgc gtccgtgtgg cagcccgggg accccgagtg   28260
gtacaccgtc tctgtccccg gtgctgacgg ctccccgcgc accgtgaata atactttcat   28320
ttttgcgcac atgtgcaaca cggtcatgtg gatgagcaag cagtacgata tgtggccccc   28380
cacgaaggag aacatcgtgg tcttctccat cgcttacagc ctgtgcacgg cgctaatcac   28440
cgctatcgtg tgcctgagca ttcacatgct catcgctatt cgcccagaa ataatgccga    28500
gaaagagaaa cagccataac acgtttttc acacaccttg tttttacaga caatgcgtct    28560
gttaaattt ttaaacattg tgctcagtat tgcttatgcc tctggttatg caaacataca    28620
gaaaacccttt tatgtaggat ctgatggtac actagagggt acccaatcac aagccaaggt   28680
tgcatggtat ttttatagaa ccaacactga tccagttaaa ctttgtaagg gtgaattgcc   28740
gcgtacacat aaaactccac ttacatttag ttgcagcaat aataatctta cactttttc    28800
aattacaaaa caatatactg gtacttatta cagtacaaac tttcatacag acaagataa    28860
atattatact gttaaggtag aaaatcctac cactcctaga actaccacca ccaccactac   28920
tgcaaagccc actgtgaaaa ctacaactag gaccaccaca actacagaaa ccaccaccag   28980
cacaacactt gctgcaacta cacacacaca cactaagcta accttacaga ccactaatga   29040
tttgatcgcc ctgctgcaaa agggggataa cagcaccact tccaatgagg agatacccaa   29100
atccatgatt ggcattattg ttgctgtagt ggtgtgcatg ttgatcatcg ccttgtgcat   29160
ggtgtactat gccttctgct acagaaagca cagactgaac gacaagctgg aacacttact   29220
aagtgttgaa ttttaatttt ttagaaccat gaagatccta ggccttttta gttttctat    29280
cattacctct gctctttgtg aatcagtgga tagagatgtt actattacca ctggttctaa   29340
ttatacactg aaagggccac cctcaggtat gctttcgtgg tattgctatt ttggaactga   29400
cactgatcaa actgaattat gcaatttca aaaaggcaaa acctcaaact ctaaaatctc    29460
taattatcaa tgcaatggca ctgatctgat actactcaat gtcacgaaag catatggtgg   29520
cagttattat tgccctggac aaaacactga agaaatgatt ttttacaaag tggaagtggt   29580
tgatcccact acaccaccca ccaccacaac tattcatacc acacacacag aacaaacacc   29640
agaggcaaca gaagcagagt tggccttcca ggttcacgga gattcctttg ctgtcaatac   29700
ccctacaccc gatcagcggt gtccggggcc gctagtcagc ggcattgtcg gtgtgctttc   29760
gggattagca gtcataatca tctgcatgtt catttttgct tgctgctata gaaggcttta   29820
ccgacaaaaa tcagacccac tgctgaacct ctatgtttaa tttttttccag agccatgaag   29880
gcagttagcg ctctagtttt ttgttctttg attggcattg tttttaatag taaaattacc   29940
agagttagct ttattaaaca tgttaatgta actgaaggag ataacatcac actagcaggt   30000
gtagaaggtg ctcaaaacac cacctggaca aaataccatc taggatggag agatatttgc   30060
acctggaatg taacttatta ttgcatagga gttaatctta ccattgttaa cgctaaccaa   30120
```

-continued

```
tctcagaatg ggttaattaa aggacagagt gttagtgtga ccagtgatgg gtactatacc    30180
cagcatagtt ttaactacaa cattactgtc ataccactgc ctacgcctag cccacctagc    30240
actaccacac agacaaccac atacagtaca tcaaatcagc ctaccaccac tacagcagca    30300
gaggttgcca gctcgtctgg ggtccgagtg gcatttttga tgttggcccc atctagcagt    30360
cccactgcta gtaccaatga gcagactact gaattttgt ccactgtcga gagccacacc    30420
acagctacct ccagtgcctt ctctagcacc gccaatctct cctcgctttc ctctacacca    30480
atcagccccg ctactactcc tagccccgct cctcttccca ctcccctgaa gcaaacagac    30540
ggcggcatgc aatggcagat caccctgctc attgtgatcg ggttggtcat cctggccgtg    30600
ttgctctact acatcttctg ccgccgcatt cccaacgcgc accgcaagcc ggcctacaag    30660
cccatcgtta tcgggcagcc ggagccgctt caggtggaag ggggtctaag gaatcttctc    30720
ttctctttta cagtatggtg attgaactat gattcctaga caattcttga tcactattct    30780
tatctgcctc ctccaagtct gtgccaccct cgctctggtg gccaacgcca gtccagactg    30840
tattgggccc ttcgcctcct acgtgctctt tgccttcgtc acctgcatct gctgctgtag    30900
catagtctgc ctgcttatca ccttcttcca gttcattgac tggatctttg tgcgcatcgc    30960
ctacctgcgc caccaccccc agtaccgcga ccagcgagtg gcgcagctgc tcaggctcct    31020
ctgataagca tgcgggctct gctacttctc gcgcttctgc tgttagtgct ccccccgtccc    31080
gtcgaccccc ggtcccccac tcagtccccc gaggaggttc gcaaatgcaa attccaagaa    31140
ccctggaaat tcctcaaatg ctaccgccaa aaatcagaca tgcatcccag ctggatcatg    31200
atcattggga tcgtgaacat tctggcctgc accctcatct cctttgtgat ttaccccctgc    31260
tttgactttg gttggaactc gccagaggcg ctctatctcc cgcctgaacc tgacacacca    31320
ccacagcagc aacctcaggc acacgcacta ccaccaccac agcctaggcc acaatacatg    31380
cccatattag actatgaggc cgagccacag cgacccatgc tccccgctat tagttacttc    31440
aatctaaccg gcgagatga ctgacccact ggccaataac aacgtcaacg accttctcct    31500
ggacatggac ggccgcgcct cggagcagcg actcgcccaa cttcgcattc gtcagcagca    31560
ggagagagcg tcaaggagc tgcaggacgg catagccatc caccagtgca agagaggcat    31620
cttctgcctg gtgaaacagg ccaagatctc ctacgaggtc acccagaccg accatcgcct    31680
ctcctacgag ctcctgcagc agcgccagaa gttcacctgc ctggtcggag tcaaccccat    31740
cgtcatcacc cagcagtcgg gcgataccaa ggggtgcatc cactgctcct gcgactcccc    31800
cgactgcgtc cacactctga tcaagaccct ctgcggcctc cgcgacctcc tccccatgaa    31860
ctaatcaccc ccttatccag tgaaataaag atcatattga tgatgattta aataaaaaaa    31920
ataatcattt gatttgaaat aaagatacaa tcatattgat gatttgagtt taacaaaaat    31980
aaagaatcac ttacttgaaa tctgatacca ggtctctgtc catgttttct gccaacacca    32040
cctcactccc ctcttcccag ctctggtact gcaggcccg gcgggctgca aacttcctcc    32100
acacgctgaa ggggatgtca aattcctcct gtccctcaat cttcatttta tcttctatca    32160
gatgtccaaa aagcgcgtcc gggtggatga tgacttcgac cccgtctacc cctacgatgc    32220
agacaacgca ccgaccgtgc ccttcatcaa cccccccttc gtctcttcag atggattcca    32280
agagaagccc ctgggggtgt tgtccctgcg actggctgac cccgtcacca ccaagaacgg    32340
ggaaatcacc ctcaagctgg gagagggggt ggacctcgac tcgtcgggaa aactcatctc    32400
caacacggcc accaaggccg ccgcccctct cagtatttca aacaacacca tttcccttaa    32460
aactgctgcc cctttctaca acaacaatgg aactttaagc ctcaatgtct ccacaccatt    32520
```

-continued

| | |
|---|---|
| agcagtattt cccacattta acactttagg cataagtctt ggaaacggtc ttcagacttc | 32580 |
| aaataagttg ttgactgtac aactaactca tcctcttaca ttcagctcaa atagcatcac | 32640 |
| agtaaaaaca gacaaagggc tatatattaa ctccagtgga aacagaggac ttgaggctaa | 32700 |
| tataagccta aaaagaggac tagtttttga cggtaatgct attgcaacat atattggaaa | 32760 |
| tggcttagac tatggatctt atgatagtga tggaaaaaca agacccgtaa ttaccaaaat | 32820 |
| tggagcagga ttaaattttg atgctaacaa agcaatagct gtcaaactag cacaggttt | 32880 |
| aagttttgac tccgctggtg ccttgacagc tggaaacaaa caggatgaca agctaacact | 32940 |
| ttggactacc cctgacccaa gccctaattg tcaattactt tcagacagag atgccaaatt | 33000 |
| tactctctgt cttacaaaat gcggtagtca atactaggc actgtggcag tggcggctgt | 33060 |
| tactgtagga tcagcactaa atccaattaa tgacacagtc aaaagcgcca tagttttcct | 33120 |
| tagatttgat tccgatggtg tactcatgtc aaactcatca atggtaggtg attactggaa | 33180 |
| ctttagggag ggacagacca ctcaaagtgt agcctataca aatgctgtgg gattcatgcc | 33240 |
| aaatataggt gcatatccaa aaacccaaag taaaacacct aaaaatagca tagtcagtca | 33300 |
| ggtatattta actggagaaa ctactatgcc aatgacacta accataactt tcaatggcac | 33360 |
| tgatgaaaaa gacacaaccc cagttagcac ctactctatg acttttacat ggcagtggac | 33420 |
| tggagactat aaggacaaaa atattacctt tgctaccaac tcattctctt tttcctacat | 33480 |
| cgcccaggaa taatcccacc cagcaagcca accccttttc ccaccacctt tgtctatatg | 33540 |
| gaaactctga acagaaaaa taagttcaa gtgttttatt gaatcaacag ttttacagga | 33600 |
| ctcgagcagt tattttttcct ccaccctccc aggacatgga atacaccacc ctctccccc | 33660 |
| gcacagcctt gaacatctga atgccattgg tgatggacat gcttttggtc tccacgttcc | 33720 |
| acacagtttc agagcgagcc agtctcggat cggtcaggga gatgaaaccc tccgggcact | 33780 |
| cccgcatctg cacctcacag ctcaacagct gaggattgtc ctcggtggtc gggatcacgg | 33840 |
| ttatctggaa gaagcagaag agcggcggtg ggaatcatag tccgcgaacg ggatcggccg | 33900 |
| gtggtgtcgc atcaggcccc gcagcagtcg ctgccgccgc cgctccgtca agctgctgct | 33960 |
| caggggttc gggtccaggg actccctcag catgatgccc acggccctca gcatcagtcg | 34020 |
| tctggtgcgg cgggcgcagc agcgcatgcg aatctcgctc aggtcactgc agtacgtgca | 34080 |
| acacaggacc accaggttgt tcaacagtcc atagttcaac acgctccagc cgaaactcat | 34140 |
| cgcgggaagg atgctaccca cgtggccgtc gtaccagatc ctcaggtaaa tcaagtggcg | 34200 |
| ctccctccag aagacgctgc ccatgtacat gatctccttg ggcatgtggc ggttcaccac | 34260 |
| ctcccggtac cacatcaccc tctggttgaa catgcagccc cggatgatcc tgcggaacca | 34320 |
| cagggccagc accgccccgc ccgccatgca gcgaagagac cccggatccc ggcaatgaca | 34380 |
| atggaggacc caccgctcgt acccgtggat catctgggag ctgaacaagt ctatgttggc | 34440 |
| acagcacagg catatgctca tgcatctctt cagcactctc agctcctcgg gggtcaaaac | 34500 |
| catatcccag ggcacgggga actcttgcag gacagcgaac cccgcagaac agggcaatcc | 34560 |
| tcgcacataa cttacattgt gcatggacag ggtatcgcaa tcaggcagca ccgggtgatc | 34620 |
| ctccaccaga gaagcgcggg tctcggtctc ctcacagcgt ggtaaggggg ccggccgata | 34680 |
| cgggtgatgg cggacgcgg ctgatcgtgt tctcgaccgt gtcatgatgc agttgctttc | 34740 |
| ggacattttc gtacttgctg tagcagaacc tggtccgggc gctgcacacc gatcgccggc | 34800 |
| ggcggtctcg gcgcttggaa cgctcggtgt taaagttgta aaacagccac tctctcagac | 34860 |

```
cgtgcagcag atctagggcc tcaggagtga tgaagatccc atcatgcctg atagctctga    34920
tcacatcgac caccgtggaa tgggccaggc ccagccagat gatgcaattt tgttgggttt    34980
cggtgacggc gggggaggga agaacaggaa gaaccatgat taacttttaa tccaaacggt    35040
ctcggagcac ttcaaaatga aggtcacgga gatggcacct ctcgcccccg ctgtgttggt    35100
ggaaaataac agccaggtca aaggtgatac ggttctcgag atgttccacg gtggcttcca    35160
gcaaagcctc cacgcgcaca tccagaaaca agacaatagc gaaagcggga gggttctcta    35220
attcctcaac catcatgtta cactcctgca ccatcccag ataattttca ttttccagc     35280 cttgaatgat tcgaactagt tcctgaggta atccaagcc agccatgata aaaagctcgc     35340
gcagagcacc ctccaccggc attcttaagc acaccctcat aattccaaga tattctgctc    35400
ctggttcacc tgcagcagat tgacaagcgg aatatcaaaa tctctgccgc gatccctgag    35460 ctcctcccctc agcaataact gtaagtactc tttcatatcg tctccgaaat ttttagccat    35520
aggaccccca ggaataagag aagggcaagc cacattacag ataaaccgaa gtccccccca    35580
gtgagcattg ccaaatgtaa gattgaaata agcatgctgg ctagacccgg tgatatcttc    35640
cagataactg gacagaaaat cgggtaagca atttttaaga aaatcaacaa agaaaaaatc    35700
ttccaggtgc acgtttaggg cctcgggaac aacgatggag taagtgcaag gggtgcgttc    35760
cagcatggtt agttagctga tctgtaaaaa aacaaaaaat aaaacattaa accatgctag    35820
cctggcgaac aggtgggtaa atcgttctct ccagcaccag gcaggccacg gggtctccgg    35880
cgcgaccctc gtaaaaattg tcgctatgat tgaaaaccat cacagagaga cgttcccggt    35940
ggccggcgtg aatgattcga gaagaagcat acaccccccgg aacattggag tccgtgagtg    36000
aaaaaaagcg gccgaggaag caatgaggca ctacaacgct cactctcaag tccagcaaag    36060
cgatgccatg cggatgaagc acaaaatttt caggtgcgta aaaaatgtaa ttactcccct    36120
cctgcacagg cagcgaagct cccgatccct ccagatacac atacaaagcc tcagcgtcca    36180
tagcttaccg agcggcagca gcagcggcac acaacaggcg caagagtcag agaaaagact    36240
gagctctaac ctgtccgccc gctctctgct caatatatag ccccagatct acactgacgt    36300
aaaggccaaa gtctaaaaat acccgccaaa taatcacaca cgcccagcac acgcccagaa    36360
accggtgaca cactcagaaa aatacgcgca cttcctcaaa cggccaaact gccgtcattt    36420
ccgggttccc acgctacgtc atcaaaacac gactttcaaa ttccgtcgac cgttaaaaac    36480
atcacccgcc ccgcccctaa cggtcgccgc tcccgcagcc aatcaccttc ctccctcccc    36540
aaattcaaac agctcatttg catattaacg cgcaccaaaa gtttgaggta tattattgat    36600
gatg                                                                36604
```

<210> SEQ ID NO 106
<211> LENGTH: 948
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Glu Leu Arg Ser Arg Tyr Trp Ala Ile Arg Thr Arg Ser Gly Arg Val
1               5                   10                  15

Lys Arg Glu Leu Arg Ser Arg His Trp Ala Ile Arg Thr Arg Ser Gly
            20                  25                  30

Arg Val Lys Arg Glu Leu Arg Ser Arg Tyr Trp Ala Ser Arg Thr Arg
        35                  40                  45

```
Ser Gly Arg Val Lys Arg Phe Met Tyr Ser Asp Phe His Phe Ile Arg
 50                  55                  60

Val Lys Arg Phe Met Tyr Ser Asp Leu His Phe Ile Arg Val Lys Arg
 65                  70                  75                  80

Phe Met Tyr Thr Asp Phe His Phe Ile Arg Val Lys Arg Phe Met Phe
                 85                  90                  95

Ser Asp Phe His Phe Ile Arg Val Lys Arg Gly Thr Phe Glu Phe Thr
                100                 105                 110

Ser Phe Phe Tyr Arg Val Lys Arg Gly Thr Phe Glu Phe Thr Ser Tyr
            115                 120                 125

Phe Tyr Arg Val Lys Arg Ile Leu Lys Gly Lys Phe Gln Thr Ala Arg
        130                 135                 140

Val Lys Arg Ile Ile Lys Gly Lys Phe Gln Thr Ala Arg Val Lys Arg
145                 150                 155                 160

Ile Leu Lys Gly Lys Phe Gln Ile Ala Arg Val Lys Arg Ile Leu Arg
                165                 170                 175

Gly Ser Ile Ala His Lys Arg Val Lys Arg Ile Leu Arg Gly Ser Val
                180                 185                 190

Ala His Lys Arg Val Lys Arg Val Leu Arg Gly Ser Ile Ala His Lys
            195                 200                 205

Arg Val Lys Arg Leu Ile Phe Leu Ala Arg Ser Ala Leu Arg Val Lys
        210                 215                 220

Arg Leu Val Phe Leu Ala Arg Ser Ala Leu Arg Val Lys Arg Leu Thr
225                 230                 235                 240

Phe Leu Ala Arg Ser Ala Leu Arg Val Lys Arg Tyr Ser His Gly Thr
                245                 250                 255

Gly Thr Gly Tyr Arg Val Lys Arg Tyr Ser His Trp Thr Gly Thr Gly
                260                 265                 270

Tyr Arg Val Lys Arg Tyr Ser His Gly Ser Gly Thr Gly Tyr Arg Val
            275                 280                 285

Lys Arg Phe Leu Ala Arg Ser Ala Leu Ile Leu Arg Gly Ser Val Ala
        290                 295                 300

His Lys Arg Val Lys Arg Phe Leu Ala Arg Ser Ala Leu Val Leu Arg
305                 310                 315                 320

Gly Ser Val Ala His Lys Arg Val Lys Arg Ile Ala Tyr Glu Arg Met
                325                 330                 335

Cys Asn Ile Leu Lys Gly Lys Phe Gln Thr Ala Ala Arg Val Lys Arg
                340                 345                 350

Val Ala Tyr Glu Arg Met Cys Asn Ile Leu Lys Gly Lys Phe Gln Thr
            355                 360                 365

Ala Ala Arg Val Lys Arg Val Ala Tyr Glu Arg Met Cys Asn Ile Ile
        370                 375                 380

Lys Gly Lys Phe Gln Thr Ala Ala Arg Val Lys Arg Val Ala Tyr Glu
385                 390                 395                 400

Arg Met Cys Asn Ile Leu Lys Gly Lys Phe Lys Thr Ala Ala Arg Val
                405                 410                 415

Lys Arg Val Ala Tyr Glu Arg Met Cys Asn Ile Leu Lys Gly Lys Phe
            420                 425                 430

Gln Ile Ala Ala Arg Val Lys Arg Val Ala Tyr Glu Arg Met Cys Asn
        435                 440                 445

Ile Leu Lys Gly Lys Phe Gln Thr Ala Val Arg Val Lys Arg Asp Val
        450                 455                 460
```

```
Val Asn Phe Val Ser Met Glu Phe Ser Leu Thr Asp Pro Arg Leu Arg
465                 470                 475                 480

Val Lys Arg Asp Val Asn Phe Val Ser Met Glu Phe Ser Leu Thr
            485                 490                 495

Tyr Pro Arg Leu Arg Val Lys Arg Asp Val Asn Phe Val Ser Met
        500                 505                 510

Glu Phe Ser Leu Thr Asp Gln Arg Leu Arg Val Lys Arg Phe Leu Ala
        515                 520                 525

Arg Ser Ala Leu Ile Leu Arg Gly Ser Val Ala His Lys Ser Arg Val
        530                 535                 540

Lys Arg Phe Leu Ala Arg Ser Ala Leu Val Leu Arg Gly Ser Val Ala
545                 550                 555                 560

His Lys Ser Arg Val Lys Arg Lys Trp Gly Met Glu Met Arg Arg Cys
                565                 570                 575

Leu Leu Gln Ser Leu Gln Gln Ile Arg Val Lys Arg Lys Leu Gly Met
                580                 585                 590

Glu Met Arg Arg Cys Leu Leu Gln Ser Leu Gln Gln Ile Arg Val Lys
            595                 600                 605

Arg Lys Trp Gly Met Glu Met Arg Arg Cys Leu Leu Gln Ser Leu Gln
        610                 615                 620

Gln Val Arg Val Lys Arg Lys Trp Gly Met Glu Leu Arg Arg Cys Leu
625                 630                 635                 640

Leu Gln Ser Leu Gln Gln Ile Arg Val Lys Arg Phe Gln Gly Arg Gly
                645                 650                 655

Val Phe Glu Leu Arg Val Lys Arg Gly Gln Ile Ser Ile Gln Pro Thr
            660                 665                 670

Phe Ser Arg Val Lys Arg Ser Gln Ile Ser Val Gln Pro Thr Phe Ser
            675                 680                 685

Arg Val Lys Arg Gly Gln Val Ser Val Gln Pro Thr Phe Ser Arg Val
        690                 695                 700

Lys Arg Gly Gln Ile Ser Val Gln Pro Thr Phe Ser Arg Val Lys Arg
705                 710                 715                 720

Trp His Ser Asn Leu Asn Asp Ala Thr Tyr Gln Arg Thr Arg Ala Leu
                725                 730                 735

Val Arg Thr Gly Met Asp Pro Arg Met Arg Val Lys Arg Trp His Ser
            740                 745                 750

Asn Leu Asn Asp Thr Thr Tyr Gln Arg Thr Arg Ala Leu Val Arg Thr
                755                 760                 765

Gly Met Asp Pro Arg Met Arg Val Lys Arg Trp His Ser Asn Leu Asn
770                 775                 780

Asp Ser Thr Tyr Gln Arg Thr Arg Ala Leu Val Arg Thr Gly Met Asp
785                 790                 795                 800

Pro Arg Met Arg Val Lys Arg Trp His Ser Asn Leu Asn Asp Ala Thr
            805                 810                 815

Tyr Gln Arg Lys Arg Ala Leu Val Arg Thr Gly Met Asp Pro Arg Met
        820                 825                 830

Arg Val Lys Arg Trp His Ser Asn Leu Asn Asp Ala Thr Tyr Gln Arg
            835                 840                 845

Thr Arg Ser Leu Val Arg Thr Gly Met Asp Pro Arg Met Arg Val Lys
        850                 855                 860

Arg Trp His Ser Asn Leu Asn Asp Ala Thr Tyr Gln Arg Thr Arg Ala
865                 870                 875                 880

Ile Val Arg Thr Gly Met Asp Pro Arg Met Arg Val Lys Arg Trp His
```

885                 890                 895

Ser Asn Leu Asn Asp Ala Thr Tyr Gln Arg Thr Arg Ala Leu Val Arg
                    900                 905                 910

Ser Gly Met Asp Pro Arg Met Arg Val Lys Arg Trp His Ser Asn Leu
                915                 920                 925

Asn Asp Ala Thr Tyr Gln Arg Thr Arg Ala Leu Val Arg Thr Gly Arg
            930                 935                 940

Asp Pro Arg Met
945

<210> SEQ ID NO 107
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 'Gly Gly Gly
      Gly Ser' repeating units

<400> SEQUENCE: 107

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 108
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 'Glu Ala Ala
      Ala Lys' repeating units

<400> SEQUENCE: 108

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Lys Glu Ala Ala Ala Lys Glu
                85                  90                  95

Ala Ala Ala Lys
            100

```
<210> SEQ ID NO 109
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(35)
```

```
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: MISC_FEATURE
<222> LOCATION: (1)..(40)
<223> OTHER INFORMATION: This sequence may encompass 1-20 'Xaa Pro'
      repeating units

<400> SEQUENCE: 109

Xaa Pro Xaa Pro Xaa Pro Xaa Pro Xaa Pro Xaa Pro Xaa Pro Xaa Pro
1               5                   10                  15

Xaa Pro Xaa Pro Xaa Pro Xaa Pro Xaa Pro Xaa Pro Xaa Pro Xaa Pro
            20                  25                  30

Xaa Pro Xaa Pro Xaa Pro Xaa Pro
        35                  40

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Val Lys Arg
1

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S-[2,3-bis(palmitoyloxy)-(2-R,S)-propyl]-N-
      palmitoyl-(R)-cysteine

<400> SEQUENCE: 111

Cys Ser Lys Lys Lys Lys
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tripalmitoyl-S-glyceryl-cysteine

<400> SEQUENCE: 112

Cys Ser Ser Asn Ala
1               5

<210> SEQ ID NO 113
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tripalmitoyl-S-glyceryl-cysteine

<400> SEQUENCE: 113

Cys Ser Lys Lys Lys Lys
1               5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dipalmitoyl-S-glyceryl-cysteine

<400> SEQUENCE: 114

Cys Ser Lys Lys Lys Lys
1               5

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ala Leu Asn Asn Arg Phe Gln Ile Lys Gly Val Glu Leu Lys Ser
1               5                   10                  15

<210> SEQ ID NO 116
<211> LENGTH: 560
<212> TYPE: PRT
<213> ORGANISM: Influenza B virus

<400> SEQUENCE: 116

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125
```

```
Phe Gln Lys Lys Lys Asn Ala Arg Asp Val Lys Glu Gly Lys Glu Glu
    130                 135                 140
Ile Asp His Asn Lys Thr Gly Gly Thr Phe Tyr Lys Met Val Arg Asp
145                 150                 155                 160
Asp Lys Thr Ile Tyr Phe Ser Pro Ile Arg Ile Thr Phe Leu Lys Glu
                165                 170                 175
Glu Val Lys Thr Met Tyr Lys Thr Thr Met Gly Ser Asp Gly Phe Ser
                180                 185                 190
Gly Leu Asn His Ile Met Ile Gly His Ser Gln Met Asn Asp Val Cys
            195                 200                 205
Phe Gln Arg Ser Lys Ala Leu Lys Arg Val Gly Leu Asp Pro Ser Leu
    210                 215                 220
Ile Ser Thr Phe Ala Gly Ser Thr Val Pro Arg Arg Ser Gly Ala Thr
225                 230                 235                 240
Gly Val Ala Ile Lys Gly Gly Thr Leu Val Ala Glu Ala Ile Arg
                245                 250                 255
Phe Ile Gly Arg Ala Met Ala Asp Arg Gly Leu Leu Arg Asp Ile Lys
                260                 265                 270
Ala Lys Thr Ala Tyr Glu Lys Ile Leu Leu Asn Leu Lys Asn Lys Cys
            275                 280                 285
Ser Ala Pro Gln Gln Lys Ala Leu Val Asp Gln Val Ile Gly Ser Arg
    290                 295                 300
Asn Pro Gly Ile Ala Asp Ile Glu Asp Leu Thr Leu Leu Ala Arg Ser
305                 310                 315                 320
Met Val Val Val Arg Pro Ser Val Ala Ser Lys Val Val Leu Pro Ile
                325                 330                 335
Ser Ile Tyr Ala Lys Ile Pro Gln Leu Gly Phe Asn Val Glu Glu Tyr
                340                 345                 350
Ser Met Val Gly Tyr Glu Ala Met Ala Leu Tyr Asn Met Ala Thr Pro
            355                 360                 365
Val Ser Ile Leu Arg Met Gly Asp Asp Ala Lys Asp Lys Ser Gln Leu
    370                 375                 380
Phe Phe Met Ser Cys Phe Gly Ala Ala Tyr Glu Asp Leu Arg Val Leu
385                 390                 395                 400
Ser Ala Leu Thr Gly Thr Glu Phe Lys Pro Arg Ser Ala Leu Lys Cys
                405                 410                 415
Lys Gly Phe His Val Pro Ala Lys Glu Gln Val Glu Gly Met Gly Ala
                420                 425                 430
Ala Leu Met Ser Ile Lys Leu Gln Phe Trp Ala Pro Met Thr Arg Ser
            435                 440                 445
Gly Gly Asn Glu Val Gly Gly Asp Gly Gly Ser Gly Gln Ile Ser Cys
    450                 455                 460
Ser Pro Val Phe Ala Val Glu Arg Pro Ile Ala Leu Ser Lys Gln Ala
465                 470                 475                 480
Val Arg Arg Met Leu Ser Met Asn Ile Glu Gly Arg Asp Ala Asp Val
                485                 490                 495
Lys Gly Asn Leu Leu Lys Met Met Asn Asp Ser Met Ala Lys Lys Thr
                500                 505                 510
Ser Gly Asn Ala Phe Ile Gly Lys Lys Met Phe Gln Ile Ser Asp Lys
            515                 520                 525
Asn Lys Thr Asn Pro Ile Glu Ile Pro Ile Lys Gln Thr Ile Pro Asn
    530                 535                 540
```

```
Phe Phe Phe Gly Arg Asp Thr Ala Glu Asp Tyr Asp Asp Leu Asp Tyr
545                 550                 555                 560
```

<210> SEQ ID NO 117
<211> LENGTH: 560
<212> TYPE: PRT
<213> ORGANISM: Influenza B virus

<400> SEQUENCE: 117

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365
```

```
Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
            435                 440                 445

Gly Gly Asn Glu Val Gly Gly Asp Gly Gly Ser Gly Gln Ile Ser Cys
        450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Val Glu Ile Pro Ile Lys Gln Thr Ile Pro Asn
        530                 535                 540

Phe Phe Phe Gly Arg Asp Thr Ala Glu Asp Tyr Asp Asp Leu Asp Tyr
545                 550                 555                 560

<210> SEQ ID NO 118
<211> LENGTH: 560
<212> TYPE: PRT
<213> ORGANISM: Influenza B virus

<400> SEQUENCE: 118

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala Tyr
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
```

-continued

```
            180                 185                 190
Gly Leu Asn His Ile Met Ile Gly His Ser Gln Met Asn Asp Val Cys
            195                 200                 205

Phe Gln Arg Ser Lys Ala Leu Lys Arg Val Gly Leu Asp Pro Ser Leu
            210                 215                 220

Ile Ser Thr Phe Ala Gly Ser Thr Val Pro Arg Arg Ser Gly Ala Thr
225                 230                 235                 240

Gly Val Ala Ile Lys Gly Gly Thr Leu Val Ala Glu Ala Ile Arg
            245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
            275                 280                 285

Ser Ala Pro Gln Gln Lys Ala Leu Val Asp Gln Val Ile Gly Ser Arg
            290                 295                 300

Asn Pro Gly Ile Ala Asp Ile Glu Asp Leu Thr Leu Leu Ala Arg Ser
305                 310                 315                 320

Met Val Val Arg Pro Ser Val Ala Ser Lys Val Val Leu Pro Ile
            325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
            355                 360                 365

Val Ser Ile Leu Arg Met Gly Asp Asp Ala Lys Asp Lys Ser Gln Leu
            370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
            405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
            435                 440                 445

Gly Gly Asn Glu Ala Gly Gly Asp Gly Gly Ser Gly Gln Ile Ser Cys
            450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
            485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
            515                 520                 525

Asn Lys Thr Asn Pro Ile Glu Ile Pro Lys Gln Thr Ile Pro Asn
            530                 535                 540

Phe Phe Phe Gly Arg Asp Thr Ala Glu Asp Tyr Asp Leu Asp Tyr
545                 550                 555                 560
```